US006316609B1

(12) United States Patent
Dillon et al.

(10) Patent No.: US 6,316,609 B1
(45) Date of Patent: Nov. 13, 2001

(54) NUCLEOTIDE SEQUENCE OF *ESCHERICHIA COLI* PATHOGENICITY ISLANDS

(75) Inventors: Patrick J. Dillon, Gaithersburg; Gil H. Choi, Rockville, both of MD (US); Rodney A. Welch, Madison, WI (US)

(73) Assignees: Human Genome Sciences, Inc., Rockville, MD (US); Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 08/976,259

(22) Filed: Nov. 21, 1997

Related U.S. Application Data
(60) Provisional application No. 60/061,953, filed on Oct. 14, 1997, and provisional application No. 60/031,626, filed on Nov. 22, 1996.

(51) Int. Cl.[7] ........................ C07H 21/04; C12N 15/63; C12N 15/85; C12N 1/21

(52) U.S. Cl. ................ 536/23.1; 536/23.1; 536/24.3; 536/24.32; 435/320.1; 435/252.3; 435/252.33; 435/325

(58) Field of Search .................................. 536/23.1, 23.7, 536/24.3, 24.32, 24.33; 435/320.1, 252.3, 69.1

(56) References Cited

U.S. PATENT DOCUMENTS 5,447,862 * 9/1995 Heim et al. .................. 435/252.3
5,457,048 * 10/1995 Pasquale et al. ............ 435/252.3

FOREIGN PATENT DOCUMENTS

386752 * 9/1990 (EP) .

OTHER PUBLICATIONS

CM Shea et al (1991) Mol Microbiol 5: 1415–1428.*
RD Fleischmann et al (1995) Science 269: 496–512.*
SR Wente et al (1992) J Cell Biol 119: 705–723.*
R Hromas et al (1993) Blood 81: 2854–2859.*
SH Fischer et al (1991) Mol Microbiol 5: 1151–1158.*
PC Maisonpierre et al (1990) Science 247: 1446–1451.*
SW Lacey et al (1989) J Clin Invest 84: 715–720.*
McDonough K.A. et al., Yersinia pestis pesticin plasmid putative insertion sequence IS100, XP002069557, AC u59875, J. Bacteriol., vol. 179, pp. 2081–2085 (1997).
Podlachikova O. et al., Yersinia pestis insertion sequence IS100, XP002069152, AC z32853, Fems Microbiol., vol. 121, pp. 269–274 (1994).
Burland et al., "Analysis of the *Escherichia coli* genome VI: DNA sequence of the region from 92.8 through 100 minutes", Nucleic Acids Research, vol. 23, No. 12, pp. 2105–2119 (1995).
Bloch, C.A. et al., "Comparative Genome Mapping with Mobile Physical Map Landmarks," *J. Bacteriology* 176(22):7121–7125 (1994).

Blum, G. et al., "Excision of Large DNA Regions Termed Pathogenicity Islands from tRNA–Specific Loci in the Chromosome of an *Escherichia coli* Wild–Type Pathogen," *Infection and Immunity* 62(2):606–614 (1994).
Felmlee, T. et al., "Nucleotide Sequence of an *Escherichia coli* Chromosomal Hemolysin," *J. Bacteriology* 163(1):94–105 (1985).
Fetherston, J.D. et al., "Loss of the pigmentation phenotype in *Yersinia pestis* is due to the spontaneous deletion of 102kb of chromosomal DNA which is flanked by a repetitive element," *Mol. Microbio.* 6(18):2693–2704 (1992).
Fetherston, J.D. and R.D. Perry, "The pigmentation locus of *Yersini a pestis* KIM6+ is flanked by an insertion sequence and includes the structural genes for pesticin sensitivity and HMWP2," *Mol. Microbio.* 13(4):697–708 (1994).
Forestier, C. and R.A. Welch, "Nonreciprocal Complementation of the hlyC and lktC Genes of the *Escherichia coli* Hemolysin and *Pasteurella haemolytica* Leukotoxin Determinants," *Infection and Immunity* 58(3):828–832 (1990).
Groisman, E.A. and H. Ochman, "Cognate gene clusters govern invasion of host epithelial cells by *Salmonella typhimurium* and *Shigella flexneri*," *EMBO* 12(10):3779–3787 (1993).
Hacker, J. et al., "Deletions of chromosomal regions coding for fimbriae and hemolysins occur in vitro and in vivo in various extraintestinal *Escherichia coli* isolates," *Microbial Pathogenesis* 8:213–225 (1990).
High, N.J. et al., "A Block of Urovirulence Genes Encoding Multiple Fimbriae and Hemolysin in *Escherichia coli* O4:K12:H–" *Infection and Immunity* 56(2):513–517 (1988).
Hultgren, S.J. et al., "Role of Type 1 Pili and Effects of Phase Variation on Lower Urinary Tract Infections Produced by *Escherichia coli*," *Infection and Immunity* 50(2):370–377 (1985).
Knapp, S. et al., "Large, Unstable Inserts in the Chromosome Affect Virulence Properties Of Uropathogenic *Escherichia coli* O6 Strain 536," *J. Bacteriology* 168(1):22–30 (1986).
Labigne–Roussel, A.F. et al., "Cloning and Expression of an Afimbrial Adhesin (AFA–I) Responsible for P Blood Group–Independent, Mannose–Resistant Hemagglutination from a Pyelonephritic *Escherichia coli* Strain," *Infection and Immunity* 46(1):251–259 (1984).

(List continued on next page.)

*Primary Examiner*—Deborah J. R. Clark
*Assistant Examiner*—Eleanor Sorbello
(74) *Attorney, Agent, or Firm*—Human Genome Sciences, Inc.

(57) ABSTRACT

The present invention relates to novel genes located in two chromosomal regions within uropathogenic *E. coli* that are associated with virulence. These chromosomal regions are known as pathogenicity islands (PAIs). In particular, the present application discloses 142 sequenced fragments (contigs) of DNA from two pools of cosmids covering pathogenicity islands PAI IV and PAI V located on the chromosome of the uropathogenic *Escherichia coli* J96. Further disclosed are 351 predicted protein-coding open reading frames within the sequenced fragments.

113 Claims, 2 Drawing Sheets

OTHER PUBLICATIONS

McDaniel, T.K. et al., "A genetic locus of enterocyte effacement conserved among diverse enterobacterial pathogens," *Proc. Natl. Acad. Sci. USA* 92:1664–1668 (Feb. 1995).

Mills, D.M. et al., "A 40kb chromosomal fragment encoding *Salmonella typhimurium* invasion genes is absent from the corresponding region of the *Escherichia coli* K–12 chromosome," *Mol. Microbiol.* 15(4):749–759 (Feb. 1995).

Mühldorfer, I. and J. Hacker, "Genetic aspects of *Escherichia coli* virulence," *Microbial Pathogenesis* 16:171–181 (1994).

Pellett, S. et al., "Characterization of Monoclonal Antibodies against the *Escherichia coli* Hemolysin," *Infection and Immunity* 58(3):822–827 (1990).

Riley, M. "Functions of the Gene Products of *Escherichia coli*," *Microbiol. Reviews* 57(4):862–952 (1993).

Ritter, A. et al., "tRNA genes and pathogenicity islands: influence on virulence and metabolic properties of uropathogenic *Escherichia coli*," *Mol. Microbiol.* 17(1):109–121 (Jul. 1995).

Strömberg, N. et al., "Host–specificity of uropathogenic *Escherichia coli* depends on differences in binding specificity to Galα1–4Gal–containing isoreceptors," *EMBO* 9(6):2001–2010 (1990).

Swenson, D.L. et al., "Two Pathogenicity Islands in Uropathogenic *Escherichia coli* J96: Cosmid Cloning and Sample Sequencing," *Infection and Immunity* 64(9):3736–3743 (Sep. 1996).

Swihart, K.G. and R.A. Welch, "The HpmA Hemolysin Is More Common than HlyA among Proteus Isolates," *Infection and Immunity* 58(6):1853–1860 (1990).

Uphoff, T.S. and R.A. Welch, "Nucleotide Sequencing of the *Proteus mirabilis* Calcium–Independent Hemolysin Genes (hpmA and hpmB) Reveals Sequence Similarity with the *Serratia marcescens* Hemolysin Genes (shlA and shlB)," *J. Bacteriology* 172(3):1206–1216 (1990).

Welch, R.A. et al., "Haemolysin contributes to virulence of extra–intestinal *E. coli* infections," *Nature* 294:665–667 (1981).

Welch, R.A. et al., "Molecular Cloning and Physical Characterization of a Chromosomal Hemolysin from *Escherichia coli*," *Infection and Immunity* 42(1):178–186 (1983).

Welch, R.A. and S. Falkow, "Characterization of *Escherichia coli* Hemolysins Conferring Quantitative Differences in Virulence," *Infection and Immunity* 43(1):156–160 (1984).

Welch, R.A., "Identification of Two Different Hemolysin Determinants in Uropathogenic Proteus isolates," *Infection and Immunity* 55(9):2183–2190 (1987).

Welch, R.A. and S. Pellett, "Transcriptional Organization of the *Escherichia coli* Hemolysin Genes," *J. Bacteriology* 170(4):1622–1630 (1988).

\* cited by examiner

SEQUENCE LISTING (1) GENERAL INFORMATION:

(iii) NUMBER OF SEQUENCES: 142

(2) INFORMATION FOR SEQ ID NO: 1:

(i) SEQUENCE CHARACTERISTICS:
        (A) LENGTH: 1178 base pairs
        (B) TYPE: nucleic acid
        (C) STRANDEDNESS: double
        (D) TOPOLOGY: linear (xi) SEQUENCE DESCRIPTION: SEQ ID NO: 1:

```
CNTANATTAG GCCTGCTNAA TGTATTTATA TCTAAAAAAA TTCGCATCCA AAAGGAATCC        60

AATCTGTACT GTTTTTTCTT GTGCTGACAT CTTCTTTTCC CTGGCTGGTA TGGCAAGTGA       120

CGGAGACAAG AGAAACGTTT TAAGCTCAGT TATCTCCGCC ATCACTTTCC ACGAATGACA       180

AGTAATTTTG CCTATTTTAA AACCATGCAA AAGGCAGGGT AAAAGGAGAA AATTCGATCG       240

AATCGATCGA CAAAATCGAT CATACATGAT GAAGATTTCT TATCGAATCC ATAAAAATAG       300

TGACAGCTAA CCGGCGTTGC AGGAACAGTC AGAAATGGGC GTTTGGGAAA GAGCCATAGC       360

ATACGTCGTC GCTGACATAG AGGAACTGTG CTTTGTTGAT AAGATCCTTT ATACGGCAAC       420

CAATCCACTG GACAAAAGAT GAACTACGTA ATCACCGGGT TCTCACTGAC GAAATACAGA       480

AGTTAATGAC ACAACTGTGC CATGCACCTT GTACAACAGC GGTGGAAAGC TCTCAGAACA       540

ATGGAATTGC AGAAAGGTGT TAAAACGATG AAAGCCTTCA TACCCAAATC GAATGTAAGA       600

ACGGCAGTAA AGACTGAATT GCGTAACCTT GCAGTAGCTC GAGTATTACA CTGCATAGTG       660

TGCAGGGTTA TCTCCCATCG AGAAAATATC GGCGCCAGCG AATAACGTCA CCTTAGATGT       720

AGCAGTTGCC AAATAGTGAC TCAAGGGCGG GCTTACCGCA TACACTGACA CTTAGCGGAT       780

CGACAGAATA TTATTAGCAG ATCATCACTG AACGCTACGT AATTATCGTA ATAAAGGCTT       840

TTTCTGGCTA CCAGGAAGAC CTGACATGGC TCTGCTCTGG AACCAGGCCG CAGGAAGCAT       900

CAATCTGGAG TTTATCAGCT ACTGGAATTC CGGTGTATTG GCAGCCCCTG ATAATCACCT       960

GACCCACGAA GAGCGCTCTG CTTTGCAGAA ACTCTGGGGC GGTTTGGAGA CAGGAGATGT      1020

AACGATTATA GGACGTTCTG ATGAAGTCCA TGATTTTACC TCCGCCTTAA TTAACTGTTT      1080

TCTTTCTGAA GAAGAAATTG TCTGGTGGCA ATCAGGTGGC ATTTTCCCGG ATCCTTGGCC      1140

CGCTAATATA TCCCGGCTGA ACTGACGATT AACGCGAT                              1178
```

(2) INFORMATION FOR SEQ ID NO: 2:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (xi) SEQUENCE DESCRIPTION: SEQ ID NO: 2:

```
ATCCTATTCA TTTTGCCATG ACGGGCGAAC TCCAGATAAA GGTTTTGAAA GTAATGAGAA        60

ATTATTAATT CATCCATGTT ACTGGCTTGG TTTGAATCTA AATCGTAATG CACTTGCTCC       120

AGAGGAAGCA GAGGAGATAA ATGACGAATA TGATATTAAT ATTATTTCAG ATAATTCAGC       180

CATTAGAAAT AAAACAATAG GTCAAATAAC TACTCATCTA GATCAGATAC CGATAGGAAA       240

TGAAGGTGCC ACTGAATTTG AACAATGGTG TTTAGACGCA CTAAGAATAG TATTTGCATC       300
```

-continued

| | |
|---|---|
| CCACCTAACA GACATCAAGT CCCATCCAAA TGGTAACGCA GTTCAGAGAC GAGATATTAT | 360 |
| AGGCACCAAT GGTGGCAAAT CTGAWTTTTG GRAACGAGTA TTGGAGGACT ATAA | 414 |

(2) INFORMATION FOR SEQ ID NO: 3:

(i) SEQUENCE CHARACTERISTICS:
        (A) LENGTH: 8752 base pairs
        (B) TYPE: nucleic acid
        (C) STRANDEDNESS: double
        (D) TOPOLOGY: linear (xi) SEQUENCE DESCRIPTION: SEQ ID NO: 3:

| | |
|---|---|
| TTGGGATCTG GTACANTCCA CCCAGCGGCA TTATCCNGAA GGCAATATTT TTAAGGATTA | 60 |
| TTCGTCCACA AAATCAGTAC TGGAACCAGG CTCAAAAAAG GCTTTAACGT GACCTGCTNC | 120 |
| CATCTACAGT AGATGTACAA CCTGTTAAGT TAATTGAAAA TGGTGTTAAT CCGGTTGTTT | 180 |
| CTCCAGGGGT AGCAAGGGCC TTATTCGATA CAGTGGGTAA TGTTACTGTA AAATTACCAT | 240 |
| CATTCCCTGT GGTCACATTG CAGGTCTGAG CTACAACTTT GCCTGTAAAC GTAATTGTTC | 300 |
| CGTCATAGGC CATAGCTGAA CCAACAAACA CAGCAGAAAC AAATGTAGCC AATGCTATAA | 360 |
| CTTTTATTTT CATAAAATGA ATTCCTGTTT AATTCCGGTA TTGATCATTT GTTCAGCAAT | 420 |
| CATCCCCAAC AAAACAATCA TTTTCAAAAT GTTTTTACCG ATCGATAACC AGCACATGAT | 480 |
| AGATTGCACC TATCATGATT GCTAAAACGA TCGGGAAAAG CGATCAAAAA CCATATTTAT | 540 |
| TGTGTTGGTA ATGACAAAAG ATATGCTTTA CCCTGAAATG AGCGACCTAT TCATGAAAAT | 600 |
| ATGTAGGTCT GTATTTGATT ACTATCATTG CTATATTTCC ACTATCCAAT TTATATTTCA | 660 |
| TGATTAAAAT ATACCTTTTT ACACTATTAT TTATTTGTTG CAGCTTGCCT GGCTTTATCT | 720 |
| TATTCCGACT ATTTTATGGT AGATACAGAA TACAATTAAT TAAACTTATT TAAAGATTTT | 780 |
| ATAAATACCA TATTGGAGTT GACCGATAGA TACCTACTAA CAAGAGCAAT CACCACCACC | 840 |
| CCATGAGGTG TTTAGGAATA CAATCAATAA ACAACATCCA TGCCCGGCGA CGTACATACC | 900 |
| TGTTTGCTAT GATATCTGTT ACGCTACGCT TGCTAATTTA CTGAAACTCA GCATCTGTCG | 960 |
| ACGGAGATTC GTCCGGGCCC TGATACAACA AGGGCAAGAA AACCACCCGA AATACAGATA | 1020 |
| TTCTTATAAA AATGGATCAT ATTTCCATGT GCAAGTTCAG CTGGCATCGT CCAGAATGCG | 1080 |
| TGTCCAAGAA ATGAAGCAAA CACGGTATAC AGGCACAGAA TAATGCTCAC TGGCCGGGTG | 1140 |
| AAAAAGCCRA AAACAATCAT TAATGCTCCA ACGATTTCGA CAAGGACCAC TATTGCTGCA | 1200 |
| GTAATCGCCG GAAATATAAG CCCAAGAGAG GCCATTTTAT CGATAGTGCC AGTGAATGAT | 1260 |
| AGCAGCTTGG GAACGCCGGA TATCATATAA AGGCATGCCA GCATCAGACG GGCAAGGAGC | 1320 |
| AACAATGCCG ACGTGTAATT TCCCATATTA AAATACCTGA TTTTATCCAC TATCAATGCT | 1380 |
| CAGTCTCCTT GTTTCTGATA AAGCCCTGAG CCAAATCCTT AAGTGTACGA GCACCACTCA | 1440 |
| GTAACATTGC CGTCCTCAGC TCCGTCTTCA GGTGCTCAAT GACACTGGCA ACGCCCCGA | 1500 |
| CACCACCTGC TGCGATGCCA TAAAGAACAG GACGTCCGAC CGCAACAGCC GTTGCCCCAA | 1560 |
| GAGAGATAGC CCTTACAACA TCAACCCCCC TGCGAATACC GCTGTCAAAA ATGACCGGAA | 1620 |
| CTTTGTGCCC GACTCTTGCA GCAACTTCCT GCAACTGGCT GATGGCAGAA GGAACACCAT | 1680 |
| CAATCTGGCG ACCACCATGA TTAGACACCT GGATGGCATC TGCTCCTGCA TCAATGGCGA | 1740 |
| CCACTGCATC CTCACCTCTG AGGATGCCCT TGACAATGAC TGGCAGCCCG GTGATTTTTT | 1800 |
| TTACAAACTC AATATCAGCC GGGGTCAGCT CAACTTTTTG GTTAAAAAAA TCACCTTTGC | 1860 |
| CACCGTAACG GGGGTCATGA TTACCGAACG TCGCTCCTGC AGGGAAAGGC GAGCTCATGC | 1920 |

```
                                                           -continued

TGAGAAAAGC ATCACTTGTC CCGGGACCAA GCGCATCCGC TGTGATAATA ATGGCTGAAT      1980

AGCCTGCCGC TTTTGCACGC TCCAGTAAAC TTCGGGTCAC ACCAGCATCC GCGTTAAAAT      2040

ACAGCTGGAA CCATTTAGGT CCTTTACTGG CTTTTGCAAT ATCCTCCAGA GAGCGGTTGG      2100

ATGCCCCTGA TGATTCATAA AGTGCCCCGG CCTTTTCTGC ACCCGCTGCA GCAATCACCT      2160

CCCCTTCCGG ATGGACGAAC ATATGCGCGC CCATAGGTGC TATCAGCAGG GGATGTTCCA      2220

GATGATGGCC CAAAAGGTCA GTCCGGATAT CAATGCTGTG GGCAGCAACT CCACTGAGTC      2280

GGTGAGGTAA CAAAGGATAA TCACTGAANT GCCTGCGGTT CTCATGATAC GTCCACTCAT      2340

CTCCAGCACC ATGAGCAATA TATGCATACG CAGCTTCCGT CATCACATCT TTTGCTGAAG      2400

TCTYCAGTCT GTCCAGACTG ATGATATGAA GAGATTTGCT GGTCGATGTA TCAGCATGTC      2460

CAGACGTTTT ACTGATGATA TGTGCCGTTG AAGATGAGAT ATTTTTGGCA AGGGCCGGCG      2520

CAGTTGACAG CCTGCGGCAG ATATTCCTAA ACGGCATTC  TGAATAAAAT TACGTCGGGA      2580

AAGAGGCATA ATAAGCTCCA TATATTATAA ATAAGCCAGG TCTCCCTGGC TTATAATGAT      2640

CATGCCACGC CCTGAAGCGG GTTGGTGTTG AAGGTATAAA GGAAAATTTT CCATTCACCA      2700

TTAATTTTAC TGAGGACAAA AACTTCACGG TTCAGGTCAA TAATGGTTTT CTGCTCTTTA      2760

AAGTTCGTTA CAACAGAACC CACATGGTGG TGAGTGCGGA CAACCGCGGT ATCTCCGTTG      2820

ATCCAGATAG AGTCAAACGC AAAATCGGTC TCAAACTTTT CACGCTTGAA CAGATCATCG      2880

TACTGCCCCT GGCGTTTTTC TGTATTGTCA GCCGTCAACT TATCATTCCA CTGGGAATAA      2940

CTTTCATCAG CAAACAGGCC CAGGATGGTT TTTGTATCCC CGGCATTCAG TGCGTTCTGA      3000

TACTTGATTA TCGTGTCATA CACGTTCTTC TGCTCAGTAG CAATCTTACT GTCTGTGGAG      3060

TATTTGAATG TACCGCCGGA TTGTTCAGGT GAGCTTTCCT TCTGTGCTGT CGACGATGAG      3120

GCAGCCAGAG CATTAGAGCC GAAAAGAAGG GATGATGCCA TGACTGCTGT TGCTATAAAA      3180

TGTTTCATAT ATTCTCCATC AGTTCTTCTG GGGATCTGTG GGCAGCATAT AGCGCTCATA      3240

CTATGCTGCT GTTTCAATAT TAGCGGCAGA CGTCAGCCTT ACCGCACTAC TTATTGGATA      3300

AGAATATCAA AAGTGACCGT GAAGTCAATT TTATCACAAC ACAGAAGGCC ACTATTTATG      3360

CCCAGAAAAT ATGAATCGTC CTCATCATGC ACGAAAGACT CGTAGTTGCA GCCCGGAAAA      3420

AACTGCCAGG ACACGACAGC AGATAGCCCG GGCAGCACTT GAGGAGTTCT CTGCACAAGG      3480

GTTCGCTCGC GCCACATNCA GCAATATCAG CAAGCGCGCA GGAGTAGCTA AAGGCACGGT      3540

ATATAACTAC TTCCCAACAA AGGAATTATT GTTTGAAGCG GTTCTGAAGG AGTTCATTGC      3600

TACCGTCCGT ACTGAACTGG AATCTTCCCC CCGCCGCAAC GGGGNAAACC GTAAAAGCCT      3660

ATCTGTTGAG AGTGATGTTA CCTGCCGTCA GGAAAATTGA CGACGCATCA ACAGGCAGAG      3720

CCAGAATAGC CCACCTGGTT ATGACAGAAG GGAGCCGGTT CCCGGTAATC GCTCAGGCTT      3780

ATTTACGGGA AATACATCAG CCACTACAGC AAGCCATGAC CCAACTGATT CAGGAAGCAG      3840

CATCAGCCGG AGAGTTAAAA GCAGAGCAAC TGCTCTGCKT CCCCTGTTTA TTGCTGGCTC      3900

CAAACTGGTT TGGCATGGTG TATAACGAAT TCTGAACCCG GCAGCACCGG TCAGTACAGG      3960

CGATCTTTTT GAAGCCGGAA TTGGTGCTTT TTTCCGATAG ACACATAACT GTCAGTATTA      4020

TGACCATGCC GTCAGGAGGA GGTATACCAG TGATACCCTG CCATGACCCG GTAACGTCTC      4080

CTGGCTGCCT TAAACCTGAA AGACCTGGCC CCACCACACT GCCGGTTACG CATCAAGATG      4140

CAGCAACCCT TGCATAAGGC TGTTTTGTGC AGAGGGCTAC CGGAAAGATA ATAACGTCAC      4200

AGCCCGTATG CATCAGATAA AACAGTGTAT TTTATCTGTC AGCAGTCACT GGAGCGGATT      4260

GTGGGGCGAG ATTCAGGTGC TGATACTGTA ACGACTCTGC GCCGCTGCTG CGGTAAAAGC      4320
```

```
GGCTGCCACC AGGCACGGTT ATCAGAGGAG GATGACCGTG TCCGCCCCTG GTGGTGATGA    4380

ACTCTCCATC ACAATCAATA ATGCCGCCGG GTGGATGAAG CAGACAGGGA TGGCAAGTCC    4440

CACTATCCCG GATAAAATGG GCTCTGGGCG CTCAGAAGAC CTGTGTGTCA GGCAGGGGTG    4500

AGAACGGTGA TGTTTTTTGT TGTCTGAAAG TCCAGCTCCA GCATTGCCTG CCAGCCTCAA    4560

GACTTCCGCT TTCTGCCCTT TCCGGCATTT TCTTCCGTTA CCATCATTCT GTTAATTCAG    4620

AGGCGTAGTA GTAGTAAACG TAATACATAT CCGGGAGGAT GAAGTCATCT AATCCTGCTC    4680

CCCGAATATC ATACAGCCAT TCCTGAGTGT GACTGCACCA TTTCCAATTA TGCAGTCTGT    4740

CCTCATCACA AAAATGTTGC AAGCAGTGCG GAGTCACGTT CCGTATTCAT GCCCTCTGCC    4800

AGATATTGAG CGGGGAGAA ATGTGTAAGC GTCAACAGAG CGCCGTATTG ACACTTATTT     4860

ATCGGTGAAA ACTACGTTCC ATGGCAGCAG TTCGTCAACA CGGTTGGAGG GCCATTCCGG    4920

CAGTACGCTC AGGATATGGC GCAGATACGC TTCTGGATCG ATACCGTTCA ACCGACAGCT    4980

CCCGATTAGT CCGTACAGCA GAGCTCCGCG CTCGCCTCCA TGATCGTTGC CGAAGAACAT    5040

GTAATTCTTT TTCCCGAGAC AGACGGCACG AAGCGCTCTT TCTGCTGTGT TATTGTCCGC    5100

CTCCGCCAGA CCGTCATCAC TGTAATAACA GAGGGCGTCC CACTGATTCA GGACATAGCT    5160

GAACGCTTSR CCCAGTCTGG ATTTTTTCGA CAACGTGCCA TTCTTCTCCA CCATCCATTC    5220

ATGCAGCGAC GTCAGTAACG CTTTGCTTCG CTGCTGCCTG GCTGCAAGAC GTTCAGACTC    5280

CGGTAAGCCC CGTATTTCAT CMTCAATGGC GTACAGTTCA CTGATGCGCT TCAGAGCTTC    5340

TTCTGCCGTC GTACTTTTGC TGCTGATGTA TACATCGTGG ATTTTTCGCC GGGCATGGGC    5400

CCAGCACGCA ACTTCTGTCA GTGCACCACC TTCACGTTCG GCACTGAACA GCCGATCGTA    5460

ACCGCTGAAT GCATCCGCCT GCAGGATACC CCGGAAGGGA CGAAGGTGTT GTACCGGATG    5520

TTTTCCCTGC CTGTCTGGTG AGTAGGCGAA CCAGACCSCC GGTGGCTCTG ATGAGCCCGC    5580

ATTCCGGTCA TCCCSGACAT ACGTCCAGAT GCGTCCTGTT TTTGCCTTTT TTCTGCCCGG    5640

TGCCAGCACT TTTACTGGTA TGTCGTCAGT GTGAACCTTG CGGGTGTTCA TCACGTAACG    5700

GTACAGGGCA TCATTCAGCG GAGTCATTAA CTGGCAGCAC GCGTCAACCC AGTTGGAGAG    5760

TAATGCACGG CTCAGTTCGG CACCCTGTCG GGCAAAGATT TCACTCTGAC GATACAGTGG    5820

CAGGTGTTCG CAGTATTTTC CCGTTAACAC GCGGGCAAGT AATCCGGAGC CCGCGATGCC    5880

GCGCTCTATC GGGCGGGACG GCGCTGGCGC TTCAACTATA CAGTCACATT TTGTACAGGC    5940

TTTTTTTACC CGAACAGTGC GGATCACTTT CAGGGCGCTA CTCACCAGTT CCAGCTGCTC    6000

AGCACTAACT TCACCCAGAT AATCCAGCTC ACTGCCACAC TCCGGGCAAC AACTTTCTTC    6060

AGGCTCCAGG CGGTGTATTT CACGGGGAAG ATGTGCTGGT AACGGACGAC GATGACGTGA    6120

TTGTCGCAAC TGGCGGGGAA CTGCGGGTCA TCCTCACGCC CACTGTAACG ATCGCTTTCC    6180

TGTTCGCGTT GTTTCAGTTG GGCCTCAGCC TGTTCAACCT CACGCTGCAG TTTTTCAGAA    6240

CGGGTACCGA ACAGCATCCG GCGCAGTTTT TCTATCTGGG CCCTCAGATG TTCTATTTCC    6300

CGCTCCTCCT CTTCGATCTT TTCTTCGGCA CGTGCCARTG CAGAGCGCAG GAAGGCCTCC    6360

GTCTCTTCAA CCAGACTCAG TTGCTGATCT TTCTGACGGA GGGCTTCAGC CTGCTCAGAG    6420

AGTAGCCTTT CCAGCTCAGT GATACGAATG AGGTATTTCC GACTCATGAC CGTTTTTATA    6480

ATCCGGCCAT GACATTTTTA CAACATTGTC AGTGCATTAA GGCGGGATGT TTTGGGTTGA    6540

CGCCAGTCCA GTTATCGAG GAGCATTGCC AGCTGCGAGC GGGTAATGGA TACCTTACCG     6600

TCACGCACCG CAGNCCAGAT AAACTGGCCT TCCTCCAGAC GTTTGGTGAA CAGGCACAGA    6660
```

```
CCATCAGCAT CAGCCCACAG GATTTTAATC GTGTCACCCC GTCGGCCGCG AAAGATAAAC    6720

AGGTGACCGG AGAAGGGGTT CTCATCCAGC ACATGTTGTA CCTGTTCACC CAGACCGTTG    6780

AAGGATTTAC GCATATCAGT AACGCCGGCA ACCAGCCAGA TTCGAGTGTC TGATGGGAGC    6840

GAGATCATCG TCCTCTCCCG GTCAGTTCAC GGATCAACAC CGTGAGCAGC TCTGGTGAAG    6900

GATTTTCCAG CGTCATGTTA CCGTGGCGGA ACTCAACTTT ACAGGAACTG GCACTGACTG    6960

TGCTTTGTGA AGGAGTGGAT AAAAGCGGAG TAAGAGCCGC CATAGGCTCT TTCTGCTCAT    7020

CAGGCGTTAT CTCAACAGGT AATAATTCAA CGCCAGCGCC AGAAGAGGTT GTTACCGGAA    7080

GACGCCGCGA TATACGCCCT TCGTTCTGCC AGAGCCTGAG CCATTTGAAC AGGAGGTTAT    7140

CATTGATATC GTGTTCCCTG GCAATACGGG CAACAGAGGC TCCTGGTTGT GAAGCCAGTT    7200

TAACCATTTG AAGTTTAAAC TCATTTGAAA ATGTTCTGCA GGGTTCTGCG GATAATATTT    7260

TCTGTTCCAT AACAGGTGTC CACTAGTTGA AAAAGTGGGC ACCTACGTTA CCAATACTGG    7320

CTTAATGGCT ACATACGGCG GTCAGTTTAC GCTTACAGAA ATGTAATGAA CACGTCCTAC    7380

CATTAACTGA AGAGCATGGT GACGGATGAA GGAAAAAGCA GGAGTGTGTG GTGCCTCACA    7440

GATTTCCGAC ATCATAGCTG TCAACGACGG ATGAAAAGCG GCTCTTCCGC AACTTGGGTG    7500

GAAGAAAATG GATGAAACTT TCTGGTGTGA GAACCTTAAG GAAACAACAT GTTGGGTGGA    7560

GCGGACAATC CAAATGGTGA ATTACCGTCT TATATCACTG GCGCTGACAT TCCGGGCGTC    7620

TTCTCCGCCA CAACGCCATT TGCAGTGCAT CACAGGCCAG TTGTGCTGTC ATTCGCGGTG    7680

ACATCGACCA GCCAATAACG GCGCGTGACC ACAGGTCGAT GACTACTGCG AGATACAACC    7740

AGCCCTCATC GGTACGCAAG TAMGTGATGT CACCCGCCCA MTTCTGGTTC GGAGCCTGGC    7800

GCTGAAGTTC CTGCTCCAGC AGATTCTCCA ATACGGGCAG GCCATGTGCA CGGTAGCTGA    7860

CCGGGCTGAA CTTCCGGCTG CTTTCGCCCG CAGCCCCTGA CGACGCAGGC TGGCGGCAAT    7920

GGTTTTAATA TTGAACTCCG GCATTTCGTC AGCAAGGCGG GGAGCACCGT ATCGCTGCTT    7980

TGCCTCAATG AATGCCTTAT GGACAGCGGC ATCGCAGGTG AGCCGAAACT GTTGGCGCAG    8040

GCTCATCTGG TGACGACGCC TGAGCCAGAC ATACCAGCCG CTGCGGGCAA CCCGAAGTAC    8100

ACGACACATC GCTTTGATGC TGAACTCTGC CCGATGATTT TCGATGAAGA CATACTTCAT    8160

TTCAGGCGCT TCGCGAAGTA TGTCGCGGCC TTTTGGAGGA TGGCCAGTTC CTCAGCCTGC    8220

TCCGCCAGTT GTCGTTTAAG GCGGACATTT TCAGCGGCCA GTTCGCTTTC GCGCTCTGAC    8280

GAACTCATTT GTTGCTGCTG TTTACTGCGC CAGGCATAAA GCTGAGATTC ATACAGGCTG    8340

AGTTCACGGG CTGCGGCGGC CACACCGATG CGTTCAGCGA GTTTCAGGGC TTCGTTACGA    8400

AATTCAGGCG TATGTTGTTT ACGGGGCTTC TTGCTGATTG ATACTGGTTT TGTCATGAGT    8460

CACCTCTGGT TGAGAGTTTA CTCACTTAGT CCTGTGTCCA CTATTGGTGG GTAAGATCAC    8520

TCAGCAACGT ATCAAAAGTC TGTAAAATCA TGGGCGTTTC GCGTGATACA TTTTATCGTT    8580

ACCGCGAACT GGTCGATGAA GGCGGTGTGG ATGCGCTGAT TAATCGTAGT GCCGCGCTCC    8640

TAACCTTAAG AACGTACCGA TGAGGCAACT GAACAGGCTG TTGTTGATTA CGCCGTCGCT    8700

TTCCCGGCAC ACGGTCAGCA CCGGACCAGC AAACAAGCTG CGTAAACAGG GC          8752
```

(2) INFORMATION FOR SEQ ID NO: 4:

(i) SEQUENCE CHARACTERISTICS:
        (A) LENGTH: 2417 base pairs
        (B) TYPE: nucleic acid
        (C) STRANDEDNESS: double
        (D) TOPOLOGY: linear (xi) SEQUENCE DESCRIPTION: SEQ ID NO: 4:

```
TGGTCAAAGA TGCAACTGCA TTTCGTCGCG GCTTTGCGGC AAATACTTAC ATCGCAGAAA      60
TACTGTGCGG AAATCTGCAT CCATTTCCAC TTGCTGTATG GCATAACTTT TCAGGCGGTC     120
CGGATACTGC CGAAGATTAT TATGCCACAT ACCACCCGTT ATGGGGGCAA TATCCGGAAG     180
CATTGCTGTT TGTAAACTGG CTCTATAATC ATTCCTCTGT GCTGCATGAA CGGGCAGAAA     240
TCATTAAATG CGCCGAAATG CTGATGCAGG AAGATGATTT CGAAATATGC GAAAGTATTT     300
TAAGACAGCA GGAGAAGTTG CGTGAAAGAA TTGATGAGAC GCTTTCTGAG AAAATTGTAC     360
AGAAATGCAG AAATATGAAT GGTGAATATG TCTGGCCCTG GATATTGCCG TTTTCAGCGG     420
CAGGCATGAA ACATACTGGC ATACAGTATC AGTAGATATT GCATTAGTGT ATCCTGCACA     480
CAAGTAATAA TTTATCCACC AATAATAACA CTGTTAATGT CCCCTTCCCC TGGTTGTCAG     540
CCAGGGGTTA TCTTCTGAAT ATTTCTTTTG AAAAGGATAA CACAATAAAT TATTTTTATG     600
AATTATCCCA TGGACTCATT AACACCCTTT CATAATGTTT TATTGTCAAA CACGTTATGG     660
CTGACATCAA AAAAAACCGG ATTTCCTCTG CCAGCGGGTA ATCACCTCCC CGGTGTTTTC     720
GGTTGGTCTG GTTACTCCTG TCTGGTTATT AGCAAGATAA TTGCTATAAA CAGTGGAAAA     780
CTCATCGTAC ATAATCTGGT GATGAACATT ACGCTTATTT TCCCTTGACC GGAAGAATCA     840
GAGGCTGCGG TTTCAGACTG TCTGCCGGTA CATTCCTCTC TCCGTTAAAA ACCATAATGG     900
GTTCATTATC TTCGTCTGTC AGTAGATTGA ATGGCGGTAT ATTTTCAGTA CGAATGCCGG     960
TCAGCCACTG AAAAATACCT GCGAAATGAC GGGCACTGAT TTTTCTGCTG ACGGACTGAT    1020
GAGACGTGAT GTCACTGGCG GTAATAATCA GGGGAACGCT GTAGCCTCCC TGCACATGAC    1080
CATCATGATG AACAGGATTA GCACTGTCGC TGACCGACAG CCCATGGTCA GAAAAGTAAA    1140
GCATGACGAA ATGACGGGAA TGCCGGCGAN GGATACCATC AAGCTGACCG AGAAAGTTAT    1200
CCAGTTTACT GATGCTGGCG AGGTAACAGG CAACCTTTCG GGGATACTGC TCCAGGTAAT    1260
GATTCGGCCA GGAGTGAAGC CGGTCACACG GGTTCGGATG AGACCCCATC ATGTGCAGGA    1320
ATATCACCTT CGGAGAGGAT TTATCCGCCA GCGCACGTTC TGTTTCCTGT AACAACAACA    1380
TGTCATCCGT TTTACGGGAA GCGAATGCSC TTTCTTGAGG AAAACGGTAT GCTCCGCATC    1440
AGAAGCAATA ACAGAGATGC GTGTGTCATG CTCTCCCAGT TTTCCCTGAT GGATATCCA     1500
CCATGTGCTG TATCCTGCTT TTGCTGCCAG CGCCACCACG TTGTTGCCGG AATCAGGGTT    1560
CTGCTCATAG TCATAAATCA GTGTCCSGCT CAGGGAAGGT ACGGTACTGG CTGCTGCCGA    1620
TGTATAGCCG TCAATAAATA AACCGGGAGC TGTCATTCCA GCCACGGCGT GGTTGGCCAC    1680
GGGATAACCA TATACCGACA TATAATCCCT GCGCACACTC TCACCAGTGA CAATCACAAT    1740
CGTGTCATAT AACGGTGTTC CCCGGCCAGG ATTTTCCCAG TTGTCAGCCC CGTGCTGACT    1800
CAGTTGTTTA TAATGCTGCA TTTCACGCAA TGTGTCAGTT GTCCCCACAA CAGTTCCTTT    1860
AACCATCCGC AACGGCCAGC TGTTTACTGA GCATAATACG AACAGCAGCA GTGCCAGCCA    1920
GTTACGGTGA CCACGGCGGT GTGTTCGCCA GAAAATCACC ATGAATACCT GAATCGCGGC    1980
ACTGACCAGA AAATGATAAA CAGGAATCAT CCCGGTAAAC TCCGCTGCCT CATCAGTTGT    2040
GGTCTGCAGC AACGCGACAA TAAAACTGTT GTTGATTTTA CCGTACGTCA TACCGGCAGG    2100
CGCATACAGT GCACAACAGA ACAGAAATAA CAGCGCTGTA ATGGATGTGA GGGTATTTCT    2160
GTGTGCAAGG AGCAGAAGGA GAAACAGAAG CAGCACATTT CCTGTTGCAT TCCTCTCAGT    2220
GTATCCGCAT GCAATTGTGG TTATTGCAGA CACAACAAAA AAGAATAAAA ACAATAAAAT    2280
CCGGGGGGGG TTGCCCGGAC AAAACAGTTT TCTGATATTC ATCGGAGTAT ATCGACAACA    2340
```

TTATTATGAA GAGAACAGGA TAATAAAAAT CAGAAATTAT TGTAAAACAG ATAAAAGCAN    2400

CNATGCAGTA ATAGACT    2417

(2) INFORMATION FOR SEQ ID NO: 5:

(i) SEQUENCE CHARACTERISTICS:
        (A) LENGTH: 6294 base pairs
        (B) TYPE: nucleic acid
        (C) STRANDEDNESS: double
        (D) TOPOLOGY: linear (xi) SEQUENCE DESCRIPTION: SEQ ID NO: 5:

AGACAAAAAC CAGTTACGGT TATCACGTAC CAGCCCCCGT ATTTCCAATT TATAATCCTG    60

GCCATCAATT ACTGGGATCT CTTCTTCTCC ATAGAAGGCA TTAAAAGGGA ATGGAGTGGT    120

AATGTCCTCT GGAAGATATT CTGGTGCCAC ACTGTTTTTG CTGAACAGAA AACTTTGAAT    180

CCGGTCATTA AATCTGGATA TACGGAACAA TGCTTTTTCA ATATCATCAT TATTGCTTAT    240

ATCACAGCCA GTCAGCATCA TAATTCCCCC AAGCGTCAGT CCCTGTTGGA GTAAACGACG    300

TCTGTCCGGC GCAAGGATTT TTTCTGCATC TTTCACCACG TAATGGGCAT CACTGTCAGA    360

CAAAAAACGT TTTTTCTTCA TTAGTGACCC CGTATCATAG ATAACAATGC ACGCGGAACC    420

AATAACACCA TAACCAGGTG AATAATAATG AACAGTACCA TAATGTTCAT GCACAGAAAG    480

TGGATATAAC GCGCTGTATC ATAACCACCG RATAGTATAG TCAGAAGGGA AAACTGAACG    540

GGTTTCCATA AAACCAGACC AGACAATAGA AGAGCAGCGC CATCTAAAAT AATCAGAATA    600

TAGGCGACTT TTTGCACCAT ATTGTATTCC TGCATATTCG TATGATGCAG CTTTCCATAC    660

AGTGCCTGCG TAAGGGATTT TTTCAGTGAG GTCCATGACA GCGGGAAAAA CTTGCTCCGG    720

AAACGTCCGC TACAAATTCC CAGAGTAAGA TAGATCGTGG CATTAATCAG CAGAATCCAC    780

ATCAGGGCGA AGTGCCACAG TAACGCACCG CCAAGCCAGC CACCGAGAGT TAATGCTGCC    840

GGATAGTTAA AAGAAAACAA AGGAGAAGCA TTATAAATGC GCCATCCACT ACATATCATG    900

CCTGCGACAG TAACAGCATT AATCCAGTGG CAACAGCGTA ACCACAGAGG RTGTATTTGT    960

TTTAACGGTA ATGGCTGCAT TATGTGATCT CTGTCTGTAA ACTAAGTATA TTATGGAAAG    1020

GAATGTTCAT CACATCCTCA CAAGAGTTTA AAAAAAATGT GACAANTCAT CGTCAAATGC    1080

TGGGGTAAAA TTCAGATAAA GAATATGTGG ATAACTTTTG ATGAATAACG TAAAAAAAAT    1140

ACTGCTGATG GAAGATGATT ATGATATTGC AGCTCTGTTG CGGCTTAATC TGCAGGATGA    1200

AGGGTATCAG ATAGTTCATG AAGCGGATGG CGCCAGAGCT CGTTTATTAC TAGACAAGCA    1260

GACCTGGGAT GCCGTAATAC TTGATCTTAT GCTGCCTAAT GTTAATGGGC TGGAGATTTG    1320

CCGTTATATC CGTCAGATGA CCCGTTATCT GCCTGTGATT ATCATCAGTG CCCGTACCAG    1380

CGAAACCCAC CGCGTCCTGG GACTGGAAAT GGGGGCTGAT GACTATCTAC CGAAACCCTT    1440

TTCCATTCCT GAGCTGATTG NCCCGCATCA AAGCGTTGTT TCGTCGTCAG GAAGCCATGG    1500

GGCAAAATAT TCTCCTGGCA GGTGGACTGA TTTGCTGTCA CGGTCTGTGC ATCAATCCAT    1560

TTTCACGTGA AGTTCATTTG CATAATAAAC AGGTTGATCT TACCCCACGC GAGTTTGATC    1620

TGCTGCTCTG GTTTGCACGT CATCCTGGCG AAGTTTTTTC CCGTCTTTCA CTGCTGGATA    1680

ATGTCTGGGG GTATCAGCAT GAAGGATATG AGCATACAGT CAACACGCAT ATCAACCGTC    1740

TTCGTGCCAA AATTGAACAG GATGCAGCAG AGCCAAAGAT GATCCAGACC GTCTGGGGAA    1800

AAGGGTATAG GTTTTCAGTT GACAATGCAG GAATGCGATA AATGAATTGT AGCCTGACAT    1860

TAAGCCAGAG GTTAAGCCTA GTATTTACAG TCGTTTTGCT GTTTTGCGCC GTGGACATGT    1920

```
GGCGTTCATA TTTACAGCAG TAATCTGTAT GGCAATGCAA TGGTACAGCG TTTATCTGCA    1980

GGCTGGCGCA ACAGATTGTC ATCACGGAGT CTCTGCTGGA TAATCGTGGG CAGGTGAATC    2040

ACCGGACATT AAAGAGTCTG TTTGAGCGTC TGATGACGCT TAATCCCAGT GTGGAGCTGT    2100

ATATTGTCTC GCCGGAAGGT CGGCTGCTTG TGGAGGCCGC CCCTCCAGGT CATATCAAAC    2160

GTCGGTATAT CAATATAGCG CCCTTGAAAA AATTTCTCTC CGGTGCTGTC TGGCCCGTAT    2220

ATGGTGATGA TCCCCGAAGT GTAAATAAGA AAAAGTTTT CAGTACCGCA CCGCTTTACC     2280

TGAGGGATGA TCTGAAAGGA TATCTGTATA TTATTTTACA GGGAGAGGAA CTTAATGCTC    2340

TTACTGATGC AGCCTGGACA AAGGCACTAT GGAATGCACT GTACTGGTCG CTGTTTCTGG    2400

TAGTGATATG TGGTCTGCTG TCGGGTATGC TGGTCTGGTA CTGGGTAACC CGTCCCATAC    2460

AGCAACTAAC TGAAAATGTC AGCGGGATAG AGCAGGACAG TATTAGTGCC ATTAAACAAC    2520

TGGCAATTCA GCGCCCTGCC ACCCCCCCTA GCAACGAGGT CGAGATATTA CACAATGCCT    2580

TCATTGAACT GGCCCGTAAA ATATCCTGTC AGTGGGATCA ACTTTCAGAA AGTGATCAAC    2640

AGCGCCGTGA ATTTATTGCC AATATCTCCC ATGATTTACG GACGCCATTA ACATCACTTC    2700

TGGGATATCT GGAAACCCTG TCAATGAAGT CGGATTCGCT ATCATCAGAG GACTGTCATA    2760

AATATCTGAC AACAGCTCTC CGGCAGGGAC ACAAGGTGAG GCATCTGTCC TGTCAGCTTT    2820

TTGAGCTGGC ACGTCTTGAG CATGGTGCTA TAAAACCTCA ACTGGAGCAA TTTTCTGTCT    2880

GTGAACTTAT TCAGGATGTA GCTCAAAAAT TTGAGCTCAG CATAGAAACC CGTCGATTGC    2940

AACTAAGAAT TATGATGTCA CATTCCCTGC CTCTTATCAG GGCAGATATT TCAATGATAG    3000

AGCGTGTGAT AACAAATTTA CTGGATAATG CTGTACGCCA CACACCTCCG GAAGGCTCGA    3060

TCAGGCTGAA AGTCTGGCAG GAAGATAATC GGTTGCACGT CGAAGTGGCT GACAGCGGCC    3120

CTGGACTAAC TGAAGATATG CGAACTCATC TTTTCCGGCG GGCATCAGTG TTATGTCATG    3180

AACCGTCAGA AGAGCCCCGG GGAGGACTGG GATTGCTGAT TGTACGCAGG ATGCTGGTAC    3240

TACACGGTGG TGATATCAGG TTGACTGATT CAACGACTGG AGCCTGCTTT CGTTTTTTTC    3300

TTCCATTATA ACATCAGGCG GCATATTTTG GGGTGGTTAT GTGTATCTGC CTTTGTAAAA    3360

GGGATACAAG TTCTGTAGTG GAGCACAAAA TCAGGACACC GGAATAACCT GTTTCCACTT    3420

TTCTTCATGT AAGCAAGGCG GTAAACCATC GTTGTTCGTG TGAGGTCGAT AAACGTTGTA    3480

ATAACCATTA ATCCACTGGT TTATATACG TACCGCATGG ATAAAATCAC CATAACCACC     3540

TTTCGGAAGC CATTCATTTT TAAGGCTGCG AAAGACTCTT CCATCGGCG AATTATCCAG     3600

GCCATTCCCT CTGCAACTCA TACTTTGCAT TACCCCATAA CGCCAGAGTA ACTTTCTGTA    3660

TTTATTGCTT TTATACTGAA CACCTTGATC TGAATGAAAC AGCAGGCGGC CATCACGCGG    3720

TCGAGTTTCC AGTCCGTTAC GCAAAGCCCT ACACACCAAC TCAGCATCAG CGGTTAATGA    3780

GAGGGCTGAA CCGATAATCC GCCGTGAATA TAAATCAACA ACGAGCGCGA GCTAACACCA    3840

TTTGTCCTGC AGGCGAATAA AACTGATGTC GCGCACCAGA CGCAGTTTGG TGCGGCGGGG    3900

TGAAATTGCC GGTTCAGTAA ATTTGGCAAT GGCGGACTTT TGTCTTCGTT TACCCGGTTG    3960

TGATGTTTAA CCGGCTGTCG ACTTGTCAGC CCTCATTCCC GCATCAGTCG TCATGCCAGC    4020

CACCGGCCTG CATCAACGCC ACTCTGGCGC AACATCTGAC TGATTGCCCG GCTACCCGGC    4080

TGCGCCACGA CTGAGAGCAT GGAAAGCCCT CACCCGGCTT CGTAATTCAA TTCTTTGCAC    4140

ATTAACAGGA CGCTTCACCT GCGCGTAATA AACGCTACGG TTAATACCGA ATAAATGACA    4200

AATAACCCAC ACTGGCCACT TTGCTTTCAG CTGTGTGATT AGCGCGACAG CTTCCCGGGG    4260
```

-continued

```
ATTTCGCTCA TCAGCACGGC AGCCTGCTTT AGTATTTCTT TTTCCATCTC AACGCGCTTT      4320

ATCTGCGCTT TAAGCTGCTG AATTTCGCGT TGTTCAGGGG TAATAGCATT ACCAGCTGGC      4380

TCAATACCCT GAAGTTCCTG CTTATACAAC CGTATCCATT TACGCAAATG GTCAGGGTTG      4440

AGCTCGAGTG CCTGCGCGAC TTCTCTGACA TCACGCTGGT ATTTAACCAC CACCTGCTCG      4500

AAAGCTTCAA GCTTGAACTC CGGGGAAAAG GTACGTTTAG TCCGACGAGT TTTGATCATG      4560

CATCACCTCA TTTTCACTGT TTTAACATTA ACAGGATTTC GAGGTGTCCT GAATTACCGA      4620

TCCACTACAA AGTACGACAG GTACTGTGGA GGTACTCCCG TAAAGACGGC CATCAAGCTC      4680

CCGCTCCGAC ATACCTGCGG GCAGAGGCCA TGAAAAGCCA GCTTTGCGAA AGCGCACGAA      4740

CATACCACAA GCTGTTGATT TTGGTACGCC CAGGCGACGC CCGACCACAA CCTGGGGTAA      4800

ATGTTCTTCA AAGTGAAGAC GTAAAGCTTC AGTGATCCAA GTCCGGTGTT TCATACGATA      4860

GTGTCCATTA AAAATGATGG ACATTATTTT TGTAAAACCG GAGGAAACAG ACCAGACGGT      4920

TTAAATGAGC CGGTTACATG TAATCCATAC TCATCCAAGG TTTAATTCTG ACACAATAAG      4980

AAAATATGGA AAGTCTCGCT CTAGAGATGG GGAGAGGGAT ATTGAAGTGT ATGATATTCC      5040

AAGAACTGCC GGAGATATCC TCGTAAATGG ATTTTCCAGT GCAAACTGAT AACAAATTCG      5100

AAGTCATTAT CTGCAACAAG ATTGATTGAT GTAGGGGATA TGTTAGAGCA TTATAATGCT      5160

CAAGGATTTG GCGTGATGAC ATCTGCGCCA ATTGATGCGA CACTATATGA TAAACTGGAT      5220

GCTATTTGCA GTAAGTGTAA AATAGAACAA ATAAATTTTT CAGTATTAGA GTCAGAACGC      5280

GCACTATATT ATGACGATAT ATTAAGATGC CGTTACTTTG GTAAATAMCA TAAAATTAAT      5340

CAATATGGTA ATATATCAGT TGTAATTGAT CGAAACAAAG CACATAAATG CCATCTTATA      5400

AAGATGGTGT TTKTTAAGCA TATAAAATAT ATTTTCTATA AGATATAGGG CAAACTAAAT      5460

TTCTTGACTT CTATGATGGA CTAACTAGAT ATACATGCCG CCAGTTTTTA TAAAACGACG      5520

GCATATATAA TCATTTATAT ATCTTTTGAT TTTATTCGTA ACCACTCATG TTGATCTAAA      5580

CCTATTCTTG ACAGATTAGC AACAATATCA GTTGTTATTT TTTGCGCGTA CGTTGTTTTT      5640

ATTTCCCCGA TCCATTTCAA TACTTTTGGA GTAGATATTT TTTCAACGAG TAAAGGAACG      5700

AATGAGATAT AGTCAGTATT AACTAGATTG TTCTTTTTCC CTATGATGAC ACCGTTTCCA      5760

TTTTCGACTC CAAATGAAAA TGAAATAATA TTAGAAGCTT TTGCCGGCAT TTTAATTTTA      5820

TAAAAACCGC CATATTCATC TTCGATTAAC AAATTGTAAT TATTATCGTC CAGTGTTCCC      5880

CTGAGGAATA AAAAATCGGC TTTTTCATGC AATCTGACGC TATCACATAA TGGTTGTATG      5940

CATAGATAGA CAAAATTATA TGCATCTAAA AGTAAAGTTC CTTGTTTTAA GGACACATTA      6000

TCTATATGAG AATGATATCT TAAACTCCTG CGCGTGATTT CCAGAGAGCA TAATTGCATT      6060

AACTTTTTAT CTTCTTCACC ATCTTGGCTT AAGTATTCCT TTTTACCTAA AGATGCGTGT      6120

TCAATAGCGT GTTGAATTTC TTCTAAAGAA TCAGCAGAGA GTATATTCCT TAGATGTTCT      6180

ACTGATAAGT CTTTTTGTTT TTTTCCAGTT AATAGAAAAT TCTTACAACC ATTTTTTGCA      6240

TAGTGAAAAA TAGGCCAATG GGATAAGGAG TTTTTGCTTA GAGATTCTG GGGA             6294
```

(2) INFORMATION FOR SEQ ID NO: 6:

(i) SEQUENCE CHARACTERISTICS:
        (A) LENGTH: 4519 base pairs
        (B) TYPE: nucleic acid
        (C) STRANDEDNESS: double
        (D) TOPOLOGY: linear (xi) SEQUENCE DESCRIPTION: SEQ ID NO: 6:

```
TATTCCTTTC TCTCCCATGA TAGGGCGAAA GGCTTTATTA CTATCCACTG CTGGTTTATT      60

AATTGCATCA TCGTCGATTA ATTTGCTGGA GGTTCCAATA GTCAACCACC TCTCTTCAAA     120

TTCATCGGTT GTCATACCTA ATCCATCATC TCTCAAGATA AGAAGATTTT CTTTCCTAAA     180

AAAATCAACT TCGACATTAT CAGCATAGGC ATCATGAGCA TTTTTAAATA ACTCACTCAA     240

GGCAGTAGGT ATACCTGCAA TTTGTTGTCT GCCAAGCATG TCCAAAGCTC GAGCCTTTGT     300

TCTTATTTTA GCCATATATC TATGAATCCT TATTAGTACA ATTTTCTATG AGATGTAGCC     360

CAAATAGTCT AGCGAGTTCG CAAGGTACAG CATTGCCGAT TTGCTTTGCC ATTGAATTCA     420

GCGAACCTTT AAAAACATAG CTTAAAGGAA ATGTTTGTAA TCTTGATGCT TCTCTTATGC     480

TAATTGCTCT ATGTTGAGTG GGGTCAGGAT GCCCAAAACG ACCATTGGAG TAACTATTAC     540

ATTTCGTCGT AAGTGTAGGC GCAGGCTTAT CCCAACTCAT TCTTCCATAA GTATCTGTGT     600

GGCCATCATA ATTTTTATGG CATTTATTAA CTAACTCTTC TGGCCAATTT CTTCTATCCC     660

CTCCTTCTGG AGTGTGCATA AKTCTTTTTA GGTTAAGAGG GCTCAGTGTT CCAGCCCTAT     720

GTAAAGGATC TTTGGGGTCG GTTTCTCCTG AACATAACTT TGTGAAGTCC TGGATATAAT     780

CTCGTACAGT TTTGAATGGG ATTTTATTTT TACCATGGGT TATCTCTGGT AGGGTAACTT     840

TACCTACTCG ACTAGCTAAG AGCACGAGTC TTTTTCTTCT TTGGGGAATC CCATAGTTCT     900

CAGCATTGGC TATAAAAGAT ATATAGTTAT ACTCTAACTC TTTAAGTAGC TTAATAAACT     960

CCTGAAATGG GCCTTCTTTT TCTTCATCAA TTTTTTGCAT TCCAGGAACA TTTTCAAGCA    1020

TAATATATTC AGGAAGAAGT TCTCTAATAA AACGATGAGT TTCATTTAGT AGATTTCTCC    1080

TTGAGTCGTC ACTAGTTTTA TTTTTATTCT GTTGCGAAAA TGGTTGACAT GGTGCACATG    1140

CACTCAGTAA CAAAGGCCGT TTAGCTTTAA TATCAATGAT GTCGGAGATA TCTTGAGGTT    1200

CGATTTTCCT AATATCATCT TGGATGAATT TTGCATCAGG GAAATTAGCT TTAAATGTTT    1260

CTGATGCTTG TTGGTCAATA TCTAATCCAA GCTCGATATC AAAGCCAGCC TGACGTAGCC    1320

CTTCACTGGC TCCACCACAG CCACAAAAAA AATCTATAAC TATCAATTTG ATACCTTCTT    1380

TGAACTAAAT AAAACAACTC GAATAAGTTG ATATTTTAAA TAAAAATAAT TGGTATGGAT    1440

ATGAACTTTG GTCACGCTAC CGCCCTGAGK TCATGGCCAT CCCCAGACCT TTTAAAGGGA    1500

TTATGAACAA CACCCAGCCG ACGTTCAACG GTGTTACCCA TACATATCAC AAAGTTAGTT    1560

AATTGGTTGG TCGTAAATTG ACCTAAAATG GATTGAGGGC AATGCAAAAA TCATTGGGAA    1620

ATCCAGGCGA CACAGATGTT CGGAAGAGAC TGAATGTTAA AAATATAGAA TGTATATTCT    1680

CAAAAAAGAG ATATTTCATT ACATTTTATA TGTGTATAGG AAAGTGAGAT TGGCGAATCA    1740

CCTCCCAATC ATCCCGCCAG CGCTCCATTC AGCGCCACGC CAACCCTCAC TCCAGCCCAC    1800

GTCATCGCCC CCAGCCAGAA TGTCGGCAAC ACCAGAAACA TCAACCTCAT CACCAGATTG    1860

ATAATCACGT CATCCTGCGT ATTCTGGATC CCGGCTAAAT TCCAGCTACT GTGGGTATCG    1920

CTGTTGTAGA GCACATCCAG CAGCCAGCTA TCAAGCCACC GTGCCAGTTC CCACCAAAAG    1980

GTGAGGAAAA ATAGTGCAAA CTGCACAAAC GTCAGCGTCA TCACTACTTT CACATCCCAC    2040

GCCGAACAGA GCGTTATCAG CGGAATACAG ATCACCAGCG CTATTTGCAG TGCGCCTGTA    2100

CCATCGGTAG TGCCTAACGC ACGCTGTCGA ATGCCGTACA TGCCGCTATG CTGCCGAGGA    2160

TATTTCTAGC GCCGGATGCC AACCGGGTGG CGGCATTGGC GACGGTGCCA TCAACGTTAC    2220

CGCCATAGCT TGGATAAACG CGCCCATTCT GCGATACCTG CATATTTCGT TCACTGACCC    2280

GCGAGCGCAG CACGGCCTCT TCATACACTA CCTGCGACTG GTCGATTTTT TTAAACGCCG    2340

TCCAGATATC TAGGGCAGGA AGTTGCAGTA GACGGGCTTT CAGCCCAAGC GGTGTCGTCG    2400
```

-continued

```
GCCCACCGCT GTTTACAAGT GGGATAGCCG CCCGCGCCCG TATCGGCCAG CCCGGCATCG    2460

CGCGATGCAC TGTACGGCCA AGCACTGTGT GGTGAAAGCG CATGGTCGGA AAAGGCCTGT    2520

TCAGCTAACC AAGCACATCC CACCATCACA AGAATCGCCA GAAAACCAAA CTCAGTCAGA    2580

ATAACTCTTC CTGATTCAGG CTTTGCTCCT GCATTATGGC TACCACTATT GTTTGCCTGC    2640

ACGTATCATC TGATAACGGT TAATTAACTG ATTTAGCGCC ATTTCAGCCT GTTTTTGCTG    2700

CTGTTCACTG CCATTCTGGT TACGGACTTC ACCGTAGCGA CGTAACTGCT CTTCCGCCGG    2760

GATATGCCGG TTAAAAGCCT GCATGATGCC AAACACCTCC GTTTTCAGTT CACTGACCGT    2820

CATGTATTTT CCCCGCTGTT CATCCTGACG GTTCAGGCGC TCAGCCAACT GCTGTAAGCG    2880

GATCATGCCT TCGTTCCAGC CCGTCATCGC CTCTTCCGGG AGCGCACGAC TCCTTACACT    2940

CTTCTGCCAG TTATCCACCA TTTCCTGAAC ACGGGGATTG CCGGGACAA GAACCCTCAG     3000

TTGCTGCAGC AGCTGCGCAC TGCACCGCAG GTTGTATGCT GGAGGTAATT CTGCCAGTCG    3060

CGTTATCTGC TGACCGGAAA GGGTTATCCA GTGCACTCAG GGCAGATACC GGATTCAGGT    3120

TAATTTTTTC AAACAGGGAA GCATATACGC TGTCGCCGGT ATGCGTTTCA GATACCACAC    3180

TCTCTGCGAC GTTCTTTTCT TTCTGTACAG ACATCAGCAT TTTCTGTAAG CGTACAGCGA    3240

GGGCCGTATT GACGGGGATG TGTTATTCAG CTGGCAGTGC TATGCGCCAC GGAAGCAGTT    3300

CGCTGACCCG GTTGACCGGC CAGTCTGCTA TGACGGCAAG CACATGGCGA AGGTAGCTTT    3360

CTGGATCCAC GTCATTCAGT TTGCACGTCC CGATCAGGCT GTACAGTAGC GCTCCCCGCT    3420

CACCACCATG GTCAGAGCCG AAGAACAGGA AGTTTTTACG ACCCAGACTG ACCGCCCGCA    3480

GGNCATNTTT CAGCGATGTT GTTGTCGATT TCCACCCAGC CATCGTTCGC ATAGTACGTC    3540

ATGCCGGCCA CTGGTTAAGT GCGTACGCGA ACGCCTTCGC CACCATCAGG CTGGACAGGG    3600

GACTTTCACC CCCAAGCTGC TGAACATGCC CGGCACACAA AGAAGATCTC GGCTCAGTGG    3660

CCGGGATTAG TTATACAATT ATCTGATTGA TTTTTAATAT ATCTTTTCTT AAATCATCGT    3720

TAATATCTGA CGGTTCTAGC TGGTTTATAA GTTGCCTTAT TTGGGTAAAG GTACTTTTCT    3780

GATCTTTTAG ATCTTCTCCT TTTATCGTTG ATAAAGCTGC AATTAGTTCA CCATCGTAAT    3840

ATTCACCCGC TAACGGCTCT TTAGTTAGAA CTTCCAACAC TCTTGGCATC AACTGATCAA    3900

TACATAAATT TTGTCGGATA GCGCGGCAAA GATCTTCCAC TGTTAACTTT TCAAGAGGCA    3960

CATCTATGAT ACGTTCGAAC CAGAGTTCAA GCGGTGATTG TTGCTCAGGC TCTTTTGTCA    4020

TATTGATGTT TCCAATCAAT TTACGTAAGG TAATCATATT CCATATCCTT TCAAGGCTGA    4080

TTCTATTTTA TTAATAGCAT CTGTTGCTCT GCCATACGCA GCCTGAGCTT CAGGATTGTT    4140

GACGTTTTTC AACGTATCCG CATGATTTCT TAATCCTCTG AGCGTATTTT GCATTTCCTG    4200

CATATGATCC CAATATCCTC CATTCTCTTT AGGAACTGGC TTACCATCCA TATCCTTGAG    4260

AGTTCCAATT AATATCATGA ATCTTTTCAG ANCATTTTTT TAATAGTGGT TAATCGANTC    4320

TTCTTTAANT CGGCAACTTT TCTTGGCCTT CCTGGAATTA AAGGCTTTAA TCCTAACAAG    4380

TTTTTTTCTC AATTTTTGGC TGGCTTTAGG GAATCAATTT TTCCCGGATT GGGTGGGTGG    4440

GTGGTAACCC GGGTTTCCCT TGAAGCCCGG GAAACCCGGC CCCAAGTTCT TACTTTTTTT    4500

CCCGCAATCG GGTCAAGAT                                                4519
```

(2) INFORMATION FOR SEQ ID NO: 7:

(i) SEQUENCE CHARACTERISTICS:
        (A) LENGTH: 1213 base pairs
        (B) TYPE: nucleic acid (C) STRANDEDNESS: double
            (D) TOPOLOGY: linear (xi) SEQUENCE DESCRIPTION: SEQ ID NO: 7:

```
ATTACAGAAT GTGGAAATTA AGTATGATTC GAAAAAAGAT TCTGATGGCT GCCATCCCCC        60

TGTTTGTTAT ATCCGGGGCA GACGCTGCTG TTTCGCTGGA CAGAACCCGC GCGGTGTTTG       120

ACGGGAGTGA GAAGTCAATG ACGCTTGATA TCTCCAATGA TAACAAACAA CTGCCCTATC       180

TTGCTCAGGC ATGGATAGAA AATGAAAATC AGGAAAAAAT TATTACAGGG CCGGTTATTG       240

CCACCCCTCC GGTTCAGCGC CTTGAGCCGG GTGCGAAAAG CATGGTCAGG CTGAGTACCA       300

CACCGGATAT CAGTAAACTT CCTCAGGACA GGGAATCACT GTTTTATTTT AATCTCAGGG       360

AAATACCGCC GAGGAGTGAA AAGGCCAATG TACTGCAGAT AGCCTTACAG ACCAAAATAA       420

AGCTTTTTTA TCGCCCGGCA GCAATTAAAA CCAGACCAAA TGAAGTATGG CAGGACCAGT       480

TAATTCTGAA CAAAGTCAGC GGTGGGTATC GTATTGAAAA CCCAACGCCC TATTATGTCA       540

CTGTTATTGG TCTGGAGGA AGTGAAAAGC AGGCAGAGGA AGGTGAGTTT GAAACCGTGA        600

TGCTGTCTCC CCGTTCAGAG CAGACAGTAA AATCGGCAAA TTATAATACC CCTTATCTGT       660

CTTATATTAA TGACTATGGT GGTCGCCCGG TACTGTCGTT TATCTGTAAT GGTAGCCGTT       720

GCTCTGTGAA AAAAGAGAAA TAATGTACCG CAATAACGGT TAAATGCGGG TGGGATATTA       780

TGGTTGTGAA TAAAACAACA GCAGTACTGT ATCTTATTGC ACTGTCGCTG AGTGGTTTCA       840

TCCATACTTT CCTGCGGGCT GAAGAGCGGG GTATATACGA TGACGTCTTT ACTGCAGATG       900

AGTTGCGTCA TTACCGGATA AATGAACGGG GGGACGCAC CGGAAGCCTG ACCGTCAGTG        960

GTGCACTGCT GTCCTCACCC TGCACGCTGG TGAGTAATGA GGTGCCGTTA ARCCTCCGGC      1020

CGGAAAATCA CTCTGCGGCA GCCGGAGCAC CTCTGATGCT GAGGCTGGCA GGATGTGGGG      1080

ACGGTGGTGC ACTTCAGCCC GGAAAACGGG GCGTTGCGAT GACAGTCTCC GGCTCACTGG      1140

TAACCGGTCC CGGAAGCGGA AGTGCTTTAC TTCCTGACCG TAASCTATCC GGCTGTGACA      1200

TCTTGTTATA CAC                                                        1213
```

(2) INFORMATION FOR SEQ ID NO: 8:

(i) SEQUENCE CHARACTERISTICS:
            (A) LENGTH: 451 base pairs
            (B) TYPE: nucleic acid
            (C) STRANDEDNESS: double
            (D) TOPOLOGY: linear (xi) SEQUENCE DESCRIPTION: SEQ ID NO: 8:

```
ACGCTCTAGT ATTCTCTGTC GTTCTGCCTG GGCCACTGCA GATAGAATAG TGACAACCAT        60

TTTACCCATC TCCCCATCGG TACTGATTCC GTCATCAATA AACCGAATGG ATACACCTTG       120

GGCGTCAAAC TCTTTTATTA ACTGGATCAT GTCAGCAGTA TCGCGCCCAA GGGGTTCAAG       180

TTTCTTCACC AAGATGACGT CACCTTCCTC CACCTTCATC CTCAGCAAGT CCAGCCCTTT       240

CCGATCGCTT GAACTGCCCG ATGCCTTGTC AGTAAAGATG CGATTTGCTT TCACGCCTGC       300

GTCTTTGAGT GCCCGAACCT GAATATCGAG AGATTGCTGG CTGGTTGATA CCCGTGCGTA       360

ACCAAAAAGT CGCATAAAAA TGTATCCYAA ATCAAATATC GGACAAGCAG TGTCTGTTAT       420

AACAAAAAAT CGATTTNAAT TAGACACCNT T                                     451
```

(2) INFORMATION FOR SEQ ID NO: 9:

(i) SEQUENCE CHARACTERISTICS:
            (A) LENGTH: 720 base pairs (B) TYPE: nucleic acid
        (C) STRANDEDNESS: double
        (D) TOPOLOGY: linear (xi) SEQUENCE DESCRIPTION: SEQ ID NO: 9:

```
GACAAGGCTT ATAAACTCAC TGACGGGGCT GGCATGTTCC TGCTGGTACA TCCTAATGGT      60

TCCCGTTACT GGCGTCTCCG TTATCGTATT CTGGGTAAGG AGAAGACTCT GGCACTTGGT     120

GTGTATCCAG AAGTTTCTCT CTCCGAAGCT CGTACAAAAC GGGATGAGGC CCGAAAACTG     180

ATTTCGGAGG GGATTGACCC TTGCGAACAG AAAAGAGCTA AAAAGTAGT CCCTGATTTA      240

CAGCTCTCTT TTGAACATAT TGCACGACGC TGGCATGCCA GTAATAAACA ATGGGCACAA     300

TCACACAGCG ATAAAGTACT CAAAAGCCTC GAAACACACG TTTTCCCCTT TATCGGCAAC     360

CGGGATATCA CAACACTCAA TACCCCGGAT CTGCTTATCC CTGTTCGTGC TGCAGAAGCT     420

AAACAAATTT ATGAAATCGC CAGTCGTCTG CAGCAAAGAA TATCTGCCGT AATGCGTTAT     480

GCCGTACAGT CTGGCATCAT CAGATATAAT CCTGCTCTGG ATATGGCTGG CGCATTGACT     540

ACGGTAAAAC GCCAGCATCG CCCCGCTCTT GATCTTTCAC GTCTGCCTGA ACTTCTGTCG     600

CGTATTAACA GTTATAAAGG NCAGCCTGTC ACCCGGCTTG CGTTGATGCT GAATTTACTG     660

GGTTTTTATT CGTTCCAGTG AACTCAGATA CGCCCGCTGG TTCTGAAAAT TGATATTGGA     720
```

(2) INFORMATION FOR SEQ ID NO: 10:

(i) SEQUENCE CHARACTERISTICS:
        (A) LENGTH: 2920 base pairs
        (B) TYPE: nucleic acid
        (C) STRANDEDNESS: double
        (D) TOPOLOGY: linear (xi) SEQUENCE DESCRIPTION: SEQ ID NO: 10:

```
NCNTTAATTT TATATCTCGT AAAATAAAAT GTTTTCTGTA CCGCTCTCCG GAGGGGGGAA      60

TGATTCGTTT ATCATTATTT ATATCGTTGC TTCTGACATC GGTCGCTGTA CTGGCTGATG     120

TGCAGATTAA CATCAGGGGA AATGTTTATA TCCCCCCATG CACCATTAAT AACGGGCAGA     180

ATATTGTTGT TGATTTTGGG AATATTAATC CTGAGCATGT GGACAACTCA CGTGGTGAAG     240

TCACAAAAAC CATAAGCATA TCCTGTCCGT ATAAGAGTGG CTCTCTCTGG ATAAAAGTTA     300

CGGGAAATAC TATGGGAGGA GGTCAGAATA ATGTACTGGC AACAAATATA ACTCATTTTG     360

GTATAGCGCT GTATCAGGGA AAAGGAATGT CAACACCTCT TACATTAGGT AATGGTTCAG     420

GAAATGGTTA CAGAGTTACA GCAGGTCTGG ACACAGCACG TTCAACGTTC ACCTTTACTT     480

CAGTGCCCTT TCGTAATGGC AGCGGGATAC TGAATGGCGG GGATTCCGG ACCACGGCCA      540

GTATGAGCAT GATTTATAAC TGAGTCATAC CCAAATGAAT AACTGTAATT ACGGAAGTGA     600

TTTCTGATGA AAAAATGGCK CCCTGCTTTT TTATTTTTAT CCCTGTCAGG CTGTAATGAT     660

GCTCTGGCTG CAAACCAGAG TACAATGTTT TACTCGTTTA ATGATAACAT TTATCGTCST     720

CAACTTAGTG TTAAAGTAAC CGATATTGTT CAATTCATAG TGGATATAAA CTCCGCATCA     780

AGTACGGCAA CTTTAAGCTA TGTGGCCTGC AATGGATTTA CCTGGACTCA TGRTCTTTAC     840

TGGTCTGAGT ATTTTGCATG GCTGGTTGTT CCTAAACATG TTTCCTATAA TGGATATAAT     900

ATATATCTTG AACTTCAGTC CAGAGGAAGT TTTTCACTTG ATGCAGAAGA TAATGATAAT     960

TACTATCTTA CCAAGGGATT TGCATGGGAT GAAGCAAACA CATCTGGACA GACATGTTTC    1020

AATATCGGAG AAAAAAGAAG TCTGGCATGG TCATTTGGTG GTGTTACCCT GAACGCCAGA    1080

TTGCCTGTTG ACCTTCCTAA GGGGGATTAT ACGTTTCCAG TTAAGTTCTT ACGTGGCATT    1140
```

```
CAGCGTAATA ATTATGATTA TATTGGTGGA CGCTACAAAA TCCCTTCTTC GTTAATGAAA    1200

ACATTTCCTT TTAATGGTAC ATTGAATTTC TCAATTAAAA ATACCGGAGN ATGCCGTCCT    1260

TCTGCACAGT CTCTGGAAAT AAATCATGGT GATCTGTCGA TTAATAGCGC TAATAATCAT    1320

TATGCGGCTC AGACTCTTTC TGTGTCTTGC GATGTGCCTA CAAATATTCG TTTTTTCCTG    1380

TTAAGCAATA CAAATCCGGC ATACAGCCAT GGTCAGCAAT TTTCGGTTGG TCTGGGTCAT    1440

GGCTGGGACT CCATTATTTC GATTAATGGC GTGGACACAG GAGAGACAAC GATGAGATGG    1500

TACAGAGCAG GTACACAAAA CCTGACCATC GCAGTCGCCT CTATGGTGAA TCTTCAAAGA    1560

TACAACCAGG AGTACTATCT GGTTCAGCAA CGCTGCTCAT GATATTGCCA TAAATGGTTT    1620

ATCCGGAGCC GGATAGTGTG TTGTGGATAT CTGGCATGCC CCGGGAAGTC ACCTTTCAGA    1680

CGGGCGGAGG GCTGGTGAAT TATCCGCGAT TACTGAGCAG TATGGATAAT CCTTTTTCAC    1740

AGACTTGTCA GCAGCCAGCA TTTATGTTCT TTTATCTGAG GGAATTTATC TGTACGCTGT    1800

GCCGGGATAT CTCAGTTATA CAGAAATCAG GCAGGAATAA ATTGTAGTGG AAAGTCGATG    1860

TTTACCGGAT GACTGATGCG CGCTTGTACA CAGACAGTGT GTTTCAGTAA TATGGAGAAT    1920

AATGAAATGA ATAACACAGA CACATTAGAA AAAATAATCA GACACCAAAA AAACAAAGAC    1980

CCCGCATATC CTTTCGGGAA CATTTGTTGA TGCAGCTCTG TATTCGCACA ATAAAAGAA    2040

TGCAGGATAA TATATCTGAA TTTCTGGGGG CGTATGGAAT AAATCACTCA GCATATATGG    2100

TCCTCACCAC ATTATTCGCA GCGGAGAACC ATTGTCTGTC ACCTTCAGAG ATAAGCCAGA    2160

AACTTCAGTT TACCAGAACT AATATTACCC GCATTACAGA TTTTTTAGAA AAAGCCGGAT    2220

ATGTAAAAAG GACGGATAGC AGGGAGGATC GCCGTGCTAA AAAAATCAGT CTGACATCTG    2280

AAGGTATGTT TTTTATTCAG AGGCTCACTC TTGCACAAAG CATGTATCTG AAAGAAATCT    2340

GGGATTATCT GACCCATGAT GAACAGGAAC TGTTTGAAGT CATTAATAAA AAATTACTGG    2400

CACATTTTTC TGATGCCAGC TCATAAAGTG CGAAATATCT GAGGATGCCG GATAGCTTCA    2460

GGCAAAATAA TAATGATTCT TGCAGATGTG TTTTTCCGGA TACAAAAACA AATGATAAAA    2520

ATTGCAGCGC CAGGCACCTT TCAAAGCAGG GAGACCTGTA CCGCGTCGAA AATTTCAGCC    2580

AGTTAATATC ATTGTCTGAA CCAGGCACTT TGCCCGGGCA GGAGAAGGAG TTGTGGCGGT    2640

CTCAGCCCGG AACAATTTGA AAACCATAAT CTCGCTTAGG GCCGTGTCCA CATTACGTGG    2700

GTAGGATCAC TCCTGGATTT TCTCTTTTTG GACATTGACG TCTCCATTGG TTTAAACACG    2760

GCAATGGAGA CTGCGGTGAA AAGAGTTAAT TCCCGGAGTG ACTGGCTGGA TGCCAATCAA    2820

TGATCGGAAG CATGCCAAAC TGTGAACGGA GATGGATGCC GCCAAATCAT GATCGATTCA    2880

GATGCCATAT TTGCAATATC GCGTTAATCG TCAGTTCAGC                          2920

(2) INFORMATION FOR SEQ ID NO: 11:

(i) SEQUENCE CHARACTERISTICS:
        (A) LENGTH: 1678 base pairs
        (B) TYPE: nucleic acid
        (C) STRANDEDNESS: double
        (D) TOPOLOGY: linear (xi) SEQUENCE DESCRIPTION: SEQ ID NO: 11:

GGTAAGGAAG TTATATATAT GAGCAACTAT ACATCTTAGA TGTATGATAA AGAAAAAGAT      60

AACAGTTCTT TAGAATATGT ATATTGAAGA GAATGCAATA GCATGGTTTA TATAAATTAC     120

GCATAAAAAT AAGCATATGT AAGCATTTTG GTTTGCTTTT TTTAACCTGC CACCGCAATG     180

AATGCTTTTT TTATGTTAAT GTGCGTTATG AAACTAAATG CAAGAAACAT ATTTAAAGGA     240
```

```
TTAATATCGT TCTCTCACAG ACTCCGTTTA CTTATTCAAG AATATAATTT AATTTATAGT    300

GAGCTTATTA TGAATATGAA CAATCCATTA GAGGKTCTTG GGCATGTATC CTGGCTCKGG    360

GGCCAGTTCC CCATTACACA GAAACYGGCC AGTTTCTTTG TTTGCAATAA ATGTATTACC    420

TGCAATACGG GGCTAACCAA TATGCTTTAT TAACCCGGGG ATAATTACCC TGTTGCATAT    480

TGTAGTTGGG GCTAATTTAA GTTTAGAAAA TGAAATTAAA TATCCTAATG ATGTTACCTC    540

ATTAGTCGCA GAAGACTGGA CTTCAGGTGA TCGTAAAKGG TYCATTGACT GGATTGCTCC    600

TTTCGGGGAT AACGGTGCCC TGTACAAATA TATGGGAAAA AAATTCCCTG ATGAACTATT    660

CCGAGCCATC AGGGTGGATY CCAAAACTCA TGTTGGTAAA GTATCAGAAT TCACGGAGG    720

TAAAATTGAT AAACAGTTAG CGAATAAAAT TTTTAAACAA TATCACCACG AGTTAATAAC    780

TGAAGTAAAA AACAAGACAG ATTTCAATTT TTCATTAACA GGTTAAGAGG TAATTAAATG    840

CCAACAATAA CCACTGCACA AATTAAAAGC ACACTACAGT CTGCAAAGCA ATCCGCTGCA    900

AATAAATTGC ACTCAGCAGG ACAAAGCACG AAAGATGCAT TAAAAAAAGC AGCAGAGCAA    960

ACCCGCAATG GGGGAAAACA GACTCATTTT TACTTATCCC TAAAGATTAT AAAGGACAGG   1020

GTTCAAGCCT TAATGACCTT GTCAGGACGG CAGATGAACT GGGAATTGAA GTCCAGTATG   1080

ATGAAAAGAA TGGCACGGCG ATTACTAAAC AGGTATTCGG CACAGCAGAG AAACTCATTG   1140

GCCTCACCGA ACGGGGAGTG ACTATCTTTG CACCACAATT AGACAAATTA CTGCAAAAGT   1200

ATCAAAAAGC GGGTAATAAA TTAGGCGGCA GTGCTGAAAA TATAGGTGAT AACTTAGGAA   1260

AGGCAGGCAG TGTACTGTCA ACGTTTCAAA ATTTTCTGGG TACTGCACTT TCCTCAATGA   1320

AAATAGACGA ACTGATAAAG AAACAAAAAT CTGGTAGCAA TGTCAGTTCT TCTGAACTGG   1380

CAAAAGCGAG TATTGAGCTA ATCAACCAAC TCGTGGACAC AGCTGCCAGC ATTAATAATA   1440

ATGTTAACTC ATTTTCTCAA CAACTCAATA AGCTGGAAG TGTATTATCC AATACAAAGC   1500

ACCTGAACGG TGTTGGTAAT AAGTTACAGA ATTTACCTAA CCTTGGATAA TATCGGTGCA   1560

GGGTTAGATA CTGTATCGGG KATTTTATCT GCGRTTTCAG CAAGCTTCAT TCTGAGSCAT   1620

GCAGATGCAG ATACCGGRAC TAAAGCTGCC AGCAGGTGTT GGATTNACCA ACGGAANT    1678

(2) INFORMATION FOR SEQ ID NO: 12:

(i) SEQUENCE CHARACTERISTICS:
        (A) LENGTH: 2676 base pairs
        (B) TYPE: nucleic acid
        (C) STRANDEDNESS: double
        (D) TOPOLOGY: linear (xi) SEQUENCE DESCRIPTION: SEQ ID NO: 12:

AAGGATTACT TTGGAATCTG ACAACAAAGT TACTATGAAA AGAACTAAC AAAGTTATAT      60

AATGACGCTA AAAATGCTTT GAAAGATGTG CAATCTAAAG CAAATAGGTT AATTTCTGAT    120

AATAAGANAA AACATAAGAG TGAACTAAAA AACATTTCTT ATGAATTCCA ATCAACTAAT    180

CTCAATGGCA AAGATACTGC GTATATATTG GATGTARAAA GAAATCTAGA AGTAAAATT    240

GAGAATACTT CAAACGAATG AGTGTAATGA AATAAGAAAA CTAACCGACC AGATTGCAAT    300

AATTAGTGAT AGTACCACTT CTGAAAATTT ATCATCGGCT CAAGTAACTG AAGCAATCGA    360

AACTGAACTT GAACATTTAC GAGACCAACA AGCAAATAAC GCAGAGTTAA TACTACTTGG    420

CATGGCTCTT TCTGTAGTAC ATCATGNATT TAATGGTAAT ATTAGGGCAA TTAGAAGTGC    480

GCTAAGGGAA TTAAAAGCAT GGGCTGACAG AAATCCTAAG CTTGATATTA TATACCAAAA    540

AATCAGAACT AGTTTTGATC ACTTAGATGG TTATTTAAAA ACCTTTACAC CATTGACAAG    600
```

```
ACGTTTAAGT CGCTCTMAAA CCAATATAAC TGGAACTGCC ATTTTAGAAT TTATCAGAGA    660

TGTATTCGAT GATCGTCTTG AGAAAGAAGG AATTGAATTA TTCACTACCT CAAAGTTTGT    720

TAATCAAGAA ATTGTAACTT ACACATCAAC CATTTACCCT GTCTTTATAA ATCTAATTGA    780

TAACGCAATA TACTGGCTTG GGAAAACAAC TGGAGAAAAA AGACTTATAC TTGATGCKAC    840

TGAAACAGGA TTTGTTATTG GTGATACTGG TCCCGGTGTT TCAACTAGAG ATCGAGATAT    900

AATATTTGAT ATGGGATTTA CACGAAAAAC AGGAGGGCGT GGAATGGGAT TATTCATTTC    960

CAAAGAGTGT TTATCTCGAG ATGGATTTAC TATAAGATTG GATGATTACA CTCCTGAACA   1020

GGGTGCTTTC TTTATTATTG AGCCATCAGA AGAAACAAGT GAATAGCGGA TATAAATAAA   1080

TGACAAGCTC TACTGATTTN CATAAACTTT CTGAAGACTG CGTTCGCCGT TTTTTACATT   1140

CTGTAGTTGC TGTAGATGAC AATATGTCTT TTGGAGCTGG TAGTGATACT TTCCCTACAG   1200

ACGAAGATAT TAATGCTTTA GTTGATCCCG ACGATGATCC TACACCAATA ATAACAGCAT   1260

CAGCATCCCC AAGGATAGAA TCAACTAAAT CAAAAGCAAA GGTAAAAAAC CATCCTTTTG   1320

ATTACCAAGC TCTAGCAGAA GCTTTCGCCA AAGATGGTAT TGCTTGTTGC GGATTATTAG   1380

CTAAGGAAGG TGCGAATAAG CGGGGAAATT CTTCTCGGCT GACTCAGTCA TTTCATTTCT   1440

TCATGTTTGA GCCGATTTTT TCTCCCGTAA ATGCCTTGAA TCAGCCTATT TAGACCGTTT   1500

CTTCGCCATT TAAGGCGTTA TCCCCAGTTT TTAGTGAGAT CTCTCCCACT GACGTATCAT   1560

TTGGTCCGCC CGAAACAGGT TGGCCAGCGT GAATAACATC GCCAGTTGGT TATCGTTTTT   1620

CAGCAACCCC TTGTATCTGG CTTTCACGAA GCCGAACTGT CGCTTGATGA TGCGAAATGG   1680

GTGCTCCACC CTGGCCCGGA TGCTGGCTTT CATGTATTCG ATGTTGATGG CCGTTTTGTT   1740

CTTGCGTGGA TGCTGTTTCA AGGTTCTTAC CTTGCCGGGG CGCTCGGCGA TCAGCCAGTC   1800

CACATCCACC TCGGCCAGCT CCTCGCGCTG TGGCGCCCCT TGGTAGCCGG CATCGGCTGA   1860

GACAAATTGC TCCTCTCCAT GCAGCAGATT ACCCAGCTGA TTGAGGTCAT GCTCGTTGGC   1920

CGCGGTGGTG ACCAGGCTGT GGGTCAGGCC ACTCTTGGCA TCGACACCAA TGTGGGCCTT   1980

CATGCCAAAG TGCCACTGAT TGCCTTTCTT GGTCTGATGC ATCTCCGGAT CGCGTTGCTG   2040

CTCTTTGTTC TTGGTCGAGC TGGGTGCCTC AATGATGGTG GCATCGACCA AGGTGCCTTG   2100

AGTCATCATG ACGCCTGCTT CGGCCAGCCA GCGATTGATG GTCTTGAACA ATTGGCGGGC   2160

CAGTTGATGC TGCTCCAGCA GGTGGCGGAA ATTCATGATG GTGGTGCGGT CCGGCAAGGC   2220

GCTATCCAGG GATAACCGGG CAAACAGACG CATGGAGGCG ATTTCGTACA GAGCATCTTC   2280

CATCGCGCCA TCGCTCAGGT TGTACCAATG CTGCATGCAG TGAATGCGTA GCATGGTTTC   2340

CAGCGGATAA GGTCGCCGGC CATTACCAGC CTTGGGGTAA AACGGCTCGA TGACTTCCAC   2400

CATGTTTTGC CATGGCAGAA TCTGCTCCAT GCGGGACAAG AAAATCTCTT TTCTGGTCTG   2460

ACGGCGCTTA CTGCTGAATT CACTGTCGGC GAAGGTAAGT TGATGACTCA TGATGAACCC   2520

TGTTCTATGG CTCCAGATGA CAAACATGAT CTCATATCAG GGACTTGTTC GCACCTTCCC   2580

TAAGAGTTTT AATGTTTGAA GAAAGAGATA TAATTACAGC ATCATCCCAC AAAGCAGATA   2640

TTACAATACC TTGACTGGGN TATTGCCAAG CGGATA                             2676
```

(2) INFORMATION FOR SEQ ID NO: 13:

(i) SEQUENCE CHARACTERISTICS:
        (A) LENGTH: 1485 base pairs
        (B) TYPE: nucleic acid
        (C) STRANDEDNESS: double
        (D) TOPOLOGY: linear (xi) SEQUENCE DESCRIPTION: SEQ ID NO: 13:

```
AAATTTGTCC TCCGGNTCTT TTCCCGTGGA TACGGGCATT GAGACCCGAA AGGSCCTGTA      60

TTTGCGACCG GAGAGGCATC CTGGGGGCTC AGTAAACCAG TGGTCGCTGT ATGGCGGGGC     120

TGTGCTTGCC GGTGATTATA ATGNCACTGG SAGCCGGTGC CGGCTGGGAC CTGGGTGTGC     180

CGGGGACCCT TTCCGCTGAT ATCACGCAGT CAGTAGCCCG TATTGAGGGA GAGAGAACGT     240

TTCAGGGAAA ATCCTGGCGT CTGAGCTACT CCAAACGGTT TGATAATGCG GATGCCGACA     300

TTACGTTCGC CGGGTATCGT TTCTCAGAGC GAAACTATAT GACCATGGAG CAGTACCTGA     360

ACGCCCGCTA CCGTAATGAT TACAGCAGTC GGGAAAAAGA GATGTATACC GTTACGCTGA     420

ATAAAAACGT GGCGGACTGG AACACCTCTT TTAACCTGCA GTACAGCCGT CAGACATACT     480

GGGACATACG GAAAACGGAC TATTATACGG TGAGCGTCAA CCGCTACTTT AATGTTTTCG     540

GACTGCAGGG TGTGGCGGTT GGATTGTCAG CCTCAAGGTC TAAATATCTG GGCGTGATA      600

ACRRTTCTGC TTACCTGCGT ATATCCGTGC CGCTGGGGAC GGGGACAGCG AGCTACAGTG     660

GCAGTATGAG TAATGACCGT TATGTGAATA TGGCCGGCTA CACTGACACG TTCAATGACG     720

GTCTGGACAG CTACAGCCTG AACGCCGGCC TTAACAGTGG CGGTGGACTG ACATCGCAAC     780

GTCAGATTAA TGCCTATTAC AGTCATCGTA GTCCGCTGGC AAATTTGTCC GCGAATATTG     840

CATCCCTGCA GAAAGGATAT ACGTCTTTCG GCGTCAGTGC TTCCGGTGGG GCAACAATTA     900

CCGGAAAAGG TGCGGCGTTA CATGCAGGGG GAATGTCCGG TGGAACACGT CTTCTTGTTG     960

ACACGGATGG TGTGGGAGGT GTACCGGTTG ATGGCGGGCA GGTGGTGACA AATCGCTGGG    1020

GAACGGGCGT GGTGACTGAC ATCAGCAGTT ATTACCGGAA TACAACCTCT GTTGACCTGA    1080

AGCGCTTACC GGATGATGTG GAAGCAACCC GTTCTGTTGT GGAATCGGCG CTGACAGAAG    1140

GTGCCATTGG TTACCGGAAA TTCAGCGTGC TTAAAGGGAA ACGTCTGTTT GCAATACTGC    1200

GTCTTGCTGA TGGCTCTCAG CCCCCGTTTG GTGCCAGTGT AACCAGTGAA AAAGGCCGGG    1260

AACTGGGCAT GGTGGCCGAC GAAGGCCTTG CCTGGCTGAG TGGCGTGACG CCGGGGGAAA    1320

CCCTGTCGGT AAACTGGGAT GGAAAAATAC AGTGTCAGGT AAATGTACCG GAGACAGCAA    1380

TATCTGACCA GCAGTTATTG CTTCCCTGTA CGCCTCAGAA ATAAATGAAA GTCCGGAATA    1440

TTAACGGCTG ATTGAATTGC GGTTTATGCC ATTTTCCCGG ACCAA                    1485
```

(2) INFORMATION FOR SEQ ID NO: 14:

(i) SEQUENCE CHARACTERISTICS:
        (A) LENGTH: 22671 base pairs
        (B) TYPE: nucleic acid
        (C) STRANDEDNESS: double
        (D) TOPOLOGY: linear (xi) SEQUENCE DESCRIPTION: SEQ ID NO: 14:

```
TTACCAATTT CATCGTCCGG TACATCCTCC AGAACATCTC GCAATAAACT CTCGTCTGCC      60

TCATTCCATG CCACACCAGC ATTTGGGAAA CGAGGATCGA TCTCTCTTTC CTTCTTCTCC     120

TTCTTACTTT GCTCTTTTCG GGATGATACA GATACGACAG AACGTTCTTT TACCGCTGTA     180

ATTGCCATAA CTGCATTGAG CAGAGATCTG CGCTCCACAT CGTTCAGCAT TTTTCCTTCA     240

CAGATCAAAT CATTCAGGAT GTCAATGACT AGATTCAGAC TTTCTTCTGT TAGCTTCATA     300

TTTCAGACCT TGAAGTATGT AGATAATCAG CACAATTACT AATGTGATAA ATATCAGAAG     360

ATAATTTACA GGTAAACCGG AAAATACATC TGAAGAATAA AGGCCTCAGC TTAACGTTTC     420

AGCCAGTTTG TGAGCTGATT GAGGTACGGC GATGACATTA ACGGGAATTA CTCCCCTATA     480
```

```
GCTCTGAGCT TATTTTTCAC CCTGGCAACA TATGGTGGCT ACTGCGCATG GTTTTGGAGT      540

AGATATCTTA CTACTCGTAG AATTGTGCTT ACTGGTCAGG CCAGCGCACA GGCATTCCGT      600

GCAATCAATA GAACACTGGT TTTTTAGTCT TCCGTTACCC ATCAGGATGT TAGTGCAGAT      660

TCCGGTGTAT TCGATCAGTT GTTCGGCGAA TCAGCGATCG ATCACGATGC GATTTCGTAT      720

GTTAGGGATG CTGGTATGAT TACTCGCTGA AAAATAATGT GAAAAGGCAG TTTTTCTTTA      780

GACATTTAGC TCATTCATGC TGTTGTTTTA CGTTTTGCTG TCGTGTGCAG GATTATCTTT      840

TCGTTACGGG ACGATTCATT CCGTTTTAAT CAGGAGCTAT TGGCGTTGCT CATTGGTGGG      900

ATGCCGTAAA GTTTTACCGC GGCGATTAAT GATGTGAAGT CAATCCAAAT CAACGGAGAT      960

CTCTCATCAT GAATCAACCA ATACACAATG ATTACTGGTT ATCCCGTTTT GAAAGTATTC     1020

TCAACAGTGC CCTGGTGCAA CACCGTGCCG TCTCGTTAAT CTGGGTGGAT TTACGTTTCC     1080

CTGAGCATAT GCCTGTCACC ATCATGGATC CCGATCCGGA TTCAGCGGTG ATTTCTCGTT     1140

TTTTCGAATC CCTGAAAGCC AAAATTCAGG CTTACCAGCG GAAAAAACGA CGTACCAACA     1200

AGCGTGTGCG TGCAACCACC CTGCATTATT TCTGGTGTCG GGAGTTTGGC AAGGAAAAAG     1260

GCAGGAAACA TTATCACGTG ATATTACTGC TCAACAAAGA TACCTGGTGC TCGCCAGGGG     1320

ATTTCACCGT TCCTTCTTCG CTGGCGACGC TGATCCAACT GGCATGGTGT AGCGCTCTGC     1380

ATCTTGAGCC CTGGCAGGGT AATGGACTGG TTCATTTTTC CAGGCGGACG CYTTTCCGTA     1440

AACCGGTATC ATCTGATGCT CGCCCTTCTT CCGATGATAC GCCTTTGTCG GGTGGATGTT     1500

CTGAAACCAG GAAGGCTTCA GACAAAAAGC CGGGTGAAGC CGCTGTTCTC TGGATCAAGC     1560

GTGGTGATGT GGAAGCGATG CAGAAAGCCA TGGAGAGAGC CCGTTATCTC GTGAAGTATG     1620

AGACGAAGCA GCATGACGGT TCTGGTCAAC GTAATTATGG TTGCAGCCGT GGAGCGGGGC     1680

GTCTACTGGA TGGCAGGTGA ACCCTGTAAA ACGGCATCCG GTGCCAGAGT ATATGTCACA     1740

GTAAGGGCGT GGTTGATGCC CTTAGCTCGT TTTCTGAAAA AGTCGTCCTG AAGTCATGTG     1800

TCACGAACGG TGCAATAGTG ATCCACACCC AACGCCTGAA ATCAGATCCA GGGGTAATC      1860

TGCTCTCCTG ATTCAGGAGA GYTTATGGTC ACTTTTGAGA CAGTTATGGA AATTAAAATC     1920

CTGCACAAGC AGGGAATGAG TAGCCGGGCG ATTGCCAGAG AACTGGGGAT CTCCCGCAAT     1980

ACGGTTAAAC GTTATTTGCA GGCAAAATCT GAGCCGCCAA AATATACGCC GCGACCTGCT     2040

GTTGCTTCAC TCCTGGATGA ATACCGGGAT TATATTCGTC AACGCATCGC CGATGCTCAT     2100

CCTTACAAAA TCCCGGCAAC GGTAATCGCT CGAGAGATCA GAGACCAGGG ATATCGTGGC     2160

GGAATGACCA TTCTCAGGGC ATTCATTCGT TCTCTCTCGG TTCCTCAGGA GCAGGAGCCT     2220

GCCGTTCGGT TCGAAACTGA ACCCGGACGA CAGATGCAGG TTGACTGGGG CACTATGCGT     2280

AATGGTCGCT CACCGCTTCA CGTGTTCGTT GCTGTTCTCG GATACAGCCG AATGCTGTAC     2340

ATCGAATTCA CTGACAATAT GCGTTATGAC ACGCTGGAGA CCTGCCATCG TAATGCGTTC     2400

CGCTTCTTTG GTGGTGTGCC GCGCGAAGTG TTGTATGACA ATATGAAAAC TGTGGTTCTG     2460

CAACGTGACG CATATCAGAC CGGTCAGCAC CGGTTCCATC CTTCGTTGTG GCAGTTCGGC     2520

AAGGAGATGG GCTTCTCTCC CCGACTGTGT CGCCCCTTCA GGGCACAGAC TAAAGGTAAG     2580

GTGGAACGGA TGGTGCAGTA CACCCGTAAC AGTTTTTACA TCCCACTAAT GACTCGCCTG     2640

CGACCGATGG GGATCACTGT CGATGTTGAA ACAGCCAGCC GCCACGGTCT GCGCTGGCTG     2700

CACGATGTCG CTAACCAACG AAAGCATGAA ACAATCCAGG CCCGTCCCTG CGATCGCTGG     2760

CTCGAAGAGC AGCAGTCCAT GCTGGCACTG CCTCCGGAGA AAAAGAGTA TGACGTGCAT      2820

CCTGGTGAAA ATCTGGTGAA CTTCGACAAA CACCCCCTGC ATCATCCACT CTCCATTTAC     2880
```

```
GACTCATTCT GCAGAGGAGT GGCGTGATGA TGGAACTGCA ACATCAACGA CTGATGGCGC   2940

TCGCCGGGCA GTTGCAACTG GAAAGCCTTA TAAGCGCAGC GCCTGCGCTG TCACAACAGG   3000

CAGTAGACCA GGAATGGAGT TATATGGACT TCCTGGAGCA TCTGCTTCAT GAAGAAAAAC   3060

TGGCACGTCA TCAACGTAAA CAGGCGATGT ATACCCGAAT GGCAGCCTTC CCGGCGGTGA   3120

AAACGTTCGA AGAGTATGAC TTCACATTCG CCACCGGAGC ACCGCAGAAG CAACTCCAGT   3180

CGTTACGCTC ACTCAGCTTC ATAGAACGTA ATGAAAATAT CGTATTACTG GGACCATCAG   3240

GTGTGGGGAA AACCCATCTG GCAATAGCGA TGGGCTATGA AGCAGTCCGT GCAGGTATCA   3300

AAGTTCGCTT CACAACAGCA GCAGATCTGT TACTTCAGTT ATCTACGGCA CAACGTCAGG   3360

GCCGTTATAA AACGACGCTT CAGCGTGGAG TAATGGCCCC CCGCCTGCTC ATCATTGATG   3420

AAATAGGCTA TCTGCCGTTC AGTCAGGAAG AAGCAAAACT GTTCTTCCAG GTCATTGCTA   3480

AACGTTACGA AAAGAGCGCA ATGATCCTGA CATCCAATCT GCCGTTCGGG CAGTGGGATC   3540

AAACGTTCGC CGGTGATGCA GCCCTGACCT CAGCGATGCT GGACCGTATC TTACACCACT   3600

CACATGTCGT TCAAATCAAA GGAGAAAGCT ATCGACTCAG ACAGAAACGA AAGGCCGGGG   3660

TTATAGCAGA AGCTAATCCT GAGTAAAACG GTGGATCAAT ATTGGGCCGT TGGTGGAGAT   3720

ATAAGTGGAT CACTTTTCAT CCGTCGTTGA CATCATGCAA TGTTTCCTGG TTTTCATGCA   3780

TCCATCATTT GTCGCTGCGA TGCCAGACTT CTGGATGCAC ACATGTTGTT TTACTTTTGT   3840

CAGCATCATA AATGCGCCGG GACTGGTGAA TGGAGATAAG CCATTTTATT ATCGACGTCA   3900

GCGAACATAC TCACCATGCC GGTATGTTCC TGAACTGAAC AATAAGTTTT GCGCTGATTA   3960

CAGTATGTGA AGGAGGTCCG TTACAATGAA TTCCGCTTAT ATGCAATCCT TGCAGACATC   4020

CCACCACTTC CCAGCTGATT TAACCTACAG ATTATTTCCT AGTGAGCTTG CATATCTCAT   4080

TGACGACTTA TATGAAAGTA CCCAACTTCC GCTGGAGCTC ATTTTTAATA CTGTACTGGC   4140

AACGCTCTCA CTCTCCTGTC AGTCACTGGT TGACGTTGTT CATCCTCACA CCAACATGCC   4200

GGAACCCTGC TCACTTTATC TGTTGGCAAT CGCAGAGCCA GGCGCGGGAA AAACAACGAT   4260

AAACAGACTG GTGATGAACC CCTGTTACGA ATTTGCCGAT CGACTCATTC AACAATACGA   4320

AGAGAGAAAC AAAGATTATA AGACTGAACT ACAGATCTGG AATACCCGGC AGAAAGCGCT   4380

TGCTGCCAAT TTAAGAAAGG CTGTTAACCG GGGGTATCCG GGGGAACAGG AAGAAGAGGC   4440

GCTGCGTAAT CACGAAAGAA ATAAACCGAC ACGTCCGGTT CGACCGAATT TTATCTATGA   4500

AGATGTTTCG CTTAAAGCGC TTGTGGAAGG GCTCAATGAA CATCCTGAGG CAGGGGTTAT   4560

TTCTGACGAG GCGGTCACTT TTTTCAGAAG CTATCTGAAA AATTATCCGG GCCTGTTGAA   4620

TAAAGCATGG AGTGGACAAC CGTTTGATTT TGGACGGGCT GACGAGAAAT ACCATATCAC   4680

GCCACGTCTG ACATTTTCGT TAATGTCCCA GCCGGATGTC TTTACGAATT ATATAAATAA   4740

AAATGACGTA CTGGCGTGGG GAAGCGGATT TCTTTCCCGG TTTCTGTTCA GTCAGACCGG   4800

AAGTCCTTCC CGGGTACGGG ATTATACGAG AGGCGAGTTC AGAACAAAAC CAACCCTGGA   4860

GAAGTTTCAT AAAAAGATTA ACGGATTTCT GTTAAGCCAT AACATTAATT CCCCCGGTAT   4920

GAGCACCGAA AGGAAAACAT TAAAACTTGC AAAGAAAGCG TTGGGGGAGT GGCAGGAAAA   4980

CCAGATTAAG ATTGAAAGAA AAGCGCTTGC AGGAGGGGAG TGGAACACA TCAGAGATAT   5040

TGTTCTGAAA GCAGGTTCTA ATATACTGAG GATAGCTGGA ATATTCACCT GCTATTGCTA   5100

TAAAGATGCT GAGGAAATTG AATCAATTGC GCTTTTTAAA GCTATGCATC TCATGGGCTG   5160

GTATCTGGAG GAGGCGAGCA CAATATTTTA TCCCATGTCT GCACGATGCC AGTTTGAACA   5220
```

```
GGATGCCTGT GAACTGTATG CATGGATTAT GACCCGAATA AGGCAGAATA ATTGGCGTGC      5280

TATCAGGAAA ACAGACATTG AAAGATATGG TCCCAATCGT CTGAGAAGAG CAGAAAAACT      5340

TACACCTGTA CTCAATCAGT TAATCGYTCA GAATTATTTC CGTATCATCM AAGATGCGAT      5400

CGCATCAGGC ACTTTATGTT TCTGCTCTTG ATAATAATGG TTACATCCTT CCTTTCGGCG      5460

CAATGTCTTA CGAACCGTTT GATATTGTTC CACCCCAGTA TAACCATAAT GCGAAAACAT      5520

ATTCCGTTGT TATTCCACCG GCATTAATTC AGTCATTTAC ACCTGATTCC TCAGCTTACA      5580

CCTTATTTTA AAACAATTTT GTGAGTAGAA ACGAAAATC ATAATCCTTC GAATGAAGGT       5640

TAATGATAAG GTGTGTTGCA TATCCTGCAC CTGTGCAAAT ATTCACCAAT CATTGGGTGT      5700

GAATGAAAAT TTCTCTGAAA AAATCGCTAT GGTAGCAACA GTAGCAGCAC ATACACTACA      5760

TCTGTGATTT GGTTTTGTTT TCATAATGAC CTGCTGTCAG AGCTGATTGA ATGCTGGGAT      5820

GTGCGCACTG GTGGAAGAGT GGTTTTCGTT TCAGATATAA CGAAAGGTAA TCGAAAGATT      5880

GTTTTAAACA TGGATTAAAG CTAATAATTA ACCATATTGT GTGAGTTTTT ATATATAAGT      5940

TTGTTTGATT CTTGCCGTGA TGAGTGCTGG GGTATATGAC GATGTCGCTC TCTTTCTGAA      6000

TAACAAATTA TTATTCGTCT GTTACTGATA AGGGATGCGA TTCATGTTTT AATAGAGGGT      6060

TGAAGAAAAT TAATTTGATA TTTTTTTGTA AGGGAATGGA ACTGTCCGGA ATATGTTCAG      6120

AACGGCGGAT TTCTCATTTC CATTCATTAA ACATGGATAA TTTTAATTTA GGTTTATTAC      6180

TATTATTATA CTCACTCCCT TTTTCATACA ATCTCTATTG TTATTTACTT CCTGTCTTTA      6240

CTCACTCTCT ATCTTTACGA TTATATTCAC TCTATCGTTA CACATTCCAT TAGTATTACT      6300

CTTGTTATCG TATTCATTCC ATCCCTCAAT CATATTTACT GTAACTCATA TGATGTTCAG      6360

GTAAGTTATT CTCTACCATT CTACTGATGA TATCCATCTG TTCTCATTTT CAGTGAAACA      6420

GCAATTGATT TTAATCTTAT CCATCATGAA CTGTATTTGC TTAACAATGA TTGTTTATCT      6480

GAAGTGTTTT AACTATTCTG GTTGGAAACA ATTTCTCTGT CATCACAGAT TAACTGAATG      6540

TTTACTCTTT GATAAGGTAT CCATGATTCC GTCATGTTTA ACAGCGCAGG ATAAACAACA      6600

GAATTAACAG AGTGAATTTC TGATTATATT TGTTGCCGGT TGTATTGTTT AAGGTACTGG      6660

GTGAAAATTA TTCATCCATG GTATGTTGTC TTATGCTATC GTGTGTCGTT AACGTTCATA      6720

TCCTGGAGAA CAGATTGAAT GAGCGCATAT AAGTTTATTG CATTGGCCTT GTACACGGTT      6780

TTTACAACCA CTGAGAGCAA GTTTGTAGTT TATGATGTGA TTGGTCGCAA TATGTTTCTT      6840

AACCTTCTGG TCGTGGTGTT TTATCGCGTA TTTTGCAGTA TTTCGTGATG TTTTATTGAG      6900

TCTGTATTTT CTTTACTCCT CGTTTATCTC ATCTCTTTAG CTAATACCAT CAGATAATCC      6960

ATTTCTTTCT GCATAATGCT GCGTATCGTT AATAACCCGT CGTATCCATT CTGCTACAGC      7020

ATGCCTGATA AATACCATCT GTAAGTTATT ACCGTTTTAG ATCTGATTAT GAGCGAAAGC      7080

ATTAATTCGT TCACAGAGCT TAAAACATCA TTAACTTTCA GGAGTCATCA ACATGCCTAA      7140

ATCTTACACA CCAAACTGGT TTTTTACCGC TTTACTTGAC AATCACATCA ATCAAATGAT      7200

GGCACGCTAT TCCTGCCTGC GGGCCTTACG CATGGATTTC TTCTACAGGA AGATACGCC       7260

CGATTTCTTA CAACCTGATC ATCGCTGGCT TGAATTGCAG TTGCGTATGA TGCTGGAGCA      7320

GGTGGAACAA TTTGAAAATA TCGTTGGCTT CTTCTGGGTG ATTGAATGGA CGGCTGATCA      7380

TGGTTTTCAT GCGCATGCGG TTTTCTGGAT CGATCGTCAG AGGGTTAAAA AAATATATCC      7440

CTTTGCGGAG CGGATTACGG AATGCTGGCG GTCTATTACG CATAACAGCG GTTCGGCACA      7500

CCGCTGCACA TATCAGCCGC ATTATACATA CAACATCAAC ATTCCTGTGC GCCACAACGA      7560

TCCTGAAAGC ATCGATAATA TTCGCGGTGC CCTGCATTAT CTGGCGAAAG AAGAGCAAAA      7620
```

```
AGACGGGCTG TGTGCTTACG GCTGCAATGA AGTTCCTGAA CGTCCTGCTG CAGGGCGTCC    7680

TCGTAAGCCT CACTTCTGAA GCTTAAGGCC TGAGCCTTCG CTCCTGGAAA CACTCCGTCG    7740

GTAAAAACTT ACCGCCTTGA TTAATGATGT GAACTGAAGT CAACGGAGAT CATTCATCCT    7800

GAACCTGCAT CCGGTGTTTT GTTCCTTGTC TTCCCGTTCT GCTTCGGTTC TTCACTTATT    7860

CCATCAATCT CATTCCGCAA GCCATAACAC GTCAGCTCAT TCACGGGCAG GACGCATTGT    7920

GGGCTGCGCA TAACGGAACA TATCTTATGA ATGCTATTCC TTATTTCGAC TATAGCCTGG    7980

CACCCTTCTG GCCATCTTAT CAGAACAAAG TCATCGGCGT CCTTGAGCGT GCGCTGCGTG    8040

AGCAGTCCGG CTCACGGATA CGGCGGATCC TGCTTCGTCT GCCGTGGGAA CATGACAACG    8100

CCTTCAGCAG CAGAAAGATC TGGTTCGGTA TGGACTTTAT CGAAACCGTC AGTGCGCTGA    8160

TGAATGCGAA ACCCGGACGC GACCTTTGCT GGCTCCTGAC CCGTCATCCG GAAAAGCCGG    8220

AATACCACGT GGTGCTGTGC GTCAGACAGG AGTATTTCGA CGGCCCCGAA CTGGATCGGT    8280

TGATACTGGA TGCCTGGAGT AATGTGCTGG GTTTCGCGTC ACCAGGTGAA GCAAAGCCGT    8340

ACCAGAAGCA GATCACCCGG GATGTGGTAC TGGATCGCCG GTCACCGGAC TGCGAAGCCC    8400

TGTTTAAGGA CCTTATCTGG GCGTTCAGTG ATTTCGCCCG CGATCGCCGT GGAGTGTGCG    8460

ATCCGGAAGC CCGTTGCCTT GCCGGCAATC CCGGTTGGCA GTGCTGAAAG CAGCACGCCA    8520

TCCCATCCCC CGTATTACCC CATTCTTCAT AAATCTCACT GAGGACATTC TGACCATGTT    8580

GACCACAACA AGCCACGACA GCGTATTGCT GCGTGCCGAC GATCCCCTGA TCGACATGAA    8640

CTACATCACC AGTTTCACCG GCATGACCGA TAAATGGTTT TACAGGCTGA TCAGTGAAGG    8700

GCATTTTCCT AAACCCATCA AACTGGGGCG CAGCAGCCGC TGGTACAAAA GTGAAGTGGA    8760

GCAGTGGATG CAACAACGAA TTGAGGAATC ACGAGGAGCA GCAGCATGAA ACGTGTTGTG    8820

ATGCCAGTAC GTTGGCAATG TGCAAAATGC CAGCGCTGGA TTGTGGAAAA TCAGCCCTGT    8880

CCCTGGTGCT GGCGACATTC CCGCTTATCT TTCCGCTGAC ACCCTCCGGT CAGCCAACTG    8940

TTAGTCATCA TTTCCTGACT GATTCGTCAT TCCATTCTTA TTGATTATAA CTGGCATTAC    9000

ACCGGTGCTG GCGTGCTTTC CTGCGTGTCT GCACCGGTTT GACAAAATTC AACAGGGTTT    9060

GAAAAGGAAC ATTTCGTGCA AATAACCGAA GCCTTAATTT CAGAGCCGGG AGACATCCGG    9120

CGTTTTATTC AACATGCTGT TGACCACTGG CCGCGTCTGC TGGCAGTCCA CTTCATACTC    9180

CATTCGACAG AAGGAAACAT CTACGGGCAA CAGATTCATG CATTCTGCAC TTCCTTTTAT    9240

CGACAACTGC ATGAACGTAT TACTGAGAGC AATCACACTG CCAGTCCATC ATCGTCGGTG    9300

GTATTACGCT GGTTGCGGGA ACAACATGGA GGAGCAACAA TTCGATGCCT GTTGCTGCTC    9360

AGCCAGACGA GTATTTGTCA CCCGCGAGCC AGTGTCACAG TTGATGAACA ATGTTCGCAA    9420

GTGGTGGATT TACTGCAACA TAGCTGGCAG GTGATAAGTG CTGGCGGACA TGCCGGGTG     9480

GAAAGGTGTT TTCGGGTTGC CCGGGGTGAT ACATCCGGTC AGTATGTTGC GTTAAAAACA    9540

GTCGCATTGT CTCTGGGGTT ACCGGTTGTG ACCGCCATTA CCCATCGTCC GGTACAGCGC    9600

TGTACATTGA TTACAGCTCA GTGAATCAGC GCTTTCTGGC TTTTCGTCGG TCATTCTGTC    9660

AACGCCACGA TGTTTGACCG TTATGGGGAT GCGGACGATT CCCTGCACAG CGTTGTTTCA    9720

CGGTGGTGGA TGACGCAACA CCGCTGTTAA AAACAGTCGT TCAGTCCTTT GTGTTACCGG    9780

TTGTGACAAC AATCAGTTGG TAATGGACGT GTGAACCATC TGCGCTTCCG TTGATTTTTA    9840

TGGACTGATA AAGTTTTGCC AGCTGAATCT TTATACGGAA TGCTCTTCAG TATGCGTACA    9900

CGAATTGACT ATCTGGCGGA TAAATACTCT TTTACCGAAC GGAATGAATC TCCACGCCTT    9960
```

-continued

```
CGCCGGCAGT GGCAGGATGT TCTGGAGGAG TGTCGGCTGA CAGAGGCCGG ACCAGAAGAA  10020
CGGCTGCGTA TTGCCCTGCT GAATGTGGAT TACGTCACCA GTTTTGAACT GCCTTTTCGC  10080
TTGTTGCTTA CTCGTACACC ACAACTGATT GCCGCGCTTC GGGAAGAATG GGGCCTCAGC  10140
CAGAAAAATG TGGTGTTCAA CGATAAACGG TTTGGCTGCG TGTACAGCCT GAAGGCCAGT  10200
CTTTCTGGTG TACCGGATAC ATTCCGGTAT CATCTGTCTC ATCGTATTCG CCGGATGGTT  10260
GGGAATGAAA ATACATCATC GCCATATCAG CAGATTGCCC GGGAAGTGAA AGTGCCCCGT  10320
GAACGGCTGA AGTATGCGCT GGAAGCCGGT TTACTGGTGA CTGCACTGGA CGGGCTGTTC  10380
TGGTCTGGTA GTCAGCGCAT TGCGGCTGAT ATCCTGAGAC TGAGAAAGAG CGGAATGCCG  10440
GTGGTGACAA CGTCCGTGGA AGCGAGCGAT AACCTGACGG GAACAACCCG CAAAATACCG  10500
GCATACCATC TCTGACATTG CGATGAAGGG CAGATTTCAC CTTGACAGGG GCAGAGTGCC  10560
GCTTTTTATA CTTTATTCCC GTGTCTGAAA AAAATGTGCA AAGGAAACGG GAATGGCAAG  10620
GTCCGATTAC GATTTTATCA ATCTGTCTCT GGGACATGAA CTGAATGAGT GGCTGGCAGA  10680
GAGAGGTTAT GCCGGACAGG CGGATAACCG GAACCGACTG GCAGAGGTGG TTACCCGCAA  10740
ATTGCGGGAC AGTTTTTATG CGGACGTCTC CTGGGATGCG CTGAATGTGG CATACAGTGA  10800
ACACCCTGAG TGGTTTTCAG AGCTTGCCTC CGGGGATGAG GATTAACAGG CAAATTATGC  10860
TGCTATCGGG CAGAGTGATT ACCTGCAGGG ATTTCCATTT ATAAGAATAC GCCGCTTCGG  10920
GAAAGCTCCG GTTCTCCGGA GAGTTACGAT TATTTTACT CAAATTCACA ACACCTGAAC  10980
TGGAACTTGC GTTGTGTCCC GGATTGTTAC TCCGCAGAAG CATCCTTTTT ACCATACGGA  11040
TGTTTGTTTT CCATTTCCCC TCCGAAAAAT ACAACTCCGA TCACATTTCT GATATTTTCC  11100
CCGGATTTTA CATAACAGGA TTGTTTCTGT ATGTTTTTTA TCTGGTGTAA ATTTCAGCAC  11160
TGACATTCCG CTTACGTTAA TTTACACTGG ATACCCCACG AGGAGAATAT GCAGCACCGG  11220
CAGGATAACT TACTGGCGAA CAGAAATTTG TTGCCTGGTA TGGTTTCCGG TCAGTACGCA  11280
TTCAGGATCC GTACCTTATC TCAGGTGGTA CGCTATTTTT CCCTCCTCCC CTGCCTTTGC  11340
ATTCTTTCAT TTTCGTCTCC GGCAGCCATG CTGTCTCCGG GTGACCGCAG TGCAATTCAG  11400
CAGCAACAGC AGCAGTTGTT GGATGAAAAC CAGCGCCAGC GTGATGCGCT GGAGCGCAGT  11460
GCGCCGCTGA CCATCACGCC GTCTCCGGAA ACGTCTGCCG GTACTGAAGG TCCCTGCTTT  11520
ACGGTGTCAC GCATTGTTGT CAGTGGGGCC ACCCGACTGA CGTCTGCAGA AACCGACAGA  11580
CTGGTGGCAC CGTGGGTGAA TCAGTGTCTG AATATACGG GACTGACCGC GGTCACGGAT  11640
GCCGTGACGG ACGGCTATAT ACGCCGGGGA TATATCACCA GCCGGGCCTT TCTGACAGAG  11700
CAGGACCTTT CAGGGGGCGT ACTGCACATA ACGGTCATGG AAGGCAGGCT GCAGCAAATC  11760
CGGGCGGAAG GCGCTGACCT TCCTGCCCGC ACCCTGAAGA TGGTTTTCCC GGGAATGGAG  11820
GGGAAGGTTC TGAACTGCGG GATATTGAGC AGGGGATGGA GCAGATTAAT CGTCTGCGTA  11880
CGGAGCCGGT ACAGATTGAA ATATCGCCCG GTGACCGTGA GGGATGGTCG GTGGTGACAC  11940
TGACGGCATT GCCGGAATGG CCTGTCACAG GGAGCGTGGG CATCGACAAC AGCGGGCAGA  12000
AGAATACCGG TACGGGCAG TTAAATGGTG TCCTTTCCTT TAATAATCCT CTGGGGCTGG  12060
CTGACAACTG GTTTGTCAGC GGGGGACGGA GCAGTGACTT TCGGTGTCA CATGATGCGA  12120
GGAATTTTGC CGCCGGTGTC AGTCTGCCGT ATGGCTATAC CCTGGTGGAT TACACGTATT  12180
CATGGAGTGA CTACCTCAGC ACCATTGATA ACCGGGGCTG GCGGTGGCGT TCCACGGGAG  12240
ACCTGCAGAC TCACCGGCTG GGACTGTCGC ATGTCCTGTT CCGTAACGGG GACATGAAGA  12300
CAGCACTGAC CGGAGGTCTG CAGCACCGCA TTATTCACAA TTATCTGGAT GATGTTCTGC  12360
```

```
TTCAGGGCAG CAGCCGTAAA CTCACTTCAT TTTCTGTCGG GCTGAATCAC ACACACAAGT   12420

TTCTGGGTGG TGTCGGAACA CTGAATCCGG TATTCACACG GGGGATGCCC TGGTTCGGCG   12480

CAGAAAGCGA CCACGGGAAA AGGGGAGACC TGCCCGTAAA TCAGTTCCGG AAATGGTCGG   12540

TGAGTGCCAG TTTTCAGCGC CCCGTCACGG ACAGGGTGTG GTGGCTGACC AGCGCTTATG   12600

CCCAGTGGTC ACCGGACCGT CTTCATGGTG TGGAACAACT GAGCCTCGGG GGTGAGAGTT   12660

CAGTGCGTGG CTTTAAGGAG CAGTATATCT CCGGTAATAA CGGCGGTTAT CTGCGAAATG   12720

AGCTGTCCTG GTCTCTGTTC TCCCTGCCAT ATGTGGGGAC AGTCCGTGCA GTGACTGCAC   12780

TGGACGGCGG CTGGCTGCAC TCTGACAGAG ATGACCCGTA CTCGTCCGGC ACGCTGTGGG   12840

GTGCTGCTGC CGGGCTCAGC ACCACCAGTG GTCATGTTTC CGGTTCGTTC ACTGCCGGAC   12900

TGCCTCTGGT TTACCCGGAC TGGCTTGCCC CTGACCATCT CACGGTTTAC TGGCGCGTTG   12960

CCGTCGCGTT TTAAGGGATT ATTACCATGC ATCAGCCTCC CGTTCGCTTC ACTTACCGCC   13020

TGCTGAGTTA CCTTATCAGT ACGATTATCG CCGGGCAGCC GTTGTTACCG GCTGTGGGGG   13080

CCGTCATCAC CCCACAAAAC GGGGCTGGAA TGGATAAAGC GGCAAATGGT GTGCCGGTCG   13140

TGAACATTGC CACGCCGAAC GGGGCCGGGA TTTCGCATAA CCGGTTTACG GATTACAACG   13200

TCGGAAGGA AGGGCTGATT CTCAATAATG CCACCGGTAA GCTTAATCCG ACGCAGCTTG   13260

GTGGACTGAT ACAGAATAAC CCGAACCTGA AGCGGGCGG GGAAGCGAAG GGTATCATCA   13320

ACGAAGTGAC CGGCGGTAAC CGTTCACTGT TGCAGGGCTA TACGGAAGTG CCGGCAAAG   13380

CGGCGAATGT GATGGTTGCC AACCCGTATG GTATCACCTG TGACGGCTGT GGTTTTATCA   13440

ACACGCCGCA CGCGACGCTC ACCACAGGCA AACCTGTGAT GAATGCCGAC GGCAGCCTGC   13500

AGGCGCTGGA GGTGACTGAA GGCAGTATCA CCATCAATGG CGCGGGCCTG GACGGCACCC   13560

GGAGCGATGC CGTATCCATT ATTGCCCGTG CAACGGAAGT GAATGCCGCG CTTCATGCGA   13620

AGGATTTAAC TGTCACTGCA GGCGCTAACC GGATAACTGC AGATGGTCGC GTCAGTGCCC   13680

TGAAGGGCGA AGGTGATGTG CCGAAAGTTG CCGTTGATAC CGGCGCGCTC GGTGGAATGT   13740

ACGCCAGGCG TATTCATCTG ACCTCCACTG AAAGTGGTGT CGGGGTTAAT CTGGGTAACC   13800

TTTATGCCCG CGAGGGCGAT ATCATACTGA GCAGTGCCGG AAAACTGGTC CTGAAGAACA   13860

GCCTTGCCGG CGGCAATACC ACCGTAACCG GAACGGATGT CTCACTTTCA GGGGATAACA   13920

AAGCCGGAGG AAATCTCAGC GTTACCGGGA CAACGGGACT GACACTGAAT CAGCCCCGTC   13980

TGGTGACGGA TAAAAATCTG GTGCTGTCTT CATCCGGGCA GATTGTACAG AACGGTGGTG   14040

AACTGACTGC CGGACAGAAC GCCATGCTCA GTGCACAGCA CCTGAACCAG ACTTCCGGGA   14100

CCGTGAATGC AGCTGAAAAT GTCACCCTTA CCACCACCAA TGATACCACA CTGAAAGGCC   14160

GCAGCGTTGC CGGAAAACA CTCACTGTCA GTTCCGGCAG CCTGAACAAC GGTGGGACAC   14220

TGGTTGCCGG GCGCGATGCC ACGGTGAAAA CCGGACATT CAGTAATACC GGTACCGTCC   14280

AGGGGAATGG CCTGAAAGTT ACCGCCACTG ACCTGACCAG CACCGGCAGT ATTAAAAGTG   14340

GCAGCACACT CGATATCAGC GCCCGCAATG CCACACTGTC CGGTGATGCC GGTGCAAAAG   14400

ACAGTGCCCG CGTTACCGTC AGCGGTACAC TCGAAAACCG CGGCAGACTT GTCAGCGATG   14460

ACGTGCTGAC GCTCAGTGCC ACGCAGATAA ACAACAGCGG TACCCTCTCC GGGGCAAAGG   14520

AACTTGTGGC TTCTGCAGAC ACACTGACCA CCACAGAAAA ATCGGTCACA AACAGTGACG   14580

GTAACCTCAT GCTGGACAGC GCGTCTTCCA CACTGGCGGG TGAAACCAGT GCGGGTGGCA   14640

CGGTGTCTGT AAAAGGCAAC AGTCTGAAGA CCACGACCAC TGCGCAGACG CAGGGCAACA   14700
```

-continued

```
GTGTCAGCGT GGATGTGCAG AACGCACAGC TTGACGGAAC ACAGGCTGCC AGAGACATCC   14760
TTACCCTGAA CGCCAGTGAA AAGCTCACCC ACAGCGGGAA AAGCAGTGCC CCGTCGCTCA   14820
GCCTCAGTGC GCCGGAACTG ACCAGCAGCG GCGTACTTGT TGGTTCCGCC CTGAATACAC   14880
AGTCACAGAC CCTGACCAAC AGCGGTCTGT TGCAGGGGGA GGCCTCACTC ACCGTTAACA   14940
CACAGAGGCT TGATAATCAG CAGAACGGCA CGCTGTACAG TGCTGCAGAC CTGACGCTGG   15000
ATATACCGGA CATCCGCAAC AGCGGGCTTA TCACCGGTGA TAATGGTTTA ATGTTAAATG   15060
CTGTCTCCCT CAGCAATCCG GGAAAAATCA TCGCTGACAC GCTGAGCGTC AGGGCGACCA   15120
CGCTGGATGG TGACGGCCTG TTGCAGGGCG CCGGTGCACT GGCGCTTGCT GGCGACACCC   15180
TCTCACAGGG TAGTCACGGA CGCTGGCTGA CGGCGGACGA CCTCTCCCTC GGGGCAAAA    15240
CACTGAATAC CGCAGGACCA CGCAGGGACA GAATATCACC GTGCAGGCGG ACAGATGGGC   15300
GAACAGTGGT TCCGTGCTGG CAACCGGTAA CCTTACTGCT TCGGCAACCG GTCAGTTGAC   15360
CAGTACCGGC GATATCATGA GCCAGGGTGA CACCACGCTG AAAGCAGCCA CCACGGACAA   15420
CCGGGGCAGT CTGCTTTCGG CCGGCACGCT CTCCCTTGAT GGAAACTCAC TGGATAACAG   15480
CGGCACTGTC CAGGGTGACC ATGTCACGAT TCGCCAGAAC AGTGTCACCA ACAGTGGCAC   15540
GCTCACCGGG ATCGCCGCGC TGACGCTTGC CGCCCGTATG GTATCCCCTC AACCTGCGCT   15600
GATGAATAAC GGAGGTTCAT TGCTGACCAG CGGCGATCTG ACAATCACCG CAGGCAGTCT   15660
GGTAAACAGC GGGGCGATCC AGGCGGCTGA CAGCCTGACT GCACGTCTGA CGGGTGAGCT   15720
CGTCAGCACA GCGGGCAGCA AAGTCACCTC GAACGGTGAA ATGGCGCTCA GTGCACTGAA   15780
TTTAAGCAAC AGCGGACAAT GGATTGCAAA AAATCTGACC CTGAAGGCGA ACTCACTGAC   15840
CAGTGCGGGT GACATCACCG GTGTGGATAC TCTCACGCTC ACGGTGAATC AGACGCTGAA   15900
CAATCAGGCG AACGGAAAAC TGCTCAGTGC AGGTGTGCTG ACGCTGAAGG CAGACAGTGT   15960
CACAAACGAC GGGCAATTAC AGGGAAATGC CACCACCATC ACGGCAGGAC AACTCACAAA   16020
CGGCGGGCAT CTGCAGGGCG AAACGCTGAC GCTGGCCGCC TCCGGTGGCG TGAACAACCG   16080
TTCCGGTGGT GTTCTGATGA GCCGGAATGC ACTGAATGTC AGTACTGCGA CCCTGAGTAA   16140
CCAGGGCACG ATACAGGGTG GTGGCGGGGT TTCCCTGAAC GCCACTGACC GTCTGCAGAA   16200
CGACGGCAAA ATCCTCTCCG GCAGTAACCT CACGCTGACG GCGCAGGTGC TGGCGAACAC   16260
CGGCAGCGGA CTGGTACAGG CTGCCACCCT GCTGCTGGAT GTGGTGAATA CTGTCAACGG   16320
CGGACGCGTA CTTGCCACCG GCAGTGCCGA CGTTAAAGGA ACCACGCTGA ATAATACCGG   16380
TACGCTTCAG GGTGCGGACC TGCTGGTGAA TTACCACACA TTCAGCAACA GCGGTACCCT   16440
GCTGGGAACC TCCGGGCTTG GCGTCAAGGG CAGTTCACTG CTGCAAAATG GTACAGGGCG   16500
GCTGTACAGT GCAGGCAACC TGCTGCTTGA CGCTCAGGAC TTCAGTGGTC AGGGGCAGGT   16560
GGTGGCCACC GGTGATGTCA CACTGAAACT GATTGCTGCC CTCACGAATT ACGGTACCCT   16620
GGCCGCAGGG AAAACCCTTT CCGTCACGTC GCAAAATGCC ATCACCAACG GCGGTGTCAT   16680
GCAGGGTGAT GCCATGGTGC TCGGTGCCGG AGAGGCATTC ACCAACAATG GAACGCTGAC   16740
TGCCGGTAAA GGCAACAGTG TTTTCAGCGC ACAGCGTCTT TTCCTTAACG CACCGGGTTC   16800
ACTTCAGGCC GGTGGCGATG TGAGTCTGAA CAGCCGGAGT GATATCACCA TCAGTGGTTT   16860
TACCGGCACG GCAGGCAGTC TGACAATGAA TGTGGCCGGT ACCCTGCTGA ACAGTGCGCT   16920
GATTTATGCG GGGAATAACC TGAAGCTGTT TACAGACCGT CTGCATAACC AGCATGGTGA   16980
TATCCTGGCC GGCAACAGTC TGTGGGTACA GAAGGATGCT TCCGGCGGTG CAAACACAGA   17040
GATTATCAAT ACTTCCGGGA ATATTGAGAC GCATCAGGGC GATATTGTTG TAAGAACCGG   17100
```

```
GCATCTTCTG AACCAGCGGG AGGGATTTTC TGCCACAACA ACAACCCGGA CTAACCCCTC   17160

ATCCATTCAG GGAATGGGAA ATGCTCTGGT TGATATTCCC CTTTCCCTTC TTCCTGACGG   17220

CAGCTATGGC TATTTCACCC GTGAAGTTGA AAATCAGCAC GGTACGCCCT GCAACGGGCA   17280

CGGGGCATGC AATATCACAA TGGATACGCT TTATTATTAC GCTCCGTTTG CTGACAGTGC   17340

CACACAGCGC TTTCTCAGCA GCCAGAACAT CACAACAGTA ACCGGTGCTG ATAATCCGGC   17400

AGGCCGCATT GCGTCAGGGC GTAATCTTTC TGCTGAGGCT GAACGACTGG AAAACCGGGC   17460

GTCATTTATC CTGGCGAATG GGGATATCGC ACTCTCGGGC AGAGAGTTAA GCAATCAGAG   17520

CTGGCAGACG GGGACAGAGA ATGAATATCT GGTATACCGC TACGACCCGA AAACGTTTTA   17580

CGGTAGCTAT GCAACAGGCT CTCTGGATAA ACTGCCCCTG CTGTCACCGG AATTTGAAAA   17640

CAATACCATC AGATTTTCAC TGGATGGCCG GGAAAAAGAT TACACGCCCG GTAAGACGTA   17700

TTATTCCGTT ATTCAGGCGG GCGGGGATGT TAAGACCCGT TTTACCAGCA GTATCAATAA   17760

CGGAACAACC ACTGCACATG CAGGTAGTGT CAGTCCGGTG GTCTCTGCAC CTGTACTGAA   17820

TACGTTAAGT CAGCAGACCG GCGGAGACAG TCTGACACAG ACAGCGCTGC AGCAGTATGA   17880

GCCGGTGGTG GTTGGCTCTC CGCAATGGCA CGATGAACTG GCAGGTGCCC TGAAAAATAT   17940

TGCCGGAGGT TCGCCACTGA CCGGTCAGAC CGGTATCAGT GATGACTGGC CACTGCCTTC   18000

CGGCAACAAT GGATACCTGG TTCCGTCCAC GGACCCGGAC AGTCCGTATC TGATTACGGT   18060

GAACCCGAAA CTGGATGGTC TCGGACAGGT GGACAGCCAT TTGTTTGCCG GACTGTATGA   18120

GCTTCTTGGA GCGAAACCGG GTCAGGCGCC ACGTGAAACG GCTCCGTCGT ATACCGATGA   18180

AAAACAGTTT CTGGGCTCAT CGTATTTTCT TGACCGCCTC GGGCTGAAAC CGGAAAAAGA   18240

TTATCGTTTC CTGGGGGATG CGGTCTTTGA TACCCGGTAT GTCAGTAACG CGGTGCTGAG   18300

CCGGACGGGT TCACGTTATC TCAACGGACT GGGTTCAGAC ACGGAACAGA TGCGGTATCT   18360

GATGGATAAC GCGGCCAGAC AACAGAAAGG ACTGGGATTA GAGTTTGGTG TGGCGCTGAC   18420

AGCTGAACAG ATTGCTCAGC TTGACGGCAG CATGCTGTGG TGGGAGTCAG TCACCATCAA   18480

CGGACAGACA GTCATGGTCC CGAAACTGTA TCTGTCGCCG GAAGATATCA CCCTGCATAA   18540

CGGCAGCGTT ATCAGCGGGA ACAACGTGCA GCTTGCGGAC GGCAATATCA CCAACAGCGG   18600

CGGCAGCATC AACGCACAGA ACGACCTTTC GCTCGACAGT ACCGGCTATA TCGACAACCT   18660

GAATGCAGGG CTGATAAGCG CGGGCGGTAG CCTGGACCTG AGCGCCATCG GGATATCAG   18720

CAATATCAGC TCAGTCATCA GCGGTAAAAC CGTACAACTG GAAAGCGTGA GTGGCAACAT   18780

CAGCAATATC ACCCGGCGTC AGCAATGGAA TGCGGGCAGT GACAGCCGAT ATGGTGGTGT   18840

GCATCTCAGC GGTACGGACA CCGGTCCGGT TGCGACCATT AAAGGCACTG ATTCACTTTC   18900

ACTGGATGCA GGGAAAAACA TTGATATTAC CGGGGCAACG GTCTCGTCCG GTGGAGACCT   18960

TGGAATGTCT GCGGGTAATG ACATCAACAT TGCCGTAAAC CTGATAAGCG GGAGCAAAAG   19020

TCAGTCCGGT TTCTGGCACA CTGATGACAA CAGTTCATCA TCCACCACCT CACAGGGCAG   19080

CAGCATCAGC GCCGGCGGTA ACCTGGCGAT GGCTGCAGGC CATAATCTGG ATGTCACAGC   19140

ATCCTCTGTT TCTGCCGGGC ACAGCGCCCT GCTTTCTGCA GGTAACGACC TGAGTCTGAA   19200

TGCAGTCAGG GAAAGCAAAA ACAGTCGCAA CGGCAGGTCA GAAAGTCATG AAAGCCACGC   19260

AGCTGTGTCC ACGGTGACGG CGGGCGATAA CCTCCTCCTT GTTGCCGGTC GTGATATTGC   19320

CAGTCAGGCT GCCGGTATGG CTGCCGAAAA TAACGTGGTC ATCCGGGGCG ACGTGATGT    19380

GAACCTGGTG GCAGAGTCTG CCGGCGCAGG CGACAGCTAT ACGTCGAAGA AAAAGAAAGA   19440
```

```
GATTAACGAG ACAGTCCGTC AGCAGGGAAC GGAAATCGCC AGCGGTGGTG ACACCACCGT   19500

CACCGCAGGA CGGGATATCA CCGCTGTTGC GTCATCCGTT ACCGCAACCG GCAATATCAG   19560

CGTGAATGCC GGTCGTGATG TTGCCCTGAC CACGGCGACA GAAAGTGACT ATCACTATCT   19620

GGAAACGAAG AAAAAAAGCG GAGGTTTTCT CAGTAAGAAA ACCACCCACA CCATCAGTGA   19680

GGACAGTGCC TCCCGTGAAG CAGGTTCCCT GCTGTCGGGG AACCGCGTGA CCGTTAACGC   19740

CGGTGATAAN CTGACGGTAG AGGGTTCGGA TGTGGTGGCT GACCGGGATG TGTCACTGGC   19800

GGCGGGTAAC CATGTTGATG TTCTTGCTGC CACCAGTACA GATACGTCCT GGCGCTTTAA   19860

GGAAACGAAG AAATCCGGTC TGATGGGTAC CGGCGGTATT GGTTTCACCA TTGGCAGCAG   19920

TAAGACAACG CACGACCGCC GCGAGGCSGG GACAACGCAG AGTCAGAGTG CCAGTACCAT   19980

CGGCTCCACT GCCGGTAATG TCAGTATTAC CGCGGGCAAA CAGGCTCATA TCAGCGGTTC   20040

GGATGTGATT GCGAACCGGG ATATCAGCAT TACCGGTGAC AGTGTGGTGG TTGACCCGGG   20100

GCATGATCGT CGTACTGTGG ACGAAAAATT TGAGCAGAAG AAAAGCGGGC TGACGGTTGC   20160

CCTTTCCGGC ACGNTGGGCA GTGCCATCAA TAATGCGGTC ACCAGTGCAC AGGAGACGAA   20220

GGAGAGCAGT GACAGCCGTC TGAAAGCCCT GCAGGCCACA AGACAGCGC TGTCTGGTGT   20280

GCAGGCCGGA CAGGCTGCGG CAATGGCCAC CGCAACCGGT GACCCGAATG CGACGGGAGT   20340

CAGCCTGTCG CTTACCACCC AGAAATCGAA ATCACAACAA CATTCTGAAA GTGACACAGT   20400

ATCCGGCAGT ACGCTGAATG CCGGGAATAA TCTGTCTGTT GTCGCAACCG GCAAAAACAG   20460

GGGAGATAAC CGCGGAGATA TTGTGATTGC AGGAAGCCAG CTTAAGGCCG GTGGTAACAC   20520

AAGCCTGGAT GCCGCGAATG ATGTTCTGTT GAGTGGCGCT GCAAACACAC AAAAAACAAC   20580

GGGCAGGAAC AGCAGCAGTG GCGGTGGCGT GGGTGTCAGT ATCGGTGCCG GTGGTAACGG   20640

TGCCGGTATC AGCGTCTTTG CCAGCGTTAA TGCGGCAAAA GGCAGCGAGA AAGGTAACGG   20700

TACTGAGTGG ACTGAAAACCA CAACAGACAG CGGTAAAAACC GTCACCATCA ACAGTGGTCG   20760

GGATACGGTA CTGAACGGTG CTCAGGTCAA CGGCAACAGG ATTATCGCCG ATGTGGGCCA   20820

CGACCTGCTG ATAAGCAGCC AGCAGGACAC CAGTAAGTAC GACAGTAAAC AGACCAGCGT   20880

GGCTGCCGGC GGCAGTTTTA CCTTTGGCTC CATGACCGGC TCAGGTTACA TCGCTGCCTC   20940

CCGGGATAAG ATGAAGAGCC GCTTTGACTC CGTTGCTGAA CAAACCGGGA TGTTTTCCGG   21000

AGATGGCGGC TTCGATATCA CGGTCGGCAA CCACACCCAG CTCGATGGTG CGGTTATCGC   21060

TTCCACGGCG ACGGCAGATA AAACAGCCT CGATACCGGG ACGCTCGGCT TCAGCGATAT   21120

TCACAACGAA GCGGATTATA AAGTCAGTCA CAGTGGAATC AGTCTGAGCG GTGGTGGCAG   21180

CTTCGGGGAT AAATTTCAGG GTAACATGCC GGGTGGCATG ATATCCGCCG GAGGTCACAG   21240

CGGACATGCG GAAGGAACGA CTCAGGCCGC AGTGGCAGAT GGCACAATCA CCATCCGGGA   21300

CAGGGACAAT CAGAAGCAGA ATCTGGCGAA CCTGAGCCGT GACCCTGCGC ACGCTAATGA   21360

CAGTATCAGC CCGATATTTG ACAAGGAGAA AGAGCAGAGG CGTCTGCAGA CAGTGGGGCT   21420

TATCAGTGAC ATTGGCAGTC AGGTGGCGGA TATCGCGCGG ACGCAGGGGG AACTGAATGC   21480

GTTGAAGCTG CGCAGGATAA ATATGGGCCT GTTCCGGCGG ATGCGACGGA AGAACAGCGG   21540

CAGGCATATC TGGCAAAACT GCGTGATACG CCGGAATACA AAAAGGAACA GGAAAAGTAT   21600

GGTACCGGCA GCGATATGCA GCGCGGTATC CAGGCTGCAA CGGCTGCACT TCAGGGCCTG   21660

GTGGGCGGCA ATATGGCAGG CGCGCTGGCA GGTGCTTCAG CGCCGGAGCT GGCGAACATC   21720

ATCGGTCATC ACGCGGGTAT TGATGACAAT ACAGCGGCAA AAGCCATTGC CCATGCCATT   21780

CTCGGTGGTG TGACAGCAGC CCTTCAGGGC AACAGTGCGG CAGCAGGCGC AATTGGTGCG   21840
```

```
GGTACTGGTG AAGTGATCGC GTCAGCCATT GCGAAAAGCC TCTACCCGGG CGTAGATCCG    21900

TCGAAACTGA CAGAAGATCA GAAGCAAACT GTAAGCACGC TGGCAACGCT GTCAGCGGGT    21960

ATGGCCGGCG GCATTGCCAG TGGCGATGTG GCTGGCGCGG CTGCTGGAGC TGGTGCCGGG    22020

AAGAACGTTG TTGAGAATAA TGCGCTGAGT CTGGTTGCCA GAGGCTGTGC GGTCGCAGCA    22080

CCTTGCAGGA CTAAAGTTGC AGAGCAGTTG CTAGAAATCG GGGCGAAAGC GGGCATGGCC    22140

GGGCTTGCCG GGGCGGCAGT CAAGGATATG GCCGACAGGA TGACCTCCGA TGAACTGGAG    22200

CATCTGATTA CCCTGCAAAT GATGGGTAAT GATGAGATCA CTACTAAGTA TCTCAGTTCG    22260

TTGCATGATA AGTACGGTTC CGGGGCTGCC TCGAATCCGA ATATCGGTAA AGATCTGACC    22320

GATGCGGAAA AGTAGAACT GGGCGGTTCC GGCTCAGGAA CCGGTACACC ACCACCATCG    22380

GAAAATGATC CTAAGCAGCA AAATGAAAAA ACTGTAGATA AGCTTAATCA GAAGCAAGAA    22440

AGTGCGATTA AGAAGATCGA TAAACACTATA AAAAATGCTC TGAAAGATCA TGATATTATT   22500

GGAACTCTCA AGGATATGGA TGGTAAGCCA GTTCCTAAAG AGAATGGAGG ATATTGGGAT    22560

CATATGCAGG AAATGCAAAA TACGCTCAGA GGATTAAGAA ATCATGCGGA TACGTTGAAA    22620

AACGTCAACA ATCCTGAAGC TCAGGCTGCG TATGGCAGAG CAACAGATGC T             22671

(2) INFORMATION FOR SEQ ID NO: 15:

(i) SEQUENCE CHARACTERISTICS:
        (A) LENGTH: 2385 base pairs
        (B) TYPE: nucleic acid
        (C) STRANDEDNESS: double
        (D) TOPOLOGY: linear (xi) SEQUENCE DESCRIPTION: SEQ ID NO: 15:

GGGCGACACG GAAATGTTGA ATACTCATAC TCTTCCTTTT TCAATATTAT TGAAGCATTT      60

ATCAGGGTTA TTGTCTCATG AGCGGATACA TATTTGAATG TATTTAGGCA ACTGAAACCC    120

GCTGACGGAT NANGTGTACA GTGGCATCAG TGGACGGMTT ACAGCATAAG TGCTTAAGGC    180

GCGTGACCAT ACAGMTACGG TCGCTGCAGA GAACAGGGAG AATATCATCC GGAACACGGT    240

GGCCATAAAC CGTAACACCA GGGGCTGCT TTCCCCGGGA GAGGTGCTGG AGATGCATGC     300

GGACGTCTGA ACAGTCAGCA GGGCTGATTA ATGAGAATCA CGAGGAAATG AAGCGGGAGC    360

CGTACAGTGA GGATAAATTT AACGCCATAG CGGCTGTGGG CGGGTATAGT GCCAAGCAGA    420

CTGCTTAAAG GCAGGTACTA CTTTCAGTGG CGGCTATGTT TCCTGGAATG TGGGTGTCAA    480

CTGGTAGTTC TGAACCCGGG CCTGAGTCAC CGGGGAGGCA GTTTTCGGTA TGAAGTAATG    540

ATTCGCTGCC TGTTTTTCTC CCCGATGGCA TAACTGACTG TTCCCGGGTA TTCCTGAAGA    600

TCTGAGAGGA AGAGTGTATA TGCTGAACTA TCGCATAAGG TCAGTGCAGC TATTTATTGT    660

AAACGGTCGG GCTGACAGGG CGCAGGTGCG TCTGGAATGC GACGATGAAG CCGTTTTTGA    720

ATGTTATCTT CTTGCTGAAG GGGAAGGGGA ACTGAAAGAA CTGAGCCTGT CAGAGCTGGA    780

AGAGCGGGCG CTGATGTATG CGGCAGACAG TTTCCGTTAT GAATGATAAG TCAGTTATAC    840

CGGTAATGGT AAACGGAGCC GGTATCCGGG ATACAAGGGG CAGAGAGTAT GCTGATTATT    900

ATTATGACCC GGGACAGATA TCTGGAATAT GGCCTGATGC GTATACTGAG CGGATATCAG    960

GTCACGACAG GCAGAGAGCT GTTTAATGCC GGAAAGCAAC GTCAGTCACT TCCCGAAGAC   1020

AGTTATGTGA TTCTCTGTGA CCGTAATCTG GAAAGGCTTA CATACTCTAT GTTCTGTGGG   1080

CGTCGGTTTC TTGTCATTCC TGTTTCCTCT GTGAGATGCC TGACAGATAT CAGGCAAACC   1140

ATCCGCCGTG GAGCGTGGCT GTTCGGACAT ACGGCAAGGC CACTGACCCG GACAGAGATG   1200
```

-continued

```
GTGGTGGTCT TCGGGGTTGT TTTCCATGAC TACGGGTTTA CCTTTCTGGC AGACCGGCTG    1260

GGGATAACCA TGAAGACGGT ATGTGCGCAT CTTTACAATG CGATGGAGAA AAATGGTATG    1320

CGCGGCGTCA GTATTAAATA TCTCTGCAAC ACCATAGACC GGTAAAAAGA TGGTTTTCTG    1380

ATAAAGGCTG TTGCGACGGG GATTTCTGTG CATGCTGTGT CACGGGCATC CCAGCTCTCC    1440

GGATAATTAA TGTTATGTAG TCAGGCGTGA TAAATTTCAT ATGGAACAGG TATGCGTTTT    1500

ATTTGTGATA ACAGTTAATG AGGTGTTTCC ATACACACTG AAGTTACCTG TAATATTAGC    1560

GGGGGATTTG AATGATGTTG CGTGTCTGCG ACCACTCGTT TATTCATGCA AATAAGTGGA    1620

CTGCTGGATC CACGGTAAGA GTACAGCGAG GGCCGTATTG ACGGGGATGT GTTATTCAGC    1680

GGGCAGTGCT ATGCGCCACG GAAGCAGTTC GCTGACACGG TTGACCGGCC AGTCAGCTAT    1740

GACGCCAAAC ACATGGCGAA GGTAGTTTTC TGGATCCTCG TCGTTCAGTT TGCACGTCCC    1800

GATCAGGCTG TACAGTAGCA CTCCCCGCTC ACCACCATGC TCAGAGCTGC GTATTACCGT    1860

GAAGGAGATC GGTGAGTAAC CCTCTGTGTC GGCACATTAT AGCCGTCACA TCGGATAACT    1920

GTTATCCTTC TGTTCTGATG TATTCTGGGA GGTGATGTTT CACTCCTGAT AAGAGCATTA    1980

CTAATTACAG CTGCTTTTCG GATAACATTC GGGCAGTTTT CTTTAATTCT GAAGTCTGAA    2040

AGAGATATCA GTAATTGTAT TGCTTTTAAA CATTGTCAGT ATTTATTTGT CCAAATCGTT    2100

CACGTTCTC ATAATCTTCC CGACAGTCAC CATCACAAAA CAATCCAGTC TTAACAGGTT    2160

CTCCGCAGTT ATAGCAGAAT CCTGTTTCAG GGAGTCTATT CCGGATACGA TTTTTTAGTC    2220

TGATGCTCAT GCTGAATTGT TCATTTTCAT AAGCAATATC TGCACTATCT GCCATAAACG    2280

ATCCTCTGAG GAGACCACAT CTTTATAACC CACCACCGAA ATATTACAAA GTAATACTCA    2340

TTGTATAATC TTTAACCRGG GGCAGGATAA TTGTATCCTG CCCCT                   2385

(2) INFORMATION FOR SEQ ID NO: 16:

(i) SEQUENCE CHARACTERISTICS:
        (A) LENGTH: 746 base pairs
        (B) TYPE: nucleic acid
        (C) STRANDEDNESS: double
        (D) TOPOLOGY: linear (xi) SEQUENCE DESCRIPTION: SEQ ID NO: 16:

CTTTCAGACC AGCGTTTCCT GTCAGGAGAT GAGGAAGAAA CATCAAAGTA TAAAGGCGGC     60

GATGACCATG ATACGGTATT CAGTGGCGGT ATTGCGGCCG GTTATGATTT TTATCCGCAG    120

TTCAGTATTC CGGTTCGTAC AGAACTGGAG TTTTACGCTC GTGGAAAAGC TGATTCGAAG    180

TATAACGTAG ATAAAGACAG CTGGTCAGGT GGTTACTGGC GTGATGACCT GAAGAATGAG    240

GTGTCAGTCA ACACACTAAT GCTGAATGCG TACTATGACT TCCGGAATGA CAGCGCATTC    300

ACACCATGGG TATCCGCAGG ATTGGCTACG CAGAATTCAC CAGAAAACAA CCGGTATCAG    360

TACCTGGGAT TATGAGTACG GAAGCAGTGG TCGCGAATCG TTGTCACGTT CAGGCTCTGC    420

TGACAACTTC GCATGGAGCC TTGGCGCGGG TGTCCGCTAT GACGTAACCC CGGATATCGC    480

TCTGGACCTC AGCTATCGCT ATCTTGATGC AGGTGACAGC AGTGTGAGTT ACAAGGACGA    540

GTGGGGCGAT AAATATAAGT CAGAAGTTGA TGTTAAAAGT CATGACATCA TGCTTGGTAT    600

GACTTATAAC TTCTGACGAC ACTGCTCCTG AACGATAATT GCGTATATTC TGTAATTAAG    660

ATAATTGCAT ATCKTCTGCA ATTAARCAGA AATACCCTGC AGTCTATTAC TGCAGGGNTG    720

TCTTTTATCT GTTTTACAGA NAATTT                                        746
```

(2) INFORMATION FOR SEQ ID NO: 17:

(i) SEQUENCE CHARACTERISTICS:
        (A) LENGTH: 411 base pairs
        (B) TYPE: nucleic acid
        (C) STRANDEDNESS: double
        (D) TOPOLOGY: linear (xi) SEQUENCE DESCRIPTION: SEQ ID NO: 17:

```
TCTGTTTGTC GTTTTTTCCC CGTTGTAGCG GYTCTGCTCC TGGCTTCCCT GATAGTCAGC        60

CCGCAGGCGC CAGGGCCCCA GATTCCCCCC CACAGTCCCG TTATAACTGA ACTGATGAGA       120

GTCTCCTCCC TGATAATTAC GGGAAACCGT CCCGTTGAGG TTATAATCCA GCATCAGTCC       180

GGGAATGCCG TCGTCCCAGC GTGAGGGAGG CAGCCAGGTG GCATCAGAAT ACTCAAGCCC       240

AGCTGCGGCA TATTGATGCG TAATACGCCC GCTCCGGTAT CAGGACGAAT ATCCACTCCC       300

GGCAACCCAT GAAAATCCGC ACACTGACCA TCATGCCAGT AAACAACTTT ATCCAGAGAT       360

TCTGCTGTTA ACCCCATCAG TCTGACCATA TCTGATGTCA GACAGGCCTG C                411
```

(2) INFORMATION FOR SEQ ID NO: 18:

(i) SEQUENCE CHARACTERISTICS:
        (A) LENGTH: 977 base pairs
        (B) TYPE: nucleic acid
        (C) STRANDEDNESS: double
        (D) TOPOLOGY: linear (xi) SEQUENCE DESCRIPTION: SEQ ID NO: 18:

```
TATTATCGCG CGCGCGCTGC ACAGGGGTTA TCTACATCTG CTGCTGCTGC CGGTTTAATT        60

GCTTCTGTAG TGACATTAGC AATTAGTCCC CTCTCATTCC TGTCCATTGC CGATAAGTTT       120

AAACGTGCAA ATAAAATAGA GGAGTATTCA CAACGATTCA AAAAACTTGG ATACGATGGT       180

GACAGTTTAC TTGCTGCTTT CCACAAAGAA ACAGGAGCTA TTGATGCATC ATTAACAACG       240

ATAAGCACTG TACTGGCTTC AGTATCTTCA GGTATTAGTG CTGCKGCAAC GACATCTCTT       300

GTTGGTGCAC CGGTAAGCGC ACTGGTAGGT GCTGTTACGG GGATAATTTC AGGTATCCTT       360

GAGGCTTCAA AGCAGGCAAT GTTTGAACAT GTTGCCAGTA AAATGGCTGA TGTTATTGCT       420

GAATGGGAGA AAAAACACGG TAAAAATTAC TTTGAAAATG GATATGATGC CCGCCATGCT       480

GCATTTTTAG AAGATAACTT TAAAATATTA TCTCAGTATA ATAAAGAGTA TTCTGTTGAA       540

AGATCAGTCC TCATTACTCA ACAACATTGG GATATGCTGA TAGGTGAGTT AGCTAGTGTC       600

ACCAGAAATG GAGACAAGAC ACTCAGTGGT AAAAGTTATA TTGACTATTA TGAAGAGGGA       660

AAGCGGCTGG AAAGAAGGCC AAAAGAGTTC CAGCAACAAA TCTTTGATCC ATTAAAAGGA       720

AATATTGACC TTTCTGACAG CAAATCTTCT ACGTTATTGA AATTTGTTAC GCCATTGTTA       780

ACTCCCGGTG AGGAAATTCG TGAAAGGAGG CAGTCCGGAA AATATGAATA TATTACCGAG       840

TTATTAGTCA AGGGTGTTGA TAAATGGACG GTGAAGGGGG TTCAGGACAA GGGGTCTGTA       900

TATGATTACT CTAACCTGAT TCAGCATGCA TCAGTCGGTA ATAACCAGTA TCGGGNAATT       960

CGTATTGAGT CACACCT                                                     977
```

(2) INFORMATION FOR SEQ ID NO: 19:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 19:

```
TTTCTTAAGT CCGGCATTGC CACGCGTAAC CCCCACTTCA ACCGCATGAT TGAGCAGATC      60

GAAAAAGTGG CGATCAAATC CCGCGCGCCG ATTCTGCTTA ACGGTCCAAC CGGCGCGGGC     120

AAGTCATTTC TGGCGCGACG CATCTTAGAG TTAAAACAGG CGCGGCATCA GTTTAGCGGC     180

GCKTTTGTGG AAGTGAACTG CGCCACCCTG CGCGGCGATA CCGCCATGTC GACGCTGTTT     240

GGTCATGTAA AAGGCGCGTT TACCGGGGCG CGGGAATCTC GTGAAGGTTT ATTACGCAGC     300

GCCAACGGGG AAATGTTGTT TCTTGATGAG ATTGGCGAAC TGGGCGCGAC GAACAGGCAA     360

TGCTGCTGAA ACCCATTGAA GRGGAAAACC TTTTACCCGT                           400
```

(2) INFORMATION FOR SEQ ID NO: 20:

(i) SEQUENCE CHARACTERISTICS:
        (A) LENGTH: 12368 base pairs
        (B) TYPE: nucleic acid
        (C) STRANDEDNESS: double
        (D) TOPOLOGY: linear (xi) SEQUENCE DESCRIPTION: SEQ ID NO: 20:

```
GTATGCGTTT TCATTAAGAT ATTCTCTGCT GTAGAGAAAC TTATAGCAAT ATAATCTGAT      60

AATATCTTTT ATGTAAAATT TAAATAGTTC ACCTGTGACA GATATATGTT TTCTGCTCAG     120

TAACTCCTGT GTATTAAGCC ATTCCCGTGA CCGAAGCACA CCCTTGTGAA AACTTTTTCT     180

TACTTGCTTT GAGGCACGGC ATTGATGTAA TATTTTTGCG TCCTCAATAA TTCTCTTTCC     240

CGTTTTATTT TTTGCAGCAT CTCTTACTCC ATAAAATATC TCCCGGTCCA GACTTTTGTC     300

ATATTTACTG ATTATACGAC AAATATTCCT GACCCGACGA TTCTCTTTAT TTCGCTTCCA     360

TAGCTTATAA TGATCATCGC ATAACCTTAA GGCATTTGCC TCATCAAATT CTGAAACAGG     420

ATTACTGCAT TTTTTATTCC GACAAATACC TTTGTTTTTA GCCATACTCT TCTTCCCGTC     480

AATGGAAAAA TTTTCACACC CATATTCCTT GAATGATAAA CCGGATTAGT GTGATCCGGT     540

TCAGTGAAAT CAACAGGATA CCGGTATGCC ATTCAGCAAT TCTTCCCTCT CCGCGCAAGT     600

GAAATCATAT CTGACGTTTC TTCCTGAAGA AATACGCCAG AAAATCCTTG AACATCTCCA     660

CGGTGTTATT CATTACGAGC CCGTGATTGG CATTATGGGT AAATCCGGCA CCGGCAAGAG     720

CAGCCTGTGT AATGCCATTT TTCAGTCCCG TATCTGCGCC ACGCATCCCC TGAACGGCTG     780

CACCCGCCAG GCTCATCGTC TTACCCTGCA GCTCGGTGAA CGCAGAATGA CGCTGGTCGA     840

TCTGCCCGGC ATTGGTGAAA CACCGCAGCA TGATCAGGAA TACCGAGCGC TTTATCGTCA     900

GTTACTGCCG GAACTGGATC TGATTATCTG GATCCTGCGG AGTGATGAAC GTGCGTATGC     960

TGCCGATATT GCCATGCATC AGTTTTTACT GAATGAGGGC GCAGATCCCT CGCGCTTTCT    1020

GTTTGTTCTC AGCCATGCCG ATCGCATGTT TCCTGCTGAA GAATGGAATG CCACAGAAAA    1080

ATGCCCGTCC CGTCACCAGG AACTCTCACT GGCGACAGTA ATAGCCCGGG TGGCCACCCT    1140

GTTCCCTTCA TCATTTCCGG TACTCCCTGT AGCCGCACCT GCAGGCTGGA ACCTTCCAGC    1200

GCTGGTGTCA CTGATGATCC ACGCGCTGCC ACCACAGGCA ACCAGCGCAG TTTATTCACA    1260

TATCAGGGGG GAAAACCGCT CTGAACAGGC CCGGAAACAC GCACAACAGA CTTTTGGTGA    1320

TGCCATCGGG AAAAGTTTTG ACGACGCCGT TGCCCGGTTC AGTTTTCCGG CCTGGATGTT    1380

ACAGCTTCTG CGTAAAGCCC GGGACCGCAT TATCCACCTG CTGATCACAC TGTGGGAGCG    1440

TCTGTTCTGA CACACTCACG CCGACAGATG TGTCGCTGGA TTAACGAGCA TTCTTCTTTT    1500

TATGAAATCA TGCTTAAAAA TCAGATAATT ARAAGAATAT TTTTTCTGCT GCATTTTATT    1560

CCTGATTATC CGGATGCGAC ACATCCTTTC AACATCATGA TGCATAATAA CATCATGAAA    1620
```

-continued

```
TAAAAGATGT TTTCTTACGG AGTGCACATC TATGTCTGAT AATCGTTCCC GGCATGATCG   1680

CCTGGCGGTT CGCTTATCAC TCATTATCAG CCGACTGATG GCCGGAGAAT CTCTGTCACT   1740

AAAAACACTG TCAGATGAAT TTGGCGTTAC AGAACGTACT TTACAGCGCG ATTTTCATCA   1800

GCGTCTGGTT CACCTAGATT TAGAGTACAG AAATGGCAGG TACAGCCTCA GACGACAGAG   1860

CAGCCCAGGT GCGATCCCTG AAATGCTTTC TTTTATACAG AATACCGGGA TCGCACGGAT   1920

ACTTCCGCTC CGGAACGGAC GACTGATAAC CTGTCTTACC GACAACCAGG AGCCCTCTCC   1980

CTGCCTTATC TGGCTACCGG CGCCGGATAT CACTGCAACG TTCCCCGAGT GTTTCTCGCA   2040

ACTCATCCTG GCAATAAGAC AGTGTATCCA CATCTCTCTG ATGACTGAGC GATGGTATCC   2100

GTCACTGGAG CCCTGCCGGC TCATTTATTA CAGCGGTAGC TGGTATCTGA TCGCGTTACA   2160

GAAGGGAAAA CTGCAGGTCT TTCCTCTGGC AGATATCAAA TCAGTCAGCC TGACATCAGA   2220

ACGGTTTGAA CGGAGAGGCC ACATCCACAG TCTGGTCGCT GAAGAGCGTT TTATCTCCGC   2280

CCTGCCACAT TTCTCTTTCA TCCATAAACT TATCAACACC TTTAACCTGT GATCGCCGGC   2340

CTGCCAAAGC CGTCCCGACA GGTATGGAGA CAATATGTTG AACAGAAAAC TAAATATACG   2400

GCTACGTCAT TCCCTGAACA GTCACTGCAT ACCTTCCATC ATTATCAATA ACACCGTACG   2460

TTCATTTCAG AGGTCAGTCA TGAATACCAG AGCTCTTTTT CCCCTGCTGT TCACTGTGGC   2520

ATCATTCTCC GCCTCCGCCG GCAACTGGGC TGTCAAAAAC GGCTGGTGTC AGACCATGAC   2580

GGAAGATGGT CAGGCGCTGG TAATGCTGAA AAATGGCACG ATTGGTATTA CCGGCCTGAT   2640

GCAGGGATGC CCGAATGGTG TACAGACGCT CCTGGGCAGC CGTATCAGTA TTAACGGTAA   2700

CCTGATCCCC ACATCACAAA TGTGTAATCA GCAGACGGGA TTCAGGGCTG TTGAGGTGGA   2760

AATCGGACAG GCGCCGGAAA TGGTCAAAAA AGCCGTTCAC TCCATAGCAG AGCGTGATGT   2820

GTCCGTTTTA CAGGCATTTG GTGTACGAAT GGAATTCACC CGCGGTGATA TGCTGAAGGT   2880

CTGTCCGAAA TTTGTCACAT CACTTGCCGG TTTTTCCCCG AAACAGACGA CCACTATTAA   2940

TAAAGATTCC GTCCTGCAGG CTGCCCGGCA GGCATACGCC CGGGAATATG ACGAGGAAAC   3000

AACAGAAACC GCTGATTTTG GCTCTTACGA AGTAAAAGGC AATAAGGTTG AGTTTGAAGT   3060

ATTCAATCCT GAAGACCGTG CGTACGACAA AGTGACCGTC ACGGTTGGTG CTGACGGTAA   3120

TGCCACCGGC GCCAGCGTTG AATTTATCGG AAAATAGCCG GTATGTCGGA CTGCCACCCT   3180

GTTTTATTGC CCGAAGGCCC TTTCTCACGC GAACAGGCGA TGGCTGTCAC AACAGCTTAC   3240

CGCAATGTGC TTATTGAAGA TGACCAGGGA ACGCATTTCC GGCTGGTTAT CCGCAATGCC   3300

GAAGGGCAGC TACGCTGGCG GTGCTGGAAT TTTGAACCTG ATGCCGGAAA ACAGCTAAAT   3360

TCGTATCTCG CCAGTGAGGG AATTCTCAGG CAATAAACGT CTTCATTTCA TCCATCAGGC   3420

CGCGTCTTCT CCGGGAGACG CGGCCTTTTC GTTTATACCG CTAATTCATT CATAAGGAGC   3480

AAAGTATGCA ATTAGCCAGT CGTTTTGGTC ATGTAAATCA GATCCGTCGG GAGCGCCCAC   3540

TGACACGCGA AGAACTGATG TACCACGTCC CGAGTATTTT TGGAGAAGAC CGGCACACCT   3600

CCCGCAGTGA ACGGTATGCG TACATTCCCA CCATCACCGT CCTGGAAAAT CTGCAGCGGG   3660

AAGGCTTTCA GCCGTKCTTC GCCTGCCAGA CCCGTGTGCG CGACCAGAGC CGCCGGGAAT   3720

ATACCAAACA TATGCTGCGT CTGCGGCGGG CCGGACAGAT AACCGGTCAG CATGTGCCTG   3780

AAATTATTCT GCTCAACTCC CATGACGGTT CATCCAGCTA CCAGATGTTA CCCGGATATT   3840

TTCGTGCCAT TTGTACCAAT GGCCTGGTCT GCGGTCAGTC GCTGGGAGAA GTCCGGGTGC   3900

CACACCGGGG AAACGTGGTG GACAGGGTCA TAGAAGGTGC TTACGAAGTG GTGGGCGTGT   3960
```

-continued

```
TTGACCTGAT TGAGGAAAAG CGTGATGCCA TGCAGTCGCT GGTCCTGCCG CCACCGGCAC      4020

GCCAGGCGCT GGCACAGGCG GCGCTGACTT ACCGTTATGG TGATGAACAT CAGCCCGTCA      4080

CCACTACCGA CATTCTGACG CCACGACGCC GGGAGGATTA CGGTAAGGAC CTGTGGAGTG      4140

CTTATCAGAC CATCCAGGAG AATATGCTGA AAGGCGGGAT TTCCGGTCGC AGTGCCAGAG      4200

GAAAACGTAT CCATACCCGG GCCATTCACA GCATCGATAC CGACATTAAG CTCAACCGGG      4260

CGTTGTGGGT GATGGCAGAA ACGCTGCTGG AGAGCCTGCG CTGATACCGT TTCCCTGAAA      4320

GCGCAGTCCT GTTCACGGCT GTCCCTTCCC CCAGACATTC CACCATTCAT TTACTTTTTA      4380

TAAGGAATAA TCTCATGACA ACCTCTTCGC ATAATTCCAC CACACCTTCT GTTTCCGTGG      4440

CCGCTGCATC AGGGAATAAC CAGTCTCAGT TGGTTGCCAC TCCCGTCCCT GATGAACAGC      4500

GCATCAGCTT CTGGCCGCAG CATTTTGGCC TCATTCCACA GTGGGTCACC CTGGAGCCCC      4560

GTGTCTTCGG CTGGATGGAC CGTCTGTGCG AAAACTACTG CGGGGGTATC TGGAATCTGT      4620

ACACCCTGAA CAACGGTGGC GCATTTATAG CACCTGAACC GGATGAAGAT GATGGAGAAA      4680

CCTGGATACT GTTCAATGCC ATGAACGGTA ACCGCGCTGA AATGAGCCCG GAAGCTGCCG      4740

GCATTGCCGC CTGTCTGATG ACGTACAGCC ATCATGCCTG TCGTACGGAG AATTATGCCA      4800

TGACGGTCCA TTATTACCGG TTGCGGGATT ACGCCCTGCA GCATCCGGAA TGCAGCGCCA      4860

TTATGCGCAT CATTGACTGA AAGGGGCCGG AATAATGCAA CAGATTTCCT TTCTGCCCGG      4920

AGAAATGACG CCCGGCGAGC GCAGTCACAT TCTGCGGGCC CTGAAAACCC TGGACCGCCA      4980

TCTTCATGAA CCCGGTGTGG CCTTCACCTC CACCCGTGCG GCACGGGAAT GGCTGATTCT      5040

GAACATGGCG GGACTGGAGC GTGAAGAGTT CCGGGTGCTG TATCTGAATA ACCAGAATCA      5100

GCTGATTGCC GGTGAAACCC TCTTCACCGG CACCATCAAC CGCACGGAAG TCCATCCCCG      5160

GGAAGTGATT AAACGCGCCC TGTACCACAA TGCCGCTGCC GTGGTGCTGG CGCACAATCA      5220

CCCGTCCGGT GAAGTCACAC CCAGTAAGGC AGACCGGCTT ATCACCGAAC GTCTGGTACA      5280

GGCACTGGGC CTGGTGGATA TCCGGGTGCC GGACCATCTG ATAGTCGGTG GCAGCCAGGT      5340

TTTCTCCTTT GCGAACACG GTCTGCTTTA ACCCGTCACC GTCACAATCA CCTTCATATC      5400

ACTTCAGTTT CTCTTTCTCA GCTGTTTCTT ACTTTCACAT TCAGGAGGAC TATTCTCATG      5460

AAAATCATCA CCCGTGGTGA AGCCATGCGT ATTCACCGTC AGCATCCTGC ATCCGTCTT      5520

TTTCCGTTCT GTACCGGTAA ATACCGCTGG CACGGTAGCA CGGATACATA TACCGGCCGT      5580

GAAGTACAGG ATATTCCCGG TGTGCTGGCT GTGTTTGCTG AACGCCGTAA GGACAGTTTT      5640

GGCCCGTATG TCCGGCTGAT GAGCGTCACC CTGAACTGAA TCAGGACGGG CATTCAGAAG      5700

AGCAGAATTA TCGCCACCAC CGGACCATTC TTAACCAATT TTCTGTGAGG ATTTTATCGT      5760

GTCAGACACT CTCCCCGGGA CAACGCATCC CGACGATAAC AACGACCGCC CCTGGTGGGG      5820

GCTACCCTGC ACCGTGACGC CCTGTTTTGG GGCACGTCTG GTGCAGGAGG GTAACCGGTT      5880

GCATTACCTT GCAGACCGCG CCGGTATCAG AGGCCGGTTC AGCGACGCGG ATGCGTACCA      5940

TCTGGACCAG GCCTTTCCGC TGCTGATGAA CAACTGGAA CTCATGCTCA CCAGCGGTRA      6000

ACTGAATCCC CGCCATCAGC ATACCGTCAC GCTGTATGCA AAAAGGCTGA CCTGCGAANC      6060

GACACCCTCG GCAGTTGTGG CTACGTTTAT ATGGCTGTTT ATCCGACGCC CGAAACGAAA      6120

AAGTAACTCT CCAGAATAAC CTTCTGCCCC GGCCTGGTGC TTTCACCACG CCACTTTTCC      6180

ATTTTTCATC TCTGCATATC AGGAAAATCT TCAGTATGAA CACATTACCC GATACACACA      6240

TACGGGAGGC ATCGCATTGC CAGTCTCCCG TCACCATCTG GCAGACACTG CTCACCCGAC      6300

TGCTGGACCA GCATTACGGC CTCACACTGA ATGACACACC GTTCGCTGAT GAACGTGTGA      6360
```

```
TTGAGCAGCA TATTGAGGCA GGCATTTCAC TGTGTGATGC GGTGAACTTT CTCGTTGAAA    6420

AATACGCACT GGTGCGTACC GACCAGCCGG GATTCAGCGC CTGTACTCGT TCTCAGTTAA    6480

TAAACAGTAT TGATATCCTC CGGGCCCGCC GGGCAACCGG CCTGATGGCC CGCGACAATT    6540

ACAGAACGGT AAATAACATT ACCCTGGGTA AGCATCCGGA GAAACGATGA AACTTTCCCT    6600

GATGCTGGAA GCCGACAGAA TTAATGTGCA GGCACTGAAC ATGGGCGAA TTGTCGTTGA     6660

CGTCGATGGT GTTAATCTCA CTGAACTGAT TAACAAGGTC GCTGAAAACG GTTATTCACT    6720

CCGCGTGGTG GAGGAATCCG ACCAACAGTC AACCTGCACA CTACCACCGT TTGCAACCCT    6780

TGCCGGCATA CGCTGCAGTA CCGCACATAT CACGGAAAAG GATAACGCCT GGCTGTACTC    6840

GCTGTCACAC CAGACCAGTG ACTTCGGTGA ATCAGAATGG ATTCATTTCA CAGGTAGCGG    6900

ATATCTGTTA CGTACCGATG CGTGGTCATA TCCGGTTCTG CGGCTTAAAC GCCTGGGGCT    6960

GTCAAAAACG TTCCGTCGTC TGGTTATCAC ACTTACCCGA CGTTATGGCG TCAGTCTCAT    7020

TCATCTGGAT GCCAGCGCTG AATGCCTGCC GGGTTTACCC ACTTTCAACT GGTAACCAGG    7080

AACAACATGA AATCATTAAC CACGGAAACC GCACTGGATA TTCTGATTGC GTGGCTGCAG    7140

GACAATATCG ACTGCGAATC GGGAATTATC TTTGACAACA ATGAGGATAA AACGGATTCA    7200

GCAGCACTGT TGCCCTGTAT CGAACAGGCC AGAGAGGATA TCCGTACCCT GCGCCAACTG    7260

CAGCTTCAGC ACCAGAACCG GTGAGTCTCA CTCATCATCT CACTCACCAG ACTTCATTCC    7320

ACTSACGCCA GCCTGAACAC GGCTGGCGTT TTCATTTATC TGCAAAAAGG AATATCGATT    7380

ATGTCTGAAA TCACAGTCTC CCGTCCGGAA GTGGTCAACG AGAATACGGA CGTTATCTGC    7440

TCCACCTCAG TCAGGTACAG GTCACTGGAA TATGATAATT TTCCGGAAAT CAGCGAAGCG    7500

AACATTCTGA GCACATTTGA ACAACTGCAC CAGAACAAAG ATGAAGTGTT TGAACGGGGA    7560

GTGATCAACG TCTTCAAAGG GCTGAGCTGG GATTACAAAA CCAACTCACC CTGTAAATTT    7620

GGCAGTAAAA TTATCGTCAA CAATCTGGTG AGATGGGACC AGTGGGGATT TCATCTTATC    7680

AGTGGAATGC AGGCAGATCG CCTGGCTGAC CTGGAAAGAA TGTTGCATCT GCTCAGCGGT    7740

AAACCGATCC CCGACAACCG AGGGAATATC ACCATTAATC TGGATGACCA CATACAGTCC    7800

GTTCAGGGTA AAGGACGCTA TGAAGATGAG ATGTTCATCA TTAAATACTT TAAGAAGGGA    7860

TCTGCACACA TCACTTTCAA AAGGCTGGAG CTGATTGACA GAATTAACGA TATAATAGCC    7920

AGGCACTTTC CTTCTGTGCT CTCAGCCTGA CCCCGAGTTT GATTCCCTTT CGATATCAAA    7980

AGGGACTGCG GGTACAAAAG AGGGTACATC TTTCACCAAA CCAAACAAAA TAAACTAATA    8040

TCAACATGAT AGAAGCATTC TTCGATTCCG AGTCCGGCAC CAAATTCATA TAAACGGACC    8100

TCCACGGAGG TCCGTTTTTC GTTTCAGGAC GCCACGATTT AAGCGTCCTG CCGCCAAATC    8160

AATTCTACCG AACTCAACCA GATTCTCCCC ACATCACCAG CAATTTGCGG GCATATCCCA    8220

ATTCGGGAAA ATTTGTTTCT GAGCTATAGC GCTGACTGAC GTGAAATGTC GTGCGGCCCC    8280

GTGATGCTGT TGAAMGTCAA ATGACGTCAT CAGGAGCGTA ACGCACCCAT AAAGCACAAC    8340

ATCGGGCAGA ACGCCAACTG ATGAGATTTT CTGAATGAGA ACAAAGAGAA ATGTATCAGT    8400

CCGTTTGCTC ATGCAAAGAC TAACAATCCA TTAAAATAGT AAGCGCTCCG GACAATTTTC    8460

CATGGATTAT TTTCTGAACA TTTTTCTTTG GCAAAGATGA TGAATTTTGA TGGTAAGGAA    8520

AATTACTTCT GGTTCTCAGT AAAATCCTTT CGTAATACTA TGTAATCAAG AAGTTTATGG    8580

CTAGTAAAAA TAACGTCTTG CATTCACCAA TAATATGTAA ATAAACCCAT CTATAGATGG    8640

AAAAAATAGG TTATGGAATT ATCATTGCAT CATTCCCTTT TCGAATGAGT TTCTATTATG    8700
```

```
CAACAACCTG TAGTTCGCGT TGGCGAATGG CTTGTTACTC CGTCCATAAA CCAAATTAGC    8760

CGCAATGGGC GTCAACTTAC CCTTGAGCCG AGATTAATCG ATCTTCTGGT TTTCTTTGCT    8820

CAACACAGTG GCGAAGTACT TAGCAGGGAT GAACTTATCG ATAATGTCTG GAAGAGAAGT    8880

ATTGTCACCA ATCACGTTGT GACGCAGAGT ATCTCAGAAC TACGTAAGTC ATTAAAAGAT    8940

AATGATGAAG ATAGTCCTGT CTATATCGCT ACTGTACCAA AGCGCGGCTA TAAATTAATG    9000

GTGCCGGTTA TCTGGTACAG CGAAGAAGAG GGAGAGGAAA TAATGCTATC TTCGCCTCCC    9060

CCTATACCAG AGGCGGTTCC TGCCACAGAT TCTCCCTCCC ACAGTCTTAA CATTCAAAAC    9120

ACCACAACGC CACCTGAACA ATCCCCAGTT AAAAGCAAAC GATTCACTAC CTTTTGGGTA    9180

TGGTTTTTTT TCCTGTTGTC GTTAGGTATC TGTGTAGCAC TGGTAGCGTT TTCAAGTCTT    9240

GAAACACGTC TTCCTATGAG TAAATCGCGC ATTTTGCTCA ATCCACGCGA TATTGACATT    9300

AATATGGTTA ATAAGAGTTG TAACAGCTGG AGTTCTCCGT ATCAGCTCTC TTACGCGATA    9360

GGCGTGGGTG ATTTGGTGGC GACATCACTT AACACCTTCT CCACCTTTAT GGTGCATGAC    9420

AAAATCAACT ACAACATTGA TGAACCGAGC AGTTCCGGTA AAACATTATC TATTGCGTTT    9480

GTTAATCAGC GCCAATACCG TGCTCAACAA TGCTTTATGT CGGTAAAATT GGTAGACAAT    9540

GCAGATGGTT CAACCATGCT GGATAAACGT TATGTCATCA CTAACGGTAA TCAGCTGGCG    9600

ATTCAAAATG ATTTGCTCCA GAGTTTATCA AAAGCGTTAA ACCAACCGTG GCCACAACGA    9660

ATGCAGGAGA TGCTCCAGCA AATTTTGCCG CATCGTGGTG CGTTATTAAC TAATTTTTAT    9720

CAGGCACATG ATTATTTACT GCATGGTGAT GATAAATCAT TGGATCGTGC CAGTGAATTA    9780

TTAGGTGAGA TTGTTCAATC ATCCCCAGAA TTTACCTACG CGAGAGCAGA AAARGCATTR    9840

GTTGRTATCG TGCGCCATTC TCAACATCCT TTAGACGRAA AACAATTAGC CAGCACTGAA    9900

CACAGAAATA GATAACATTG TTACACTGCC GGAATTGAAC AACCTGTCCA TTATATATCA    9960

AATAAAAGCG GTCAGTGCCC TGGTAAAAGG TAAAACAGAT GAGTCTTATC AGGCGATAAA    10020

TACCGGCATT GATCTTGAAA TGTCCTGGCT AAATTATGTG TTGCTTGGCA AGGTTTATGA    10080

AATGAAGGGG ATGAACCGGG AAGCAGCTGA TGCATATCTC ACCGCCTTTA ATTTACGCCC    10140

AGGGGCAAAC ACCCTTTACT GGATTGAAAA TGGTATATTC CAGACTTCTG TTCCTTATGT    10200

TGTACCTTAT CTCGACAAAT TTCKCGCTTC AGAATAAGTA ACTCCCGGGT TGATTCATGC    10260

TCGGGAATAT TTGTTGTTGA GTTTTTGTAT GTTCCCGTTG GTATAATATG GTTCGGCAAT    10320

TTATTTGCCG CATAATTTTT ATTACATAAA TTTAACCAGA GAATGTCACG CAATGCATTG    10380

TAAACATTGA ATGTTTATCT TTTCATGATA TCAACTTGCG ATCCTGATGT GTTAATAAAA    10440

AACCTCAAGT TCTCACTTAC AGAAACTTTT GTGTTATTTC ACCTAATCTT TAGGATTAAT    10500

CCTTTTTTCG TGAGTAATCT TAGCGCCAGT TTGGTCTGGT CAGGAAATAG TTATACATCA    10560

TGACCCGGAC TCCAAATTCA AAAATGAAAT TAGGAGAAGA GCATGAGTTC TGCCAAGAAG    10620

ATCGGGCTAT TTGNCCTGTA CCGGTGTTGT TGCCGGTAAT ATGATGGGGA GCGGTATTGC    10680

ATTATTACCT GCGAACCTAG CAAGTATCGG TGGTATTGCT ATCTGGGGTT GGATTATCTC    10740

TATTATTGGT GCAATGTCGC TGGCATATGT ATATGCCCGA CTGGCAACAA AAAACCCGCA    10800

ACAAGGTGGC CCAATTGCGT ATGCCGGAGA AATTTCCCCT GCATTGGTT TTCAGACAGG    10860

TGTTCTTTAT TACCATGCTA ACTGGATTGG TAACCTGGCA ATTGGTATTA CCGCTGTATC    10920

TTATCTTTCC ACCTTCTTCC CAGTATTAAA TGATCCTGTT CCGGCGGGTA TCGCTGTTAT    10980

TGCTATCGTC TGGGTATTTA CCTTTGTGAA TATGCTCGGC GGTACCTGGG TAAGCCGTTT    11040

AACCACGATT GGTCTGGTGC TGGTTCTTRK TCCTGTGGTG ATGACTGCTA TTGTTGGCTG    11100
```

-continued

```
GCATTGGTTT GATGCAGCAA CTTATGCAGC TAACTGGAAT ACTGCGGATA CCACTGATGG   11160

TCATGCGATC ATTAAAAGTA TTCTGCTCTG CCTGTGGGCC TTCGTGGGTG TTGAATCCGC   11220

AGCAGTAAGT ACTGGTATGG TTAAAAACCC GAAACGTACC GTTCCGCTGG CAACCATGCT   11280

GGGTACTGGT TTAGCAGGTA TTGTTTACAT CGCTGCGACT CAGGTGCTTT CCGGTATGTA   11340

TCCGTCTTCT GTAATGGCGG CTTCCGGTGC TCCGTTTGCA ATCAGTGCTT CAACTATCCT   11400

CGGTAACTGG GCTGCACCAC TGGTTTCTGC ATTCACCGCC TTTGCGTGTC TGACTTCTCT   11460

GGGCTCCTGG ATGATGTTGG TAGGCCAGGC AGGTGTACGT GCCGCTAACG ACGGTAACTT   11520

CCCGAAAGTT TATGGTGAAG TCGACAGCAA CGGTATTCCG AAAAAAGGTC TGCTGCTGGC   11580

TGCAGTGAAA ATGACTGCCC TGATGATCCT CATCACTCTG ATGAACTCTG CCGGTGGTAA   11640

AGCCTCTGAC CTGTTCGGTG AACTGACCGG TATCGCAGTA CTGCTGACTA TGCTGCCGTA   11700

CTTCTACTCT TGCGTTGACC TGATTCGTTT TGAAGGCGTT AACATCCGCA ACTTTGTCAG   11760

CCTGATCTGT TCTGTACTGG GTTGCGTGTT CTGCTTCATC GCGCTGATGG GCGCAAGCTC   11820

CTTCGAGCTG GCAGGTACCT TCATCGTCAG CCTGATTATC CTGATGTTCT ATGCTCGCAA   11880

AATGCACGAG CGCCAGAGCC ACTCAATGGA TAACCACACA GCGTCTAACG CACATTAATT   11940

AAAAGTATTT TCCGAGGCTC CTCCTTTCAT TTTGTCCCAT GTGTTGGGAG GGGCCTTTTT   12000

TACCTGGAGA TATGACTATG AACGTTATTG CAATATTGAA TCACATGGGG GTTTATTTTA   12060

AAGAAGAACC CATCCGTGAA CTTCATCGCG CGCTTGAACG TCTGAACTTC CAGATTGTTT   12120

ACCCGAACGA CCGTGACGAC TTATTAAAAC TGATCGAAAA CAATGCGCGT CTGTGCGGCG   12180

TTATTTTTGA CTGGGATAAA TATAATCTCG AGCTGTGCGA AGAAATTAGC AAAATGAACG   12240

AGAACCTGCC GTTGTACGCG TTCGCTAATA CGTATTCCAC TCTCGATGTA AGCCTGAATG   12300

ACTGCGTTTA CAGATTAGCT TCTTTGAATA TGCGCTGGGT GCTGCTGATG ATATTGCTAA   12360

CAAGATCC                                                          12368
```

(2) INFORMATION FOR SEQ ID NO: 21:

(i) SEQUENCE CHARACTERISTICS:
        (A) LENGTH: 833 base pairs
        (B) TYPE: nucleic acid
        (C) STRANDEDNESS: double
        (D) TOPOLOGY: linear (xi) SEQUENCE DESCRIPTION: SEQ ID NO: 21:

```
GCACGGCACT CTGATGTANC TTTTATCTGT TCCCAGTGGA AGCATGCCCC ACAACTGAGT     60

CATTAAGTGT GGAAGAACAG TTTTGTCCCC GCCTGCAATC TCTCCCTTTC NAAAAACCAG    120

TATGTCGCCA TGCCTCGCCT TAATGGAGAG CGCTGAACCA TACCTTCTTT TTCCCAGTAA    180

TAACAGGTAA TAGCGTGCCT GGTAATCCGT TACCGCCAGC GCCTCCGCAA TTTCTGCGGT    240

TTTCCCTCCA TTATGCCTGT TCAGAAATYC CAGTATTTCA TTCTTCATAT ATTCACTCAT    300

CTCACTGTAA CAAAGTTYCT YCGAATAATA AAAATCATGC TTTCTGTTAT CAACGGAAAG    360

GTATTTTTAT TCTCTGTGTT TGCTTTATTT GTGAAATTTA GTGAATTTGC TTTTTGTTGG    420

CTTTATTTGN ATGTGTGTCA CATTTGTGT GTTATTTTTC TGTGAAAAGA AAGTCCGTAA     480

AAATGCATTT AGACGATCTT TTATGCTGTA AATTCAATTC ACCATGATGT TTTTATCTGA    540

GTGCATTCTT TTTGTTGGTG TTTTATTCTA GTTTGATTTT GTTTTGTGGG TTAAAAGATC    600

GTTTAAATCA ATATTTACAA CATAAAAAAC TAAATTTAAC TTATTGCGTG AAGAGTATTT    660

CCGGGCCGGA AGCATATATC CAGGGGCCCG ACAGAAGGGG GAAACATGGC GCATCATGAA    720
```

| | | |
|---|---|---|
| GTCATCAGTC GGTCAGGAAA TGCGTTTTTG CTGAATATAC GCGAGAGCGT AYTGTTGCCC | 780 |
| GGCTMTATGT CTGAAATGCA TTTTTTTTTA CTGATAGGTA TTTCTTCTCA TTC | 833 |

(2) INFORMATION FOR SEQ ID NO: 22:

(i) SEQUENCE CHARACTERISTICS:
        (A) LENGTH: 2916 base pairs
        (B) TYPE: nucleic acid
        (C) STRANDEDNESS: double
        (D) TOPOLOGY: linear (xi) SEQUENCE DESCRIPTION: SEQ ID NO: 22:

| | |
|---|---|
| TGCACCATCA CTGATACCAC CGGGACCCCG GATTTTATCC GGTCCCCGCG GACTGACAGG | 60 |
| GTTTGTGACA CCTGAGTCAT ATCCGATGTA AACTTCATTT TCACGGGTTG TACAGGAAAA | 120 |
| CTCCCCTGTG CCATTGAGTT CTGATGTGTG CCCTTCGCCA CAACTCCCAC CGTCACGGCA | 180 |
| CCAGTTGCAT CTGACGCCGA CCAACTGCTG AGAGCCATGC CGTTTCCGGC TTTGTCGACA | 240 |
| ACGCATGCTG CAGTTCCCAG CGATGCGAAC TGGTCTGGCA TGCATTCACG AACCAACAGC | 300 |
| AGTGGTGCTA CGTCCGGATG CAATTCGCAT GAGCTCCAAC CGCGGTTGTA AGTTCAGCAG | 360 |
| CCCGGGCCTC TGCCCCCGGC ACAGTCGCAT AAGTATTCGA TACCGTGCGA CACCATTACC | 420 |
| TTCAGGATAC GCCACGGACC CGTCACCCTA CGAAAACGCC GGAGCACCGG CAATCAGCAA | 480 |
| AGGCAGCAGT GATAAAAGAC TGATATATTT CCTGTCATTA TTTTTCATAT TAATTTAACT | 540 |
| CCTGATTAAC CGGTTTTTAT TGATATGAGA AGTAATAGT TGCAATAGCC TTCACACTTC | 600 |
| CAGGTGTAGT TGCATCAGCA ATTTTTATAT AATTGGCTCT TAAATTGATA TGTGGATTTA | 660 |
| CCTCTCCCCT GTAATCGGAG AAGTGCCATT GACTGCCATT TCCTTTCACA GGGGAGTCTT | 720 |
| CACCATAGCT GATGGCAGTT ACATCACTGT CTTTATATAG CCTGATGCCA AATCCTTTTG | 780 |
| CAGTGGATTC ACTGCTTAAG GTCAATATAT CTGTTCTGTT CACTGGCTGT GATGCATCTG | 840 |
| TCAATGTAGC ATAAACATCA ATTCCATCCG GGCATTGTAG GTGTATGTCA ATTTTACCTC | 900 |
| CCTGTATTTC TTTATACAAA GATGTGAACT GTGATTGATA TACGGTATTT AATGGCACCA | 960 |
| CATAGTTTTT TTGCCCCATG GTACATGTCT GACTCTGTAC CTGAATGCGC CCACCATTTA | 1020 |
| ACATAACAGG TGCTGTCAGT CCTTTATTAT TTAAACTTGT ACGTTTTGCT TCCAACAAAA | 1080 |
| TAGTACCAAG CTGCCTGGTG GGTATTGTTA TATATCCATT GGGTAATCTT CCCGTTGCGA | 1140 |
| CAAAAGCAAC AAACAAACGA GCTCCGAAGC TTGCTGTCGC ACCGTTATAA GTATTGGGGT | 1200 |
| TTGTATTGGC ACCTACAGGG TCAATATATA TACCTGAGCT ATTTATGGGG ACCAGAGGCG | 1260 |
| TTGCGGGCCA ATAGCCCGCC ATGCCAATAA TAATACCCAG TCCGGATACA CCAATATCAT | 1320 |
| AGATATCAAA ATCAGATGAA TCACGGCTGT TTCCTTGATG GAAAGTATAC GTAATACTTC | 1380 |
| CAATTTTAGG CAGTGCGGGT GTAAACTTTC CACGCATCAG AGCGATGGCA CCGCCATTAA | 1440 |
| AAACATACTG GTTACTTGTT CCCGCCAGCT CTCCTATCAC CCGGGGATAG GTATGGGCAT | 1500 |
| CAGCAGGACC AATCACAACA CCTGGCAATG TGGATGTATT AACCGCTATC TGCGAAGGCA | 1560 |
| CATAATCATC CGGACCCGCT ACCGCCAGCT TAGGGAGTAA AATTAAAAAC AATGGTATGA | 1620 |
| AAAAGATTCT TTTCATGTTT TTTCCTGATT AGGGTGCTGT ATACACAGAA CAGGAACGAG | 1680 |
| CTGAGATTGC ATATCATCTT TATTGTGTGC AACATGATAT ACAAATGAAC ATCTGTCTTT | 1740 |
| ATTATCTGGT CCCCATACAA CGCTGAGATG ACCTTTTTCA GGGAGTCCCC TGGTAAATAC | 1800 |
| CTTCCCGGCC TGAGCGACAT ATCCGGCCAA CTGTCCATGT TCATCCAGAA CTTCAGAAGC | 1860 |
| CATTGGAGGG GGATTGCCAG TAGACATACG AATATCAAAT AACAGACTTC TTCCTGTTTT | 1920 |

```
AGTGTCAAAT TTYACTAACG TGGCGCTATT AGCACGAGGA ATGATTTCCT GCTCCGTCGC    1980

CGATAATTCA ACATTCAAAT CTAAATTGGA GGGATCGATG CTAATTTGAT TTTTCTCATA    2040

GGGTGTAACA TAAGGAACAA TACCATTTCC CCAAAAATCC AGACGACTAC CAGAGGCATT    2100

ATTGATGGCA GCCCCCTGAG CTCCTTCAGC ATGGATAATG GCAAAAGTAT CACTCAGGTC    2160

ATTACTCAAT GTCACTCCAT AGGGGTGTGC GACCACCGCT CCCGACGCAC CAAATGACCT    2220

TTGATTATTA TTCTGAGTAT CATGCCCGAC TGTTGTGGTT ATATTTACAT AAGGTGAACG    2280

ATAACCCCCA TTCATTGCAT AACCGGAAGG CCCGTTTTCC TGGCTGTTTC CTGAAAGACC    2340

ATAAGAGAAC TGATTATCCT CCCCGCCAGT ACCACTAATT GATGTCTGAA TACTATTTTT    2400

CTCTTCTTTG CTATAATTTA AAACAGTGGA AAACACCGGG CTTTGAACAC TTNCCTCCCA    2460

GAGGGAGAGT AAAATTAATA TAAAATCTGT CATCACGGCG TTGTTGCTCA TTATCTCTTG    2520

ACTGAGACAA TCCAATTTGA TAGCCGAGTT GTTTCCAGAA GTTGCTGTAC CCCATCTGGT    2580

ATTCATTACG ACTTCCTTTA TGTCCCCAGT AATTATAGGT TGTTCCTGTT AAATACATCC    2640

CACCCCATTT TTCACCTAAT TCCTGGTTGA TTGAAATCTG GAATTGATTC CTGGGACGAT    2700

AAAACGCTGT ACTTTTTACA GAAACATCAT CAATAAACGC GTTGTGATTA GCTGATAGCG    2760

CATCCTTCAG ATGATAAAAA TCTTTTGATG AATAACGATA AGCCGCCAGA GTTATATTTG    2820

TGTTTTGAGG GCTGGGAATA TTGGATGGCT AATAACTTGG AGTNGCAGGA CTAATAAACC    2880

TTTTACGGCG GTTACACCGG GAATACCNGG AAATGC                              2916

(2) INFORMATION FOR SEQ ID NO: 23:

(i) SEQUENCE CHARACTERISTICS:
        (A) LENGTH: 2677 base pairs
        (B) TYPE: nucleic acid
        (C) STRANDEDNESS: double
        (D) TOPOLOGY: linear (xi) SEQUENCE DESCRIPTION: SEQ ID NO: 23:

ACCGCATCGC CAATCTCAGC GGCAGTGGTT TACATGTCTT CCGTGATGGA AGGTCATGGC      60

ATCAGCTACC TCCATCTGCT CTCCGTGGTC ATCCCGTCCA CCCTGCTGGC GGTTCTGGTG     120

ATGTCCTTCC TGGTCACTAT GCTGTTCAAC TCCAAACTCT CTGACGATCC GATTTATCGC     180

AAGCGTCTGG AAGAGGGCCT GGTTGAACTG CGCGGTGAAA AGCAGATTGA AATCAAATCC     240

GGTGCAAAAA CGTCCGTCTG GCTGTTCCTG CTGGGCGTAG TTGGCGTGGT TATCTATGCA     300

ATCATCAACA GCCCAAGCAT GGGTCTGGTT GAAAAACCAC TGATGAACAC CACCAACGCA     360

ATCCTGRTCA TCATGCTCAG CGTTGCAACT CTGACCACCG TTATCTGTRA ARTCGATACC     420

GACAACATTC TCAAYTCCAG CACCTTCAAA GCAGGTATGA GCGCCTGTAT TTGTATCCTG     480

GGTGTTGCGT GGCTGGGCGA TACTTTCGTT TCCAACAACA TCGACTGGAT CAAAGATACC     540

GCTGGTGAAG TGATTCAGGG TCATCCGTGG CTGCTGGCCG TCATCTTCTT CTTTGCTTCT     600

GCTCTGCTGT ACTCTCAGGC TGCAACCGCA AAAGCAYTGA TGCCGATGGC TCTGGCACTG     660

AACGTTTCTC CGCTGACCGC TGTTGCTTCT TTTGCTGCGG TGTCTGGTCT GTTCATTCTG     720

CCGACCTACC CGACACTGGT TGCTGCGGTA CAGATGGATG ACACGGGTAC TACCCGTATC     780

GGTAAATTCG TCTTCAACCA TCCGTTCTTC ATCCGGGTA CTCTGGGTGT TGCCCTGGCC      840

GTTTGCTTCG GCTTCGTGCT GGGTAGCTTC ATGCTGTAAT GACCCATYGC GGGGCGTTCA     900

CGCCCCGCTT TCTTTCCCGC CGACTAACAT CCTTTCCCCG TCCGTTGTAT AGTGACCTCT     960

CTCTTGCGGT TCCATCTGTT CTTGCGAGGT GTTTATGCTT GATGAAAAAA GTTCGAATAC    1020
```

```
CACGTCTGTC GTGGTGCTAT GTACGGCACC GGATGAAGCG ACAGCCCAGG ATTTAGCCGC      1080

CAAAGTGCTG GCGGAAAAAC TGGCGGCCTG CGCGACCTTG ATCCCCGGCG CTACCTCTCT      1140

CTATTACTGG GAAGGTAAGC TGGAGCAAGA ATACGAATGC AGATGATTTT AAAAACTACC      1200

GTATCTCACC AGCAGGCACT GMTGAATGCC TGAAGTCTCA TCATCCATAT CAAACCCCGG      1260

AACTTCTGGT TTTACCTGTT ACACACGGAG ACACAGATTA CCTCTCATGG CTCAACGCAT      1320

CTTTACGCTG ATCCTGCTAC TTTGCAGCAC TTCCGTTTTT GCCGGATTAT TCGACGCGCC      1380

GGGACGTTCA CAATTTGTCC CCGCGGATCA AGCCTTTGCT TTTGATTTTC AGCAAAACCA      1440

ACATGACCTG AATCTGACCT GGCAGATCAA AGACGGTTAC TACCTCTACC GTAAACAGAT      1500

CCGCATTACG CCGGAACACG CGAAAATTGC CGACGTGCAG CTGCCGCAAG GCGTCTGGCA      1560

TGAAGATGAG TTTTACGGCA AAAGCGAGAT TTACCGCGAT CGGCTGACGC TTCCCGTAAC      1620

CATCAACCAG GCGAGTGCGG GAGCAACGTT AACTGTCACC TACCAGGGCT GTGCTGATGC      1680

CGGTTTCTGT TATCCGCCAG AAACCAAAAC CGTTCCGTTA AGCGAAGTGG TCGCCAACAA      1740

CGAAGCGTCA CAGCCTGTGT CTGTTCCGCA GCAAGAGCAG CCCACCGCGC AATTGCCCTT      1800

TTCCGCGCTC TGGGCGTTGT TGATCGGTAT TGGTATCGCC TTTACGCCAT GCGTGCTGCC      1860

AATGTACCCA CTGATTTCTG GCATCGTGCT GGGCGGTAAA CAGCGGCTTT CCACTGCCAG      1920

AGCATTGTTG CTGACCTTTA TTTATGTGCA GGGGATGGCG CTGACTTACA CGGCGCTGGG      1980

TCTGGTGGTT GCCGCCGCAG GKTTACAGTT CCAGGCGGCG CTACAGMACC CATACGTGCT      2040

CATTGGCCTC GCCATCGTCT TTACYTTGCT GGCGATGTCA ATGTTTGGCT TKTTTACTCT      2100

GCAACTCCCC TCTTCGCTGC AAACACGTCT CACGCTGATG AGCAATCGCC AACAGGGCGG      2160

CTCACCTGGC GGTGTGTTTA TTATGGGGGC GATTGCCGGA CTGATCTGTT CACCYTGCAC      2220

CACCGCACCG CTTAGCGCGA TTCTGCTGTA TATCGCCCAA AGCGGGAACA TGTGGCTGGG      2280

CAGCGGCACG CTTTATCTTT ATGCGCTGGG CATGGGCCTG CCGCTGATGC TAATTACCGT      2340

CTTTGGTAAC CGCTTGCTGC CGAAAAGCGG CCCGTGGATG GAACAAGTCA AAACCGCGTT      2400

TGGTTTTGTG ATCCTCGCAC TGCCGGTCTT CCTGCTGGAG CGAGTGATTG GTGATATATG      2460

GGGATTACGC TTGTGGTCGG CGCTTGGTGT CGCATTCTTT GGCTGGGCCT TTATCACCAG      2520

CNTACAGGCC AAACGCGGCT GGATGCGCGT GGTGCAAATA ATCCTGCTGG CAGCGGCATT      2580

GGTTAGCGTG CGCCCACTTC AGGATTGGGC ATTTGGTGCA ACACATACCG CGCAAACTCA      2640

GACGCATCTC AACTTTACAC AAATCAAAAC AGTAGAT                              2677
```

(2) INFORMATION FOR SEQ ID NO: 24:

(i) SEQUENCE CHARACTERISTICS:
        (A) LENGTH: 537 base pairs
        (B) TYPE: nucleic acid
        (C) STRANDEDNESS: double
        (D) TOPOLOGY: linear (xi) SEQUENCE DESCRIPTION: SEQ ID NO: 24:

```
ATCCTGATGA CGCCGTAAAT GTGCATTTGC CAGGATTGCC GCATAGAGGG CACGAAGAAA       60

AGGTCGGTTG TCAGGATGTA TCCAGATGAT TCTGCCACTG AAACCTTCAG GGATAAGACG      120

ATTGCCAACT GCCAGTCCTT TAAGGGCAGC ATTCAGCGCC TTACGCGGGG CATTCTGCTC      180

CAGAAATACG TATGCCAAGT GAGCGTGTAC ATCAATAAAG TCATTCTCCT GTCGGGCAAG      240

GCGCCTGAGT TTGTTGATGT AACTTGTTTC GCTGATTTCA TCCGCATCGT ATGCATCAAT      300

CAGTTCTTCA AACTCATCCA GCAACGAGCC AAACCAGGTT TCCGGAAATA TGAAACAGCC      360
```

```
CTGGTTATCG TTCACTTCAA AGCGTAATTT GCCAGTCATA TTCTGAACCT GTAAAAAAGG      420

ATAGACCATA ATCTGCAGGC TATAAAAATT GTGGATGCCT GGCATCGGGT GTCCTTTTAT      480

TGTCCGGGAT TAACGTTGCC CATGATAATA CAGTGAATCC NGTTCTGTGG TAAGACG         537
```

(2) INFORMATION FOR SEQ ID NO: 25:

(i) SEQUENCE CHARACTERISTICS:
        (A) LENGTH: 1128 base pairs
        (B) TYPE: nucleic acid
        (C) STRANDEDNESS: double
        (D) TOPOLOGY: linear (xi) SEQUENCE DESCRIPTION: SEQ ID NO: 25:

```
CGCTCGAGCA CCAGATTCAC TGACATGCGC AAACTCATGT GTAAATCCTG TCTGGGCATC       60

TATCTCAAGT AACAGTTCCG TTAAATCTAC CGGTGGGAGT AGCTGTTTGA TCCGATTATT      120

TAGACGAAGC AATGATGGTG GCTCTTCCTG TTTCTCCAGA CAACTGATAG TCAGGGATGG      180

ATATTTACCT TCATTACAGA TATGAACTTC CGCATTCTTT TCAAATCGTG ATGCCAGGCT      240

TTCCAGGTCT CATCCAGCTG AATAGCCAGT TGTTGCACAC CTTTACGTCC ATCGACAGGA      300

TGTCCCAGTG CCCGACAGAC AGGAATACGC TGAGTCTGCC ACTCTTCACC TTGCAACAAC      360

TTCTCGCGAG GATCTCCCCA GCGATCACTG TTTTCAAGCC CAGATGTCCC CGGCGGCGCA      420

RTGCATCCTG AAGGCGTTCC AGCAAACATA GTGAATAACC TGCACGCTGT ATCCCGTCCC      480

TCCGCATCGT ATACGAGGCG TTTCCAGGGA CCGGTGATAA TATGTTCAGC GCATCATCAA      540

GGATGCGCTT TTTCGAACCA TTCAGTTCTG CCAGATAATG AATCGCAGCC AGTACATGTC      600

ACCTGCCGGT GCCGCACGGA AATGCAGGTC CCGCAACACC GCCGGAAGAA AACGTTTAAC      660

CCGACCGTAC TGCTCAACCA TTTCGTCATG GAAATTATTG TTCTGTGGAC GAGCAAGTTC      720

ATTAACCTTG CTTACAGATT CTGCCAGTCT GTTTTTGGGT ACGCACTTGA AGATAACCTG      780

CCTGAGATCT GGGACATCTG TATTATCATC CAGCAACAAT GCACATGCCC GCGCCAGTAA      840

CAATGCGGCC TGATCAAGAT CTTTCAGTGT CCTGAGTCTT TTTTTTTGCC CGGTTTTCTT      900

TGCTTCGCGG ATAATGTCCA GAATTAGCAT ATCAAGCACA TCAACGGCAT CGTCTAATGC      960

CGTTATTTCC TGTGCTTTAA CGAATGCAGT AAGTACAGCA AGCTTTCTCT GCTGTGGCAT     1020

TCGAGCGATA TATTTTACCG ACGCCATGCC AGCATGAACG AGCCAGATTA CGCNTTGGNA     1080

ATGGTCAGGC AGACCGGGAA AAGTTCCAGT CGGGNAAAAC TCCAAGAA                  1128
```

(2) INFORMATION FOR SEQ ID NO: 26:

(i) SEQUENCE CHARACTERISTICS:
        (A) LENGTH: 2311 base pairs
        (B) TYPE: nucleic acid
        (C) STRANDEDNESS: double
        (D) TOPOLOGY: linear (xi) SEQUENCE DESCRIPTION: SEQ ID NO: 26:

```
GGNTGATAAA AATCYTTTGA TGAATAACGA TAAGCCGCCC AGAGTTATAT TTGTGTTTGA       60

GGCTGGAATA TTGATGCTAT AACTTGAGTG CAGACTATAA CCTTTACGCG TTACACCGGA     120

ATACCTGAAT GCTGTTCTGG ACAATGTAAT GTCAGATGCT ATAGCACCCA GATGGGTATT      180

AAAGGCCAGG CCAGCTAACC CCGCTGTATA TCCTGAAGCT GTGGTAAGAC CACTGTTTAA      240

AGTAATATCA TTCGTCAGGC CGTATTGATA GGTGCCTTGT GCTATTAAAT CATTATATGT      300

TTTATTCGCA TAACGATACT TTCCCACTGA CATTTGCCAG CGACTAAATC CGGGACGAAT      360
```

```
GAGTTGAGCA ACGGCCGCAA AAGGAACCGT GAACATTCGT GTCTGGCCAT TAGACTCTGT    420

TATCTTAACG AGAAGGTCAC CAGCATATCC ACTGGGATAT AAATCATTGA TGACAAATGG    480

TCCGGCTGGC ACCGTCGTTT CATAGAGGAT ATGAGCATTT TGATAAATGG TTACTTTAGC    540

ATTACTGTTA GCTATTCCCC GGACAGCAGG RGCATAGCCA CGTAAAGAAC CGGGTAACAT    600

TCGTTCATCC GATGCTAACC TGACTCCCCG CAAACTGAGG CTATCCATTA GCTCACCATT    660

CGTATAAAAA TCCCCTAATG TGAATTGTGC TCTCAATGGG GCAAGGTCAT GCATTATACT    720

TGTTTCTATA TTCTGATATC CGGCAGGATA GCTATTATTC CAGCTCTCAC TGCCACGGTG    780

GCGCAAAGCC ATCCCCACAA ATTGAATCCA GCTTTTAATC CCAGATAAGT CTGTTCGTTA    840

CTCGTCCCGG AAGAGCTATA CTGGTAATAG TTAGCATCAT AGTTTATAAA TGCTGCAGGA    900

ACACCACTTT GCCACTGAGA AGGGGAAATA TATCCTCTTG GACGTGTATT CAGCAGTGCT    960

GCGGGATTTC GATATTCAAC CTTAAAGTCG ATAAGTCAAA ATTAATTCTG GCTGAAGAAA   1020

GCCCTGTTGA CGCCGGAAAG CAGGAGGTGT TTCCCGACAT AGTATCTTTG ACTAAATCAA   1080

TCAATGAAAG CAGCTCAGGC GTCAGGCATA ACGTCGGAGC ACCGGTATTG GCAGTACGTA   1140

AATACTGCAA ATCAGCCTTC CCCTTCCATA CATTATTAAC ATAAATATCA GAATAATACC   1200

TGCCCTCAGG CACAGGGTTA CCATGACTAA AGCGGCGGAT ATCAATAGCA TTTATCCCTT   1260

TATCCAAATG CAAAAACTCA GAATCAAACT CAGCCTCTTC AGCAGCAAAT GAATGGTTTG   1320

TTACTGTTAA CCCTAATGCA GCAAAAAGCA GAAGAGAACA ACGACAGTAA ATCAGGCATG   1380

ACAGATTATT AGCGTTCATT ATTACCTTAC TCCAGAACAG ATTCTCCTTG CTGATATCCT   1440

CCGTAATCAT TAACAATAAC CCAGGAAACT TTGCTGGTGG CGCAGTTCTG CCTTTAAGTG   1500

CAAATACTGT TGAAGAGAAA GGGGGAATCA TTCCACCATG TTCAACAGGC GTTAAGTGCT   1560

TATTCTGGTC AACTGCAATT TTGTTGTAGG TTATGTAATA AGGTGTTGGA TTAACTGCTT   1620

TAATTCGGCC TTCCTCCTGG TGCCAGGTAA CTTTCAGATA AGCATCATTT GGTGTTAACT   1680

TCAGGTGAGC AGGACGAAAG AAAAATTTTA TGCGACTACG AACAGCTAGT TGCAAATAAT   1740

TATTATTCCG CTGCTCTGAG TTATCGGAGT CTTTTTTTGC CCTGGGCTTT GCTGGAATAT   1800

CCAGAACATT TAGATAGAAA AGAGATTCTC GGTCTTTCGG TAGTGACTCG CCTGTATATA   1860

CAATTCTGAC TGTTTGTCCT GATTTAGAGT CCATACGAAA TATTGGCGGA GTAATGATAA   1920

AAGGACGTGG ACTGACTCAG GGGGAGCTGC TGCATCTCCA TCGYCAACCA GGACTGGACT   1980

AATGCCGAGA TTTCATTGTC ATTATTTNAA CGTATGCTAA TACTCTTTTG AGTCGCCGGA   2040

TAAACAACAC GGGTTCCCAT GATAACTACA CTACCCTGAA CAACTGCAGA TACAGATAGA   2100

GTAAAAAAAA ACAGCACAAA CCTTAGCATG GTATCTCCAG AAGAAAGCAG GGCAGTATTT   2160

CCTGCCCCAA AATACAAAAC CGTTTGTTAT TCGTAGGCGA TGGTATAATT GACTGTTGTT   2220

TTTACATTGC CTGGAGTTGA TGTCCCGGTC GCATAATATT GAGCCATATA ACGTAATGTG   2280

GCATTACCAT CCCCACCAAT AGTTTCAGAA T                                 2311
```

(2) INFORMATION FOR SEQ ID NO: 27:

(i) SEQUENCE CHARACTERISTICS:
        (A) LENGTH: 1118 base pairs
        (B) TYPE: nucleic acid
        (C) STRANDEDNESS: double
        (D) TOPOLOGY: linear (xi) SEQUENCE DESCRIPTION: SEQ ID NO: 27:

```
TATTACCTGT GATTTTTCCG GGCGTAAATG GAGTCCCTAA AGTTATCGCA GTCCCAATAT     60
```

```
TTCCTGCATT ACTGTTATAA AGATAAACGA GTAACCCATC AGAAGATGTG TTTGATGTAT    120

TCTGAACTAA AATAGCATTG TNATAAGTGT TTGTTGCCGT TATCGTAACC TTCATTGTTC    180

CCAGATTATA GGGACACCGC ATATTCACAG TAAACTCTTT TTCGTGANTT CCATTTTGAC    240

TCAGGGTCTG AATCTCTACA NCCTGCCAGT CAACAGTTGT GTTGCTTACA GTACAGGCAG    300

GAATAATCAG TTTTCCTCTG AAGGTCAGAT TATCAACTGC ATGTACATGC TGAGACATTA    360

ACACTGCCCC CAGCATTACC GGAAGACACA AACCTCTTAT CTTTTTCATC TGAAATATCC    420

TGTACAAAAA TTTTGCTAAC GATATGTCAA TTCAAACGTG GCTGTTGCTT CATAATCACC    480

GGGTACCACA CTCTTCGTCC GCAGGGCTTC CGGCGTTGCC ACAACATACG CGCCGAAAGG    540

AAGCTCAAGA CTGTTTCCGG TAACCTTTTC CCCCTGGCCT TTGTTATGGG AGGTGCCGGG    600

TTTCAGCAGA CTGCTGCCAT CGGTGTCCAG CAGTGCAATG CCTAACCGGC CAGCATTCAC    660

TCCGGTTACC TTCAGATGGC CCGGGAGRCG CYNTCTTCCG TCCCCTTAAA GGTCAGGGTC    720

ACAATTTTGC CAACTGCTGT TGCATGGCAG TTTTCCAGCC TGATGACAAA CGACTCTGTC    780

GGCGAACGTC CGGGCGGATA CCAGAAATCC CTGGACGCCC GGGTTTTGAA GACGACATGT    840

TTATTCAGAC TGTCACCGGA CACATGGCAG GGTCTGTCAA GCAGATTACC CCTGAATGCC    900

ACATCTGAGG CTATTGCCTG TCCGGCAGAC AGTGCGGCAA ACAGTAAAAG AGCGCCTGTG    960

CTTTTTATCA TCACATTCCC TTACTCATAT TTTATGCTCA GACGCAGCAT GGCCGGATTG   1020

CTCCTGGCAT CAGAATACTC AACCTCCTGT GGCGGCCTTT TCCTCCAGGC GGGCAAGCAT   1080

CTCCTCCTGG CGGCGGGTAA GGCGGGGACA GTAAAAAA                          1118

(2) INFORMATION FOR SEQ ID NO: 28:

(i) SEQUENCE CHARACTERISTICS:
        (A) LENGTH: 562 base pairs
        (B) TYPE: nucleic acid
        (C) STRANDEDNESS: double
        (D) TOPOLOGY: linear (xi) SEQUENCE DESCRIPTION: SEQ ID NO: 28:

TTCGTGGGTG AAATCGTAGG CCGCGCTTTT TTGCTGATCG GCCAGTTGAT GAATAGGGTG     60

GCCAKGATCG GGATAAAACG TACAGGCAGC GATAAACAGA CAGCCCGGAT AGCGGTTGTT    120

TTTAACGCAC TCCGATAACG CCTGATAACG TGCCAGCAAC TTTTGTTCGG CGGTTTGCGT    180

TTCGTCCAGC ATCAGCTGAC GACGCCAGAC ATCTATCTGT TGGCTAAGAT AACGCAGCGC    240

ATCGTAGAGG ATTGCCTCTT TGTCTGGCCA GAAGCGGCGT ACTCGTCCAG TGGATAATCC    300

ACACGTTCAG CAACCATCTC CAGCGTGGTG TTGGCAATCC CTTGTAATTC TAATAATTTC    360

AGGGCTTCTC CCAGTACATC TTCACGTTGC ACGCTATTTT CCTCCGKCTT TCCCACTGCA    420

ATGTTCGKTC ACGGTTGGCG ATCGCGCAAA TGTGCGCTGG AAGGTTTCAG CATCCATAAA    480

GCCCGTGACG CGTGCTTGTG GATGCTCCTG GCCTTGGTCC GGTCAAAAAA GAGAATTTGT    540

CCGGTAGGGC CAAGGATATT AA                                            562

(2) INFORMATION FOR SEQ ID NO: 29:

(i) SEQUENCE CHARACTERISTICS:
        (A) LENGTH: 745 base pairs
        (B) TYPE: nucleic acid
        (C) STRANDEDNESS: double
        (D) TOPOLOGY: linear (xi) SEQUENCE DESCRIPTION: SEQ ID NO: 29:

CCATCGCTTT ACCCCAGAAA AGTTAAGCCA TATAATGTGA GGGATATAAG TCGTCGTATC     60
```

```
CGGTAAGTAC AGATAACCAC AACATAAGCT CATTCAGTAA ATTTTATCTC TGAACAAACG      120

ACTATGGCAT GCTCATTTAT ACTATTCATA AGAAAGTGTG ATTATCTGTA AGCATTAACC      180

ATCAAATCAT ATAACCATAC TAAACTGGCG GATCATCAGC ACCATTAGCA GGTAACTTAT      240

TGAAATTTTA TTATGTGTTT TTTGTTGATA ATTAATATGC AATATGAATT TGCTATTTTA      300

GAATCATGAA CACCATTTAA AATTACCATC ATTAACATCA TATAAAAATA TATTTTTACT      360

AAAACATGAA TTGTATATAT TTATTAGCTC AGGAAAATTA TCAGGGTTCA CCTTCAAATT      420

AACCTGAATG TTATGCTTAA TTTCACCCAG TAGTTCTTCA TGTGTAGATT TTATTATCCC      480

ATTATTATAA TCGATAAATG CACACATGTT TTTTATGAAT TCAAAACCTT TTCCTGTATA      540

CAGTTTAATG AATGCCACCA GAGCAAACAT TTCAAGATGT AGCCATAATG CTACGTTAGT      600

TTTTTGCAAA GTATAAAAAA TTGAATTCGC CACTTTTTTA CTTATTGCTC TTTTATACTG      660

TGATCGAGCA AGATTCAGTA GCGGAAGTCC TCGTTCAATA AATGAATGTG AAAAGACTGG      720

ATAAATTGAT GTCGGAAACC TTTCA                                            745

(2) INFORMATION FOR SEQ ID NO: 30:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 30:

GCGTTNATGC ATTTCGASAT TTTCCACTTC GTTCTGACGT TGCACTGCTT TGGCGTCATC      60

ATTACGTAAC GTATCGAGGA AATCGAGGTA GCCCTGATCA ACATCTTTGG TGACGTAGAC      120

GCCGTTGAAC ACCGAGCATT CAAACTGCTG GATATCCGGA TTTTCAGCGC GAACGGCGTC      180

GATCAGATCG TTCAGATCCT GGAAAATCAA CCCGTCAGCA CCGATGATCT GGCGAATTTC      240

ATCAACTTCG CGACCGTGAG CGATCAGTTC CGTGGCGCTC GGCATATCAA TACCATAAAA      300

CGTTCGGGAA AGCGAATTTC CGGTGCCGCA GAAGCGAGGT ACACTTTCTT CGCTCCGGCT      360

TCGCGTGCCA TCTCGATAAT CTGTCAGAAG TGGTGCCACG                            400

(2) INFORMATION FOR SEQ ID NO: 31:

(i) SEQUENCE CHARACTERISTICS:
        (A) LENGTH: 824 base pairs
        (B) TYPE: nucleic acid
        (C) STRANDEDNESS: double
        (D) TOPOLOGY: linear (xi) SEQUENCE DESCRIPTION: SEQ ID NO: 31:

TGTCGACGAT GAGGCAGCCA GAGCATTAGA GCCGAAAAGA AGGGATGATG CCATGACTGC      60

TGTTGCTATA AAATGTTTCA TATATTCTCC ATCAGTTCTT CTGGGGATCT GTGGGCAGCA      120

TATAGCGCTC ATACTAGGGG TTTGAGGGCC AATGGAACGA AAACGTACGT TAAGGAGATA      180

ATTCGTTGTT TATATTTAAA TTTAGAGCTC TCAGTTCCCC TTTTAAAATA TCCTCTGGCA      240

ACGTGAATGT ATAATGGCCC AACATATTGA TATGCCCGTG CATCAGGGGA GATAGCCGAG      300

CGATATCTTC ATCTATAATT TCTTCGCCAT TACGGCGCAT CCAGCTCAAC GCTTCCTCCA      360

TATAGAGCGT GTTCCACAGA ACCACTGCAT TAGTAACCAG GCCCAGCGCC CCCAGTTGAT      420

CTTCCTGCCC TTCACGATAA CGCTTTCTGA TCTCTCCGCG TTGTCCGTAA CAAATCGCAC      480

GAGCCACAGC GTGCGKTCCT TCTCCTCGAT TAAGCTGCGT CAGGATCCGC CGACGATAAT      540
```

-continued

```
CTTCATCATC AATATAATTG AGGAGATATA GCGTTTTGTT TACACGCCCT ACTTCCATAA      600

TTGCCTGTGC CAGTCCTGAT GGGCGCGAGC TTTTCAGTAA AGAGCGAATG AGTTCTGACG      660

CATGAATTGT ACCCAACTTC AGGAACCAGC GGTTCGCATC ATCTCATCCC ACTGACTCTC      720

CGCTTTTGAC AGATCTGCAT ATCCTCGGGC CAACTTATCC AGTACTCCGT AGTTTGCCGA      780

TTTATTCACC CGCCAGAACA CCGCCTCACC TGCATCGGCA AGCC                       824
```

(2) INFORMATION FOR SEQ ID NO: 32:

(i) SEQUENCE CHARACTERISTICS:
        (A) LENGTH: 911 base pairs
        (B) TYPE: nucleic acid
        (C) STRANDEDNESS: double
        (D) TOPOLOGY: linear (xi) SEQUENCE DESCRIPTION: SEQ ID NO: 32:

```
ACAAATCAGA CCAGTTAACC AGTCAGTCGG TTTTATGATT TCACTCACTA TACTTTGTTT       60

CATAAGGATT TCAGGATCTG CCAGACTGCG CAGAAATGAT GCTTACGAAT ACACAGTAAA      120

GGCAATGTCA TTTCCGATAC AGAGCCTGAC ATTGCCATAA TGAGCTATTT ATCTGAAAAA      180

CGACAGAATA TGATGTTTTA TCGTAACGTA ATTTTAAGTT CTCAACTTAT TGAGACATAT      240

TGTCTTTTTT ACCCATGTGG TCATTTTTCA TCCCATCCGT TTTGCTCATG TGTTCTTTCT      300

CCATTTTCTC TTTATCCATT GCATTTTTGC ACATACCATC CTTGCACATT TTATCATGCG      360

CGCTGGACAT GCTGCCTTTT ACTTCATGTG TTTTATCCAT TGTGTCTGCT GCCTGAGCAT      420

TGAACATGAA CAGCGCGGAT AGTACAGTTG CAGAAATAAT ATTTTTCATG GTTCTTCCTC      480

ATTTTTAACA ATTGTATCAA CAACCACCAA ACCAGTTATA ACCCTGGTCT TCCCAGTACC      540

CCCCCGGAAA ATGATTAGTG ACCTCTATAA CCTGAACATG CTTGGGGTTT TTATATCCCA      600

GCTTAGTAGG GATACGTATC TTTATGGGAT AGCCATATTC TTTTGGCAAT ACCCTGTTAT      660

TCCATGTCAA TGTCAGCAAT GTTTGTGAAT GTAGTGCTGT CGCCATATCA ATACTGGTGT      720

AGTAACCATC GACGCAACGA AAACTGACGT ATTTTGCCCG CATATCGGCA CCAATCAGCG      780

TCAGGAAATG CCGGAATGGT ATCCCTCCCC ATTTTCCTAT TGCACTCCAT CCTTCAACAC      840

NGATATGACG GGTTATCTGA CTCACATGCT GCATGTTATA CAATTCAGAC CAAAAACCAG      900

TTACGGGTTA T                                                          911
```

(2) INFORMATION FOR SEQ ID NO: 33:

(i) SEQUENCE CHARACTERISTICS:
        (A) LENGTH: 463 base pairs
        (B) TYPE: nucleic acid
        (C) STRANDEDNESS: double
        (D) TOPOLOGY: linear (xi) SEQUENCE DESCRIPTION: SEQ ID NO: 33:

```
NGGGGCAGGA TAATTGTATC CTGCCCNGTA TATAATTCTC AGCACAGGTG TTGACTAAAG       60

AGCGTGAAAC TTTGCTATTA TGTCTTCGTA AGATTCACGG ACGGTTATAC TTGAGCCTGA      120

TTCTGTGAAG TAAACAACAG CAGAAGCATC GTTGCCTTTT TCAATGTATG AAACATTCCA      180

GTCATGGATA GCCACTGCGG GCTGACCATT ATCCCGACGG TGCGTCTTAA TGAATCGCGG      240

AAGTAATTCT GCAATATCGT TAAAAACACC ATTTACGGTA TGAGTGATAC CACCAACGCA      300

ATGTAGATGA GTTGACTCCG GGGTATCATT GTCTGCTTCT GCAAAGAGTA TAGCTGTCTT      360

GCTAATTGTA ACAGGCGCCT GTGARCGGGA TAATTCGAGA GAAATAAACC CGGATTCTGC      420

CATAAAAACT CCAGTTTGTG ATGTTATATC ATTTCATATG TTT                       463
```

(2) INFORMATION FOR SEQ ID NO: 34:

(i) SEQUENCE CHARACTERISTICS:
        (A) LENGTH: 565 base pairs
        (B) TYPE: nucleic acid
        (C) STRANDEDNESS: double
        (D) TOPOLOGY: linear (xi) SEQUENCE DESCRIPTION: SEQ ID NO: 34:

```
TTCTAACCTC TGACCAAAAA CAGAATTACG GTTGTTATGC TGCAGAACCT AATGACGTGC    60
AACTGGCGCG CTATTTTCAT CTTGATGAAC GGGATCTGGC CTTCATTAAC CAACGACGGG   120
GCAAACATAA TAGGCTGGGC ATTGCGCTTC AGCTCACCAC AGCCCGTTTT CTGGGAACAT   180
TTCTGACGGA TTTAACTCAG GTTCTGCCTG GTGTTCAACA TTTTGTCGCG GTACAGCTTA   240
ATATCCACCG TCCAGAAGTT CTCTCCCGCT ATGCTGAACG GACACTACC CTTAGAGAAC    300
ATACTGCATT AATTAAGGAA TATTACGGCT ATCATGAATT TGGTGATTTT CCATGGTCTT   360
TCCGCCTGAA GCGTCTGCTA TATACCCGGG CGTGGCTCAG TAATGACGAC CGGGTCTGAT   420
GTTTGATTTT GCCACTGCAT GGTTGCTTCA AAATAAGGTA TTACTGCCCG GAGCAACCAC   480
ACTAGTACGT CTCATCAGTG AAATTCGTGA AAGGGCAAAT CAGCGGCTGT GGAAAAAGCT   540
GGCCGCACTG CCGAACAAAT GGCAG                                        565
```

(2) INFORMATION FOR SEQ ID NO: 35:

(i) SEQUENCE CHARACTERISTICS:
        (A) LENGTH: 512 base pairs
        (B) TYPE: nucleic acid
        (C) STRANDEDNESS: double
        (D) TOPOLOGY: linear (xi) SEQUENCE DESCRIPTION: SEQ ID NO: 35:

```
CGATGGCGTC CGGGGTGAAC GCCGGATAAG TTTAATTTAT CCGGTCAGGC AAAAGGCATT    60
AATCTGCAGA TAGCTGATGT CAGGGGAAAT ATTGCCCGGG CAGGAAAAGT AATGCCTGCA   120
ATACCATTGA CGGGTAATGA AGAAGCGCTG GATTACACCC TCAGAATTGT GAGAAACGGA   180
AAAAAACTTG AAGCCGGAAA TTATTTTGCT GTGCTGGGAT TCCGGGTCGA TTATGAGTGA   240
GTCACTCCGG TGAGATGTCC GGTTATTTAT CTTTTTTGTG AATCTGGTGA TGCGTGGAAT   300
GAAAGACAGA ATACCTTTTG CAGTCAACAA TATTACCTGT GTGATATTGT TGTCTCTGTT   360
TTGTAACGCA GCCAGTGCCG TTGAGTTTAA TACAGATGTA CTTGACGCAG CGGACAAGAA   420
AAATATTGAC TTCACCCGTT TTTCAGAAGC CGGCTATGTT CTGCCGGGGG CAATATCTTC   480
TGGGATGTGG AATTGTTAAC GGGGCCAAAG TA                                512
```

(2) INFORMATION FOR SEQ ID NO: 36:

(i) SEQUENCE CHARACTERISTICS:
        (A) LENGTH: 827 base pairs
        (B) TYPE: nucleic acid
        (C) STRANDEDNESS: double
        (D) TOPOLOGY: linear (xi) SEQUENCE DESCRIPTION: SEQ ID NO: 36:

```
TTGCCGGTGC GGTTANTAGT GGCAGTGGTG TCTTTTGGTG TAAATGCTGC TCCAACTATT    60
CCACAGGGGC AGGGTAAAGT AACTTTTAAC GGAACTGTTG TTGATGCTCC ATGCAGCATT   120
TCTCAGAAAT CAGCTGATCA GTCTATTGAT TTTGGACAGC TTTCAAAAAG CTTCCTTGAG   180
GCAGGAGGTG TATCCAAACC AATGGACTTA GATATTGAAT TGGTTAATTG TGATATTACT   240
```

```
GCCTTTAAAG GTGGTAATGG CGCCAAAAAA GGGACTGTTA AGCTGGCTTT TACTGGCCCG      300

ATAGTTAATG GACATTCTGA TGAGCTAGAT ACAAATGGTG GTACGGGCAC AGCTATCGTA      360

NTTCAGGGGG CAGGTAAAAA CGTTGTCTTC GATGGCTCCG AAGTGATGCT AATACCCTGA      420

AAGATGGTGA AAACGTGCTG CATTATACTG CTGTTGTTAA GAAGTCGTCA GCCGTTGGTG      480

CCGCTGTTAC TGAAGGTGCC TTCTCAGCAG TTGCGAATTT CAACCTGACT TATCAGTAAT      540

ACTGATAATC CGGTCGGTAA ACAGCGGAAA TATTCCGCTG TTTATTTCTC AGGGTATTTA      600

TCATGAGACT GCGATTCTCT GTTCCACTTT TCTTTTTTGG CTGTGTGTTT GTTCATGGTG      660

TTTTTGCCGG TCCGTTTCCT CCGCCCGGCA TGTCCCTTCC TGAATACTGG GGAGAAGAGC      720

ACGTATGGTG GGACGGCAGG GCTGCTTTTC ATGGTGAGGT TGTCAGACCT GCCTGTACTC      780

TGGCGATGGA AGACGCCTGG CAGATTATTG ATATGGGGGA ATACCCC                   827
```

(2) INFORMATION FOR SEQ ID NO: 37:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 37:

```
CCAGGGGCCC AAAATCCGTG TATCCACCTT TAAAGAAGGC AAAGTTTTCC TCAATATTGG       60

GGATAAATTC CTGCTCGACG CCAACCTGGG TAAAGGTGAA GGCGACAAAG AAAAAGTCGG      120

TATCGACTAC AAAGGCCTGC CTGCTGACGT CGTGCCTGGT GACATCCTGC TGCTGGACGA      180

TGGTCGCGTC CAGTTAAAAG TACTGGAAGT TCAGGGCATG AAAGTGTTCA CCGAAGTNAC      240

CGTCGGTGGT CCCCTCTCCA ACAATAAAGG TATCAACAAA CTTGGCGGCG GTTTGTCGGC      300

TGAAGCGCTG ACCGAAAAAG ACAAAGCAGA CATTAAGACT GCGGCGTTGA TTGGCGTAGA      360

TTANCTGGCT GTCTCCTTCC CACNCTGTGG CGAAGATNTG                           400
```

(2) INFORMATION FOR SEQ ID NO: 38:

(i) SEQUENCE CHARACTERISTICS:
        (A) LENGTH: 578 base pairs
        (B) TYPE: nucleic acid
        (C) STRANDEDNESS: double
        (D) TOPOLOGY: linear (xi) SEQUENCE DESCRIPTION: SEQ ID NO: 38:

```
CCGATTTTTT GCGAAACGTT CCGCCTGGCA TCAGGATAGT TGTTCGTTA TCCAGTTCGG        60

ATAGCGCATT GACGATATGC AGGCTGTTGG TCATCACCGT GATGTNATTA AAGCGCGAGA      120

GCAGGGGAAC CATCTGCAAA ACGGTACTGC CAGCATCAAG AATGATCGAA TCGCCATCAT      180

GGATAAAACT AACGGCAGCT TCTGCAATCA GCTCTTTCTT GTGGGTGTTG ATGAGTGTTT      240

TATGATCGAT AGGCGGATCG GATTCCTCTT TATTCAACAC CACTCCGCCA TAAGTACGAA      300

TGACGGTTCC GGCATGTTCC AGAATGACCA GATCTTTGCG AATGGKTGTG CCTGTGGTGT      360

CAAATATTGC GCCATTCTTC AACCGAGCAT TTACCCTGCT TTGCAGATAC TCCAGAATGG      420

CGGCCTGACG CTGACGAGTT TCATGGGCGT GATACCTGAT TTAGGTTCAA ATGATAACTC      480

GCAAGCAGTA ACATCACACG NAATATCCAC GTTCAGTTAA GCGCCATGAT AGAGCATCCG      540

TGATAGGGNC AGGGGNAGTC ACACGGCGTA ATCACCGC                             578
```

(2) INFORMATION FOR SEQ ID NO: 39:

(i) SEQUENCE CHARACTERISTICS:
    (A) LENGTH: 399 base pairs
    (B) TYPE: nucleic acid
    (C) STRANDEDNESS: double
    (D) TOPOLOGY: linear (xi) SEQUENCE DESCRIPTION: SEQ ID NO: 39:

```
TGTTAGGTCA GGGCCCACAG TCAAGCTTAG GTTTTACTGA ATATACCTCA AATGTTAACA    60

GTGCASATGC AGCAAGCAGA CGACACTTTC TGGTAGTTAT AAAAGTGCRC GTAAAATATA   120

TCACCAATAA TAATGTTTCA TATGTTAATC ATTGGGCAAT TCCTGATGAA GCCCCGGTTG   180

AAGTACTGGC TGTGGTTGAC AGGMGATTTA ATTTTCCTGA GCCATCAACG CCTCCTGATA   240

TATCAACCAT ACGTAAATTG TTATCTCTAC GATATTTTAA AGAAAGTATC GAAAGCACCT   300

CCAAATCTAA CTTTCAGAAA TTAAGTCGCG GTAAATATTG GATGTGCTTA AAGGACGGGG   360

AAGATTTCAT CGACACGTCN GCGTGCAATC TATCCGTAT                          399
```

(2) INFORMATION FOR SEQ ID NO: 40:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (xi) SEQUENCE DESCRIPTION: SEQ ID NO: 40:

```
CAGCCTCCGT TACCGGACAG CAAGGAGGCT GAATGGAGTT TACAGGATTT GCTTTTTTAT    60

AATGTCTGGC CATGCAGTMA AACCGGACAG GTTTTATTAT CATGTGAGGT ATTCTGACAT   120

AAAATGCTGG ATTTTTATTT TGTGACGAAT GCTGCAAAAT TGCATCTGCA CTCTGATGTA   180

GCTTTTATCT GTTTCAGTGA AGCATGCCCA CAAACTGAGT TATTAAGTTG TGGAAGAACA   240

GTTTTGTCCC GCCTGCATAT CTCCTTTCAA AAACCAGTAT GTCGCCATGC CTCGCCTTAA   300

TGGAGAGCGC TGAACCATAC CTTCTTT                                       327
```

(2) INFORMATION FOR SEQ ID NO: 41:

(i) SEQUENCE CHARACTERISTICS:
        (A) LENGTH: 314 base pairs
        (B) TYPE: nucleic acid
        (C) STRANDEDNESS: double
        (D) TOPOLOGY: linear (xi) SEQUENCE DESCRIPTION: SEQ ID NO: 41:

```
GGAGATGGGC ATGGAACTCA CTTCATAATA ATGCCTACCG AAGAAATATT AATAGATGAC    60

ATTTCCACGA GNGATAGCAA TAAAACATCA GAGCAGTCTT CTCGCTTAGA AAAAGCTTTA   120

TTAGGTTTTA CAAACACAAT GTACAGTGAT TCAAACCCTC CTATTATAGC TCGTTTTAGA   180

GACTATCTGG AAGATGGTGA GTGCATTGAC AGAATTAGCG AATCAATTTT TTTTACACCG   240

CAAGAATTCA ATCTTGCAGA TCACCACATT GAAGGATGGT TCAATGAATT TGGTCAATTC   300

AGTGGAACTG TTTC                                                     314
```

(2) INFORMATION FOR SEQ ID NO: 42:

(i) SEQUENCE CHARACTERISTICS:
        (A) LENGTH: 590 base pairs
        (B) TYPE: nucleic acid
        (C) STRANDEDNESS: double
        (D) TOPOLOGY: linear (xi) SEQUENCE DESCRIPTION: SEQ ID NO: 42:

```
TCCCAAGATC TTTTTGGCCG CAAATCCACA AAACCCGTCG TTANTGTCGC GCAGCCANTT      60

GCAGGCCGAA TTTGCACCGT TTTAGAAAGC GGCGTTTTGT AGAGCAGCAC GCAGTGAGAA     120

GCCACCGCGC CACGACCTAC GNGCNCGCGC AGCTGGTGTA ATTGCGCCAG ACCCAGACGC     180

TCCGGGTTTT CGATAATCAT CAGACTGGCG TTAGGCACAT CAACGCCGAC TTCAATAACG     240

GTTGTGGCAA CCAGCAGGTG TAGCTCACCT TGTTTAAACG ACGCCATCAC CGCCTGTTTC     300

TCGGCAGGTT TCATCCGCCC GTGTACCAGG CCAACGTTCA ACTCTGGTAG CGCCAGTTTC     360

AACTCTTCCC AGGTAGTTCC GMCGCCTGCG CTTCCAGCAA TTCCGACTCT TCAATCAACG     420

TACAAACCCA GTATGCCTGA CGACCTTCAG TTATGCAGGC GTGGTGCACC GGGTGCAATG     480

GATGTCGGTA NNGCGGGTAT CAGGAATAGC GACCGTAGTC ACTGGGCGTG CGGCCTGGGC     540

GGCACTCCAT CTATCACCGA GGGTATCGAG ATCGGGCATA CGCNTGCATT                590
```

(2) INFORMATION FOR SEQ ID NO: 43:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 43:

```
GACGAAAGGG CCTCGTGATA CGCCTATTTT TATAGGTTAA TGTCATGATA ATAATGGTTT      60

CTTAGACGTC AGGTGGCACT TTTCGGGGAA ATGTGCGCGG AACCCCTATT TGTTTATTTT     120

TCTAAATACA TTCAAATATG TATCCGCTCA TGAGACAATA ACCCTGGATA AATGCTTCAA     180

TAATATTGAA AAAGGAAGAG TATGAGTATT CAACATTTCC GTGTCGCCCT TATTCCCTTT     240

TTTGCGGCAT TTTGCCTTGC CTGTTTTTGC TCACCCAGAA ACGCTGGTGA AAGTAAAAGA     300

TGCTGAAGAT CAGTTGGGTG CACGAGTGGG TTACATCGAA CTGGGATCTG CAACAGCGGT     360

AAGATCCTTG AGAGTTTTTC GCCCCGAAGG AACGTTTTTC                           400
```

(2) INFORMATION FOR SEQ ID NO: 44:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 44:

```
ATTCGGAAAG ATGCTTCTAN TTTTTTTAAG CACGTATAAA CTGTTAATTC AGGTTCAATG      60

CTACGAAATG CACTAGTTAT AACCTGTATT GAAGGAAAGA TCTTCTGATA CTCTTTCCAG     120

AGATCTTCAA GTCTGGCCAT GGAAATTGAC TTGGCTGCAT ATTCTAGGTC AGTGTTTATG     180

ATAGTTTCTC TATTCTCTCT GAATGCGGAA AAAAAAGCTT CATTCAACAA TGATAGTAAA     240

TCCCTGGGCC GGTAAAGGGT AAATTGCAAA CATCGCTTAA AACCATTCCT CCCTTTAAGA     300

TCATCCGCTG TGCATCTATC CCAAACTCGT TGATCTTTCT CAATATCTAG CTTAAATGCT     360

ACTTTCATTC TTTTAGCTGA CAGCATTAGG AGTTGTGCCC                           400
```

(2) INFORMATION FOR SEQ ID NO: 45:

(i) SEQUENCE CHARACTERISTICS:
        (A) LENGTH: 585 base pairs
        (B) TYPE: nucleic acid
        (C) STRANDEDNESS: double
        (D) TOPOLOGY: linear (xi) SEQUENCE DESCRIPTION: SEQ ID NO: 45:

| | |
|---|---|
| TAATGTTGAA GACAGAGATA TAATNTACAG CATCATCCCA CAAGGCAGAT ATAACAATAC | 60 |
| TTGACTGGGA TATGCAAAGC GATAGTGGGC AATTTGCTAT TGAAATAATA AAATCGATAA | 120 |
| TCGTTTCAGA TATAAATTCT GGAGGACGTT TACGTCTTCT TTCTATTTAT ACTGGTGNAC | 180 |
| ATGTTACTGC TGTTATAACT AAGTTGAACA ATGAGTTAAA GAAAACATAC CGTAGCGTAA | 240 |
| TAAAAAATGA TGATAGTATT TTTATTGAAG ATAACTATGC ACTCGAACAA TGGTGTATAG | 300 |
| TTGTTATTAG TAAAGACGTT TATGAAAAAG ATCTTCCAAA TGTGTTAATA AAAAAATTCA | 360 |
| CTAACCTTAC AGCTGGGTTG CTATCCAACG CCGCACTCTC TTGCATTTCT GAAATAAGAG | 420 |
| AWAAAACCCA TGGGATATTA ACAAAATATA ATAATAAATT AGACACTGCA TATGTTTCCC | 480 |
| ACATCTTAAA TTTAATAAAA TCCAAGGRGT CAAGGGCATA TGCTTATGAA AATGCTCATG | 540 |
| ATTATGCAGT AGATTTAATT TCTGAAGAAA TAAGATCAAT ATTGC | 585 |

(2) INFORMATION FOR SEQ ID NO: 46:

(i) SEQUENCE CHARACTERISTICS:
        (A) LENGTH: 390 base pairs
        (B) TYPE: nucleic acid
        (C) STRANDEDNESS: double
        (D) TOPOLOGY: linear (xi) SEQUENCE DESCRIPTION: SEQ ID NO: 46:

| | |
|---|---|
| ANTCATCCAA CTGGCCGATC AGCAAAAAAG CGCGGCCTAC GATTTCACCC ACGAACTGTT | 60 |
| AACCACGCTG GAAGTTGACG ATCCGGCGAT GGTAGCAAAG CAGATGGAAC TGGTGCTGGA | 120 |
| AGGCTGTTTA AGCCGAATGC TGGTGAATCG TAGCCAGGCG GATGTCGACA CCGCACATCG | 180 |
| GCTGGCGGAA GATANTCNTT GCGTTCGCCC GCTGCCGTCA GGGTGGTGCA CTGACCTGAC | 240 |
| AGAAACACAG AAAAGAAGCG ATTTGCCGCA ATCTTAAGCA GTTGAATCGC TTTTACTGAA | 300 |
| ATTAGGTTGA CGAGATGTGC AGATTACGGT TTAATGCGCC CCGTTGCCCG GATAGCTCAG | 360 |
| TCGTAGAGCA GGGGATTGAA AATCCGTTGT | 390 |

(2) INFORMATION FOR SEQ ID NO: 47:

(i) SEQUENCE CHARACTERISTICS:
        (A) LENGTH: 473 base pairs
        (B) TYPE: nucleic acid
        (C) STRANDEDNESS: double
        (D) TOPOLOGY: linear (xi) SEQUENCE DESCRIPTION: SEQ ID NO: 47:

| | |
|---|---|
| GGATGCCAGT GTCAGCGACT GGTTAAAGTG GTCGATATCG ATGAGCAAAT TTACGCGCGC | 60 |
| CTGCGCAATA ACAGTCGGGA AAAATTAGTC GGTGTAAGAA AGACGCCGCG TATTCCTGCC | 120 |
| GTTCCGCTCA CGGAACTTAA CCGCGAGCAG AAGTGGCAGA TGATGTTGTC AAAGAGTATG | 180 |
| CGTCGTTAAT TTTATCTCGT TGATACCGGG CGTCCTGCTT GCCAGATGCG ATGTTGTAGC | 240 |
| ATCTTATCCA GCAACCAGGT CGCATCCGGC AAGATCACCG TTTAGGCGTC ACATCCGTCG | 300 |
| TCCCCTGGCA AACGGGGGCG ATTTTCCTCC ATTTGCCTCA GTGGCTGGCG TTTCATGTAA | 360 |
| CGATACATGA CAGCGCCCGA CAAGATCCTG ATACTCTTTG GGTATTCAAC CGTTTCCAGT | 420 |
| GTAATTCGTC GTTCACNAAC ATTGGCGTTA CAGGCGGGGC TGGCNGTNAC CCA | 473 |

(2) INFORMATION FOR SEQ ID NO: 48:

(i) SEQUENCE CHARACTERISTICS:

(A) LENGTH: 482 base pairs
        (B) TYPE: nucleic acid
        (C) STRANDEDNESS: double
        (D) TOPOLOGY: linear (xi) SEQUENCE DESCRIPTION: SEQ ID NO: 48:

GAAGTGACGG ATGGCTGTGG TTTCTCCATC GGTCACCAGC AGCAGTTNGC ATCATGGATT    60

GCCTATAAAG TCGCGCCGTT CCTCGGNAAA AAGAGGAGA GCGTTGAAGA CCTCAAATTG    120

CCGGGCTGGC TGAACATTTT CCACGACAAC ATCGTCTCCA CGCGATTGTG ATGACCATCT    180

TCTTTGGTGC CATTCTGCTC TCTTCGGTAT CGACACCGTG CAGCGATGGC AGGCAAAGTG    240

CACTGGACGG TGTACATCCT GCAAACTGGT TCTCCTTTGC GGTGGCGATC TTCATCATCA    300

CGCAGGGTGT GCGCATGTTT GTGGCGGAAC TCTCTGAAGC ATTTAACGGC ATTTCCCAGC    360

GCCTGATCCC AGGTGCGGTT CTGGCGATTG ACTGTGCAGC TATCTATAGT TCGCGCCGAA    420

CGCCGTGGTC TGGGGCTTTA TGTGGGGCAC CATCGGTCAG CTGATTGCGG TTGGCATCCT    480

AG    482

(2) INFORMATION FOR SEQ ID NO: 49:

(i) SEQUENCE CHARACTERISTICS:
        (A) LENGTH: 185 base pairs
        (B) TYPE: nucleic acid
        (C) STRANDEDNESS: double
        (D) TOPOLOGY: linear (xi) SEQUENCE DESCRIPTION: SEQ ID NO: 49:

GACGACCTGC AGGCATGCAA GCTTGGCACT GGCCGTCGTT TTACAACGTC GTGACTGGGA    60

AAACCCTGGC GTTACCCAAC TTAATCGSCT TGCAGCACAT CCCCCTTTCG CCAGCTGGCG    120

TAATAGCGAA GAGGCCCGCA CCGATCGCCC TTCCCAACAG TTGCGCANCT GAATGGCGAA    180

TGGCG    185

(2) INFORMATION FOR SEQ ID NO: 50:

(i) SEQUENCE CHARACTERISTICS:
        (A) LENGTH: 491 base pairs
        (B) TYPE: nucleic acid
        (C) STRANDEDNESS: double
        (D) TOPOLOGY: linear (xi) SEQUENCE DESCRIPTION: SEQ ID NO: 50:

TAACGCTTCA ATACGCGCGA CCAGCTGGCG GCGCTCATAC GGCGTAATTT TGGCGTCGGC    60

GAGCAAAATC CCTTGTTTAA AGGTATTTTG CCAGCTGCCG TCGTCATATT GGCGAGCTTG    120

CTGACGCGAC TGCGCAGGCA TTAAACGATC AGCACAATCC ATCGCCCGCA GCCAGTAAAG    180

CGGATTGGTT TCGGTTGATT TACCTTGCAG CGCCCAGATG TCGCTACATT CAGTAGAAAG    240

ATAGTCAGCC AGTTGATAAA CCGGAATTTT TTCTTCTGCT GGCGTATCAA TGGCTGGCTT    300

ATTGTGATTC TGCACGCAAC CCAGCAATGC CAGACATGGA GACCCTGCCA GCCACAGCCG    360

TCGGGCAAT AATCGTTGAA AAATGTGTCG CATATTCACC AGACTTAAAG CCTATCCCAG    420

TGGGCGTAAT TGTTGCAGAC AGTCTGGACA TGGACAGCGC GGAGAAACCG GNAGCGTACA    480

TATCGTACGT G    491

(2) INFORMATION FOR SEQ ID NO: 51:

(i) SEQUENCE CHARACTERISTICS:
        (A) LENGTH: 106 base pairs
        (B) TYPE: nucleic acid

```
            (C) STRANDEDNESS: double
            (D) TOPOLOGY: linear (xi) SEQUENCE DESCRIPTION: SEQ ID NO: 51:

ACTTGAACGG CAATTATTAT TTATCCATGC AACTTCAAGT TGCAGTATCG GAACATTAAC      60

TTTTCTGGGG TGAATATCAC TCTGATATCG TTTTTTGTAT GCGTNT                   106

(2) INFORMATION FOR SEQ ID NO: 52:

(i) SEQUENCE CHARACTERISTICS:
        (A) LENGTH: 481 base pairs
        (B) TYPE: nucleic acid
        (C) STRANDEDNESS: double
        (D) TOPOLOGY: linear (xi) SEQUENCE DESCRIPTION: SEQ ID NO: 52:

TTTATGTGCG GTATTGATGG CTGAAGCCTG TAATATCGGA CTGGAACCGC TGATAAAGCA      60

CAATATACCA GCACTGACCC GCCATCGGCT CAGTTGGGTG AAACAGAATT ACCTTCGTGC     120

AGAAACGCTG GTCAGCGCCA ATGCCCGCCT GGTTGATTTT CAGTCCACAC TGGAGCTTGC     180

TGGTCGTTGG GGAGGTGGAG AAGTGGCATC AGCTGACGGC ATGCGCTTTG TCACACCAGT     240

GAAGACCATC AACTCAGGAT CTAACAGAAA ATATTTTGGT TCTGGGACGA GGCATCACCT     300

GGTATAACTT CGTATCTGGA TCAGTACTCT GGGTTCCATG GCATTGTGGT ACCCGGTACA     360

TTACGGGRCT CGATTTTGTA CTGGAAGGAC TTCTTGAGCA GCAGACAGGG CTGAATCCAG     420

TTGAAATCAT GACAGACANT GCGGGTAGCA GCGATATTAT TTTCGGTCTG TTCTGGCTAC     480

T                                                                    481

(2) INFORMATION FOR SEQ ID NO: 53:

(i) SEQUENCE CHARACTERISTICS:
        (A) LENGTH: 558 base pairs
        (B) TYPE: nucleic acid
        (C) STRANDEDNESS: double
        (D) TOPOLOGY: linear (xi) SEQUENCE DESCRIPTION: SEQ ID NO: 53:

TGGNCCGTAA TTCCCAACCA TTTGCCGAGG TCCAGNTTTT TCACCATGTT ACTCGGGATA      60

GCCAAAACNG ATACCGATGT TGCCGCCGTC CCGGTGCGAG GATCGCGGTG TTGATACCGA     120

TCAGTTCGCC GTTCAGGTTA ACCAGCGCAC CACCGGAGTT ACCACGGTTG ATCGCTGCAT     180

CGGTCTGGAT GAAGTTTTCG TAGTTTTCGG CATTCAGGCC GTACGCCCCA GCGCAGAGAC     240

AATCCCGGAA GTTACCGTCT CGCCCAGACC AAACGGGTTA CCAATCGCTA CGGTGTAATC     300

ACCCACGCGC AGTGCATCAG AATCCGCCAT CTTAATTGCG GTCAGGTTTT TCGGGTTCTG     360

GATTTGGATC AGCGCGATAT CAGAGCGCGG ATCTTTGCCA ACCATCTTCG CGTCGAACTT     420

ACGGCCATCG CTCAGTTGAA CTTTAATGAC CGTCGNGTTA TNAACAACGT GGTTGTTGGT     480

GACGACATAG CCTTTATCGG CATCAATGAT GACGCCGGAA CCCAGCGCCA TGAATTCTGT     540

TGCTGGCCGC CACCATTA                                                  558

(2) INFORMATION FOR SEQ ID NO: 54:

(i) SEQUENCE CHARACTERISTICS:
        (A) LENGTH: 263 base pairs
        (B) TYPE: nucleic acid
        (C) STRANDEDNESS: double
        (D) TOPOLOGY: linear (xi) SEQUENCE DESCRIPTION: SEQ ID NO: 54:
```

```
CACCTGCGTG ACGTGACCGA CCTTTTCTCC TCGCTGNTTG TTTCCCCTAT CGTCGGCCTG        60

GTCATTGCGG GAGGCCTGAT ATTCCTGCTG CGACGCTACT GGCGCGGGAC GAAAAAAGCG       120

TGACCGTATT CGCCGCATTC CGGAAGATCG CAAAAAGAAA AAACGGCAAA CGTCAACCGN       180

CATTCTGGAC GCGTATTGCG CTGATTGTTT CCGCTGCGGG CGTGGCGTTT TCGCACGGCG       240

CGAACGACGG ACCAAAAGGG ATC                                               263
```

(2) INFORMATION FOR SEQ ID NO: 55:

(i) SEQUENCE CHARACTERISTICS:
        (A) LENGTH: 683 base pairs
        (B) TYPE: nucleic acid
        (C) STRANDEDNESS: double
        (D) TOPOLOGY: linear (xi) SEQUENCE DESCRIPTION: SEQ ID NO: 55:

```
GTAACGCGTC TGGAAGATGG CCTGCCAGTG GGCGTCGTCG ATGTGGTCGA GGGGCTGGAC        60

GGTTGCCATT CCGCCAATAT CTCACCGGAC AACCGTACGC TGTGGGTTCC GGCATTAAAG       120

CAGGATCGCA TTTGCCTGTT TACGGTCAGC GATGATGGTC ATCTCGTGGC GCAGGACCCT       180

GCGGAAGTGA CCACCGTTGA AGGGGCCGGC CCGCGTCATA TGGTATTCCA TCCAAACGAA       240

CAATATGCGT ATTGCGTCAA TGAGTTAAAC AGCTCAGTGG ATGTCTGGGA ACTGAAAGAT       300

CCGCACGGTA ATAATCGAAT GTGTCCAGAC GCTGGATATG ATGCCGGAAA ATTCTCCGAC       360

ACCCGTTGGG CGGCKGATAT TCATATCACC CCGGATGGTC GCCATTTATA CGCCTGCGAC       420

CGTACCGCCA GCCTGATTAC CGTTTTCAGC GTTTCGGAAG ATGGCAGCGT GTTGAGTAAA       480

GAAGGCTTCC AGCCAACGGA AACCCAGCCG CGCGGCNTCA ATGTTGATCA CAGCGGCAAG       540

TATCTGATTG CCGCCGGGCA AAAATCTCAC CACATCTCGG TATACGAAAT TGTTGGCGAN       600

CAGGGGCTAC TGCATGAAAA AGGCCGCTAT GCGGTCGGGC AGGGACCAAT GTGGGTGGTG       660

GTTAACGCAC ACTAACCGCT GAT                                               683
```

(2) INFORMATION FOR SEQ ID NO: 56:

(i) SEQUENCE CHARACTERISTICS:
        (A) LENGTH: 282 base pairs
        (B) TYPE: nucleic acid
        (C) STRANDEDNESS: double
        (D) TOPOLOGY: linear (xi) SEQUENCE DESCRIPTION: SEQ ID NO: 56:

```
TGGATGCAGG GAAAAACATT GATATTACCG GGGCAACGTG CTCGTCCGGT GGAGACCTTG        60

GAATGTCTGC GGGTAATRAC ATCAACATTG CCGTAAACCT GATAAGCGGG ACAAAAGTCA       120

GTCCGGTTTC TGGCACACTG ATGACAACAG TTCATCATCC ACCACCTCAC AGGGCAGCAG       180

CATCAGCGCC GGCGATAACC TGGGCGATGG CTGCAGGCAG AGATKCTGGG NTGTCACAGC       240

ATCCTCTGTT TCTGCCGGGC ACAGCGCCCT GCTTTCTGCA GT                          282
```

(2) INFORMATION FOR SEQ ID NO: 57:

(i) SEQUENCE CHARACTERISTICS:
        (A) LENGTH: 697 base pairs
        (B) TYPE: nucleic acid
        (C) STRANDEDNESS: double
        (D) TOPOLOGY: linear (xi) SEQUENCE DESCRIPTION: SEQ ID NO: 57:

```
ATGAACGGCC CCCCCACAG CCCGTTAACA AACGGNTGCC CCGGCGATAA TCGTACTGAT         60
```

-continued

```
AAGTTAACTC CAGCAGGCGG TTAATTGAAA GCGAACGGGA GGCTGATGCA TGGTAATAAT        120

CCCTTAAAAC GCGACGGCAA CGCGCCAGTA AACCGTGAGA TGGTCAGGGG CAAGCCAGTC        180

CGGGTAAACC AGAGGCAGTC CGGCAGTGAA CGAACCGGAA ACATGACCAC TGGTGGTGCT        240

GAGCCCGGCA GCAGCACCCC ACAGCGTGCC GGACGAGTAC GGGTCATCTC TGTCAGAGTG        300

CAGCCAGCCG CCGTCCAGTG CAGTCACTGC ACGGACTGTC CCCACATATG GCAGGGAGAA        360

CAGAGACCAG GACAGCTCAT TTCGCAGATA ACCGCCGTTA TTACCGGAGA TATACTGCTC        420

CTTAAAGCCA CGCACTGAAC TCTCACCCCC GAGGCTCAGT TGTTCCACAC CATGAAGACG        480

GTCCGGTGAC CACTGGGCAT AAGCGCTGGT CAGCCACCAC ACCCTGTCCG TGACGGGGCG        540

CTGAAAACTG GCACTCACCG ACCATTTCCG GAACTGATTT ACGGGCAGGT CTCCCCTTTT        600

CCCGTGGTCG CTTTCTGCGC CGAACCAGGG CATCCCCCGT GTGAATACCG GATTCAGTGT        660

TCCGACACCA CCCAGAAACT TGTGTGTGTG ATTCANC                                697

(2) INFORMATION FOR SEQ ID NO: 58:

(i) SEQUENCE CHARACTERISTICS:
        (A) LENGTH: 4835 base pairs
        (B) TYPE: nucleic acid
        (C) STRANDEDNESS: double
        (D) TOPOLOGY: linear (xi) SEQUENCE DESCRIPTION: SEQ ID NO: 58:

TTCGACTGAG CACCACAAAT ACTGGGTATC TCCCCAGATA GTTCATTGCG GTACAAGCAA         60

TATAGGTGCA GAAAGTCAAC CTGCTGCACC CTATTGGATA ATTATATATG GCCTTCAATA        120

AAGTTTGCGG TTGTCGACGT TGGCTATATC AGCCATTTCC AATGCATAGT TCTTTGGTTT        180

AGCACCATCA AGTTATAGAT TTGGGAATAG TTTCAACTGG TATTGATTGA ATTGGGTTTC        240

ATCGTCGATG ATTAATACTA TTTGTAAAGA CTTTATTGTT GATTTCTTAT TATACCACAA        300

ACCCAAACTG GTCTAGGTCA TCATTTGGTG TTGATAACGG GCTCTGATAA TTTCTGCTCT        360

TCTGCTATAC TGGGGATTAT GAAGAATATT AAGGCTGAGT GTATTGAGGT AGTGTTCTTT        420

GAACCGACCA TTCATGACAA TATATTCTTC AATTCGTGAG TGATCCAGCA ACTGGTTGAA        480

TTTAAAACAC TGAGTGATGT TATCCTCTGT AATCGTATGT TGCTGAACT AGTTGATGTA        540

GCCGATAAGG TTTATACCAG ATATCTTTTG GGGGATTAG ATAACGTAGC CGCGGATAGC        600

AAACGAGATA GTTGAATTTT ATTACCGTAA TTTCTTCCAT TGAGAAAAGC TTATTTTTCT        660

TGGTGGTATT CGCAGTTATG TATCTTCCAT AAAGACTTGG GAATATCTTG CTTGAAARGC        720

TATCTGGAGA TAGCCTTAGT TATTTGATAA ATATTTCAAA TAGGAGGAGC CGTATGGCTG        780

TCATTTATAC CCTCACTAAA TCGTCACTTG TCAAGTCTGG TGGTCAATTA CATTGGAATA        840

TTGATTCGCC ATCAGAACAA CAGCCACAAA AGATCGTCAA TGGTCGGGTT GCGCTTCGGG        900

GATGGTTACT GGCAGATGTG GAAAAGATC TCCGTGTTGC GGTTAAAATT GAACATTTGA        960

CATACAGTTT TCCCTTCAAT ATAAAGCGCC CTGATGTTAT TTCAGCTATA CTGAAACAGC       1020

CACCTGAAAA ACATCAAAGA CTTCATTGTG GATTTGATAT CAATGTCCCA TTTTCTACTA       1080

AAATAATTAT TGGCCTTGAG TCTGATGGGT TGATTACCTG GTTGGAAGAG TTATTATTTC       1140

TCCTGCCTGA TAATTGAATT AAGTATCTAT ACCGATAGTA TCGCGATAGA TATATTTTTT       1200

TACAGGATGA TAATTTGAGA ATCTATATAG CCGCTATTAT CAAGGATGAG TATTCAAGTT       1260

TACTTGAATG GATTGCCTAC CATCGAGTAT TAGGTGTTGA TGGGTTTAKT ATTGCAGATA       1320

ATGGCAGTCG TGAWGGTAGC CGAGAATTAC TATTTTCCCT CGCTCGCCTA GGTATTGTGA       1380
```

```
CGATGTTCGA ACAACCGACT TTGGTGAATC AAAAGCCACA ATTACCTGCA TATGAACATA    1440

TTTTACGTAG CTGTCCCAGA GACATAGACC TGCTTGCATT TATAGATGCT GATGAATTTT    1500

TATTGCCACT TGAATCGGAT ACCAATTTGT CAGATTTTTT TTCTGAAAAG TTTCAGGATG    1560

AGAGTGTCAG CGCTATTGCA TTGAATTGGG CAAATTTTGG TTCTAGTGGT GAATGGTTTG    1620

CTGAAGAGGG GTTGGTTATT GAACGTTTTA CCTATCGTGC CCCGCAATCC TTTAACGTTC    1680

ATCATAACTT CAAAAGCGTG GTCAAACCCG AACGAGTTAA CCGCTTTCAT AATCCGCATT    1740

ATGCTGATTT GCGTTATGGT CGATATATCG ATGCATTGGG TCGTGATTTG ATTCTGCACC    1800

CGAGGCATGG TAATGGGGTT AGTGCTGAAG TGACTTGGAG CGGTGTCAGG GTAAATCACT    1860

ATGCAGTTAA ATCACTTGAG GAATTCTTGT TGGGCAAGCA TCTGCGTGGT AGTGCTGCCA    1920

CTGCTAATCG AGTAAAGCAT AAAGATTATT TCAAGGCACA TGATCGTAAT GATGAAGAGT    1980

GCCTTCTCGC TGCCGCATTC TCAGAACAAG TAAAAGCTGA ATGGAACGA TTAAGTGTGA     2040

AGTTGACTGA GTTACCAGCA GTTGAACCTA TTCCTACTGG TTCTTGGTTC AAAAAAAAAA    2100

TGAAGAAATG GATGGTTTGA ATATATTGAG CAAGCACTTT GGTATTTATT CTGCTCTTA     2160

TCTACAGGTC TGCTAATAAG GATCTGTATC CCCCAGGTGT TACCTTGGAC TGTAAGTTAT    2220

ATTATGTGTA GCTATTGCGA TTGGCAGCCT CTGACATTGC CAGACTCGTT TTCTCTTCAT    2280

TCTGGTTGGC TTCTGATTCG GGGGCGCGTG TTGACGACTC AAACTCGAGG TGAAACTCGT    2340

CTGCGCTGGC AATGCGGACA AGGAATATGG CATGAACAGA AGTTGCCGGT CACTCGTCGA    2400

GGCACGTTGC TGGAGCTGGT TTATCTACCY TCGGGAGCTA GTCATTKGTC TTTGCTGGCA    2460

AGTAATAAGG GCGCTGAGTG TAATGTTGAA ATTACTCAGC TTTGTTGTGT ATCCCGTGCC    2520

GAGAGTCTCT GGCGTCGATT GCGCCGGGTT GTACCTTTTT ACCGACGCTT AACGAAGTCC    2580

AGACGCAAAA GGTTAGGCCT TTCATGGCAT TTGTGGCTCA CGGACTTGCA GCAAGCTTAC    2640

CAACTTGTCA GCAGAGTTCG CGATGATAAA CCACTCAATA GCTATGATGA GTGGCTAGCA    2700

GACTTCGACA CCCTTGAACC CGCCGAATAC AAGCTGATTA AGCGCCAGCT GGCTCGCTGG    2760

GGCACATTAC CACGTTTCTG TTTGCATCTT GTTGGCGTTG GGGATGAACA GAGCCGCCAC    2820

AAGACCCTGG AGAGTATTCA GGCACTCTGT TATCCGGCAA GCAATATAAA CCTGCAGGAG    2880

CATGGTGCAT ATCCAGAAAT CTCCAGTCAG TCAAGCGGCG AATGGCAGTG GGTGTTGCCT    2940

GTAGGGGCAG TGGTTTCGCC AAGCGCCTTA TTTTGGGTTG CCCACCAGTT ACGCCAGAAT    3000

CCTGATTGTT TATGGATATA CGGTGATCAC GATCTGCTTG ACGAGAGAGG TGAACGTCAC    3060

TCTCCCAACT TCAAACCTGA TTGGAATGAA ACGCTGCTAC AGAGCCAAAA CTATATTAGT    3120

TGGTGTGGTT TGTGGCGTGA ACAAGGTGCT GGCCGTGTTC CCTTTGATGC GGCGACATGC    3180

CATCAGTGGT GGCTACAGTT GGCAAAGATG TGTGAACCGA AACAGATAGT CCATATTCCA    3240

TCATTGATGA TGCATTTGCC TGCAAGAGCG TTGATTTCGG ATGATTTTGA GTCGCTGAAA    3300

GATAAAGAAG ATTTACTGCC ATCAGGAGTG AGCATTGAGG CAGCACCTCA TGGTGTATGT    3360

CGTTGGCGCT GGCCGTTGCC AGCGCAATTG CCATTGGTTT CAGTGATTAT CCCTACTAGA    3420

AATGGTATTG CTCATTTACG CCCTTGTATC GAAAGCCTGA TACAAAAGAC GCAATATGCC    3480

AATATGGAAG TCATAGTGAT GGATAATCAG AGCGATGAGG AGGAGACGCT TGCTTATCTT    3540

GCTCATATCG AACAGGTTTA TGGCGTTAGG GTGATTTCTT ATGATCAACC GTTTAACTAT    3600

TCAGCCATCA ACAATCTGGC AGTGAGAAAC GCACATGGAG ATATGGATATG TTTGCTGAAT    3660

AATGATACTC AGGTAATCAG TATTGACTGG CTGGATGAAA TGGTTTCTCA TTTATTACGC    3720
```

```
CCCGGCGTGG GTGTGGTAGG AGCAAAGCTG TATTACGGAA ATGGCTTGAT TCAGCATGCA      3780

GGCGATGCTG TCGGCCCTGG CGGTTGTGCA GATCATTTTC ATAATGGTTT GTCAGCTAAC      3840

GATCCTGGAT ATCAGCGTAG GGCTGTTAGT GCCCAAGAGC TGTCAGCTGT GACTGCAGCT      3900

TGTTTATTGA CTCATAAAGA GTTATATCTG GCGCTCGGAG GACTTGATGA AACGAATTTG      3960

CCGATAGCTT TTAATGACGT RGATTATTGT CTCAGAGTTC GAGATGCTGG CTGGAGAGTA      4020

ATCTGGACTC CCTTCGCTGA ATTGTATCAT CATGAGTCTA TTTCCCGTGG TAAAGATGTA      4080

TCAAAACAAC AGCAGATACG AGCGAAATCT GAGTTGCGCT ATATGAAAAA ACGATGGGCA      4140

TGTGCACTTA AACACGATCC AGCCTACAAC CAAAATTTGA GTTATGAACG TCCTGATTTC      4200

TCTTTAAGTA GAGCTCCTAA TATAGTATTG CCATGGATGA ATTAATTCGC AGGAAACTAT      4260

TTAAGCCTTA TCGTAAATTA AATAAACAGA GTTATAGAAG TCCGCAAAGC TCTGAGATTA      4320

ACTTTGAACG ATTGTTTATA TTACATGAGG GAAAATCACC TACATTAGCC TATTTTGAAT      4380

CGGCTATTAT AAGTCGGTTT CCTGATGCAG AATGTCATTT TATCGACACA TTAGCATCCA      4440

CTGATATATT TATTCCTAGA GGATCTGCCC TTGTCGTCAT TAGATTCATC TCCCCAAAAT      4500

GGCAACAGCA CATAGAAAGA TATAACGACA GGTTTTCTCG AATTGTTTAT TTTATGGATG      4560

ACGACCTGTT TGACCCGACT GCACTATCTA CGTTACCAAA AGAGTATCGT ACCAAGATAA      4620

TAAGGAGGTC GGCGGCTCAG CATCGATGGA TTACGCAATA TTGTGATAAC ATTTGGGTTT      4680

CAACTGCCTA TTTGGCTAAT AAATATGCAC ATCTTAACCC GGAGATTGTT TCTGCTAAAC      4740

CGTCACTGGC ACTCATTGAA ACACATCGAT CAGTAAAAAT CGCTTATCAT GGCTCAAGTT      4800

CTCATCGGGA AGAAAAATAT TGGTTGAGAC AAATC                                4835
```

(2) INFORMATION FOR SEQ ID NO: 59:

(i) SEQUENCE CHARACTERISTICS:
        (A) LENGTH: 1746 base pairs
        (B) TYPE: nucleic acid
        (C) STRANDEDNESS: double
        (D) TOPOLOGY: linear (xi) SEQUENCE DESCRIPTION: SEQ ID NO: 59:

```
GAAAAATGNC ATAACCGCAT TCCATCAAGC CCGTNAATAT CCCGGACTTT CATTTATTTC        60

TGAGGCGTAC AGGGAAGCAA TAACTGCTGG TCAGATATTG CTGTCTCCGG TACATTTACC       120

TGACACTGTA TTTTTCCATC CCAGTTTACC GACAGGGTTT CCCCCGGCGT CACGCCACTC       180

AGCCAGGCAA GGCCTTCGTC GGCCACCATG CCCAGTTCCC GGCCTTTTTC ACTGGTTACA       240

CTGGCACCAA ACGGGGCTG AGAGCCATCA GCAAGACGCA GTATTGCAAA CAGACGTTTC        300

CCTTTAAGCA CGCTGAATTT CCGGTAACCA ATGGCACCTT CTGTCAGCGC CGATTCCACA       360

ACAGAACGGG TTGCTTCCAC ATCATCCGGT AAGCGCTTCA GGTCAACAGA GGTTGTATTC       420

CGGTAATAAC TGCTGATGTC AGTCACCACG CCCGTTCCCC AGCGATTTGT CACCACCTGC       480

CCGCCATCAA CCGGTACACC TCCCACACCA TCCGTGTCAA CAAGAAGACG TGTTCCACCG       540

GACATTCCCC CTGCATGTAA CGCCGCACCT TTTCCGGTAA TTGTTGCCCC ACCGGAAGCA       600

CTGACGCCGA AAGACGTATA TCCTTTCTGC AGGGATGCAA TATTCGCGGA CAAATTTGCC       660

AGCGGACTAC GATGACTGTA ATAGGCATTA ATCTGACGTT GCGATGTCAG TCCACCGCCA       720

CTGTTAAGGC CGGCGTTCAG GCTGTAGCTG TCCAGACCGT CATTGAACGT GWCAGTGTAG       780

CCGGCCATAT TCACATAACG GTCATTACTC ATACTGCCAC TGTAGCTCGC TGTCCCCGTC       840

CCCCAGCGGC ACGGATATAC GCAGGTAAGC AGAATCNTTA TCACGCCCCA GATATTTAGA       900
```

```
CCTTGAGGCT GACAATCCAA CCGCCACACC CTGCAGTCCG AAAACATTAA AGTAGCGGTT      960

GACGCTCACC GTATAATAGT CCGTTTTCCG TATGTCCCAG TATGTCTGAC GGCTGTACTG     1020

CAGGTTAAAA GAGGTGTTCC AGTCCGCCAC GTTTTTATTC AGCGTAACGG TATACATCTC     1080

TTTTTCCCGA CTGCTGTAAT CATTACGGTA GCGGGCGTTC AGGTACTGCT CCATGGTCAT     1140

ATAGTTTCGC TCTGAGAAAC GATACCCGGC GAACGTAATG TCGGCATCCG CATTATCAAA     1200

CCGTTTGGAG TAGCTCAGAC GCCAGGATTT CCCTGAAAC GTTCTCTCTC CCTCAATACG      1260

GGCTACTGAC TGCGTGATAT CAGCGGAAAG GGTCCCCGGC ACACCCAGGT CCCAGCCGGC     1320

ACCGGCTGCC AGTGCATTAT AATCACCGGC AAGCACAGCC CCGCCATACA GCGACCACTG     1380

GTTACTGAGC CCCCAGGATG CCTCTCCGGT CGCAAATACA GGCCCTTCGG TCTCATGCCC     1440

GTATCCACGG GAACGACCGG AGACAAGTTT GTACCGGACC TGTCCCGGAC GCGTCAGATA     1500

AGGAACCGAG GCCGTATCGA CCTGAAAGTT TTCTTCCGTC CGTTCTGTTC AATAACCTCA     1560

ACATCAAGAC GTCCGCGAAC TGAACTGTCC AGGTCCTGAA TACTGAATGG CCCTGCGGGG     1620

ACCATCGAGT CGTACAGCAC CCGTCCCTGC TGCGACACCA CAACACGGGC ATTAGTCTCC     1680

GCAATCCCGG TAATCTGCGG TGCATAAGCC TTCGCATTCT TGGGGCGGCA CATTCCGGGT     1740

CAGCGN                                                               1746

(2) INFORMATION FOR SEQ ID NO: 60:

(i) SEQUENCE CHARACTERISTICS:
        (A) LENGTH: 723 base pairs
        (B) TYPE: nucleic acid
        (C) STRANDEDNESS: double
        (D) TOPOLOGY: linear (xi) SEQUENCE DESCRIPTION: SEQ ID NO: 60:

TGTACTGAGC ACGGCGAATA TCCAGTGTTC AAATTCCACT TTGCAGCGAC TGCATGATGT       60

CTGCGGCGCG GTAACAATCA GGGCATTACT GTGTTTGCTG GCGGCGATGG AGACAACCTC      120

ACGCCCGCTA CCGACCGTGC CTTCCGCCTC TTCTTTAGCC GCCGTGAGCG TGCCGCTGAC      180

CTGCTTCAGC ACATCGACCA GATCTTCGGC TTTGCTGTAT TTGAGATAGA AAACCTGGCT      240

GTTGCCGCTG CGTTCCATTT CTGAGTCCAG CCGACGGATC AGGCGGCGCA TTTTGTCCCG      300

CGTGGCCGGG TCACCACTGA CAATCACACT GTTGGTGCGT TCGTCGGCGA CAATTTGAGA      360

TTTCAGCGTC GCAGGCTGGT TCTCGCCGCT GTTTTTAGTC AGGCTTTCCA GCACGCGGGC      420

GATTTCCGAA GCAGAGGCGT TATCCAGCGG GATCACCTCT TCAGTGCGAT TANCCGCGTG      480

ATCCACACGC TGGATCACTT CCGTCAGCCG CTCCACGACG GAGGCGCGCC CGGTGAGCAT      540

AATCACGTTG GAGGGATCGT AATTAACAAC GTTGCCTGAG CCTGCGCTGT CGATCATCTG      600

GCGCAGAATC GGTGCCAGTT CGCGTACCGA AACATNACGT ACCGGCACGA CTTTGGTGAC      660

CATTTCATCG CCCGCGTATT GTCGCTGCCT TCACCAACCA GCGGCAGGGC TCGACTTTCG      720

CGG                                                                    723

(2) INFORMATION FOR SEQ ID NO: 61:

(i) SEQUENCE CHARACTERISTICS:
        (A) LENGTH: 2556 base pairs
        (B) TYPE: nucleic acid
        (C) STRANDEDNESS: double
        (D) TOPOLOGY: linear (xi) SEQUENCE DESCRIPTION: SEQ ID NO: 61:

TAGAGGATCC CCGGCGTTGC GATCGTCACG AACATAGACC CACAKCCGTC CGGTAGGTAT       60
```

| | |
|---|---|
| TTACCCTGAC CCGGYTCCAG TACATTTACC GGCGTGTCAT CGGCATGCAC TTTACCCGGC | 120 |
| ATCAGCACAT AGTGCTTCAG TTCATCATAC AGCGGGCGAA GCTGCTCTCC CATGATGTCA | 180 |
| ACCCAGCGCC CCATCGTATT GCAGTGCAGC TCCACGCCCT GGCGGGCATA GATTTCCGAC | 240 |
| TGACGGTACA GCGGCAGATG CTCGGCGAAC TTAGCCATGA TTATGCGGGC CAGCAGAGCC | 300 |
| GGACTGGCGT AACTGCGCTC GATGGGTTTT GGTGGCTGCG GAGCCTGAAC TATACAGTCG | 360 |
| CACCGGCTGC AGGCCAGTTT TGGGCGAACC GTTTCGATTA CCCTGAACGC GGTGTTGATG | 420 |
| ATATCCAGTT GTTCAGAGAT GCTTTCTCCC AGCGGTTTCA GTTGCCGCT GCAGACGGGG | 480 |
| CATTCGGTTT CTGCCGGGGA GATAACCTGC CTGTCACGGG GAAGTGTTGC CGGAAGTGCT | 540 |
| TTGCGGACGG GAGAGTCTGA TGTTTTCGGC GCTGTCTCTC CGGCCATTGA GGTGAGTTGC | 600 |
| AACTGCGCCT CACCAAGCCT GTTCTGGAGC TCGGTTATAC GCGTTTCTGC CCGTGCGATC | 660 |
| TTCTTTTCTA TCTTCTCGCG GCTTTTCTCG CTGCTGCGAC CGAACAACAT TCTCTGTAGT | 720 |
| TTAGCGACCA GCGCTCTGAG TGAGCTGATC TCGCGGCATA GCCGGTTATT TCACCAGACA | 780 |
| GACGGACGAT AACAGCCTGC TGTGCGATCA GCAGGGCCTT CAGTTGCTCG ATGTCGTCGG | 840 |
| GGAGTGTGTT GTTCATTCCC CTGTTTTATC ACGGGTTATA TCCGGATGCC AGGCCGTTCT | 900 |
| GTCCGTTTGG GATGTTGCCA CGCGATCCCC TCCAGTAGCA TGGATAACTG AGCTGGCGTC | 960 |
| AGGTGCACTT TCCCTTCCCG GGTTACCGGC CAGACGAAGC GGCCCCGTTC CAGGCGTTTG | 1020 |
| GCGAACAGGC ATAACCCGTC ACGATCGGCC CACAGTATTT CACCATTTT GCCACTGCGG | 1080 |
| CCCCGGAAGA CGAAGATATG CCCGGAGAAC GGGTCATCTT TCAGCGTGTT CTGCACCTTC | 1140 |
| GAAGCCAGGC CGTTGAAGCC ACAACGCATA TCTGTGATGC CAGCGATGAT CCAGATTCTG | 1200 |
| GTACCGGTTG GCAGCGTTAT CATCGGGTAC CTCCTTTTAT TTCGCGGATT AGCGCCCGTA | 1260 |
| ACATTTCCGG AGTGAGAGGG TCAAACAGTT TTACCACACC TGATTAAGA TGCAGCTCGC | 1320 |
| ACCGTGGGAC GTTTCCGGGA TCACACTCAG GGCACTCATC AGGCTTGTTA CGCCAGAAGG | 1380 |
| GATTTGTAAC TGGTCTGGTC GGCTCTGGCG TATCAGTCAG AGCCACCGGG ACAGGCATGC | 1440 |
| ATTCCTGTAT GTCATCATCG CTCAGTAAGC CGTCCTCGTA CTGGCTTTTC CATTTAAACA | 1500 |
| GCAGGTTATC ATTGATACCG TGCTCTCTGG CGATCCGGGC AACAACAGCA CCGGGCTGTA | 1560 |
| ATGCCTGCTT AGCCAGACGG ACCTTAAATT CACGGCTGTA GCTGGCTCGC CGTTCTTTTC | 1620 |
| GCCATGTGCC TTCGCTGATT TGAGGCTCTG TTAATTCCTT CTTTCTGTTG GCATAAAGGA | 1680 |
| TGGCGTCAAG CTGAGCTAAT GAAACTGAAT CGGGCAATGG CCATGCGATA CCGGATGCAA | 1740 |
| TAAATCGCTG AAAAAGCGTA TGTATTGTGG AATGACTGAG ACCTAGACGC TGAGCGATGG | 1800 |
| CCCGGATGGT CAGTTTATCT TCAAATCTTA AACGCAGAGC ATCAGGCAAA TAAGAACGGA | 1860 |
| AGCAGGGAAT ATCTTTTTTT GTCTGGGAAT TCATCGTTCG TGTCCATCTA TATAGATGGG | 1920 |
| CGCGATTGTT GCCAGACAGG ACAATTTTCA CAAGACGTCG CAGATGGGGC GCTTACCAGA | 1980 |
| AATGCGCGGG TACGACAGTG ACTCGTCAAA TCTCAGTTGT AGCACACGCG GGATCAATTC | 2040 |
| CGGATTGTCT GCCAGTACCG CCTTTCGTGC ATTCATCTTA AATGTCCCTT TACTGCAAAA | 2100 |
| ATGGACATTA GTATCGGAAA CAGGAAAGGG AGGCGAAAGA CGGTTTAAAT GAGACGGTTA | 2160 |
| CCATTGTGTC GGGCTGTGTA CGTTCTCCCC GGACAGACAG CCTCAGTTCG TAGAATCTAT | 2220 |
| AAATTACTGC TACTGATGCT GCCGGGGAAA GGCGTAACGA AAAACAGCC TCCGTTACCG | 2280 |
| GACAGCAAGG AGGCTGAATG GAGTTTACAG GATTTGCTTT TTTATAATGT CTGGCCATGC | 2340 |
| AGTAAAACCG GACAGGTTTT ATTATCATGT GAGGTATTCT GACATAAAAT GCTGGATTTT | 2400 |

```
TATTTTGTGA CGAATGCTGC AAAATTGCAT CTGCACTCTG ATGTAGCTTT TATCTGTTTC    2460

AGTGAAGCAT GCCCACAAAC TGAGTTATTA AGTTGTGGAA GAACAGTTTT GTCCCGCCTG    2520

CATCTCTCCT TTCAAAAACC AGTATGTCGC CATGCC                              2556
```

(2) INFORMATION FOR SEQ ID NO: 62:

(i) SEQUENCE CHARACTERISTICS:
        (A) LENGTH: 790 base pairs
        (B) TYPE: nucleic acid
        (C) STRANDEDNESS: double
        (D) TOPOLOGY: linear (xi) SEQUENCE DESCRIPTION: SEQ ID NO: 62:

```
CAGTTAGTGT TAAAAAATNT CCTCTGCTNC AGAAATTACA CCCACCAATA TACAATNATT      60

AATAAATTTT CGGTTGGGTT AGGTAATGGC TGGGATTCGA TAATATCTCT TGATGGGGTT    120

GAACAGAGTG AGGAAATATT ACGCTGGTAC ACAGCCGGCT CAAAAACAGT AAAGATTGAG    180

AGCAGGTTGT ATGGTGAAGA GGGAAAGAGA AAACCCGGGG AGCTATCTGG TTCTATGACT    240

ATGGTTCTGA GTTTCCCCTG AATAAGATGA TGGATTATCT GACTGGCTGT TCATCAGTCG    300

GATAATGATG AAAACTGATG AGCAACAGGT TGTGCGGGCA ATGTGCAGGA TCCGTCACCA    360

AAGGGTGGAA GTTGCGGGCG ACTCAGATAA ACGGGTTACA TGAGCTATTT CTGGAGTTTG    420

ACGAAGCCGT CTGGAAGGGA GAAGAGGCGA TTCCATTGAT GTCTCTGGAA ACATCTGTC     480

AGTCGTGCTG CTGGAAATAT TGATAGAGCA ATGGGAATGG TTATCCAACA TTGATGAACA    540

TATTGTATAT TTACAGAAAT TTTTAAAAAC AGGACTCAGC AGGTTAAATC GTGTAAAAAT    600

TACTCATGAA TACCATTATG GGCTTACAAA GCGATGTGGT TAAGCAGATC TTATTCAGGC    660

CTGTGCAGCG TAGGATTACA ATAGGATCGA ATAACGCCAT ACAGGGGAAT GGGAGATAGG    720

CTGATTCATC CTGTGGCTAT AACCAGGAGC ATATCGGGAA TCMANTATGT TACCCCAGAT    780

GGAACACCAT                                                            790
```

(2) INFORMATION FOR SEQ ID NO: 63:

(i) SEQUENCE CHARACTERISTICS:
        (A) LENGTH: 10906 base pairs
        (B) TYPE: nucleic acid
        (C) STRANDEDNESS: double
        (D) TOPOLOGY: linear (xi) SEQUENCE DESCRIPTION: SEQ ID NO: 63:

```
GCGGCCGCAG TACTGGATCT CTTTGCGGCA TGACGATGAG GGGGAGAGAA ATAAACTTAA     60

CCCAGTCATG GCAGATGAAG AACAGGCTTA CGTAAAAGGG TTATATGAAG GGATTATGCT    120

GATTGGTAAT ATAATCAATA AGCCTGAAGA AGCTAAAGCG TTAATCAAGG CAACTGAAAA    180

TGGCTGCAGA ATGGTGAGTA ACCGGCTGCA ACTTCTACCC GAAGAGCAGC GTGTTCGTGC    240

CTATATGGCG AATCCTGAAT TGACCACTTA TGGTTCCGGA AAATATACAG GATTAATGAT    300

GAAACATGcT GGCGCAGTAA ACGTCGCCGC TTCCACCATT AAAGGTTTCA ACAGGTCTC    360

GATAGAGCAA GTCATTGAAT GGAATCCTCA GGTAATTTTT GTGCAGAATC GTTATCCTGC    420

TGTAGTGAAT GAAATACAGT CAAGCCCACA GTGGCAGGTA ATAGATGCTG TCAAAAATCA    480

TCGTGTTTAT TTGATGCCAG AGTATGCCAA AGCATGGGGC TATCCGATGC CCGAGGCTAT    540

GGGGaTTGGG GAATTGTGGA TGGCGAAAAA GCTGTATCCA GAAAAATTCA ATGATGTTGA    600

TATGCATAAA ATAGTCAATG ACTGGTATAG AACGTTTTAC CGTACTGATT ATCAGGGTGA    660

AGACTAATGC GAGTGCTTGC TGCGGGCAGT TTACGCCGGG TATGGAAATC ACTTGTGTCA    720
```

```
GAGTATCAGG CCGATAATAT ACAGTGTGAT TTTGGACCAG CGGGTATATT AAGGGAGCGT    780
ATTGAGGTGG GTGAGGCATG CGATTTTTTT GCATCAGCCA ATATGACTCA CCCACAGATA    840
TTAATGtCCG CAGGanGAGC ATTGTGTATT AAACCTTTTG CCAGAAATCG TTTGTGTTTG    900
TATGTTCGGG CGAATAAATT CAATGAGAAT GACGACTGGT ATTCTTTATT AAATCGGGAA    960
ACATTGCGAA TCGGAACATC AACGGCGGGA TGTGATCCAT CTGGTGATTA CACTCAGGAA   1020
CTGTTTGAAA ATATGGGAG TGTCGGTGAA AAAATAAGGC AACGGGCTGT AGCATTAGTT   1080
GGGcgGGAGG CATTCGTTTC CTCTTCCAGG AAATGCGATA gcAGCGCAGT GGTTAATTGA   1140
AAATGATTAT ACTGATCTGT TCATCGGTTA TGCCAATTAC GCTCCTGGCT TGCAATCAAT   1200
TGATTCAGTA AAAGTTATAG AAATACCGGA ACCTTATAAT CCGATTGCTA TCTATGGATT   1260
TGCCTGTCTG ACCGATAATG CCCTGCCACT TGCCGACTTT TTAGTTTCAC CTGTTGCCAG   1320
AGGTATACTT GAACAGCATG GGTTTATGCC TCCAGGTACG TTATAGCCCC CTGTCTTACA   1380
GCTGtCTCTT gATCAGATCT CCTGATCAAG AGACTTCATC ACCAGGTAAC CCTCAACCAT   1440
ATCCTGCATA TCCTGAAGTC TGAACCAGCC ATCCCACATA ACTACCCAAC CGGGGCGGCC   1500
TGTGCGTTTG CTGTCATGCC ATCGCCCCAG TTTCGCCAGT TTCAGACAGG CCCATTTCAG   1560
TGTCGGCGTC TGTGACGGAA GCGGTTTTCC TTCCAGCTTA ACCCACAGCA GTTTCCACTC   1620
TGTCGGCGTC AGTATTTTCT TACAGCTGTC ATTTTGTGTT TCTTCACTGA TACCTCCCTG   1680
CCGCAGGCCa GCACCCGTAC CGCGATAAAC GCCTTGATAA CCACCATGCG CTCAAGGTTA   1740
TCCCGGGTCT GCATTCGCAG CGATTCCACA CATGTACCAC CACTTTTCCA CGCCTTGTGG   1800
TATTCCTCTA TCAGCCaGCG TCGCTCGTAA TGGCTGACGA TACGTCGCGC ATCGGCGGCA   1860
CTCGCCACTT TTTCTGACGT CAGCAGATGC CAGCAGGCAC CGTCCTCTGC CTGCTCCCGG   1920
CAACAGACAT ACGTGAGCGG GAGCGCCTGG CCGCTGTTGT CGGGATTTTT TATGCTGAcT   1980
TCGTTGTAAC TGATGAACAT CCGGGCCtgg CGGGCTGCCC GCCCGCCTTT TTGCATCACA   2040
TTCAGCGTGT GGCTTCCCGC GGTTGCCAGG ACTTCCGGCA GTTCGAAGAG CTTGCCGGGT   2100
GCTTCTTCCA GCCGGCGATT CTGTGCAGCA CGCACCACGA AGCGCTGTCC GTGGCTGACT   2160
TTATAATGCA GGTAATGCTA GATATCCGCT TCCCGGTCAC AGACAGTGAT TACCCGTTTC   2220
TGTATCTCCC CCAGCCGTTC GGCCATACGC TCCGAAGCCT GCTGCCAGCG GTAACTTTCT   2280
TTTTCTTCAT AGGGACGTTC TTTTCGCTGG TGCTTAACAC CATAGGtgtC CGTGACCCGA   2340
CTCCAGCGCT GCTGTTCGAT AAGACCGACT GGCAGGGCGC TGTCGGGGGC GTACATCAGG   2400
ACAGAGTGAG CCAGCAGCCC GCGCGTCTTC GGGTTAGTGG TGGTATTCCC CAGGTCATCA   2460
GATGCCGTAC TGTGGCTGAA GTTAATGGTG GTGGTGTCTT CCAGTGCGAG GAGCAGCGGA   2520
TGAGCCTCAC ATGCCCTTAC AGTGGCGGTA AATCCGGCTT CGGCAATGGC TTGCGGGGAC   2580
ACAGACGGGT TACGTATCAG GCGGTACGCA CCTTCAACCT GAGCAGTGGA CTGGGATGAT   2640
TTCACAATAG AAAGACCTGC ATGCTGAGCG AGAGAAGAGG TCAGTGACAC AAGGCGTCGT   2700
GTACGACGCG GATCACCGAG ACGGGCATGT CCAAACTGCT CGTTAGCCCA TGAATAACAA   2760
TCAGAAAGTA CCATAACAGA GTCGAATAAA ATGAAATATA AGAGAAGATC AACGGGTGAA   2820
GAAAAAGTTC AAAAAATGGC TACCGGGGAG GAAGGAAAGT ACCGGATGGA AGAGCCCCC    2880
CTAAAGCAGA CTGACAGACA TCACAAATCC CCGGGGGGA CTTGTGTATA AGAGACAGGT   2940
CTTACAGGGG GAGCGTCCGT CTTTTTATCA ACATCAGGCA ATGACATAAC ATTATGAACA   3000
AGCTCACAAG TCTGATGGTT AAATTTTATA ATGCTCCTTA CTAAGACCGT ATTTTTTCAT   3060
```

```
TCTGAGATAG AGTTTTTTCC GCGGGATTTG TAAATATTCA GCAACCTCAT TGATACGCCC    3120
CTGATGGATA TTAAGTGCCT CTGTGATTAT CTGTCGCTCA GCGTCCTCCA CTCGTCTGTC    3180
AAGCGGTGTC GGGGTTCCGA CGTGCATCAA CGGATTTGCT GTTTCTGCCA GCGGTAATAC    3240
TCCTACAGTA AATAGTTCTG CTGCATTGGC CAGCTCTCGC ACATTATTTG GCCACATGCG    3300
GCGCATCATC TCTTTGAGCA TCTCTTTTCC CACTTCCGGA ACAGGATGGT TAAGCCGTTG    3360
ACATGCTTTA CAAAGGTAAT GGCGAAACAG TGGTTCAATA TCATCGGGGC GTTGAGTTAA    3420
TGGCAGGCAA GCGATTTGTG TCATTGCAAA GCAGTAATAG AGCTCCGCGA TGATATGGTT    3480
GCTGGCGGCC AGCTCGACCA GCGAAGTGTC TCCAATACCA ATCAGGCGAA AAGGTCGGTG    3540
TTCCTGGCTT TGTAACTGAA CCAGATGGTA CTGCTGTTCA CGCGTCAGGT GTTCAGGATG    3600
GCTGAGCACT AATGTTCCCC CCTGAGCCAG CGCAATGAAA TCATTAAGCT GTGGTGCATT    3660
GTCTGGTGTC AGCTCGCGGT AGATAAATTC GCCTTGTGCA TTACGTCCAA ATTGGTGCAG    3720
ATAACGTGCA CCGGTCATCC GTCCTGTGCC TGGGGCACcG TAGAGCCAGA CGGCAATATC    3780
TGTTTCAGAC AACTGCTGTA AACGTCGCCG ATACTGATTT ATCCATTCAC TTCTCCCTAT    3840
CAACTCCACC TGCAACGTCT GTTGGCAATA CTGACGACGC GCAATGATTG ATTGACGCTG    3900
GCGTAgcGCC TCTTCAACCA GAGAAAGCAA TTTGCCGGGA TCAACCGGTT TTTGCAAAAA    3960
ATCCCACGCG CCTTTTTTTA CCGCATCAAC TGCCATTGGC ACGTCGCCGT GCCCGGTaAT    4020
AAGCAGAATG GGGATCTGTT GATCATCCTG GTGAAATAAC ATCATCAAAT CGATACCAGA    4080
GCAGCCAGGC ATACACACAT CACTTAGCAC AATACCTGGC CAGTCTGGTT GTATCCACGT    4140
CTGCGCCTCA AAAGGATTGT TACAGGCAAA AACCCGATAG CCTGACTGTT CAAGTAACTG    4200
TGTGTAGGCG TCCAGCACGT CAGCATCATC ATCAATCAGC AGAATCGAAT ATTCACTACT    4260
TAGCATCTTC CACATCCGTT AGTCTGAATT GCAGTACCAC ACAGGCATTC CTGGTCATCG    4320
TTGATGCCAG CCGTAATTCA CCTTTCATTT GCTCCATCAA CGACACACAA ATTGAAAGAC    4380
CAATACCCAG TCCTACTTCT TTACTGGTGG TAAACGGCTT CAATAACGAA GGCAACAATG    4440
CCTCAGGCCA GCCCGGGCCA TTATCGCCAA TGAATACGTT CAGCGTTTTA CCCTGCATTT    4500
GCCAGTTAAC GGTAATGACA GCGCCTTGCC CACAAACATC AAGCGCATTC GCCAGTACGT    4560
TAACCAGTAC CTGCTGGGTT CTGACCTCAT CGCCTGAAAC TGTGGCTGTA CCTTGCGGCA    4620
GAACAAGCGT AGCTTGCAAA GGGCGATGAC GCATGGCCAG AAGTTCCCAG GCCGCACTGA    4680
ACATCTGTGC TAAATCAACG GAATGGAGTG ATATTTCCAG TTCGGCGCGC CGGGTAAACT    4740
GCCGTAGTGA ACGGATAATG GCGTCAATGC GACCAATCAC CCcTTCGGCT TTACCAAGCA    4800
TCATGCTGGC CTGTTCTGTC TGGGTCTGTT cAaTGcCTGC GGGCTGTAAA CAGATACATC    4860
GACAGCGCAT TTAGCGGCTG ATTGATCTCG TGGGCCAGCG TGGTCATCGT TGCCCGACT    4920
AnCCGCaGct TCGCTGTCTG AATCAGTTCG TCCTGGGTGG CTCGCAGATC GGCTTCTATC    4980
ACCTTTCGAT CGGTAATTTC TTGTTCAAGT TGCTGTTTTT GCACATTGAG CTGCCCGAGA    5040
GTATGGCGTA ATAATCCTGC AATTCTCCCC AGTTCATCAT TCCCATAAAC AGGAATAGCC    5100
GTTTCCGTGC CTCCCAGACC AATTTGCACA ACGGCCTGAT TCAGTAGGGT AAAGCGTTTC    5160
ACCAACCGTG AGCGGATAAA ATAATGGTTG AATACCCATG CCAGCAGTAA CGCCAGTGcT    5220
GTCGCCACCA GGATCAGCCC ACCgctAACG CGAACAATTT GTTCCATTCG TTGATTAAAC    5280
ATCTGCATTT GTTGATGAGT ACTGCcAAGT GCGCTTCCAG TAACGTTCTG AAGCGACCCA    5340
GTGTCGCTTc CCTGGTGCGA CTGGCATCCT CTAAGGCTTT TTGGGCGGTG ACATATTCAC    5400
GCATCGTAGC CGGCATTTTG TTTTTTACGA TTCCCATATC CAGCAATTCA TCGATAGTCT    5460
```

```
GCCTCAGGGT AATGGTGCCA GGCCAGTCAT CCAGCATACG TATATTTTCA TCTGCCGTTT    5520

TTTTCAGATT TTCAAAATAA CGGAGATGAG TTTCCACCTG TGTGTCGTCA TCACGTCCTG    5580

ATTTGAGTTC ATTGAGTCTG TCACGCAGAT CGTCAACAAT CTGATTTTCA ATGCGTGCCA    5640

GGGTATAAAC CTGCTGCTGT TCATTTTGCA CTTCACGAGA TCGCTTCAGG TATTGCGCCG    5700

TATCGCCyTG TCGGGAGGCG ATTTGATCCA GCAGCGTTCC CTGCTGCCAG GTGAAATCCT    5760

GCACTAAAGA ATTAAGCTCG GTAGTAAAAT CATCGTGTAA CCAGTCAATC CTCGCTGATA    5820

GCTCACTCAC CTTTTCCCGT AGTAAAAACA TGTTGTAAAG CGCACGATCC AACTCGGATA    5880

ACAGTGATCG ACTGTCCTGC AAAAtGACCG TCAGTTGTTG GCGTTCCCGG GATGACAGCC    5940

CCCGACTAAG CCGTTCTATG GTGTCGAGAT GCTGAATAAT CTGGGTACGA AGTTGCAATC    6000

GCACCGTGGT GTTGGGAGCC TGCAAAAATT CATTTAGCTG GTCTACCACC AGATTCAGGT    6060

TCCCTTCAAT AAGGAAAGCA GAGTGAATAC GGGGAAAATA CTCATCCAGC GAGTAACGAA    6120

TTTGTGAGCT TTGTTCATGC CATGAATACA GACTGACACT ACTGACAATC AGGGTCAGAA    6180

GTGCCCCCAT CAGAAATGCG CAACGTAAGC TGGTACTGAT ACTGACCTGT CTTAAACGCT    6240

GCCACAGCGT TATGTTTTTC ATTTCAGCTC TTCCAGTTTT TTTATCGCCA GGCGCTGGTT    6300

ATTCAGAAAC CAGAGTTGCC ATTCCATCAT TTGCTGCTCG GCAAAGCTTT TGTTATCGAA    6360

CTGTGCCAGC CAGACGGGAT CTTCACTGCT GGCCGCTGCA ACGGGCACTT GTGTTAACAG    6420

TGCACGTATT TCTGGTAATG GTTTCTTCAG ACGTGCCTCG GTACTGTGCA GCGCTCGCCA    6480

GGCATCTTTT AGCTGTGCTA ACCGAAAGCT AATTGCCGTA TCAAACAAGC GCTGCACCAG    6540

ACGCTGACGT TCAGGATAAA GGTGATAATT CAGCGGGGGT TGATTCATCA GGAGCTGTTG    6600

TTGCGTTGCC CGCGGATTGT CTGCGGCAAG TGGTGTCACC GGATATTTTC CTGTATTGGC    6660

ATCGGCCAGA ATACGCTGTC CTTTCGGACT TAACAGGTAG TGAATAAAGC GACGGGCTGC    6720

ATCGACGTGT GGGCTTTTCC TGAGAATTGC AACGTAGGTG GGGGATACCG CAGACCGGGG    6780

GAAATAGGTA AAAGAGAGAT GGGGGTCATT TAACAGTAAA TTAGCATAGT TATCGATAAC    6840

GGGGCCGGCA ACGCCGAGTC CGCTTTTTAT TTTAnTCGcT ACGCCAAAAC TGCGGGAGGA    6900

GATTGTCACC AGGTTTCCTG CACTTGTCAG CAACGTTTCC CATCCTTTCA CCCAGCCTTT    6960

TTGCTGTAGT AATGACTCAA CCATTAAATG GTTAGTATCT GAACGCGACG GACTACTCAT    7020

CAATAAAGCG TCCTGATAGA TCGGCAAAGC AAGATCGTCC CAGTCAGCAG GGGCAGGAAG    7080

GTGTTTTACA GAAAGCGCCG GACGATTAAT GAGCAGACCA AAACCTGATA TTGCTACTGC    7140

AACGGAGGTT GCACGGATCG ACTCCGGCAC CAGGTTTTGG CTTTCTGCGG GTGCATCATC    7200

AAACGGGGCC AGTTCTGGT GCTCCTGAAG GTGCTGGAGC AGCATTGGTG ATGAAGTCAG    7260

GATAAGATCG ACGTTTTCTA CGTTGGCCGT ATCAAGCAAc TGTTCCAGTG AGGCACTGGT    7320

GCGGTTAAGC GTACGGATCA TTACCGACTC AGGCTCTGTT TGCCAGCGCT GTATTATCCA    7380

CGCGGTAGCT CCGGGTGAGA ATGTGGTGGC CATCACCAGT TCATTTCGTT GAGCCcTGAC    7440

GGCCCCGGCG TCCATCAGCA ACAGTAAAAG AATCATGGTT TTGATGCCGA TTTCGCACCA    7500

GCTAAAAAAT CGGTTTGTGA TCCAGGTCAT AAATATTAAT ACACCGCAAA ATCGCATTG    7560

AGACAAAAAT TACCCGTTTC AGACATTCGT CTGATAACAC GTCTGCTCAA AGAGACCGTT    7620

AATATATTAA TCAGAGATTA CCCGATAATC AGCATGAGAT TGTTAATAT CCGCACATGC    7680

TAACAACAAA CCAGATAAAG CATAAATCTA CCTTGTCTAT GCATCAATAA AATGGGTCAA    7740

AAACAGGCTT TGATTTTATT ATTTTGTGTC AATTGTGACA CATTTTTTCA GTTTGATGTT    7800
```

```
TCATYTCAAT TATATGACTC TCATTGTCAG AATACTCCTG ATGTTCATAT CAATATAAAA    7860

TACAGGTGAA GACATGTTAT CAATATTTAA AACGGGGCAA TCGGCGGATA GTGTTCCGGT    7920

GGAGAAAATT CAGGTGACAT ATCGTCGCTA TCGTATGCAG GCGTTACTTA GCGTATTTCT    7980

GGGGTATCTT GCATACTATA TCGTGCGTAA TAATTTCACT TTATCGACGC CTTATCTTAA    8040

AGAGCAATTA GATCTCAGCG CCACACAAAT TGGCGTACTG AGTAGCTGTA TGCNTATCGC    8100

CTATGGTATC AGCAAAGGAG TGATGAGTAG CCTTGCCGAT AAAGCCAGTC CGAAAGTCTT    8160

TATGGCGTGT GGGCTGGTGT TATGTGCCAT CGTTAACGTT GGCCTGGGAT TCAGCACTGC    8220

ATTCTGGATT TTTGCGGCAT TGGTTGTTCT GAATGGTCTT TTCCAGGGAA TGGGCGTTGG    8280

TCCTTCTTTC ATCACTATTG CTAACTGGTT CCCTCGCCGG GAGCGTGGTC GGGTTGGTGC    8340

TTTCTGGAAT ATCTCTCATA ACGTCGGTGG TGGTATTGTT GCCCCTATTG TTGGTGCCGC    8400

TTTTGCCCTA CTCGGCAGCG AGCACTGGCA AGGTGCGAGC TATATCGTTC CGGCCTGCGT    8460

GGCTATCGTT TTTGCGGTAA TTGTGCTGAT TCTCGGTAAA GGTTCCCCAC GTCAGGAAGG    8520

TCTACCCTCT CTGGAAGAGA TGATGCCGGA AGAAAAAGTC GTCCTGAATA CCCGACAGAC    8580

GGTAAAAGCA CCAGAAAACA TGAGCGCCTT TCAGATTTTC TGCACTTATG TATTACGCAA    8640

CAAAAATGCC TGGTATGTCT CACTGGTTGA CGTATTTGTA TACATGGTGC GCTTCGGGAT    8700

GATTAGCTGG TTGCCTATTT ACCTGCTGAC GGTGAAACAT TTTTCTAAAG AACAAATGAG    8760

CGTCGCGTTT TTATTTTTTG AATGGGCCGC AATCCCTTCC ACGCTACTTG CCGGTTGGTT    8820

GTCAGACAAA CTGTTTAAAG GGCGTCGTAT GCCATTGGCG ATGATTGTA TGGCGCTGAT     8880

TTTCATTTGC CTGATTGGCT ACTGGAAAAG TGAATCGCTG TTTATGGTGA CAATTTTTGC    8940

TGCCATTGTT GGTTGCCTGA TTTACGTTCC ACAATTTCTG GCTTCCGTTC AGACTATGGA    9000

GATCGTTCCC AGCTTTGCTG TTGGTTCTGC AGTAGGCTTA CGCGGTTTTA TGAGCTATAT    9060

CTTCGGTGCG TCTCTGGGCA CCAGCCTGTT TGGTATTATG GTCGATCATA TTGGCTGGCA    9120

TGGCGGATTT TATCTTCTTG GCTGCGGTAT TATTTGTTGC ATCATTTTCT GCTGGTTATC    9180

ACATCGTGGT GCAATTGAAC TTGAACGTCA CAGAGCCGCA TATATAAAAG AACACTGATT    9240

ACCTTCCCCA GGGCCGTCTC CCTGGGGAGT GGAGTATATT ATGATTTATA AGATATCTGG    9300

AAATCAGAGA TTAATATGGA AATTTTATAA GACTGATTAC AATAAATGGA GATGGTATTG    9360

TCATGAGAAA AATGGATATC TTTTGTCTCA ATCAGATAAC GCATATAATT CGCAATTGTT    9420

ATGCATTGAA AATGCTAAAA AACAGGGATA CTCAGACGAA TCGGTCTTGC CACTTTTTCT    9480

ACATATTTCC TATATTCAGG AAAAAGGCTG GAAATGGTAT CAATGTTATG ATTGTGGATA    9540

TATTGTAAAA GAAACCTCTG TTTTTTTTTC GACATACCAG GAATGTGTCA ATGATGTTAA    9600

AAGGAATATA CTAGCATCTA TGTGTAGTGG TTGTAGTGGC ACAGTAAATT TGGCCACCTG    9660

ATTAAAGGTG ATATTCTCAC CACAACATAA AACAACAAGA AAACAAAGCG TACCTTCTCT    9720

CCTGAGTTTA AACTGGAATG CGCCCAACTT ATCGTTGATA ACGGTTACTC ATACCGGGAA    9780

GCTACTGAAG CTATGAATGT TGGTTTCTCT ACTCTGGAGG CATGGGTACG TCAGCTCAGA    9840

CGGGAACGTC AGGAGATCAC GCCTTCTGCT GCAGCACCAC TCACATCAGA GCAGCAACGT    9900

ATTCGTGAGC TGGAAAAGCA GGTGCGTCGT CTGGAGGAAC AAAATACGAT ATTAAAAAAG    9960

GCTACCGCGC TCTTGATATC AGACTTCCTG AATAGTTACC GATAATCGGG AAACTCAGAG    10020

CGCATTATCC GGTGGTCACA CTCTGCCATG TGTTCAGGGT TCATCGCAGT AGCTACAGAT    10080

ACTGGAAAAA CCGTCCTGAA AAACCAGATG GGCTGTATTA CACAGTCAGG TACTTGAGCT    10140

ACATGGCATC AGCCACGGTT CGGCCGGAGC AAGAAGCATC GCCACAATGG CAACCCGGAG    10200
```

| | |
|---|---|
| AGGCTACCAG ATGGGACGCT GGCTTGCTGG CAGGCTCATG AAAGAGCTGG GGTTGGTCAG | 10260 |
| CTGTCAGCAG CCGACTCACC GGTATAAACG TGGTGGTCAT GAACATGTTG CTATCCCTAA | 10320 |
| AAGCAACAGC AAACAGCGAC CACTGGGGAG CCCTGCATTG CGGGATTGTA TTGTTCAGCG | 10380 |
| GGCCATGCTG ATGGCGATGG GGCCGAGGAG AGTGATTTTC ATACGCTCTC ATATGGTTTT | 10440 |
| CGACTTGTGC GAAATGTCCA CTACGCGATC CGCACGGTGA AACTGCAACT CACCGACTTC | 10500 |
| AGGGGAAACT CGGGGCCGCT GGGTAATCTC ACATAAAAGT TCTTCGGTGT CATAAACAAC | 10560 |
| GAGAGTATTT GATTCCTTTA TGGTGGCCTG GTGCAGAGCT GCCCTTTCCC AGGACCTCCA | 10620 |
| TATAATTTTT GTAGCGGCAG TCAGTGGCAC ACTCAGTTAA CTACTTTCAC TTCAGTGACT | 10680 |
| TTGAATGAGT CAGGGCTGCC GTTAAAGGTG TTAATGAAGG CTTGTATTTT CCACTTCTGG | 10740 |
| CCTGGTTCAA GATTGGATGC TGTGTCGATT GTTTGACCGA TAACGACTCC ATCTTTTAAN | 10800 |
| AGATTAAATT TTACATAAGC ATTTTTGACA ACAGAGTTTG ATTTATTTNC AGCATAACCC | 10860 |
| ACAATTGCCT TCGTCCCACT TGGGGTGTTT TCCACATGAA GGTTAG | 10906 |

(2) INFORMATION FOR SEQ ID NO: 64:

(i) SEQUENCE CHARACTERISTICS:
        (A) LENGTH: 7430 base pairs
        (B) TYPE: nucleic acid
        (C) STRANDEDNESS: double
        (D) TOPOLOGY: linear (xi) SEQUENCE DESCRIPTION: SEQ ID NO: 64:

| | |
|---|---|
| ATGGTTATTT TTATTTCCTG CACCTTGCTT CATTTGAAAT AAAAACATAT GCATACGACG | 60 |
| CTGCCATTGA GCAGAAAAAT ACAGGAATTA ATGTTATGAG TTAACCATAA TACCTGTGTT | 120 |
| ATGAATATCT GACATAAACA AGAACAATTC ATATCTTCTG TATTCAGCAG AATAATAAAA | 180 |
| GTTCGTCTGC CATTCTCAAA CTTATTCTTC GGAATACGTT GTTTCATGAA AGAAGGGGCC | 240 |
| GGAATAAAAG CTGGTCACCG TAATGCTAAT ATTAATGCAG ACTACCGCCT TCTGGAATTA | 300 |
| ACAGTCATCA ACCAGCACAA ACCATTAGCA ATCAAACAAA TTTTAATTAA CAAAATTTTA | 360 |
| GCTAATACAA TTACTGCATT AACCACTCTG CAGTTTGCCT TCTCAATAAG TTACAGATGC | 420 |
| CAAACAATAC TCTTTTATAT GTTATAACAT AACACAAACA ATAAATAAAG AACAGACGGC | 480 |
| ACTCCATTTC TCCACGTAAG TGAGCCATCA GAATCGCTTA TGAATGTGTA CGGCAGACGT | 540 |
| ATACTCGTGT TTTACTGCAG CAACCGGAGC AAAAGTTGCA CTTCCACAGC CTGGGTTAAG | 600 |
| TTTTTCATGC TTGTGGGCTC GTCCTCCCTC CATTTCCACC GCGGGCAAAC AAGGCCATCT | 660 |
| TTTGTCTGGC CACACAGCAG ATGGAGAGTC GAATTATGCT GTCTGACGAC ACCGGGAACA | 720 |
| AATATGCCAT GCCTTCGCAC AATGAACCCG GCATCATCG TTTTATCTTT ATAATCGAGA | 780 |
| CAGGTATGAG GGAAAGTCGG ATGATAAGCA GATAGTGAGT GAGGCGCTGG AACATGGCGC | 840 |
| TCTGGCAAGA GAAGTGTCAC AGGTTACCTG ATGATATGGG GCAACCTGAT ATCTACTTAC | 900 |
| TTTTTTGCCT ACTCTCTTAC TTCATGCCAG CAGCGAGGGT ATCGACATTG TGTTTGAACG | 960 |
| CTGCCGTGTA GGTAGCAGCG AGGCCGCTAC TGTCGGTAAG TGCTTCCGGA TAAAGCTCTC | 1020 |
| CTCCCGCTTG TGCACCACTG GCATTGGCGA TTTGTTTCAC CAAACGGGGA TCTGTCTGGT | 1080 |
| TTTCGATAAA GTACAATTTT ACGTGCTCTC TCTTAATTTG ATTAATCAGT TCGCCACAT | 1140 |
| TTTTACTGCT AGCTTCCGAC TCAGTGGAGT ACCCCACTGG CGACAGAAAG CGAACCCCGT | 1200 |
| AGGCGGCAGC GAAATACCCA AACGCATCAT GACTGGTCAG TACTTTACGT TTTTCTCTTG | 1260 |
| GAATAGCAGC AAACGTCTGC GTGGCGTAAT TATCCAGTTG CTTCAACTGC TGGATATAGC | 1320 |

```
TGTCACCCTG TTTTCGATAA TCGCTGGCGT GCTCCGGGTC TGCTTTGCTC AGGCCATTGA      1380

CAATGTTGTG AGCATAGACA ATACCGTTTT TCATGCTGTT CCAGGCGTGC GGATCAGTGA      1440

TGGTGATCCC ATCCTCTTTC ATTTTCAGTG TATCTATTCC GTTAGACGCG GTAATTACCT      1500

CACCTCTGTA GCCAGAGGCT TTCACCGAC GGTCCAGCCA TCCCTCCAGT CCCAATCCAT       1560

TGACAAAGAC AACATCCGCC TGTGCCAGCG TTTTGCTGTC TTTCGKCGAC GGTTCAAATT      1620

CATGTGGATC ACCATCCGGT TGCACCAGAT CAGTGACATG AACGTATGGG CCGCCAATCT      1680

GGCTGACCAT ATCGCCCAGT ACCGAGAAAC TTGCCACCAC ATTCAACTCT TTTGCAATCA      1740

CCAGTGGGCT CACTAGTAGG CTGGACAGTG CCACAACCAA AATGGACCGT TTCATCTTTC      1800

CTCCTTCATC TCGTTGCTAT GTGTAAAAAC ACTTCTTGTC AGCGACATCT GCATAACATG      1860

CCGCCATTAG AGCCAAACAG AACTGAAAAG CAGAAAAACA GAGTGCTCGT GAGGATGACT      1920

GCAGGACCTG CAGGCAAATC AGCGTAATAA GACCAGATCA GTCCAACCAG ACTGGCGCAG      1980

GTACCAATAC CCACTGCAGC TAACAACATG ATGGACAGAC GTTGACTCCA GAAACGCGCG      2040

CTGGCAGCCG GTAACATCAT AATACCGACT GTCATCAGGG TGCCAAGTAG CTGGAAACCT      2100

GCCACCAGAT TGAGTACCAC CATTGACAAA ACAGGCAGT GGATCAGCGC CCGCGACCGA       2160

CGTGACAGAA CTTTCAGGAA AGTGACATCA AACGACTCAA TCACCAGCAC CCGGTAGATC      2220

AACGCCAGTA CCAGAACCGA ACCGGAACTA ATTATGCCGA TAGTGATCAG AGCATTGGCG      2280

TCAATAGCCA GAATGGAACC GAACAGCACA TGCAGCAGGT CGACACTGGA GCCACGCAAA      2340

GAGACCAGGG TGACGCCAAG TGCCAGCGAG CCGAGGTAAA ACCCGGCGAA ACTGGCGTCT      2400

TCTCTCAATC CAGTGCGGCG GCTGACCACA CCAGACAACA TCGCCACAGA CAGCCCGGCA      2460

ATGAAGCCAC CGACTCCCAT CGCAACCAGC GACATGCCCG ATACCAGGTA GCCAATTGCT      2520

ACTCCCGGCA ACACCGCATG GGACAGTGCA TCACCGATCA GGCTCATACG GCGCAGTAGC      2580

AAAAAACAGC CAAGTGGCGC GGCGCTCAGG GTCAACGCCA GACATCCGAC CAGCGCCCGA      2640

CGCATAAAAC CGAAATCGCC AAATGGCTCG CACAACAGGT GCAGTAACAT CATGGCAGCA      2700

GCCCCTGCTG CGGTGGCGTG GCTGCAGCCG TGAGGGAATG GAGTATATCG GCACTTCTCC      2760

CCCATCGGTG GCCTTCCGCA CTGAGCATCA GTACATGAGG AAAGTATTTT TCTACCTGTT      2820

CCATGTCATG CAACACCGCA AGAATTGTAC GTCCTTCCAG ATGTAGCTGC CGAATAACAA      2880

CCAGCAGAGT ACGGATAGTC TGAATATCAA TGCCAGTAAA TGGTTCATCC AGCAGAATAA      2940

CCGACGGCTG CATCACCAGC AGTCGTGCGA ACAGTACGCG CTGTAACTGA CCACCGGAAA      3000

GTGTGCCGAT GTGCATCGGC GAAAATTCTG TCATACCGAC GGTATCCAGC GCTTCGATAG      3060

CTTTTTTTCG CCATAGACCG GAAATACGAC CGAACATCCC GCTGTGTGGA ATACATCCCA      3120

TCAGCACCAG ATCGTTAACA CTCAGTGGAA ACTGGCGATC AAATTCAGTC AATTGGGGCA      3180

AATAACCTAA CTGGCGTTGC CCCTGCGGTG CCATGCAGAA GCAACCACCC AGAGGTGGCA      3240

GCAGACCGGC CAACGTTTTA AGCAAGGTGG ATTTACCTGT GCCATTCGCT CCGATAATGG      3300

CAGTCAGTGA ACCGGTGTCA AAACATCCAT TCAGCGTACC CAGCGGGTGC TGTCCCGAAT      3360

AGCCAAATGC CAGTGAATGT AATGCGATCA TGTCAGTACC ACCGCCCAGG AAATAAGAGT      3420

CCATAACAGT ACCAGCAGCA CACCGACGAT ACCCAGTCGG GCTATTGCGG AAAAAGCATA      3480

AAGACTGACC ACAGTATCCC CCATCAAAAT TGTTATAGTA TAACATTATT GCTTTATGGG      3540

TGCCGATGAT AGGTAAGAAA ATGTGTCATG GCTTCTGCAG CGTAAGCATA CAGCGAGAGC      3600

AGTATTGACA GGGATGCGTT AGTCATTTAG CAGTGTAATG CGCTAAATAG NTGCGCGGAA      3660
```

```
TAGTAGATCA CTTTGAGGGT ACTCAGCCCG GATTGTGCGC TCTGATCAAT CGCCAAATCA  3720

AAACAAATCA CCAACCGAAC TGAGCAATGC CGATCATAGC ACCAATTTCC CGTGACGAAC  3780

GACACCGGAT GCAGAAAGCC ATCCATAAAA CACACGATAA AAATTATGCC CGCAGACTGA  3840

CTGCCATGCT GATGCTGCAC CGGGGCAACC GTATCAACGA CGTTGCCAGA ACGCTCTGCT  3900

GCACCCGTTC ATCTGTTGGA TGCTGGATTA ACTGGTTACT AAAATCATTC CCTGCCGGGC  3960

GTGCCCATCG CTGGCCATTT GAGCATATCT GCACACTGTT ACGTGAGCTG GTAAAACATT  4020

CTCCCGACGA CTTTGGCTAC AAGCGTTCAC GCTGGAATAC AGAACTGCTG GCAATAAAAA  4080

ATCAATGAGA TAACCGGTTG CCTGTTAAAT GCCGGAACCG TTCGCCGTTG GTTGCCGTCT  4140

GCGGGGATAG TGTGGCTAAG GGTTGTGCCA GCTCTGCGTA TCCGTGACCC GCATAAAGAT  4200

GAAAAGATGG CAGCAATCCA TAAGGCACTG GACGAATGCA GCACAGAGCA TCCGGTCTTT  4260

TATGAAGATG AAGTGGATAT CCATCTTAAT CCCAAAATCG GCGCTGACTG GCAGTTACGC  4320

GGACAGCAAA ACGGGTGATC ACGCCGGGAC AGAATGAAAA ATATTATCTG GCCGGAGCGC  4380

TGCACTGCAG GACAGGTTAA AGTCAGCCAT GTGGGCGGCA ACCGCAAAAA TTCGGTGCTG  4440

TTCATCAGTC TGCTGAAGCG GCTTAAAGCG ACATACTGTC GAGCGAAAAC CAGCACGCTG  4500

ATCGTGGGCA ACAACATTAT CCACAAAAGC CGGGAAACAC AGCGCTGGCT GAAGGAGAAC  4560

CCGAAGTTCA GGGGCATTTA TCAGCCGGTT TACTCGCCAT GSGTGAACCA TGTTGAACGG  4620

CTATGGCAGA CACTTCTCGA CACAATAATG TGTAATCATC AGTACCGCTC AATGTGGCAA  4680

CTGGTGAAAA AAGTTCGCCA TTTTATGGAA ACCGTCAGCC CATTCCCGTA GGGGAACATG  4740

GGCTGGCAAA AGTGTAGCGG TATTAGGAGC AGCTATTTAG GAGAACAGCT CGCTGACCCG  4800

GTTGACTATG ACTCAAGCCC ATGACGAAGA TAGCTTTCTG GATCAACATC GTTCAGTCTG  4860

CACGTCCCAA TCCAGCCACC AGCCACCAGC CACCAGCCAC CAGCCACCAG CCACCAGCCA  4920

CCAGCCAGGC TACAGTGCCA TCCCGACCTC CCCACGTAAA CCCAGGGACA GGCTAAAGGC  4980

AGAAAATGGG GAAGGCAGTA TGACTCTCCG TGACACAGAT GCGGGTACCT GATGGGAGTG  5040

AGATCATCTT CCCCTCCCGG TCAGTTCCCG GATCAACACC GTGAGCAGCT CTGGCGAAGG  5100

TTTTTCCAGC GTCATTTTAC CGTAACGAAA TTCAACCTTA CAGGAACTGG CACAGACTGT  5160

GCACTAAGTG GCAGTGGATA AAAGCGGAGT AAGAGCCGCC ACAGGCTCTT TCTGCTCATC  5220

AGGCATTATC TCAACAGGTA ATAATTCAAC GCCAGCGCCA GAAGAGGTTG TTACCGGAAG  5280

ACGCCGCGCC CCCCTTCGTT CAGCCAGAGC CTGAGCCATT TGACCAGGAG GTTATCATTG  5340

ATATCGTGTT CCTGGTCAAT ACGGGCAACA GAGGTGCCTA CGACGTTTTT TCAGTTCGGT  5400

TATCTATTGA CTTAACTCTT TGGCCAGTAA TGCTGCAGCC CCCGTGCCAT GAATAAACGA  5460

GTGGTCGCAG ACCACGCAAC ATGCAACATC ATTCAGATCC CCGCTAATA TTACAGGTAA  5520

TTCAGAATCA GCAATACTTT TCCCGACCAT TAAAAGTTCT GAGTCACGAT CAGTTGACTC  5580

ATCACTTTCA GTCGGGCTCG GTGGAACAGG ATGAAGACAA TGTAATCTTA TTCTCAAACC  5640

TTCTGGCATA TGAACTATCA TATTCATGGA GGGAATTTCC TTGTCCACTA AATACTGTAT  5700

TTCTGCATCA CTTAAAATCA TCCAGGAATA TACATGCATG CCATATAAAT TTTCTTTCGG  5760

GCATTTCAGG GAGTATGGAA ACACTTCATC CAGAGGTGAT AGTTTCTGTT CCCACCATAA  5820

GTTTGTTTCA AGAAGAACAA GTATATCAGG TTTTTCTTTA TTTATAAGTT CAAGAATGGG  5880

TATATATTTT TTATTGGTCA TAAGAACATT GAATACCAGT ATACTTAAAC CCAGAAATCC  5940

ATCAGAGTCC TTTATTTCCT TTACCTGCTT CTTGCCAATT ACTGTATAAG GAATTATCCA  6000

TACCAACTGG TAAGCGACAC AAATTAAACT TATTATCCCA ACAACAACT CTGTAAATAA  6060
```

```
GTCAAGAAAA ACAACAGACA GAAAAACATT CAAAGTACAC AGCAAAAGTA TCTGTAGTCG      6120

GGGAAAATCC CATCCCCCGA CAACCCATGA TGTATTACCG GAAACAGGGA TAAAAGTTAT      6180

GACTGCCAGA AGGATAGCAG TAAAAATAAA AACACAAGTT ATCACAAATC GCTCCTTGTT      6240

CTGAACCGGA ACACAAAACT GTCATATACG TTTCAAAAGT AAAAATACAC TGCTGCCACA      6300

AGATTTACAG CGTAACCGGA CAGCATATCC TGATTACGGA CAATCCATGA AACCGCCTCA      6360

CCAGAAGCGT CCATCACATC CGTTTTTTCC CTGTTTTATA TTCCCCGAAA CATTTTATTT      6420

TCAGGAATCT CCGGGCCTTT ATCCCGCATC ATTGCAAAAT GGCATCTGAA TCGATCATGA      6480

TTTGGCATCC ATCTCCGATC ACAGTTTGGC ATCACAATCG ATCACGATTT GGCATGCTTC      6540

CGATCATTGA TTAGCATCCT GCCAGTCACT CCGGGAATTA ACTCTTTTCG CCACAGTCTT      6600

CATTGCCGTG TTTAAACCAA TGGAGACGGC AATGTCCAAA AGAGAATAT  CCAGGAGCAC      6660

TATGGATACC TGTTTTAAGA TCCTTCAGCT CAAGTTCGAC CAGAAGCTGG CTAACCGTTG      6720

TATCGGACTT GCAAAACACC AATGGGGATT GATCTCTATT TTGCGACACA GACGCATTAT      6780

CAATACATCG ATGGTGCGAT CAAATACCTC AGTGGTCTCA CCGTGGATCA AATCCAGCAA      6840

TTGCTCACAG ATTAAGACTC GTCGGGAGTT TTGAGCCAAC ACCAGCAGTA ACCCATATTC      6900

ACCTTGAGTG AAATCTACAG GCTGTTGATG AGCATCAACC AGCACGTAAC GGTCCGGGAT      6960

CAAGTGTCCA GCCGTTAAAA AAACCACTCT ACTACCCTGC TCGACCTAAG CCTCGGCGTT      7020

CAGCCGCCTG AACGGGTATG GCAAGGGTGA AAAGAAACAG CATCCCCACA GTACCGACCA      7080

GACGACAGGA TGATGCTGGA ACAGAAAGCA TTCGCACCTC TCTTAGAATT AGACAGTGCG      7140

TACAGGATAC GTAAGACAGG GTGACGGGGC GGCGATAAAC TCTATTTACA AAGCTGAAAA      7200

TTTTCTGACG ATGAAAAACT ATTCAACAAG GTTATCTGAG GCGTTAAAAT AACCAGCTCG      7260

ATTAACGACT AACTTGAGGT GAATATGAAT TTAAAAAATA TAATTTTAAG TACTGTTTTA      7320

TCAATCGCTA GTTGTCATGC CCTGGCTGTA GGTAATTCTC CAAATAGCGC TATCTAACCT      7380

TCATGTGGGR AAACACCCCC AGTGGGACS AAGGSCAATT GGTGGGGTTA                  7430
```

(2) INFORMATION FOR SEQ ID NO: 65:

(i) SEQUENCE CHARACTERISTICS:
        (A) LENGTH: 6681 base pairs
        (B) TYPE: nucleic acid
        (C) STRANDEDNESS: double
        (D) TOPOLOGY: linear (xi) SEQUENCE DESCRIPTION: SEQ ID NO: 65:

```
AGATTATTCT GGCTCAGATT CATTTTTCAT CAGTCGCTTT CCCCTATAAA CCGTAAGGTT        60

CCATAGTGTC GACGCTCTCG CTTAATTCCC ATATCGTCGA TAGTCTTATT AGCCGCTTCT       120

GTCAGGTCAG AAAAAGTATC ACGCTTCTTT GGGAGTTCAA GTCAGATTTC TCGCCGTCGG       180

GCGATGCGCT CAAAATGTTT GTCTGTATGG GGTCGCTTCA TCACGTCAAG CCATCGCGCT       240

GCCGCTCTCC GCCAGAGTAC AAGCTCTTCC AGTTGTTCTG CTTTTTATCT TATCTGTGGC       300

GATGCAGTAT CCTCCTCCGT TTGTGTAAAT CGTTGAGTGG TGAATCACGC AAAGGGGCTT       360

CTTTTTTCTG ATCTATCCCC ATATTCTTTA GCGTTCTGGT CGCAGCATCT CTGATGTCGC       420

AGACACTGAA CCTTTGTATT TTCCATGATC TTGTGGAGTT TTCGATACAT CTGCTCCGAT       480

GCTGGGTTAT AAAGATCCGC TCTTTATCAT CCTTGGCTTG TGTAAGCAAT CTCCCCAAC        540

GTTCTGCTGC ACGCCGCCAT AACTCTCTTC TTTCCAGTTC CTCAGCTTTT TCATCATGTA       600

CCATTCGTGT ATCCCCGTTT ATCCAGTCTG AACCGCACCG GGTTTCCTGG AGAATGTTTT       660
```

```
CTCTGTGAAC TCAGGCTGCC AGATCATCGT TTCCGATGGA AGCATAATAA GCTTTTTCTG    720

CTTCTGCCGG ARGAATATGG CCCAGCTTTT CCAGCAATCG TCGATTGTCA TACCAGTCCA    780

CCCACGTTAG TGTGGCCAGC TCCACTTCTG TCCGTTTTTT CCAGCTCTTA CGGTTATTAC    840

CTCCGTTTTG TAAAGACCAT TGATGCTCTC CGCCATTGCG TCGTCATACG AGTCGCCTGT    900

ACTCCCTGTT GATGCCAGTA ATCCGGCTTC CTTAAGCCGT TGCGGACACA TAATGAGAGC    960

CTTTATCGCT GTAATTGTCA ACGACGGATG AAAAGTGATC CACTTATATC TCCACCAACG   1020

GCCCAATATT GATCCACCGT TTTACTCAGG ATTAGCTTCT GCTATAACCC CGGCCTTTCG   1080

TTTCTGTCTG AGTCGATAGC TTTCTCCTTT GATTTGAACG ACATGTGAGT GGTGTAAGAT   1140

ACGGTCCAGC ATCGCTGAGG TCAGTGCTGC ATCACCGGCG AACGTTTGAT CCCACTGCCC   1200

GAACGGCAGA TTGGATGTCA GGATCATTGC GCTCTTTTCG TAACGTTTAG CGATGACCTG   1260

GAAGAACAGC TTTGCTTCTT CCTGACTGAA CGGCAGATAG CCTATTTCAT CAATGATGAG   1320

CAGGCGGGGG GCCATTACTC CACGCTGAAG CGTCGTTTTA TAACGGCCCT GACGTTGTGC   1380

CGTAGATAAC TGAAGTAACA GATCTGCTGC TGTTGTGAAG CGAACTTTGA TACCTGCACG   1440

GACTGCTTCA TAGCCCATCG CTATTGCCAG ATGGGTTTTC CCCACACCTG ATGGCCCCAG   1500

TAATACGATA TTTTCATTAC GTTCTATGAA GCTGAGTGAG CGTAACGACT GGAGTTGCTT   1560

CTGCGGTGCT CCGGTGGCGA ATGTGAAGTC ATACTCTTCG AACGTTTTCA CCGCCGGGAA   1620

GGCTGCCATT CGGGTATACA TCGCCTGTTT ACGTTGATGA CGTGCCAGTT TTTCTTCATG   1680

AAGCAGATGC TCCAGGAAGT CCATATAACT CCATTCCTGG TCTACTGCCT GTTGTGACAG   1740

CGCAGGCGCT GCGCTTATAA GGCTTTCCAG TTGCAACTGC CCGGCGAGCG CCATCAGTCG   1800

TTGATGTTGC AGTTCCATCA TCACGCCACT CCTCTGCAGA ATGAGTCGTA GATGGAGAGT   1860

GGATGATGCA GGGGGTGTTT GTCGAAGTTC ACCAGATTTT CATCAAGATG CACGTCATAC   1920

TCTTTTTTCT CCGGAGCAGT GCCAGCATGG ACTGCTGTCT TCGAGCCAGC GATCGCAGGG   1980

ACGGGCCTGG ATTGTTTCAT GCTTTCGTTG GTTAGCGACA TCGTGCAGCC AGCGCAGACC   2040

GTGGCGGTTG GCTGTTTCAA CATCGACAGT GATCCCCATC GGGCGCAGGC GAGTCATTAG   2100

TGGGATGTAA AAACTGTTAC GGGTGTACTG CACCATCCGT TCCACCTTAC CTTTAGTCTG   2160

TGCCCTGAAG GGGCGACACA GTCGGGGAGA GAAGCCCATC TCCTTGCCGA ACTGCCACAG   2220

CGAAGGATGG AACCGGTGCT GACCGGTCTG ATATGCGTCA CGTTGCAGAA CCACAGTTTT   2280

CATATTGTCA TACAACACTT CGCGCGGCAC ACCACCAAAG AAGCGGAACG CATTACGATG   2340

GCAGGTCTCC AGCGTGTCAT AACGCATATT GTCAGTGAAT TCGATGTACA GCATTCGGCT   2400

GTATCCGAGA ACAGCAACGA ACACGTGAAG CGGTGAGCGA CCATTACGCA TAGTGCCCCA   2460

GTCAACCTGC ATCTGTCGTC CGGGTTCAGT TTCGAACCGA ACGGCAGGCT CCTGCTCCTG   2520

AGGAACCGAG AGAGAACGAA TGAATGCCCT GAGAATGGTC ATTCCGCCAC GATATCCCTG   2580

GTCTCTGATC TCGCGAGCGA TTACCGTTGC CGGGATTTTG TAAGGATGAG CATCGGCGAT   2640

GCGTTGACGA ATATAATCCC GGTATTCATC CAGGAGTGAA GCAACAGCAG GTCGCGGCGT   2700

ATATTTGGC GGCTCAGATT TTGCCTGCAA ATAACGTTTA ACCGTATTGC GGGAGATCCC    2760

CAGTTCTCTG GCAATCGCCC GGCTACTCAT TCCCTGCTTG TGCAGGATTT TAATTTCCAT   2820

AACTGTCTCA AAAGTGACCA TAAACTCTCC TGAATCAGGA GAGCAGATTA CCCCTGGAT    2880

CTGATTTCAG GCGTTGGGTG TGGATCACTA TTGCACCGTT CGTGACAGTA ATGGATTGTG   2940

TCAGACGGAC GACGGGCCCA TAACGCCTGC TCCAGTGCAT CCAGCACGAA TGTTGTTTCC   3000
```

-continued

```
ATGGACGATG AGACTCGCCA TCCCACGATG TATCCGGCGA ACACATCAAT GATGAACGCC    3060
ACATAAACAA AGCCCCGCCA TGTGCTTATC CCGGTAAAAT CAGCTACCCA CAACTGGTCC    3120
GGGCGTTCTG CGATGAACTG ACGGTTTACA CCGTTGCATG CGGCAACAGC TTTCCGGCTG    3180
ATTGTCATGC GAACCTTTTG CAAACCCCAT ATATTTCAGA CGATACCGTT CAACGGTAGT    3240
GAACCCACCA TCACCGCTCC CGGTATCCCG CTCATGCTGG TATACCCAGA CATGCAGGGG    3300
TTCCAGCGTA CAGCCAATCT TTGGGGCAAT GGAACAAATT GACGCCCACT ACGAGTCATA    3360
CGACTTTCCA GAACAATACG GAGCGCCCGC TGACGGACCA CCAAAGAGCC GCCATTATTC    3420
TTATTACCTT TAACTAATAA TGCCAATTCA GACCCAAACA CGGCATCATT CGCTTCAGCC    3480
TCTGCGCCAT TAATTAATGC CAGGACTTGG TCAAGAAAGC GTTGCGCTTC GTTTACATCT    3540
GTTGCTTGTC GCAGGTAATA AGGTATTCGT TCAACAAACT CGGAACGTGA TAAAGGCTGA    3600
TGCTCCAGCA AAACCTCAAG CATTGCGGGC CGCAACAAAC GACGCTCAGC ATCAACATTG    3660
GGAAACTTAA CCTCAATGGC ATATGTGGCA AAATACTTAA GTTGCTCCTT AAGCCCCAAA    3720
TTAGGCATAA GAGAATCAAT TGAGCCAGAC GCCACTGCAG CGCTTGATTC AATTGTTTCT    3780
ACATACTCGT AGGAAGGTAC AACAACATCT GGAGCCAATG TTTTAAGCTC ATGGAGTTGA    3840
CGGATAATCG GGGATAGAAC CTCATCAGGA TTACTGAACC AATCAGTGGA CCAAATACGG    3900
CTAATTCTCC ACCCCAAACG CTCCAAAACC TCTTGACGCA AACGATCACG GGCAGATTTA    3960
GCTGAATGAT AAGCCGCACC ATCGCACTCT ATACCCATTA AGTAACAACC CGGATCTTCT    4020
ACCGACAGAT CAATAAAGAA TCCTGCAACC CCACCTGAGG TTCACACTCA AACCCAGCGT    4080
GATTGAGTGC TTCCATTATA GCAACCTCAA AGTCACTATC CGGAGCCCTG CCCGTATACG    4140
TCGTGAGGGA ATCTAATTTG CCACTTTCGG CAAACTGTAA AAAACCTTTC AACGAAATAA    4200
CACCAAATTT ACTGGTTTCA CTCGTCAATA CATCTTCAGA ACGCATTGAA CTAAACACAT    4260
GCATCCGTTT CTTTGATCGA GTTAAAAGCA CATTCAAGCG GCGCCAGCMA ACATCGGAAT    4320
TGACAGGCCC AAAGCGTTAA TAAACCTTTC CACCATGCTC AGAAGGTCCA CAGGTAAAGG    4380
AAATAAAGAT TACATCACGC TCATCACCTT GAACGTTCTC AAGTTTTTTC ACAAAAAGTG    4440
GCTCTTCCAT GGCATATAAG CCATCAATTG CATCGTTAAA TTCAGTGCGA TTTCGGCGCA    4500
ATTCATCAAT AGCGCGCTCA ATCTGATCGC GTTGCCTGGA ACTCATGGCC ACTACCCCAA    4560
GAGATTCATC CAGCCGGTGT TGCGCATGAT GAAGTACAGC CTCAGCAACT GCTTGGGCTT    4620
CTTCAATATT GTGTTGATTA GAGCAACGAC CTTTTGATAC ATAAGTAAAT TTGATTCCAT    4680
ACTCTGGAGA CTCAGCATTT GGAGAAGGGA ATATCACCAA ATCACTGTTA TAAAAATGGC    4740
GGTTAGAGTA TGCAATTAAC TTTTCGTGTC GTGAACGATA GTGCCAATGC AAACGTCTCA    4800
TAGGAAACAG TGGCAAAGCA GCATCCAAAA TGCCGTCAGT ATCACTTAAA GCCGCGACAT    4860
CATCGTCATC TTCTCCGGCG GAACTTCGAT CTGAAGTGGC ACACTGAATT TGGCCACCTG    4920
AACAGAGGTG ATATGCTCAC CTCAGAACAA CACAGGTGCT CCAATGAAAA AAAGGAATTT    4980
CAGCGCAGAG TTTAAACGCG AATCCGCTCA ACTGGTTGTT GACCAGAACT ACACGGTGGC    5040
AGATGCCGCC AAAGCTATGG ATATCGGCCT TTCCACAATG ACAAGATGGG TCAAACAACT    5100
GCGTGATGAG CGTCAGGGCA AAACACCAAA AGCCTCTCCG ATAACACCAG AACAAATCGA    5160
AATACGTGAG CTGAGGAAAA AGCTACAACG CATTGAAATG GAGAATGAAA TATTAAAAAA    5220
GGCTACCGCG CTCTTGATGT CAGACTCCCT GAACAGTTCT CGATAATCGG GAAACTCAGA    5280
GCGCATTATC CTGTGGTCAC ACTCTGCCAT GTGTTCGGGG TTCATCGCAG CAGCTACAGA    5340
TACTGGAAAA ACCGTCCTGA AAACCAGAC GGCAGACGGG CTGTATTACG CAGTCAGGTA    5400
```

-continued

| | |
|---|---|
| CTTGAGTTGC ATAACATCAG CCATGGTTCT GCCGGGGCAA GAAGCATCGC CACAATGGCA | 5460 |
| ACCCGGAGAG GCTACCAGAT GGGGCGCTGG CTTGCCGGCA GGCTCATGAA AGAACTGGGA | 5520 |
| CTGGTCAGTT GCCAGCAGCC TGCGCACCGT TATAAACGAG GTGGTCGTGA ACATGTCACT | 5580 |
| ATCCCGAATC ACCTTGGGCG GCAGTTCGCA GTGACAGAGC CAAATCAGGT ATGGTGCGGC | 5640 |
| GACGTGACGT ACATCTGGAC GGGGAAACGT TGGGCATACC TTGCCGTTGT TCTCGACCTG | 5700 |
| TTTGCAAGGA AACCGGTAGG TTGGGCAATG TCGTTCTCTC CGGACAGCAG ACTGACCATC | 5760 |
| AAAGCGCTGA AAATGGCCTA GGAAATCCGC AGTAAACCAG CCGGGGTAAT GTTCCACAGC | 5820 |
| GATAGTAATA ATGCCGGTAT CAGTTTTTAT CATCACTCTG TTTGCTGTTT AACCAGACTG | 5880 |
| GTGTGATTAC TGATGCAGTG AAGACCTTCC CGCATCCTGA CTCACACAGC GATCGACCCT | 5940 |
| TTGTGTCCTG CCCTGGACCT GTCGGTTGCC GGAAGCGCCT TCATGCGAGG CGTCTCCTCA | 6000 |
| CCGATGCGCG TGACTCAAGA AGGGCCTGAC GGTTTGTCTC GTTACTGTCC TGTCCGGGTT | 6060 |
| ATCTGTCTGG AGATTCAACT CTGTTTCCTC ACAGGAGCTC TGTTATGGCA GGTAAAGTTA | 6120 |
| CGGAAACCGC TGTTGTGGGT GGCGTGGATA CACATAAAGA TCTGCACGTT GCCGCTGTCG | 6180 |
| TAGATCAGAA CAATAAAGTT CTGGGGACCC AGTTTTTCTC CACAATACGG CAAGGTTACC | 6240 |
| GGCAGATGCT GGCATGGATG ACTTCGTTTG GGGCATTAAA GCGAATTGGT GTTGAGTGTA | 6300 |
| CTGGCACCTA TGGATCAGGT CTGCTTCGCT ATTTACAGAA TGCCGGGTTA GACGTTCTTG | 6360 |
| AGGTGACTGC GCCAGATCGG ATGGAGCGAC GCAAACGGGG TAAAAGTGAC ACGATTGATG | 6420 |
| CTGAATGTGC CGCTCACGCC GCATTCTCCC GAATAAGAAC CGTCACACCC AAAACGCGCA | 6480 |
| ATGGCATGAT TGAGTCTCTG CGGGTATTAA AAACTTGCCG AAAAACAGCA ATATCAGCCC | 6540 |
| GCAGAGTCGC TCTCCAGATT ATCCATTCCA ATATTATCTC TGCCCCGGAT GAATTACGTG | 6600 |
| AACAGCTCAG AAATATGACG CGCATGCAGC TCATCAGGAC TCTGGGATCC TGGCGGCCTG | 6660 |
| ATGCCAGTGA ATACCGCAAT G | 6681 |

(2) INFORMATION FOR SEQ ID NO: 66:

(i) SEQUENCE CHARACTERISTICS:
        (A) LENGTH: 1342 base pairs
        (B) TYPE: nucleic acid
        (C) STRANDEDNESS: double
        (D) TOPOLOGY: linear (xi) SEQUENCE DESCRIPTION: SEQ ID NO: 66:

| | |
|---|---|
| TATTCGCGCA TACGCGTTGC ACATGTTCTT TTGGCGAACG ATCATCGGCA ATACAGAGTT | 60 |
| CCCAATGGGG ATAGCTTTGA GCCAGGACAG AATCCAGACA GGCACGCAMG TAGATCTCCG | 120 |
| CTGGATTATA AACAGGAATC ACAATAGATA TAACTGGAGG GTGAGTCATA CTGGCAAGCA | 180 |
| TCAGACTCAC CWCTTCKTTG CCAGGCAACG AAGGTAATTC CACCGTTTCT ATCCATTCCT | 240 |
| CATAACCGAC AGAAGACGGG GTAACGCTGA ACGTYTCGTT ATAGAATGCT TGCAGGCGCT | 300 |
| CTATTGACAT ATCGCCATTG TSCATCAATA TGGATTTTWT GATTTTTTCT AGCGGCATGT | 360 |
| CACGATAGCT TTGGTGTTCT TTTTGAATGC GAGCCAATAG TGCAGACTCG ACTACTTTCA | 420 |
| CATCAACAGC CGCTATTTCA AACTGATTAA TTGCAAATTT TGCTGCCTGT TCTAATGGAT | 480 |
| CAAATCGTAA TGCACAAGAG GCGATTCCAG ATAGAACAAC GACTGACGCT GACCGCTCGT | 540 |
| TTATATGGCA ACGTTACTGT TTCAAACTCA TTGAACCCTT TACCTGTATC CAAATRTAAC | 600 |
| TTAGCTAATC CTTGCTTTGG TTGGGCAATT AATAGAGATA TTAAATTGAT ACCATCCCTT | 660 |
| GCTAATATTT GAGAGCTGCT CCAAATCAAT AATGAAAAAT GGATCATTTC CCTCTGCAAC | 720 |

-continued

```
CCAACTTTGT GAATTATCTA TATCTATCGA GAGCTGATTT GTTGCCAGAT AGGGCAGCAC      780

AACTGTATTT TGCATTTTAC TCACTGCAGG AGAAACGTCC CATGCTTCGC ATGGTTTCCT      840

ACCAAGTAAC ATCCCATAAC GCTTAAAATG TTCTCTTGCT GACAACCCGG TCTGTTTCAC      900

ATCCAAATAG TTATGCAGAT ACCAATGTTC ATCAAAGTGA GCTAGCAACT CGTCTTGGTG      960

ATTTTTAACC ATCACTTTTA TTCTCCCTTA TTGACAGGCA GGCAACTGCG CTGCTCAAAC     1020

TTCCCATACA TAATGTAATG AAGCAGCGGA TTAATGCCTC CTTGGGCCAC ATCCGGATAG     1080

GTTTGCAAAT ACCAGCGAGT ATCAAACTGC TCACTAGGGC TATAACCTTT ATCCGCCCCC     1140

ACGCTAATAA AATGCTCAAG AGCTGAGAGC CCAGTGTCTG CAACCTCTGG GTAGCGATGT     1200

TGATACCAGA GTTCATCAAA CAATCCTGAA GCGGCAANTA CTCCGCGGCA CTCTCTGTAG     1260

CTGTTGTTCT GGATGGAGTC TCCTCCTTAA ATGTTCTGCC AAGAGCACGA ACTGGGGCTG     1320

TAATCTTCCA AGAGACGGTT CT                                              1342
```

(2) INFORMATION FOR SEQ ID NO: 67:

(i) SEQUENCE CHARACTERISTICS:
        (A) LENGTH: 1580 base pairs
        (B) TYPE: nucleic acid
        (C) STRANDEDNESS: double
        (D) TOPOLOGY: linear (xi) SEQUENCE DESCRIPTION: SEQ ID NO: 67:

```
CGAAGGAAGC AGTNTGCNGC CTGCGCTGGC GGAGTTGCGC CTGTTCCCAC CGATGATGCT       60

GTACATGAAT CCTCCGGCGA ACAGAGCGGT GAACTGGAAA CCATGCTTGA ACAGGCCGCG      120

GTCAATCAGG AACGGGAATT TGATACCCAG GTGGGGCTGG CGTTAGGGCT GTTTGAGCCG      180

GCGCTGGTGG TGATGATGGC GGGCGTGGTG CTGTTTATCG TCATCGCCAT CCTCGAGCCG      240

ATGCTGCAAC TGAACAATAT GGTTGGAATG TAATTTACGG AGTTATCACA TGAATTCGTT      300

ATCCCGCACA CAAAAACCAC GGGCAGGTTT TACCCTGCTG GAAGTGATGG TGGTGATTGT      360

TATTCTTGGC GTCCTGGCAA GTCTGGTGGT GCCTAACCTG TTGGGCAACA AGAGAAARC      420

CGATCGGCAA AAAGCCATCA GCGATATCGT GGCGCTGGAG AATGCGCTGG ATATGTACCG      480

ACTGGATAAC GGGCGTTATC CGACCACTGA GCAGGGGCTT GAGGCGCTGA TCCAGCAACC      540

GGCCAATATG GCGGATTCCC GTAACTACCG TACCGGTGGA TACATTAAAC GACTGCCAAA      600

GGATCCGTGG GGCAATGATT ATCAGTATCT CAGCCCGGGT GAAAAGGGC TGTTTGATGT       660

TTATACCCTG GGGGCAGATG GTCAGGAAAA TGGGGAGGGC GCTGGCGCAG ATATCGGTAA      720

CTGGAATTTG CAGGAGTTTC AGTAATCAGT GCCTGAACGC GGATTCACAC TTCTGGAAAT      780

CATGCTGGTG ATTTTCCTTA TCGGCCTTGC CAGTGCGGGC GTGATACAGA CGTTTGCGAC      840

CGCTTCAGAG CCGCCTGCGA AAAAGCGGC GCAGGATTTT CTGACTCGCT TTGCGCAGTT      900

TAAGGACAGG GCAGTGATCG AAGGGCAAAC ACTCGGTGTG CTAATCGACC CGCCTGGCTA      960

TCAGTTTATG CAGCGTCGTC ACGGACAGTG GCTACCCGTT TCTGCGACCC GCTTATCGAC     1020

ACAGGTTACG GTGCCAAAAC AGGTGCAGAT GCTGTTACAA CCCGGCAGTG ATATCTGGCA     1080

GAAGGAGTAT GCGCTGGAGC TGCAACGTCG TCGCCTGACG CTGCACGATA TTGAACTGGA     1140

GTTGCAAAAA GAGGCGAAAA AGAAGACGCC ACAGATCCGT TTTTCGCCTT TGAACCCGC     1200

CACGCCGTTT ACGCTGCGCT TCTACTCAGC GGCGCAAAAC GCATGTTGGG CGGTAAAACT     1260

GGCACACGAT GGCGCGTTAT CCCTCAGTCA ATGTGATGAG AGGATGCCAT GAAGCGTGGA     1320

TTTACCTTGC TGGAAGTGAT GCTCGCGCTG GCGATTTTTG CGCTGGCTGC CACGGCGGTG     1380
```

| | | |
|---|---|---|
| TTACAGATTG CCAGCGGCGC GCTGAGTAAT CAGCACGTTC TTGAGGAAAA AACGGTAGCG | 1440 |
| GGCTGGGTAG CTGAAAACCA GACCGCACTG CTCTACCTGA TGACCCGCGA ACAACGGGCG | 1500 |
| GTCAGGCACC AGGGCGAGAG CGATATGGCA GGAAGCCGCT GGKTCTGGCG AACCACACCA | 1560 |
| CTGAATACCG GTAATGCGCT | 1580 |

(2) INFORMATION FOR SEQ ID NO: 68:

(i) SEQUENCE CHARACTERISTICS:
        (A) LENGTH: 3241 base pairs
        (B) TYPE: nucleic acid
        (C) STRANDEDNESS: double
        (D) TOPOLOGY: linear (xi) SEQUENCE DESCRIPTION: SEQ ID NO: 68:

| | |
|---|---|
| CTTAACCATT ACCCAGCATT TGGTAGTTAA ATAGTCGTTA AAAGCATAAA ACATGGACAT | 60 |
| TGTGCCATCC CAGCTAAAGC ATCCATTACC GCCTGACAGG GATAAAAATA AAAAAGCAGG | 120 |
| GAACCATTTT TTCATCAGAA ATCACTTCCG TAATTACAGT TATTCATTTA GGTATGACTC | 180 |
| AGTTATAAAT CATGCTCATA CTGGCCGTGG TCTGGRAATC CCCGCCATTC AGTATCCCGC | 240 |
| TGCCATTACG AAAGGGCACT GAAGTAAAGG TGAACGTTGA ACGTGCTGTG TCCAGACCTG | 300 |
| CTGTCACTCC GTAACCATTT CCTGAACCAT TACCTAATAT AAGAGGTGTT GACATTCCTT | 360 |
| TTCCCTGATA CAGCGCTATA CCAAAATGAG TTATATTTGT TGCCAGTACA TTATTCTGAC | 420 |
| CTCCTCCCAT AGTATTTCCC GTAACTTTTA TCCAGAGAGA GCCACTCTTA TACGGACAGG | 480 |
| ATATGCTTAT GGTTTTTGTG ACTTCACCAC GTGAGTTGTC CACGTGCTCA GGATTAATAT | 540 |
| TCCCAAAATC AACAACAATA TTCTGCCCGT TATTAATGGT GCATGGGGGG ATATAAACAT | 600 |
| TCCCCCTGAT GTTAATCTGC ACATCAGCCA GTACAGCGAC CGATGTCAGA AGCAACGATA | 660 |
| TAAATAATGA TAAACGAATC ATTCCCCTCC GGAGAGCGGT ACAGAAAACA TTTTATTTTA | 720 |
| CGAGATATAA AATTAACGTA TTTTAGTTGA TACTATTACG AATATGATGC AACCAGCGTT | 780 |
| GCTGTTGCAG AGAAAGGACC GGCTATCAAA TTCTGCATAT TCCCTTTATA TCCAAGTTTG | 840 |
| GCATGAAGTG ATATAGTTTT ATCTGCATTA TTACCTGTGA TTTTTCCGGG CGTAAATGGA | 900 |
| GTCCCTAAAG TTATCGCAGT CCCAATATTT CCTGCATTAC TGTTATAAAG ATAAACGAGT | 960 |
| AACCCATCAG AAGATGTGTT TGATGTATTC TGAACTAAAA TAGCATTGTT ATAAGTGTTT | 1020 |
| GTTGCCGTTA TCGTAACCTT CATTGTTCCC AGATTATAGG GACACCGCAT ATTCACAGTA | 1080 |
| AACTCTTTTT CGTGATTTCC ATTTTGACTC AGGGTCTGAA TCTCTACATC CTGCCAGTCA | 1140 |
| ACAGTTGTGT TGCTTACAGT ACAGGCAGGA ATAATCAGTT TTCCTCTGAA GGTCAGATTA | 1200 |
| TCAACTGCAT GTACATGCTG AGACATTAAC ACTGCCCCCA GCATTACCGG AAGACACAAA | 1260 |
| CCTCTTATCT TTTTCATCTG AAATATCCTG TACAAAAATT TTGCTAACGA TATGTCAATT | 1320 |
| CAAACGTGGC TGTTGCTTCA TAATCACCGG GTACCACACT CTTCGTCCGC AGGCTTCCGG | 1380 |
| CGTTGCCACA ACATACGCGC CGAAAGGAAG CTCAAGACTG TTTCCGGTAA CCTTTTCCCC | 1440 |
| CTGGCCTTTG TTATGGGAGG TGCCGGGTTT CAGCAGACTG CTGCCATCGG TGTCCAGCAG | 1500 |
| TGCAATGCCT AACCGGCCAG CATTCACTCC GGTTACCTTC AGATGGCCCG GGAGGGCGCC | 1560 |
| TCTTCCGTCC CCTTAAAGGT CAGGGTCACA ATTTTGCCAA CTGCTGTTGC ATGGCAGTTT | 1620 |
| TCCAGCCTGA TGACAAACGA CTCTGTCGGC GAACGTCCGG GCGGATACCA GAAATCCCTG | 1680 |
| GACGCCCGGG TTTTGAAGAC GACATGTTTA TTCAGACTGT CACCGGACAC ATGGCAGGGT | 1740 |
| CTGTCAAGCA GATTACCCCT GAATGCCACA TCTGAGGCTA TTGCCTGTCC GGCAGACAGT | 1800 |

-continued

```
GCGGCAAACA GTAAAAGAGC GCCTGTGCTT TTTATCATCA CATTCCCTTA CTCATATTTT    1860

ATGCTCAGAC GCAGCATGGC CGGATTGCTC CTGGCATCAG AATACTCACC CTCCTGTGTC    1920

GCCCTTTTCC TCCAGGCGGC CAGCATCTCC TCCTGCCGCC GGTCAGGCCG GCACAGTAAA    1980

AAGGTATCAC CATCGTGTAT AACAAGATGG TCACAGCCGG ATAGCTTACG GTCAGGAAGT    2040

AAAGCACTTC CGCTTCCGGG ACCGGTTACC AGTGAGCCGG AGACTGTCAT CGCAACGCCC    2100

CGTTTTCCGG GCTGAAGTGC ACCACCGTCC CCACATCCTG CCAGCCTCAG CATCAGAGGT    2160

GCTCCGGCTG CCGCAGAGTG ATTTTCCGGC CGGAGGYTTA ACGGCACCTC ATTACTCACC    2220

AGCGTGCAGG GTGAGGACAG CAGTGCACCA CTGACGGTCA GGCTTCCGGT GCGTCCCCCC    2280

CGTTCATTTA TCCGGTAATG ACGCAACTCA TCTGCAGTAA AGACGTCATC GTATATACCC    2340

CGCTCTTCAG CCCGCAGGAA AGTATGGATG AAACCACTCA GCGACAGTGC AATAAGATAC    2400

AGTACTGCTG TTGTTTTATT CACAACCATA ATATCCCACC CGCATTTAAC CGTTATTGCG    2460

GTACATTATT TCTCTTTTTT CACAGAGCAA CGGCTACCAT TACAGATAAA CGACAGTACC    2520

GGGCGACCAC CATAGTCATT AATATAAGAC AGATAAGGGG TATTATAATT TGCCGATTTT    2580

ACTGTCTGCT CTGAACGGGG AGACAGCATC ACGGTTTCAA ACTCACCTTC CTCTGCCTGC    2640

TTTTCACTTC CTCCCAGACC AATAACAGTG ACATAATAGG GCGTTGGGTT TTCAATACGA    2700

TACCCACCGC TGACTTTGTT CAGAATTAAC TGGTCCTGCC ATACTTCATT TGGTCTGGTT    2760

TTAATTGCTG CCGGGCGATA AAAAGCTTT ATTTTGGTCT GTAAGGCTAT CTGCAGTACA    2820

TTGGCCTTTT CACTCCTCGG CGGTATTTCC CTGAGATTAA AATAAAACAG TGATTCCCTG    2880

TCCTGAGGAA GTTTACTGAT ATCCGGTGTG GTACTCAGCC TGACCATGCT TTTCGCACCC    2940

GGCTCAAGGC GCTGAACCGG AGGGGTGGCA ATAACCGGCC CTGTAATAAT TTTTTCCTGA    3000

TTTTCATTTT CTATCCATGC CTGAGCAAGA TAGGGCAGTT GTTTGTTATC ATTGGAGATA    3060

TCAAGCGTCA TTGACTTCTC ACTCCCGTCA ACACCGCGC GGGTTCTGTC CAGCGAAACA    3120

GCAGCGTCTG CCCCGGATAT AACAAACAGG GGGATGGCAG CCATCAGAAT CTTTTTTCGA    3180

ATCATACTTA ATTTCCACAT TCTGTAATTT CACCTGGTCC GGAAAATGGC ATAACCGCAT    3240

T                                                                     3241
```

(2) INFORMATION FOR SEQ ID NO: 69:

(i) SEQUENCE CHARACTERISTICS:
        (A) LENGTH: 398 base pairs
        (B) TYPE: nucleic acid
        (C) STRANDEDNESS: double
        (D) TOPOLOGY: linear (xi) SEQUENCE DESCRIPTION: SEQ ID NO: 69:

```
AACGTGGATC TCCAGCTGAT CGGTGCCGTA TTCCAGGTCG TAAGTTTCAC TGATGGTTTC      60

ACGCGGCAGT TGCCCGGTT TACGGACCGG TACAAAGCCA ACGCCCAGAC CCAGAGCTAC     120

CGGAGCGCCA AACAAGAAGC CACGCGCTTC GGTGCCGACA ACTTTGGTAA TGCCCGCATT     180

TTTGTAACGC TCAACCAGCA AGTCGATGCT GAGAGCGTAA TTTTCGGGTC TTCCAGTAAG     240

CTGGTGACAT CGCGGAAAAG AATGCCGGGT TTTGGGTAGT CCTGAATGCT TTTGATGCTA     300

TTTTTGAGAT ACTCAAGCTG CTGTGCATCG CGGGKCATAA GTGTATGCCT GCTTGTTACG     360

GTGGTACTCA CGGCGCGTTT TTAAACGTAT CAAAAGTT                              398
```

(2) INFORMATION FOR SEQ ID NO: 70:

-continued (i) SEQUENCE CHARACTERISTICS:
    (A) LENGTH: 17710 base pairs
    (B) TYPE: nucleic acid
    (C) STRANDEDNESS: double
    (D) TOPOLOGY: linear (xi) SEQUENCE DESCRIPTION: SEQ ID NO: 70:

| | | | | | |
|---|---|---|---|---|---|
| CAGTTNCNGT | TCTCATAGAC | AGATTGATAA | AATCGTAAAC | AGCCCCTAGC | ATTCCCGTTT | 60 |
| CCTTTGCACA | CATATTCAGG | CACGGGGATA | AAGTATAAAG | AATGTCGTAC | TGCTGCTACC | 120 |
| AGAGCAATAT | TCCCCCCTGA | TGGCCGTATC | AGAGATAGTA | TGCCGGTATT | TTGCGGGTGG | 180 |
| TTCCCGTCAG | GTTATCGTGT | ACCTCCACGG | TCGTAGTCAC | CACCGGCATT | CCGGCYTTTC | 240 |
| TCAGCCTCAA | AACATCAGCT | GCAATACGCT | GACTGCCGAA | CCAGAACAGG | CCGTCCAGTG | 300 |
| CAGTCACCAG | CAACCCCGCC | TCCAGCGCAT | GCTTCAGCCG | TTCACGGGGC | GCTTTCACTT | 360 |
| CCCGGGCAAT | CTGCTGGTAT | GGCGATGATG | TGTTTTCATT | CCCAATCACC | CGGCGAATAC | 420 |
| GATGAGACAG | ATGATACCGG | TATGTATCCG | GCACACCGGA | AAGGCTGGCC | TTCAGGCTGT | 480 |
| ACACGCAGCC | AAATCGTTTA | TCATTGAACA | CCACATTTTT | CTGGCTGATG | CCCCATTCTT | 540 |
| CACGCAGCGC | GGCAATCAGT | TGTGGTGTAC | GGGTAAGCAA | CAAGCGAAAA | GGCAGTTCAA | 600 |
| AACTGGTGAC | ATAATCCACA | TTCAACAGGG | CAATGCGAAG | TCGTTCTTCT | GGTCCGGCTT | 660 |
| CTGTCTGCCG | GCACTCCTCC | AGGACATCCT | GCCACTGCAG | GCGAAGACGG | GAAGACTCAT | 720 |
| TCAGTTCTGT | AAAGCAGTAT | TTATCCGCCA | GATAGTCAAT | TCGTGTATGC | ATACTGAAGA | 780 |
| GTATTCCGTA | TAAAGATTCA | GCTGGCAAAA | CTTTATCAGT | CTGTAAAAAC | TAACGGAAGA | 840 |
| GTCGATATTT | CTCCCGACAA | TCACCGGATG | ATTGTTGCAA | TACCTCGTGG | CATCAGAGAC | 900 |
| TGAACAGCAG | TTTTTAACGC | AACGTATTGC | TCTGATGTAT | CAGGCCGGAC | AACCCGAAAA | 960 |
| CAGCCTTCCA | CCCGGCATTG | TCCGCCAGCG | CTTATCACCG | GCCAGGTCTG | TTGCAGTAAA | 1020 |
| TCCGCCACTT | GCGAACATGC | TTCATCAACT | GTGACACTGG | CCCGCGGATG | GCAAATGCTC | 1080 |
| GTCTGGCTGA | GCAGCAACAG | GCATCGCATT | GTTGCTCCTC | TATGTTGTTC | CCGCAACCAG | 1140 |
| CGTAATACCA | CCGGCGAGGA | TGGACAGGCA | GTGTGATTAC | GCTCCGTAAT | ACGTTCGTGC | 1200 |
| ACCCGTCGGT | GAAAGGAACT | ACAGAATGTC | TGAATCTGTT | GCCCGTTGAT | GTATCCTTCT | 1260 |
| GTCGAATGAA | GTGTGAAGTG | GATTGCCAGC | AGATGCGGCC | AGTGATCCAC | CGCCTGCTGA | 1320 |
| ACAAAACGCC | GGATTTCCCC | CGGCTCTGAA | AGTAAGGCTT | CGGTTATTTG | CACTATTTTA | 1380 |
| TCTCTGTTGA | ATTTGGTTAA | GTCGGTGCAG | ACGCATCAAC | ACAAGTACGG | TTCGATGCAA | 1440 |
| ACAGCTGTGA | CTGGCAATAT | GAAAGGAATG | ATGAATCAGT | CAGGATGACA | AAGTGCCGGC | 1500 |
| TGACCGGAGG | GGACGCAGGA | AGATTCACGG | GGGGACCAGC | ACCAGGGAAC | AGCGCCACAA | 1560 |
| TACCAGCGCT | GACACGTTGA | ACATTGCCAG | CGTACCGGTA | TCACAACACG | TTTCATACTT | 1620 |
| CTGCCCCGT | GATTCTTCGA | TTCGTTACTG | TATCTACTGT | GACACTTCGC | TTTTATACCT | 1680 |
| GCGGCTGGAT | CGGCCCGGCT | TGATGAATCT | TCACTGATCA | GCTTATAAAA | CCCTCTGTCG | 1740 |
| GTCATACCGG | TGAAACTGGT | GATATAGTTC | ATGTCAATCA | GGGAATTATC | GGCACGCAGA | 1800 |
| AATACGCTGT | CGTGGCTTGT | TGTAGTCAAC | ATGGTCAGAA | TGTCCTCTGT | GAGATTTATG | 1860 |
| AAGATTGTGC | GAATGCGGGG | AATCTACTGA | GCTGTGCTTT | CAGAACTGGC | CTGTTACGGG | 1920 |
| AKRSCAGGGA | TTACCGGCGG | GGTAACGGGC | TTCCGGATCA | TACACACCAC | GATTATCGCG | 1980 |
| GACAAAATCA | CTGAACGCCC | ATATCACCTC | TTTAAGTATG | TCTTCGCAGC | CCGGTACATG | 2040 |
| ACGATCCAGC | GCCACATCCC | GAGTGGTACT | ACTTTGATGC | GCCCGGTGAC | ACAAAGCCCG | 2100 |
| GATTGTTCCA | GACATCCTGA | ATCAAACGCC | CCAGATTAGG | GGCGTCGAAA | TATGCCTCTC | 2160 |

```
TGACCATTAT ATTCCGGTGT ACAGGTAGCA GGTCAGAAGT GACAATGCGT CACCTGACGT   2220

TAAAAGTCAC TACACCCAAG ATGACGTTCA ACAGCACCAT GCGATTCAAT GTAAGCCCGG   2280

GCTGTCTGTT CCAGTACACC AGGCTCAGCG TTGTATGTGT TAGCTGCATC AAATACCAAC   2340

GACAGCACTT CAGGATACAC AACCAGATGT GTAATGGAGT TATCTTCACC CAATACTTTT   2400

CCCCACGCCT GCTCAATCAG ATTTCTGAGA ACCACCACCT CACGACTCTT ACACCAGACA   2460

TCGTTATTAA GTAGCAGCAC CATAAGATAA GGAGTGGTAT CGTTAGTCAC AGCCTCCCTA   2520

CTCCAGAGAT AATATAAAGG GGTGGGCTCA ACAGATTTAT CTTTACGTCG CTTACACTGC   2580

AAATATTCAG AAATGAGTCT ATGCAGTTCA CCAGTAAAAT CCGCCATCAG AGAGGGAATG   2640

GCCTTATTAA TACCAGGGCA AGGTATTAAT TTAAATTGTA ATAATTTAAT TTCAGGATGT   2700

GTGGCTGCAG CCCGATACAG AGTTGCAAGG ACACACTTTT GCCAGAGGGC GTTACTGGAA   2760

AGCTTAACGT TTGATTCTGT ATACATAATA AATCACCTTA CAGTTACAAC AGGTCAAAAA   2820

CCGCTGTAGC CAGAGTTACG CTGGCCTGAT GCTTTAGTAC CGGGCTTCGT CAGATAATCC   2880

AGACGCTCCA ATAAGCGCTG ATACTGCTCA GGGAAATCAG GATCATGAAT ATCCTGGATG   2940

TCACGTCCAT TAGCAGGGAA ATGAATAACG CAGCCCCCTG GATTAACAAT GCAGAAATCG   3000

TCCTGAGGTA CTGATCAATA CGGAGAGGAC TCTCGCGTGT GGTTTATTGA CACCACAGTG   3060

CAGATTCGGC GAATCCGCGA TCACGGTGCG ATTTCGTTCC ACAGCACACA ATCATGACCC   3120

CGGGTTTTAT TCAGGTAAGC AGGATTGCGG ATATCCGGTG TCGCGCCTTT CTGTCACGAA   3180

CGGGGTAGGT GCGAAACACC GGATAAAATG CAGGCTGGCA ATACCTCTGA ACGCCCTGCG   3240

CAGAGCGGAT ATTTTGGATT AAGTACTCGC ACCTCCGCAG TCCTGAAACA AGTCTGGCTG   3300

GTAGCTGTAA ACAGACTTCG TACATGTTGC TCTGGAATAG ATCCCCGTGC CACAGGCTTC   3360

GCAGAACTTT TTCCCGGGAA AATGCTGCCC GCACATCACA CAATGCCACT CCAGCACGAC   3420

CGGTAATGGC GATAGAAACA TCGCCATATC CTCAATGTAA GGGTGGGACT TTTCCGGATT   3480

CAGCACCACG CAGGCCGCCT TCTGTTGCGC GCTCAGGGCA TGTAAATCGT GCTCAAACCA   3540

CGCCCCCTGA GCATCTGTCT GCAAAATCAA CCGACCACGA CAGGAAAGGC AGAAACAATG   3600

CCTGATATTT CTGCTAAGGC TGAGGCCGCA CTGATAATGT GTTCACCCGG CGTGATCCCC   3660

AGCCCCGTTT TTATACCGTT CATTCAGCCA CTCCCTCCTC ACTGAAGTGC CCTGTATGGC   3720

AGTGAGTGCA GTACCGCTCC CCATAATAAT CGTGGTGACA TTGTCTGCAG TGCCAGCTGG   3780

CTTTACGCAC CACGGGTAAG GCATCCGGTA CGAATTTCTG CAGACGCTTA ATCAGTTGTA   3840

TTTCTCTGCG CTCCGGTCTG ACATAAGGGC ACTGTTGACC GTGCTCCGTC AGCCCGTCGT   3900

CAGTGTGTTC AAACCAGGGA AGTTCAGTGT CGTATTGCGG ATGGTATCTG AGCGCACTGC   3960

CGCAAAGGTG GCAGGTGTAG CGGTCGTAAG GTGCAGTCTG TGCGGTACGG GCAGCGGTCA   4020

GACGTCCGTT GCCATCAAAT GCGAGAAAAG ATTTTGCGTA CATAGTATAT GTTCCTTACC   4080

GCCAGACGAC ACGCAGGCGT CAGCGTCCCT TTACGGGCAG CGTGGGCAGG GTGTGAATGG   4140

CGGTACAGTT AAGGGGGGGG TGGAAAATGG GCGGGCTGTT GTTACAGCAC TGTGGATGTC   4200

ACATCATGGC GTACCAACGT AAAAAATAAT CAGCAGGCCC GGATACATCG TTGTCGCCGG   4260

ACATCAGCCC GTCCTGCTGG TTTTGCCGGG CTCAGCCCCG ACTGCAGCCG AAATTACGCT   4320

CACCAGTGGC GTGAGCTTTG GTATGTTCCT TCGCCAGATA GTCAGCACGT TCCAGCACCT   4380

GCTGAAAGCC AGTGTCATCA CCGCGTTCCA GCCACACCGC CGGCGTGTCA GGAAAATGCG   4440

CCAACGTGGC ATAAGGCCCG GCATCCACCC CCAGGGCACT GCACCAGGCN TGWTTAATCA   4500
```

```
TCCCGGCCAG TGACCCCGGA TCGCGGTAAT CGCCGGCACG ACACCAGGTA TCCCGGTTGA    4560

CCAGCAGCAG GAGGTGATAG TGTTTTTTGC CCCTGAGTAC CCCGAACTCC CGGGCCCAGG    4620

CGTAATGCAG GGTGGTGGGA TGCACGCGTT TACCTTCACG NCGTTACGCT TCTGGTAAGC    4680

GTCGATTCGG GCTTTCAGGG CATTGATGAA GCGGGATATC ACAGCCGCGT CCGTAGCTGC    4740

CGGTACATCC GGGAGACGCA GATCAACCCG AAGTGCCGTC AGGCGGGGAT GAACATTCAG    4800

TGCGTGCCGC ACCGTCTCAC GAATACGTTG CTGCCAGAAG GGGTTGTATT TGTAGGTCAT    4860

GGTTAAATCT CCGTATGGTT CATACGGAAT AGCCACGTCG TAAAAAATGC GCAGAGCCCC    4920

TGACGTGGCC ACCGACAGAA CACGGCCTCA GGCGCGTTGT GATAACCCAG CTATCGTTTC    4980

CGGACTGACG GTTGAATTTC CTGCGTTGTT TTCTTAATGT AAAAAACCTG CTACGGGTAA    5040

GGCTGTGAGG AGGAAGTGAT GGTGATACGC AAAAAGAAGT GCAGGGACTG CGGAGAAGCG    5100

ACAGAGCATA ACACGGTATG TTGCCCACAC TGCGGTTCTG TCGATCCCTT CGGCTATTAC    5160

CGCAATACAG ACAGAATATT CACCCTCCTG ATGGTCCTGC TGGTTGTGGT TCTGCTGATG    5220

ACGGCTGCGG TCAGCGTGTA TGTGCTGTGG TAGTCGGAGG GGCAGGGAGC AGACGATGAC    5280

GTAAAATATC TCCGGTGCTC AGATATCACG GCCGGTCAGA CCGCAAACCA ACGGTTAATC    5340

GTAACCGGAT CAGGCAAATG TGTGATTAGC CCCCTGGCGC TCATACCCGC ACCGCAGACC    5400

ACCTTAAGTA CTTCCCGCCC GACACCATTC CCTGCTCCCG GATAATTTGT TGTCGCTATA    5460

CCGCTTAACA TCACCGATAC CACACCGGCG CAGATAGCAC CGGATTCATT GTAGAGATGA    5520

CTTAAGGTTC AGGTAACATA TTTCCAGACA GAAGCGGGAA CACGATCGTA AAGTTTGTTC    5580

ATGGTCAGTT CTGCCAGCCG GTGATCAACC GCAGAGTTGA AATTTTCCAG CTCCGCCGGG    5640

GTGAGTTTAT ACCGTGCGTG GGAAATCACT TTTTCCAGTG TCTCCCGGGA TGAACAACGA    5700

CGGAACTGAT ACAGCCAGTC TTCTTTGGTT TTTACTTCCA TTCGTCTCTC GTTACTTTAT    5760

GCTGCGGTTA ACAGGATGCC GTCAGTATAC CGCATGCAGA CACTCTCCCG CTCCCCCGCT    5820

TGCTGCGATA CAACTTAACG TTTCAGGAAT CCAGTCATCG CACCGGGAAA GGCTTTCTGG    5880

TGACAGGAAA CGTCAGGAAC AGGAGTTTCT CAGACTCCCA CTCATCGGAT CAGGCTCAGA    5940

CAGGATTATT AATACGCTCA GTTCATGTGT CATATACAGG GCATCGGGGA TGAATATATG    6000

GGTATAACTC AGAGCCTGTA CTACAGCTTT CACTGCTGAC TGATTTTACG TATCAGCGTT    6060

CATGTATCTG CACTCTGATA TAGAATACTT CTACCGGAGC TACTCTTACG TTAGCTCACT    6120

CTCACATCAG GCAACATCAC TTATTCAGCT CACTTACCTC TTACCACTCA CTACTTCTTT    6180

ATATTTATAA TATCAATCAG ACAGCCTTAT CCCCCCGGTA ATATCTGTTG CCTTCCCGCC    6240

AGCCACAGGC TTATTCACCA CAACCACCTC CGATAACAAC TCTGCAATTA TCAGAACGCC    6300

TGCTTCTCTC CCTGTCCTCA CGAAAACTAT CCCCTCTTTA TCGCGCGTGC GTGCGGAAGC    6360

ATCTTTTCGC AACAACCACC CGGGATTCCG CTACGGCTCT GCCATCGCAA TCCCCCCGTT    6420

TATCTCCGGA CAGCCACATT CCCGATTATT TTTTACGTTT CTCCCCGGTT GTTATGCCGG    6480

TGAAGGTGGT GCGTCGTTTT CATCACCACA CCGGTTGCGA TTAACAACAT CCGGAGGAAC    6540

ATTCTCATGA CCACACCCTT TTCACTGATG GATGACCAGA TGGTCGACAT GGCGTTTATC    6600

ACTCAACTGA CCGGCCTGAG CGATAAGTGG TTTTACAAAC TCATCCAGGA CGGAGCCTTT    6660

CCGGCCCCCA TCAAACTGGG CCGCAGCTCC CGCTGGCTGA AAAGTGAAGT GGAAGCCTGG    6720

CTGCAGGCGC GTATTACACA GTCCCGTCCG TAATTTCTGC CCCTTATCCG TTCACCCGCA    6780

GCAGACGCCT CCCCGGCCTG CCGTTGACAT TCTGCTGCCT GTTTTATCCC CGTGAGGAAT    6840

ATGAAAATGA AACAACAGTA CCAGACCCGC TACGAATGGC TCCACGAAAG CTACCAGAAA    6900
```

```
TGGCTGACCG GCTTCAMCCG GCACGCCGTA TCCTGGGCG TGTGTCATCC GAATATCTAC    6960

TATTTCCATA ATCTGACGCC CGGGTGGGTG TCATTCAACG GCGAACAGTC GGAGATTGCC    7020

ATTGTTCCCG GCAGTCTGCA CCGGCTGATT TATGGTCATG ACAAACGGGC CATGCCGCCC    7080

CTGGATGATG ATCTGGTGGT GAATTTATGC ACCAGTGAGA ATCTGCTGGT TCATCATCCG    7140

ATGCTGGAAG GCATTCTGCT GTCTGAGTGC ACGCGCCTGC ATAAAAAATC ACTGGCGAAC    7200

AAACTGATCA GTATATTCCG TCAGTTTGAC GGCACGGAGC TGCGTCTCAA ACTGGTCTGG    7260

CTTTGCTGGT TTGATTTAAT GACCGGAAAC TGCCTTGACG ACTGGACGGA GAACCTGNAA    7320

CGGAAATCAG AAAAGAGCT GGAGAAATGG ATCATTGAGC GCCAGAACCG GAACGCACCG    7380

CTGACGAATC TGATGGATCA GTACGTGCTC CTGGCATTCC GCACAACGGT TGACGATAGC    7440

CGCAACTGAT GTCTGCATGC TGCCSGCTGA AGCCATATTC ACGGGCAGG GACGCCCCTG    7500

CTTCCGCAAC AATCCGGGGT AATGGCGACG TACGCCTGCA GAGTGTGTTC ATCGTTGTCA    7560

CAGCCGGACA AGGTGAATAC CGTTGATGAT GCGGGGATGA ACCTGCTGGT CCACCGCGCT    7620

GTCACTCAGA CGCGTCAGCG TGTATGGACG CCCCGATCGA ATGGTTCTTC CGCCAGAGTG    7680

CACAGAAATG AGGCACGGAA CGTTACCTGA AGGGTGACCG GCACGGACTG CAACTTGTTG    7740

CCATTGATGG CGCACAAGTC ACATACAGCA GAATGTCGTG ACCGCACCTT ACCGGTGAAG    7800

CGAAACGGTG CTGCCCCACT CCACCACCAT CCCGGATAAC GCCATTACGC TGTCTGATAA    7860

GCGCTTTTAC AGCGCAAATC TGGTGCAGAA AAGCGTAAAG CTGACCTGCC GGAGCAGGAT    7920

GTGGGCATGT TGCGGGCTTA CAACCTGATA CGGCATGAGG CACTAAAAGC AGCATCAGAA    7980

ATCAGCCTGA GTTCGCGTTC CGGTTTATCC CGACAGAGAG GACAGTGCCG GGCAACACGG    8040

TGTCACCGGG GAGCATCCCG AAACGACCGG AGCATCTGCG GGATGCTCTG TAAGTGGTGT    8100

TAAGGTGGGC GGTAAGGTA TCAAAAAAAT CGTTATCCTG TGAAAGACAG TGCGCTCTGC    8160

TGAAGTGAAC GTCACTGCCG GGAAGCATCG GGTTTCGCTA CCGGACAGTC GCGGTAACGC    8220

GTTTACCGGC ATCTGTCTGT GTGGCAGGGA TGGCTGATAT TGTCGGTTAT ACCAGCGGCA    8280

GGTGCGTCCT GTTATCTGTA AAATCAGGGC GTGCCGGTAC ACAACGCCTC GTTGATGCCG    8340

GTCACTGAAC GAATCATCCT CTGACGAAAA CAACCGTCGA TACAACGCCG GCGTAAAAAG    8400

AAAACCGGAA ACCATCTTGT GCACGACAGG TACTCAGGGG GGTATAACGC CTGCGCACCA    8460

TCACATCCGG GAACAGGGCT GCTCCTCAGT GTCTTCGTGT GGCGAAGCAT CTGCAACCGG    8520

ACGGTACTGC CCTCAGAGCA ATCTCCCTGC TGCAGTGCAC AGAGTAAGCC GGAAAGCTGG    8580

TGAATGCCGC CATGACACAC TGCGACGTGG AGAAACAAAC GACACACTCC GTCCGCAGTA    8640

ACACTGAAGG TAGTCCCGCA AACCTCAGAC TTCTTCCTGC ACGTTATCAG CGGACTGAAC    8700

CCCGGTCAGC CACTTAAACC TGCTAATCGT GTTGCTGCAT ACCCGCCCGG CCGGAAGGTG    8760

TTATGAAGCC CGCCACCGGA GCGCTTCTGC AAATATCCGG GGAGATAAAA TTTTCGTGAC    8820

AGGATGACGG TCGTGCTGCA GACGTAAAGC CGCAGGAGCG GACACGACAG ACAGTGTTCA    8880

CTGTGGCGTC CTTTGCCGTC GGTATCGTGC TCACGCTGAG GTCCCGGGGG TACACCTGAC    8940

GACAAATACC TGCGATTCCC GGGACGGTCT GTTCTCCGTA AAATAAAGAA AATGCGGGAT    9000

GCCTCCCGGA CTGCAGAGAA GAGGGATTGA CAGACAGTGT ATATTGCGTA CGATTACAGG    9060

GGAAAAACAC AGTAAATATG GAGGTCAGGT CCGAAAACAA CCTACGAAAT TTCTATGAAA    9120

AACGATTGAA AAAATCATCA AATTCAGTTC GTTTTTCTAT GGTAATTTTT AAACACTCCC    9180

GATGATAACC TGTTGTATGT GCATGTGGGG AACGCACCGA AACATCAGA ATCATCTGAA    9240
```

```
AAAAACAACG AACACACCAG AAAAACAGGA GCAACCATAA CGAAGCAACA TATTGATTTT    9300

AAACAGAATT TAAGGTTAAC AGACAAAAAA CACTTTCAAC TGAAGGAGAA ATATACACTG    9360

GCGACAGTGC AGGGTTTTTC ATGCAAAAAA AATGAGCTTT TATCTCCGGC GCATACTGAC    9420

CGGGATGCAG CCATGACAGA GCAAAAACCA TTAAATATCA GGAGGTTAAA CACACAAAAA    9480

GCTGACATGC ATCAGGGAGC AATCCCTCAC AACAGAGGCT GAGCGGCAAC GCTTCCTCAC    9540

AGGACGGCAT TCCTGAAAGG ACAGGCAGCC ACGGCTTTTT ACTGCCCGTA TCCGGTATAT    9600

TTATCTGCCG TGACGTGCAG AGGATTTTGT GTTTCCGGAA ATCAGGAAAA CAGGAGAACC    9660

GCGGGAGATA TGATGGAAAA AGAACCGGAT GATATCTGCG CAGACTGTCC GAATATTGAT    9720

GCAATAAAAC GGCACAAACA ACAGGCCGGA GCCATCAGGG AATACACTGA GTGGTTAAAA    9780

AAACAACCGC GTGCTTCTTA CTTTTTTCTC TTCCGGTTGT ACGCATACCT TCAGAATGAA    9840

GTGATATCCC GAAAACAAAA ACATTCGCTC ACCAGCGATA ACAGCCATCC CCCGGAATCT    9900

GATGTCACCC CTCCGGATTT AACCCTTCCC CGTCGCTACT ACTGTGATTA CGGTTACACG    9960

CCCTACCCCA TGATGGGCGG ACAGATGTCT GTTTTTGCCA CAACGTCAGA AACCACCAGT   10020

TCGACGAATG CAGTCCCCGG AAACGCAGTT ACCGGGAATG AGACTGAAAA GCATGAAAAC   10080

GCGGTACCGG CGACATTCCC CGTCAGCCGT TCTGCAATGC CCCCGGAACC TCTGCGGTTT   10140

GCCACGGGTT TTCCATCGCA ACCACTGCTT GCCGGTCCCC GGGAAAAGCC GATGCGCACC   10200

GTGCATCCTG ACATCCACAG CGAAATTATA TGGTTCTGCT CCACTTACCT GCTGAAATCC   10260

GGACCACAGA TTACGAAGAC GATTATCAAC TCAGTATTCT CTGAATGGGC CCGCATCAGC   10320

AATGATTACC CCTCCCCCTT TTCGTGGGTG GACAGCAGGG ACAGTGAACA GTGTGACTGG   10380

TTATGGAACG CCATGCAGCT CCGGTGTGTG GGAACCCCGC TGAATCCCCT TACCCCGGAG   10440

CAGAAATACT GGTTTGCCTG CGCCACGTTT GATAACTGGG AGGGCTGGAA TGAGCAACAG   10500

ATACAGTTTT TACTGAAAAG TAATCCCAGA CGAAACAGAG CGAAGTTTAC GGTCACCTTC   10560

GGCCCTCCCT GGATTCAGCA TAAAGCCATT CTTCTTGATG AGCTGAAGAG TGCCCGGGAG   10620

CAACAAAAAA GGCGCGATGA ACGCGCTGAT GGTTCCGTCC CGCTGAAACT GTCCGGAAAA   10680

ATCCACAAAC ACCTTGAAAG TATTGCCCGG AGTCGTGGTA TCCCCCCAAA AAAACTGCTG   10740

AATGAAATGA TTGAGCAGGC GTACCAGGAC TCAGTGGTGA ACAGCCGGAA TAAACCACTG   10800

ATTTAAAATA ATTTCAGACA GATATTATCT CCGTGAATCC CCCGCCACCT TTCCGGTGCG   10860

CGGGGTTTTG TCTTTTTTCA CCGGGAATAC ATGTATGAAT CCGTCTGATG CCATTGAGGC   10920

AATTGAAAAA CCGCTCTCCT CCCTGCCTTA CTCGCTTTCC CGTCACATCC TGGAACATCT   10980

GCGCAAACTC ACCCGTCACG AACCCGTGAT TGGCATTATG GGTAAAAGCG GGGCCGGTAA   11040

ATCCTCACTC TGTAATGCAC TGTTTCAGGG GGAGGTCACC CCGGTCAGTG ATGTTCACGC   11100

CGGCACCCGG GAAGTGCGGC GCTTCCGTCT GAGTGGCCAT GGTCACAACA TGGTTATCAC   11160

TGACCTGCCC GGGGTGGGCG AGAGCNGGGA CAGGGATGCA GAGTATGAAG CCCTGTACCG   11220

TGACATTCTG CCTGAACTGG ACCTGGTACT GTGGCTGATT AAAGCCGATG ACCGTGCCCT   11280

GTCTGTGGAT GAGTATTTCT GGCGACACAT CCTGCAACGC GGACATCAGC AGGTGCTGTT   11340

TGTGGTGACG CAGGCCGACA AAACGGAGCC CTGCCATGAA TGGGATATGG CCGGCATTCA   11400

GCCCTCTCCC GCACAGGCAC AGAACATTCG CGAAAAAACG GAGGCGGTAT TCCGTCTGTT   11460

CCGGCCTGTA CATCCGGTTG TGGCCGTATC GGCCCGCACC GGCTGGGAAC TGGATACGCT   11520

GGTCAGTGCA CTCATGACAG CGCTTCCCGA CCATGCCGCC AGTCCCCTGA TGACCCGACT   11580

GCAGGACGAG CTGCGCACGG AGTCTGTCCG CGCTCAGGCC CGTGAACAGT TTACCGGTGC   11640
```

```
GGTGGACCGG ATATTTGACA CAGCGGAGAG CGTCTGTGTT GCCTCTGTTG TCCGTACGGC   11700

CCTGCGCGCT GTTCGTGACA CCGTGGTCTC TGTTGCCCGC GCGGTATGGA ACTGGATCTT   11760

CTTCTGAACC TGTTGTGGAT GATGTCCTCC CTGCCTCTGA GTCTGCTCAC AAAAGCGCTG   11820

TTTTCGTTAC TGTCTCTCTT GTCCGTGCAA TAGCTCAATA ATAGAATAAA GCGATCGATA   11880

ACTATTTCAT CGATCGTTTA TATCGATCGA TATGCTAATA ATAACCTTTA TTACCAACAT   11940

GCGCAGATAC GCACAGACAG ACATTCAGGG GACGACAGAA CAACACTTCA GAAACTCCCG   12000

TCAGCCGGAC CTCCGGCACT GTAACCCTTT ACCTGCCGGT ATCCACATCT GTGGATACCG   12060

GCTTTTTTAT TCACCCTCAC TCTGATTAAG GAAATGCTGA TGAAACGACA TCTGAATACC   12120

TGCTACAGGC TGGTATGGAA TCACATTACG GGCGCTTTCG TGGTTGCCTC CGAACTGGCC   12180

CGCGCACGGG GTAAACGTGG CGGTGTGGCG GTTGCACTGT CTCTTGCCGC GGTCACGTCA   12240

CTCCCGGTGC TGGCTGCTGA CATCGTTGTG CACCCGGGTG AAACAGTGAA TGGCGGAACA   12300

CTGGTAAACC ATGACAACCA GTTTGTATCC GGAACAGCTG ATGGCGTGAC TGTCAGTACC   12360

GGGCTTGAGC TGGGGCCGGA CAGTGACGAA AACACCGGCG GCAATGGAT AAAAGCGGGT   12420

GGCACAGGCA GAAACACCAC TGTCACCGCA AATGGTCGTC AGATTGTGCA GGCAGGAGGA   12480

ACTGCCAGTG ATACGGTTAT TCGTGATGGC GGAGGGCAGA GCCTTAACGG ACTGGCGGTG   12540

AACACCACGC TGGATAACAG AGGTGAGCAG TGGGTACACG GGGGAGGGAA AGCAGACGGT   12600

ACAATTATTA ACCAGGATGG TTACCAGACC ATAAAACATG GCGGACTGGC AACCGGAACC   12660

ATCGTCAACA CCGGTGCAGA AGGTGGTCCG GAGTCTGAAA ATGTGTCCAG CGGTCAGATG   12720

GTCGGAGGGA CGGCTGAATC CACCACCATC AACAAAAATG GCCGGCAGGT TATCTGGTCT   12780

TCGGGGATGG CACGGGACAC CCTCATTTGC GCTGGTGGTG ACCAGACGGT ACACGGAGAG   12840

GCACATAACA CCCGACTGGA GGGAGGTAAC CAGTATGTAC ACAACGGTGG CACGGCAACA   12900

GAGACGCTGA TAAACCGTGA TGGCTGGCAG GTGATTAAGG AAGGAGGAAC TGCCGCGCAT   12960

ACCACCATCA ACCAGAAAGG AAAGCTGCAG GTGAATGCCG GCGGTAAAGC GTCTGATGTC   13020

ACCCAGAACA CGGGCGGAGC ACTGGTTACC AGCACTGCTG CAACCGTCAC CGGCACAAAC   13080

CGCCTGGGAG CATTCTCTGT TGTGGAGGGT AAAGCTGATA ATGTCGTACT GGAAAATGGC   13140

GGCCGTCTGG ATGTGCTGAC CGGACACACA GCCACCAGAA CCCGTGTGGA TGATGGCGGA   13200

ACGCTGGATG TCCGCAACGG TGGCACCGCC ACCACCGTAT CCATGGGGGA TGGCGGTATA   13260

CTGCTGGCCG ATTCCGGTGC CGCTGTCAGT GGTACCCGGA GCGACGGAAC GGCATTCCGT   13320

ATCGGGGGCG GTCAGGCGGA TGCCCTGATG CTGGGAAAAG GCAGTTCATT CACGCTGAAC   13380

GCCGGTGATA CGGCCACGGA TACCACGGTA AATGGCGGAC TGTTCACCGC CAGAGGGGGC   13440

ACGCTGGCGG GCACCACCAC ACTGAATAAC GGTGCCACGC TTACCCTTTC CGGGAAAACG   13500

GTGAATAACG ATACCCTGAC CATCCGTGAA GGTGATGCAC TCCTGCAGGG AGGCGCTCTT   13560

ACCGGTAACG GCAGGGTGGA AAAATCAGGA AGTGGCACAC TCACTGTCAG CAACACCACA   13620

CTCACCCAGA AAACCGTCAA CCTGAATGAA GGCACGCTGA CGCTGAACGA CAGTACCGTC   13680

ACCACGGATA TCATCGCTCA TCGCGGCACG GCCCTGAAGC TGACCGGCAG CACCGTGCTG   13740

AACGGTGCCA TTGACCCCAC GAATGTCACC CTCGCCTCCG GTGCCATCTG GAATATCCCC   13800

GATAACGCCC CGGTTCAGTC AGTAGTGGAT GACCTCAGCC ATGCCGGACA GATTCATTTC   13860

ACCTCCGCCC GCACAGGGAA GTTCGTACCG GCAACTCTGC AGGTGAAAAA CCTGAACGGA   13920

CAGAATGGCA CCATCAGCCT GCGTGTACGC CCGGATATGG CGCAGAACAA TGCTGACAGA   13980
```

```
CTGGTCATTG ACGGTGGCAG GGCAACCGGA AAAACCATCC TGAATCTGGT GAACGCCGGC    14040
AACAGTGCGT CGGGGCTGGC GACCACCGGT AAGGGGATTC AGGTGGTTGA AGCCATTAAC    14100
GGTGCCACCA CGGAGGAAGG GGCCTTTGTC CAGGGGAATA TGCTGCAGGC CGGGGCCTTT    14160
AACTACACCC TCAACCGGGA CAGTGATGAG AGCTGGTATC TGCGCAGTGA AGAACGTTAT    14220
CGTGCTGAAG TCCCCCTGTA TGCCTCCATG CTGACACAGG CAATGGACTA TGACCGGATT    14280
CTGGCAGGCT CCCGCAGCCA TCAGACCGGT GTAAGCGGTG AAAATAACAG CGTCCGTCTC    14340
AGCATTCAGG GCGGTCATCT CGGGCACGAT AACAACGGTG GTATTGCCCG TGGGGCCACG    14400
CCGGAAAGCA GCGGCAGCTA TGGCTTCGTC CGTCTGGAGG GTGACCTGCT CAGAACAGAG    14460
GTTGCCGGTA TGTCTGTGAC CGCGGGGGTA TATGGTGCTG CTGGCCATTC TTCCGTTGAT    14520
GTTAAGGATT ATGACGGTTC CCGCGCCGGC ACGGTCCGGG ATGATGCCGG CAGCCTGGGC    14580
GGATACCTGA ATCTGGTACA CACCTCCTCC GGCCTGTGGG CTGACATTGT GGCACAGGGA    14640
ACCCGCCACA GTATGAAAGC GTCATCGGAC AATAACGACT TCCGCGCACG GGGCCGGGGC    14700
TGGCTGGGCT CACTGGAAAC CGGTCTGCCC TTCAGTATCA CTGACAATCT GATGCTGGAG    14760
CCACGACTGC AGTACACCTG GCAGGGGCTC TCCCTGGATG ACGGTAAGGA CAACGCCGGT    14820
TATGTGAAGT TCGGGCATGG CAGTGCACAA CATGTGCGTG CCGGTTTCCG TCTGGGCAGC    14880
CACAACGATA TGACCTTTGG TGAAGGCACC TCATCCCGTG ACACCCTGCG TGACAGTGCA    14940
AAACACAGTG TGCGTGAACT GCCGGTGAAC GGGTGGGTAC AGCCTTCTGT TATCCGCACC    15000
TTCAGCTCCC GGGGAGACAT GAGCATGGGT ACAGCCGCAG CCGGCAGTAA CATGACGTTC    15060
TCACCGTCCC GGAATGGCAC GTCACTGGAG CTGCAGGCCG GACTGGAAGC CCGTGTCCGG    15120
GAAAATATCA CCCTGGGCGT TCAGGCCGGT TATGCCCACA GCGTCAGCGG CAGCAGCGCT    15180
GAAGGTTATA ACGGCCAAGC CACACTGAAT GTGACCTTCT GATAATTCGG CATTGTCTCT    15240
CTGTGGTCCC GGTCATCATG ACCGGGACCC GGACAGGTGC AAAACGCTTCA GTGCCACATT    15300
CACTGGCATT CACAATAACA TGATATTCAT CACGGAGTGA CTATGTTACA GATAGTCGGT    15360
GCGCTGATTC TGCTGATCGC AGGATTTGCC ATTCTTCGCC TTTTGTTCAG AGCATTAACC    15420
AGCACAGCGT CTGCGCTGGC AGGGTTCATA TTGCTGTGTC TGTTCGGCCC GGCTTTACTG    15480
GCTGGCTATA TCACTGAACG CATAACCCGG TTATTCCATA TTCGCTGGCT GGCAGGCGTA    15540
TTTCTGACGA TTGCCGGAAT GGTCATCAGC TTCATGTGGG GACTTGATGG TAAACATATC    15600
GCACTGGAGG CTCATACCTT TGACTCTGTA AAATTTATTC TGACCACCGC TCTCGCCGCT    15660
GGTCTGCTGG CTCTTCCCGT GCAGATAAGA ACCATTCAGC AGAACGGGCT CACACCAGAA    15720
GATATCAGCA AGGAAATTAA CGGGTATTAC TGCTGTTTTT ATACTGCTTT TTTCCTTATG    15780
GCGTGTTCTG CATACGCACC ATTGATCGCA TTGCAGTTCG ATATTTCACC CTCACTGATG    15840
TGGTGGGGCG GGTTGTTGTA CTGGCTGGCT GCATTAGTGA CGCTGCTATG GGCGGCCAGC    15900
CAGATCCAGG CGCTGAAAAA ACTGACCAGT GCCATCAGCC AGACACTGGA AGAACAACCG    15960
GTGCTCAACA GTAAATCGTG GCTGACCAGT TTGCAAAACG ATTACAGCCT TCCTGACTCA    16020
CTGACGGAGC GCATCTGGCT CACGCTCATT TCACAACGGA TTTCCCGGGG AGAACTGAGG    16080
GAATTTGAAC TGGCAGACGG AAACTGGCTA CTGGACAATG CCTGGTATGA AGAAACATG     16140
GCGGGTTTCA ACGAAAAGCT GAGAGAGAGC CTGTCATTTA CCCCTGATGA ACTGAAAACC    16200
CTCTTCCGGA ACCGCTGAA TTTATCACCG GAAGCGAATG ACGATTTTCT CGATCGTTGC     16260
CTGGACGGCG GTGACTGGTA CCCCTTTTCA GAAGGCCGCC GTTTTGTATC ATTCCACCAC    16320
GTGGATGAGC TTCGTATCTG TGCCTCCTGC GGGCTGACAG AAGTACATCA TGCCCCGGAA    16380
```

```
AATCATAAGC CGGATCCGGA ATGGTACTGC TCCTCTCTTT GTCGCGAAAC AGAAACACTG    16440

TGTCAGGACA TTTATGAACG TTCTTACACC GGTTTTATTT CCGATGCAAC GGCGAATGGT    16500

CTGATTCTCA TGAAACTGCC GGAAACCTGG AGTACAAATG AGAAAATGTT TGCTTCCGGA    16560

GGGCAGGGAC ATGGGTTTGC CGCTGAACGG GGAAACCATA TTGTCGACAG AGTCCGTCTG    16620

AAAAACGCAC GGATCCTCGG TGATAATAAT GCCAAAAATG GAGCAGACAG ACTGGTCAGC    16680

GGAACAGAAA TCCAGACGAA ATATTGTTCA ACTGCAGCCC GTAGCGTCGG TGCGGCATTC    16740

GACGGACAGA ACGGACAGTA TCGTTACATG GGAAATCATG GTCCCATGCA ACTGGAAGTC    16800

CCCGTGATCA GTATGCCGGC GCTGTGGAAA CCATGAAGAA TAAGATCCGC GAAGGTAAAG    16860

TACCCGGTGT AACCGATCCC GAAGAAGCGT CCCGGCTGAT TCGTCGGGGA CATCTGACTT    16920

ATACCCAGGC CCGTAATATC ACCCGGTTCG GGACCATCGA ATCGGTCACT TATGATATTG    16980

CCGAGGGGTC GGTTGTCAGT CTGGCGGCCG GAGGGATCAG TTTTGCCCTG ACGGCATCGG    17040

TCTTCTGGCT CAGCACCGGC GATCGCGATG CTGCCCTGCA GACAGCTGCT GTCCAGGCAG    17100

GAAAAACCTT CACCCGCACA CTGGCTGTCT ACGTCACAAC CCAGCAACTT CACCGGCTCA    17160

GTGTTGTTCA GGGTATGCTG AAGCATATTG ATTTTTCGAC GGCCAGCCCG ACTGTCCGGC    17220

AGGCGCTTCA GAAGGGGACC GGTGCAGGAA ATATCAGTGC CCTGAACAAA GTGATGAAGG    17280

GGTCGCTGGT GACATCTCTG GCACTGGTAG CTGTCACAAC CGGCCCTGAC ATGATCAAAA    17340

TGTTGCGGGG ACGGATCTCC GGTGCGCAGT TCATCAGGAA TCTTGCCGTG GCATCTTCCT    17400

GTGTGGCAGG TGGTGCTGTC GGGTCAGTGG CGGGCGGGAT ATTGTTCAGT CCACTGGGAC    17460

CATTTGGTGC ACTGACAGGG CGTGTGGTTG GCGGTGTTCT GGGGGGAATG ATTGCCTCCG    17520

CTGTATCAGG AAAAATTGCC GGAGCGCTGG TTGAAGAAGA TCGCGTCAAA ATTCTGGCAA    17580

TGATTCAGGA GCAGGTGACA TGGCTTGCCG GCAGTTTCCT GCTGACCGGA CATGAGATTG    17640

AAAATCTGAA CGCGAATCTG GCCCGTGTTA TCGATCAGAA TGCTNCTGGA GATCATTTTC    17700

GCCGCCGGTA                                                          17710

(2) INFORMATION FOR SEQ ID NO: 71:

(i) SEQUENCE CHARACTERISTICS:
        (A) LENGTH: 1803 base pairs
        (B) TYPE: nucleic acid
        (C) STRANDEDNESS: double
        (D) TOPOLOGY: linear (xi) SEQUENCE DESCRIPTION: SEQ ID NO: 71:

AATAACCAAT AGATGCTTAA GTTTACGATA TGCCTCAACC CGCGTCTGCT CTAAGCTGAT      60

AAGGCCAGTT TTGTAGAGAT CCGCTGCCAA GGTTGCCTGC GTTTGCACAT CCATGTAACC     120

GGCGGTGATT TCATTCATGG CATCGTTATC TTGACCAGTC AGCTTAGCAC GCTCCTGTTC     180

AAGCTGCTTG GTTAGGGCGT CAACTCGGCT CTGTAATGAG ACTACGGCCG GTGCGGTTTC     240

CTTCATATAG CTGCGCAGTT GTTTTAGCTC CGCCTGTTGA CGCACCAGCT CTCCTTCAAT     300

CTGGCTGACC ACTCCCAAGC GTGCGCTGCT GGTAGATTCA GGGCTGAGAA GTTGGTGGCT     360

ATTCTGAAAT GCTAATACTT TAGCTTTTTC ATCCTGTAAG CGTTGATATG CTCTATTTAC     420

TTCTTTTTCA ACAAAGGCCA ATTGTTCGAG CGCAACCTGA TGACCTAATT TGTTAATAAA     480

ACGCTCCGAT TCTTTGAGCA TTAACTCAAC AACTCGCTGA CCGTATTGGG GATCAAATGT     540

CTGCAACTCA ACGGTAAGTA CTCCTGATAA TTCATCAAGG TGTAACGTCA AATGTTTGCG     600

GTAATAATCA AGAAAATCTT CCCTACTGAC TCCCTTATGC AACCGCGAGA ATAATCTGC      660
```

| | |
|---|---|
| ACTATCACTC TGGAAATGTG CTTTAAGTGC AAGTTCTTTG TCCAACTTGG CCAGCATATC | 720 |
| CCATGACTTC ATATAATCCT GAACGAGTAA TATATCCTGA TGATTACTAC CACCTATCCC | 780 |
| TAACATTGAT AACGCATCAG GCAACATTTT AACTTGATCG GCTTGTTTAA TCATTAATTC | 840 |
| AGCCCGGSTC ACATAACGAT CGGAAGCAAT GAAGCCAAAA TAGAGCACTG CGATAGAAAA | 900 |
| GCAGATAACT ACCCAAAGAA AACTGCCTAG CTGTAAACTT TTCTTCCACG AGCGGTGTAC | 960 |
| AATTTGATAT CCTCTCGAAT CAATCAAAAA TAGTTTTGGA TTATTGCTCA GTTTTCTTAA | 1020 |
| CTTTCGCGTA AGGCGAGATA TTGAGGATGA AGAATTCGGA GATGTCATAA TCAGTTGCTG | 1080 |
| CTCAAAGTGA CTGGTAAATT TTGATGGCAT CATCAATATT ATCAAAAACT TCTAATTTAC | 1140 |
| CATCACGTAA CAAGATGCCC ATATCGCATT GTTGTCGTAG ATTTTTCATA TCATGCGAAA | 1200 |
| CCATAATCAA ACTAGCTGTT CTCGCTTTT TGTTAAATAC ATCAATACAT TTTTGTTTAA | 1260 |
| AACGTGCATC ACCTACTGAG GTAATTTCAT CGGTAAGATA TATATCAAAA TCAAAAGCCA | 1320 |
| TACTAACAGC AAAAGAAAAT TTTGATTTCA TGCCGCTAGA GTATGTTTTA ATAGGCAGCT | 1380 |
| CATAATGTTG TCCAATTTCA GAAAACTCTT TAACCCACTC TTCTACGGGG CTTGTATCGC | 1440 |
| GTACACCATG AATGCGGCAA ACAAATCGCG TGTTTTCACG ACCAGTCATA CTACCTTGAA | 1500 |
| ATCCCCCAGC TAGTGCTAGA GGCCAAGATA CTCGGCAGAG ACGAGTTACT TTCCCCCTGT | 1560 |
| TAGGCGTATC CATCCCTCCT AACAAACGTA ACAAAGTAGA TTTYCCKGCT CCATKGATAC | 1620 |
| CTAGAATACC TATATTACGG TCCCTTGGTA GCTCAATATT TACATTCCTC AGGACATAAT | 1680 |
| TTCGTCCAAA TTTAGTTGGA TAATATTTTG ATACATTATC AAGAATAATC ATTTTTCTTA | 1740 |
| ACGCTAACTA GCAATCAATT GGCGATGCCG TAATCGGTAA CAACTCATAG CAAAAGTGAG | 1800 |
| CAA | 1803 |

(2) INFORMATION FOR SEQ ID NO: 72:

(i) SEQUENCE CHARACTERISTICS:
        (A) LENGTH: 1283 base pairs
        (B) TYPE: nucleic acid
        (C) STRANDEDNESS: double
        (D) TOPOLOGY: linear (xi) SEQUENCE DESCRIPTION: SEQ ID NO: 72:

| | |
|---|---|
| NGGACCCAAG GTAAAAACNG GTAAAAAAAA CMATTGACCG ATTAAACTTT ATTTCTCTGC | 60 |
| CCGCATTAGT CTGGAGAGAG GATGGATGTC ATTTTAATTT NACTAAAGTC AGTAAAGAAG | 120 |
| CAAACAGATA TCTTATTTTT GATCTGGAGC AGCGAAATCC CCGTGTTCTC GAACAGTCTG | 180 |
| AGTTTGAGGC GTTATATCAG GGGCATATTA TTCTTATTGC TTCCCGTTCT TCTGTTACCG | 240 |
| GGAAACTGGC AAAATTTGAC TTTACCTGGT TTATTCCTGC CATTATAAAA TACAGGAAAA | 300 |
| TATTTATTGA AACCCTTGTT GTATCTGTTT TTTTACAATT ATTTGCATTA ATAACCCCCC | 360 |
| TTTTTTTTCA GGTGGTTATG GACAAAGTAT TAGTACACAG GGGGTTTTCA ACCCTTAATG | 420 |
| TTATTACTGT CGCATTATCT GTTGTGGTGG TGTTTGAGAT TATACTCAGC GGTTTAAGAA | 480 |
| CTTACATTTT TGCACATAGT ACAAGTCGGA TTGATGTTGA GTTGGGTGCC AAACTCTTCC | 540 |
| GGCATTTACT GGCGCTACCG ATCTCTTATT TTGAGAGTCG TCGTGTTGGT GATACTGTTG | 600 |
| CCAGGGTAAG AGAATTAGAC CAGATCCGTA ATTTCCTGAC AGGACAGGCA TTAACATCTG | 660 |
| TTCTGGACTT ATTATTTTCA TTCATATTTT TTGCGGTAAT GTGGTATTAC AGCCCAAAGC | 720 |
| TTACTCTGGT GATCTTATTT TCGCTGCCCT GTTATGCTGC ATGGTCTGTT TTTATTAGCC | 780 |
| CCATTTTGCG ACGTCGCCTT GATGATAAGT TTTCACGGAA TGCGGATAAT CAATCTTTCC | 840 |

| | |
|---|---:|
| TGGTGGAATC AGTCACGGCG ATTAACACTA TAAAAGCTAT GGCAGTCTCA CCTCAGATGA | 900 |
| CGAACATATG GGACAAACAA TTGGCAGGAT ATGTTGCTGC AGGCTTTAAA GTGACAGTAT | 960 |
| TAGCCACCAT TGGTCAACAA GGAATACAGT TAATACAAAA GACTGTTATG ATCATCAACC | 1020 |
| TGTGGGTTGG GGTGCACACC TGGTTATTTC CGGGGATTTA AGTATTGGTC AGTTAATTGC | 1080 |
| TTTTAATATG CTTGCAGGTC AGATTGTTGC ACCGGTTATT CGCCTTGCAC AAATCTGGCA | 1140 |
| GGATTTCCAG CAGGTTGGTA TATCAGTTAC CCGCCTTGGT GATGTGCTTA ACTCTCCAAC | 1200 |
| TGAARTTCAT CATGGGAAAC TGGSATTACC GGRAATTAAW GGTGATATCA CTTTTCGTAA | 1260 |
| TATCCGGTTT CGCTATAAGC CTG | 1283 |

(2) INFORMATION FOR SEQ ID NO: 73:

(i) SEQUENCE CHARACTERISTICS:
        (A) LENGTH: 6836 base pairs
        (B) TYPE: nucleic acid
        (C) STRANDEDNESS: double
        (D) TOPOLOGY: linear (xi) SEQUENCE DESCRIPTION: SEQ ID NO: 73:

| | |
|---|---:|
| TCAACCTGAC CAACCACTAG AATCAACTCA CGTCCGTCGT TAGGGGGCTC ATATTCTTGT | 60 |
| GTACTCCCCA CATTGTATTT ACTGACTCGT GATGATTGTA ATTGCGCTAA TAATGACTCT | 120 |
| GCGCGTGCTT CTTCTTTCGC ATCTAAAACG TACGTAGTGA GTAACTGCTC AAGCTTACTC | 180 |
| GGACGGCGGC TATCAAAATA GATTCCAACG GGGTCAATCG AGAGTGATGA AGGTCGACAT | 240 |
| AAATTAGACC CCAATCCGTT GGAGCGGATA AAACCATCTT CAATCCGGAT CACTGATTGC | 300 |
| AGTTCAGGAT AACGGTTTCC CCACACCAAC ACCTGTTCAT CATCTTTTAA CTGTGAGGGC | 360 |
| ACAGTACGAA CAAAACAAAG TTCATCTGCC AAATACGCAC AAAATGTGCG TATAAAAGCA | 420 |
| CGCTTCCACA GAGAAAAACC AACGAGATAA AGACGACGCC AAGGTTTGGG CTCTACCTGC | 480 |
| TGCTGAGCCA AAATCGCTAC AACATCTTCT ACCTCACAAC GTTTTCCCAA TATAGGATCT | 540 |
| AAATAACGCG GATAACGGAT CAACGCCGCC GCAACTAAGC GGGGCAATGA AATAGATGAA | 600 |
| ACGCCTTCGG CTGACATTGC TTCTTCACGG CGTATACAAC GTTTACTGTC ATGCGTTAAC | 660 |
| CCCCACCCAG CATAAAATGG CATACCGAAG CAATATACAG GTTTGCCCAA CAGCAACGCT | 720 |
| TCCAAAGCCA ACCTGCGATG AAACTGTGTA CACCGCATCC ACCATACGAA TTATTCTATG | 780 |
| CGGATGGCAA GTTCACTCAC CACCTCAACA TCAGCCAGTC GAGGATCACG CCCCACTAAA | 840 |
| CGTGCTAACA CGCCGCTTTT TTTGCTAAAG CGTGTATCTG GGTGTGTTCG CAACAATAGA | 900 |
| CGCGCATTAG GGTGATTACG GCGAGCCTCG ACCACCATAG AAACAAAATC AGCTTCGCAA | 960 |
| GCAAGAGCCC CAGAAATTGA CAAGTCTCCC GCTACTTGAT CCACAAGCAA AATACGCGGT | 1020 |
| CTTGGATCAT CCAGTAAACG TGCTAAGTTT GAATGAGCCG TGAGGTGAAT AACTCAGGTT | 1080 |
| GTATATGTGT CGGTAAATCT AAAGAAGGCC CGTCAGTAGC ACGGGACAGA GCCATTAAAT | 1140 |
| GTATGCTCAG TGCTATTGGG TATAGCAGTT ATACTTGGTG ATTCCTAAAC GCAAAATATC | 1200 |
| MGAGATCAGA TGCTCCAGCG CGCGCAAAGT AAAGCCGTAT CCAACAGGTT CCAATAATAA | 1260 |
| GCTGTTCTAA TTGACTCGTC TGATGTGCAT CATAATATAT CCCCAGAGGG TCAGCAATAA | 1320 |
| GAGAAACCGC CTTTCCTCCT TTTGCTGGGT GCCCGATATA GCCAATAAAA CCATCTTCAA | 1380 |
| GTTGCCAATA AGATATTCCT AACTCTTGAG CTTTCTGTTT AATCTGCTTA GTATTAGATT | 1440 |
| TTTTTCCCCA GCCAACTAAA ACGTCATTTT TAGAAAAAGC CTCGTCTCCT TTCATATAAA | 1500 |
| GCAATGGGTG ACCAAGCATA GGCTCAATAT TATTTTYTCT GGCAAGAATC CCTTTCGATC | 1560 |

-continued

```
CCGTATATAA ATACATGTTG TCTCTGTGAA CTGAAGATTC TCTACAATGG TGTATAAAGT    1620

GTGATTTAGA TGAACAGCTC TGCGCTCTCT AATGACTTTG CAATACTATC TTTTGCTGAA    1680

GTGAGAATGT CCGCCTTTAA CTCGGGCCAC CTAATACCAA TTGTAGGATC ATTCCATGCA    1740

ATGCCTCTAT CACTGGCAGG GGCATAATAA TTAGTTGTTT TATACAAAAA TTCGGCCGAT    1800

TCAGTCAGTG TTACAAAACC ATGGGCAAAT CCTTCCGGAA TCCATAATGT CGTTTGTTTT    1860

CCCCTGAAAG ATGAACGCCA ACCCATTGTC CGRAGCTCGG TGAGCTTTTG CGAATATCTA    1920

CCGCAACATC AAACACTTCA CCGGCTACAC AACGCACTAA CTTGCCCTGG GCATGGGGAG    1980

GTAACTGATA GTGCAAGCCA CGCAGTACCC CTTTAGAAGA TTTTGAGTGA TTATCCTGCA    2040

CAAAGGTAAC TGGATATCCT ACAGCCTCTT CAAACAACTT GTGATTAAAA CTCTCAAAGA    2100

AAAAACCACG CTCATCTCCA AATACTTTTG GCTCAAAAAT AAGCACACCA GGAATTGCTG    2160

TCTTGATTAC ATTCATCTAT ATGCCCACAT TTAATTAAAT ATTTTTAGGG GAAGCATATT    2220

CCCTCCCCCT TCTCAATTAC ATCACGCCTT ATCAATCATT TTTAATAAAT ATTGCCCATA    2280

GGCGTTTTTT GCCAACGGAG CAGCAAGYTC ACGAACCTGG TCGGCACTAA TAAACTTCTG    2340

GCGATAAGCA ATCTCTTCCG GACAAGCCAC TTTCAATCCC TGACGCGTCT CGATGGTCTG    2400

AATAAAGTTA CTCGCTTCAA TTAGGCTTTC GTGGGTACCG GTATCAAGCC AGGCATAACC    2460

ACGCCCCATC ATTGCCACCG ATAGATTGCC TTGCTCCAGG TAAATACGGT TCACATCGGT    2520

GATTTCCAAC TCACCACGCG GCGATGGCTT GAGACCCTTG GCAACGTCCA CAACGCTGTT    2580

GTCGTAGAAA TAGAGGCCGG TGACTGCGTA STACTCTTAG GCTCCAGTGG TTTTTCTTCC    2640

AGTGAAATAG CGGTACCTTG ATTATCAAAT TCGACCACTC CATAACGTTC CGGGTCGTGC    2700

ACATGATAGG CAAATACAGT AGCACCGGTC TCTTTGGCCG CGGCTGCCTC CAACTGTTTC    2760

TGTAGGTCAT GACCGTAGAA GATGTTATCC CCCAGCACCA GTGCACACGG GGCTGAACCA    2820

ATGAATTCTT CACCTAGAAT AAAAGCTTGT GCCAACCCGT CTGGGCTTGG CTGAACCTCA    2880

TATTGTAAAT TCAGTCCCCA GTGGCTGCCA TCACCCAGCA ATCGCTGAAA GGANGGAGTA    2940

TCTTGTGGAG TGCTAATGAT CAAAATATCG CGAATTCCAG CCAGCATCAG GGTGCTCAGC    3000

GGCCGCAGTA CTGGATCATC GGCTTGTCAT AGATGGGCAA CAACTGCTTG CTCACCGCCA    3060

TAGTAACCGG ATAGAGACGT GTACCAGATC CACCGGCCAG AATAATACCT TTACGTTTAG    3120

TCATGATGCT TGTTTCTTAT TTTTAAATTA CATAAGAATA AAGTGGCTTG AGCCGCGCCT    3180

TTCTGTTTTA TCCTCACCTG TGGTTTACTT CCCCATGATC TCAGTCAACA TCCGCTCAAC    3240

ACCGACTGAC CAGTCCGGCA AAACCAGATC AAATGTACGC TGGAATTTTT TAGTATCAAG    3300

TCGGGAATTA TGAGGGCGTT TCGCCGGGGT CGGAAAGGCG CCTGTCGGCA CTGCATTAAG    3360

CTGTGTGACT GCCAGTTCAA CTCCTGCGTC TCTGGCTTTG TCAAACACCA ACCGGGCGTA    3420

GTCAAACCAA GTGGTAGTAC CGGAGGCAGC CAAATGGTAC AGCCCGGCAA CGTCGGGTTT    3480

GCTCTGTGCA ACTCGGATTG CATGGGCGGT ACAATCGGCC AGCAACTCAG CTCCAGTTGG    3540

AGCGCCAAAC TGATCATTAA TGACCGATAT CTCGCGACGC TCTTTGCCAA GACGCAGCAT    3600

AGTTTTGGCG AAGTTGGCAC CGCGCGCAGC ATAAACCCAA CTGGTACGAA AGATAAGGTG    3660

ACGTGAGCAG AGTGCCGCAC CGTGTTCCCC TGCCAGCTTG GTTTCGCCAT AGACGTTGAG    3720

CGGGGAAATC ACATCGGTTT CCACCCAAGG ACGTTCACCA CTTCCATCGA AACATAGTC    3780

GGTGGAATAA TGTACTAGCC ACGCACCTAA TGCTTCAGCT TCTTTGGCAA TAACCGCCAC    3840

ACTAGTTGCA TTGAGTAACT CGGCAAATTC CCGCTCACTC TCCGCTTTGT CGACTGCAGT    3900
```

```
ATGGGCCGCT GCGTTAACAA TCACATCCGG CTTGACGAGA CGTACCGTTT CAGCCACCCC    3960

TGCAGAATTG CTAAAATCAC CGCAATAGTC GGTGGAGTCA AAATCAACGG CAGTGATGTG    4020

CCCCAGAGGC GCCAATGCAC GCTGCAGCCC CCATCCACTT TCTGGCCACA CCAGACTCGC    4080

CAGCAAAAAA GTGAGTGCTG TCAATAACTC AACCAGCGGA TAACGCTTGC TGATTTTCGC    4140

CTGACAGTCG CGGCAGCGCC CTTTGAGCAT CAACCATGAG AGCAGCGGAA TATTGTCACG    4200

AACGCGGATG GTCTGCTGGC AATGCGGACA GTGCGAACGC GGTAGCGCAA GGCTTATTTT    4260

TGACTGCGCA CTCGGCATTT CACCATGAAA CTCCGCCATT TGTTGGCGCA GCATGATGGG    4320

GTAACGCCAA ATCACCACAT TCAAAAAACT GCCGATGATC AATCCTCCGA CGGTTGCCAG    4380

TATGGGCATC GCCGCGGGGT ATTGCTGAAA ACATCAAAA AGCATGGTTA AAGGTTATTT    4440

GTTGTAACTT GCCGGATGCG GGCCTGCGGG TGTATGCCAT ACGGCTTTCC TTCAGGCCCG    4500

ATGCGCCTTA TTTCATGCCG GATGCGGCGC GAGCGCCTTA TCCGGCATAC AGGCTTACTC    4560

AGCTGACATC TTATGCTCGG TAACCTGATT AATGGTTTCC GGCCCTTGCT GCGGTTTCGG    4620

CAGATTAAGC GCCGCCAGTG TCTCGTAAGC CGACTGGCTC ACACCGCCCT CGAAGTTCAT    4680

CTCGCTCGCT CCCGGCAACT GGTAAGCATT CGCGCCCGGA TTCCATTTCT TAAAGAACTC    4740

CGAAAGATCC GTCTGGGCGA CCCAGGATGC ACACAGCATC AGCTTGTCGG CAGCGTTACC    4800

GTTGGATTCG GCACAGTAAT TTCTTTCGCC AAACTTGGTT TTGCCAACCT CATCGCCGCG    4860

TGCTTTACGG TGCATCAACT GGAACAGGTT CCAGCCTTTC ATCCCTTCAC GATCGCTGTA    4920

GAACTTAGGC AGGTCACCTT CTGGATACCA CTGTTTGATA TCAAAGTTTT TCTCTGCCCA    4980

CTCTTTCAGC TGTGCGTACA TCAGCAGACG GTCACCCGCA CCGCCGCGCG CCCATGCCTG    5040

ACCGTTGCTC TCCTCCAGAT ATTCCGGCGC GACGGTAATG TCGTCAGCGA CACGGTTCAT    5100

CTTGCCGAGA TAGCGATCCT GCATGTACAG CGCCAGCACG TTGTTCGCTA CTTCAGTTGC    5160

GCCAGGAACA GTCAGCGGCG TTTCGGCGGC GTTGTGACCA ACTTCGTGCC AGATCAGCCA    5220

GTCGTTCAGC GGCGTCGTCG GCAGCGTGGT GCTGTTCGTC GAGAAGCTGC TGTTCATTAC    5280

CGGATAACCA GAGTGCGCAT CACCGATGGA GATCTGCACA TCGTTGGTGA AACGATGCTT    5340

GTGGCCCGTC AAGTTTTTAT AGGTAAACAT CCGGTGCTTA CCGTCTTCAT CATTACGACC    5400

GTAGAAGTCA TTCATCGAGC TGGCAAAGGT ATCCAGATCT TTAGCGAATT CTGCTACGCC    5460

ACCAGTGAAA TTGCTGGCCT CAAGGTTCTT CTTCGGCGTG GTGTAGACGA AAGCGTCTGA    5520

CTCCAGCTCG CCCAACGGCG CAGGGAGTT CAGAGCGTTT TTCCATGCGC CATCTTTATA    5580

GAACGGCGCT TTCACCACAC CAGTAAAGGT GAATTCGGCT GACTCATTCT GTGGGCTGTT    5640

GCCCTTGATA TAAATCAGAC CACCGTAAGG AACCGTAAAC TTCACCTCAC CATTGGCTTT    5700

CAGCTCATAG GTTTTCGTCA CTTTTGGCGG ACGGTTCAGA GCGACTTCAT GCTTCTCACG    5760

TCCGGTAAGG TCGTCGGCCA GCGCCACGGT GACAGTCACA GGAACTGATG CAGAAGACTC    5820

AATGGTGACC TCTTTCTGAG CCGGAGCCCA CAGGCCAGTA GACTGCATGT TACCCGCAAA    5880

CCATTTGGTC GGATTCGAGT ACAGGCTGAT GGTTTCAGTA ACCTTCTCAC CTTCTGCCGA    5940

TACCGCTCCC GGATACTTCT CGACATCAAC TTTGATGTTC AGATCCCACC AGGAACGACC    6000

CAGCATCAGG CGCGTCAGCG GTTTTTCCAT ATAGTTGAGC GGATAGCTCG GGTTCATCAT    6060

GCCCGCTTTA TTAACGCTCT TCTCGCCGTA GATCATGTTG TTATCGACCA GCGATTTTTT    6120

CAGCTCATCA GAAACACTGC GTGCCGCCAG TATAGGCATC GTTGGCGTAG CAGTTCAGGA    6180

ACTCGGTGAA CGTTTTAAAG CCCAGCTCGT CATCCTTGTC GTTTTCATAG CGATATTCAA    6240

TTTTATTCCA CAGCCAGACC GACATGTTCT GGTACAGACG TTCCAGATCG ACGCTGCTCA    6300
```

```
GACGCTCACC TTTGCGACCA TTGGTCCGGA AGTAGAGCTC ATGCTGATAC AGACGCTGAA    6360

TGTTGGTGCC TAAATCCGCA GCCTGCACCA TCGCTTTTGC CGTGTCGGCG TTAAGGCTTA    6420

GTTGCGTATA CTGTGGAACA TACATGCCAC CAGTAACCGG AACCCCCGTG CCAGGACGAT    6480

ATTCCAGACA GTTGACCTCG TAGTGGTAAG TTGGGTCCTT ACACTCCTTT AATCCAGGAA    6540

ACTTCTCAAA GATTTTTGCC TTCGCAGCCT TCAGAGAATC CTCTGTTTTA TGATCGGCCT    6600

CATCAATAAA GGCATAACGC GTTTCCTGTT TGCCATCTAC ATCTTCCAGC CAGCTGGCAA    6660

CTTCCAGCTT CGGTTTGTCA TCAGGTTTGT TTTCTACCTG ATATTTCCAC TTAACTTCCC    6720

CTGTCTTACT ATCGATGGTG TACGGCAGCG CACCATCTAC GGCAGGATAA CGTTCATAGA    6780

CCCAAATGCC CGTTGCGCGC TGCTGACGAA CGCGGTTCGG ATACCCTTGC GGATCC       6836
```

(2) INFORMATION FOR SEQ ID NO: 74:

(i) SEQUENCE CHARACTERISTICS:
        (A) LENGTH: 1332 base pairs
        (B) TYPE: nucleic acid
        (C) STRANDEDNESS: double
        (D) TOPOLOGY: linear (xi) SEQUENCE DESCRIPTION: SEQ ID NO: 74:

```
GGAAAAACNC GCCGTATATT AGCCCGCGCG GAAAAAGCCC CGTNACGGGC AAACGCAGCA      60

AGGTTTTATC CCAGCGCAGG CGCATGGCAG GATTTTTGAG TAGCCGTTGC CCCAGCACCA     120

GAAGCCCCAG CAATCCCGCC AGCCAGTAAA CGCCGCTGGT CTGTAACGTG TCGCTCATGG     180

CGATGAGCGT GCGGGTGGAG GCGGGCAGCG CGTGTCCGAG ATGATCAAAC TGTTCGATGA     240

TTTTTGGCAC CACTGCCGTC AGCAAAATAG TGACCACGCC CGTTGCCACC ACCAGCAGTA     300

CCAGCGGGTA GAGCATGGCC TGCAGCAGGC GTGAATTTCC AGNACCTGCC GCTGTTACGG     360

TGTAACCCGC CAGGCGATTG AGCACCACGT CGAGATGTCC GGATTTTTCT CCGGCAGCAA     420

CCATCGAACA AAACAGGGAA TCAAAGACGC GGGGATGTTC GCGCAGGCTG TCCGACAGGK     480

TGTAACYTTC CTGAATCCGC TGCGCAGCGC CATTCCGAGG CTTTTTACAT GCAGTTTTTC     540

ACTTTGCTCA CTGACCGCCT GTAAGCAGGT TTCCAGCGGC ATTGCTGCCT GTACCAGCGT     600

TGCCAGTTGG CGCGTGAACA GCGCAAGATC TGCCGCCGCC ACGCGACGAT GTGCGTGCCG     660

CCGACGCTGC AACATCCCCC CTGACGAAGT ATTCATCCGG GCTTCAATAT GCACGGGGAT     720

AAGCTCTTTA CCGCGCAACA ACTGGCGGGC ATGACGCGCG GAATCCGCCT CAATCATACC     780

TTTGGTTTTG CGACCATTAC GCTCCAGCGC CTGATAGTAA AACAGTGCCA TTACGCCTCC     840

ATGGTTACCC GCAGAACTTC ATCGAGAGAG GTTTCTCCGG CGAGCACTTT CTCAATGCCG     900

TTGCTGCGGA TACCCGCAGA GTGTTGTCGG ACATAACGTT CCAGCTCCAG CTCCCCGGCC     960

TGACGGTGGA TCAAATCACG CAATGTGGCA TCCACCACGA TCAGCTCATG GATGGCAGTC    1020

CGTCCGCGAA AACCTTTGTG ATTACAGGCG GGACAGCCCT GTGGATGGTA CAGAGTGACG    1080

GTACGGGCGT CGGTAATTCC CAGCAGGCGT TTTTCTTCGT CGGTGGCAGG CGCGGCCTGA    1140

CGGCAGTCGG AGCACAGCGT GCGGACCAGT CGCTGCGCCA TCACGCCCGT CAGACTGGAA    1200

GAGAGCAGGA AAGGCTCCAC GCCCATATCC TGCAAACGTG TGATCGCCCC CACCGCTGTG    1260

TTGGTATGCA GCGTGGAAAG TACCAGGTGT CCGGTCAGTG AAGCCTGAAC AGCGATTTCT    1320

GCGGTTTCGG TA                                                        1332
```

(2) INFORMATION FOR SEQ ID NO: 75:

(i) SEQUENCE CHARACTERISTICS:
    (A) LENGTH: 4407 base pairs
    (B) TYPE: nucleic acid
    (C) STRANDEDNESS: double
    (D) TOPOLOGY: linear (xi) SEQUENCE DESCRIPTION: SEQ ID NO: 75:

```
CCCAACGTTT ATCGTATTTC ATTAAAGTCC CTTGCCCGAT GCTATCTCGA GTTACATGAC      60
GAAATCGCTG ATTTGGATGT CATGATTGCG GCAATTGTCG ATGARCTGGC GCCTGAACTG     120
ATTAAACGTA ATGCTATTGG ATACGAAAGC STTCGCAGTT GCTGATCACG GCAGGAGACA     180
ATCCCCAACG ATTAAGATCA GAATCAGGTT TTGCGGCACT GTGTGGTGTC AGCCCTGTTC     240
CCGTATCTTC AGGAAAAACG AATCGTTATC GACTTAACCG GGGTGGAGAT CGTGCTGCAA     300
ATAGTGCACT TCACATCATT GCCATCGGAC GTTTGCGAAC TGACGATAAA ACGAAGGAAT     360
ATGTCGCCAG ACGAGTAGCG GAAGGGCATA CAAAAATGGA AGCAATACGC TGCCTGAAGC     420
GCTATATCTC ACGCGAAGTT TATACATTAC TGCGTAATCA AAACAGGCAG CTCAACAGCA     480
TCCCGATAAC GGCTTGACTC TTAGAAGGGC GTCCAGGGCA GCCACTATAC AAGCAGGCAG     540
TTCCGGCAGT TACTGTGGCG TTACCAGATC AAACAGAGTC TGAGTCGACG AGGAAATTGC     600
TGGGATAACA GCCCGATGGA GCGCTTCTTC AGGAGTCTGA AAAACGAGTG GATACCGGTG     660
ACGGGTTACA TGAACTTCAG CGATGCTGCC CATGAAATAA CGGACTATAT CGTTGGGTAT     720
TACAACGCGC TCAGGCCGCA CGAATATAAC GGTGGGTTGC CACCAAATGA ATCGGAAAAC     780
CGATACTGGA AAAACTCTAA AGCGGTGGCC AGTTTTTGTT GACCACTACA TTTAGTGCGA     840
CACGGGAAGC GCGATATGAA CGATACGATA CATCAATGGT TTATTGCGGT GATAACCTGA     900
AGGGTGAGAT TGAGGCTATT TATAATAGTC TTGAGAGGCG TCAGGTTTAG AGCAGGAATG     960
CTGAGTAGCC ATCTTATCGA TTGTTTTCGA GCGTAAGATG GCTGAATGGA ATGGCTATTA    1020
TTGCACAGTC CTTAATTATA ACATTCATAC CGACATGATT ATCTTCTGTC CGGAAGAATC    1080
AGAGGCTGCG GTTTCAGACT GTCTGCCGGT ACATTCCTCT CTCCGTTAAA AACCATAACG    1140
GGTTCATTAT CTTCGTCTGT CAGCAGATTG AATGGCGGTA TATTTCAGT ACGAATGCCG     1200
GTCAGCCACT GAAAAATACC TGCGAAATGA CGGGCACTGA TTTTTCTGCT GACGGACTGA    1260
TGAGACGTGA TGTCACTGGC GGTAATAATC AGGGGAACGC TGTAGCCTCC CTGCACATGA    1320
CCATCATGAT GAACAGGATT AGCACTGTCG CTGACCGACA GACCATGGTC AGAAAAGTAA    1380
AGCATGGCAA AATGACGGGA ATGCCGGCGA AGGATACCAT CAAGCTGCCC GAGAAAGTTA    1440
TCCCAGTTTA CTGATGCTGG CGAGGTAACA GGCAATTTTT CGGGGATACT GCCCCAGGTA    1500
ATGATTCGGC CAGGAGTTAA GCCGGTCACA CGGGTTCGGA TGAGACCCCA TCATGTGCAG    1560
GAATATCACT TCGGAGAGGA TTTATCCGCC AGTGCACGTT CTGTTTCCTG TAACAACAAC    1620
ATGTCATCCG TTTTACGGGA AGCAAAGCTG CCTTTCTTGA GGAAAACGGT ATGCTCCGCA    1680
TCAGAAGCAA TAACAGAGAT GCGTGTATCA TGCTCCCCCA GCTTTCCCTG ATTGGATATC    1740
CACCATGTGC TGTATCCTGC TTTTGCTGCC AGCGCCACCA CGTTGTTGCC GGAGTCAGGG    1800
TTCTGCTCAT AGTCATAAAT CAGTGTCCGG CTCAGGGAAG GTACGGTACT GGCTGCTGCC    1860
GATGTATAGC CGTCAATAAA TAAACCGGGA GCAGTATTCA GCCACGGTGT GGTTGGCACG    1920
GGATAGCCAT ATACCGACAT ATAATCCCTG CGCACACTCT CACCAGTGAC GATAACAATC    1980
GTGTCATACA ACGGTACACC CGGCAGGATT TTCCAGTTGT CAGCCCCGTG CTGATTCAGT    2040
TGTTTATAAC GCTGCATTTC ACGCAATGTG TCAGTTGTCC CCACAACAGT TCCTTTAACC    2100
ATCCGCAACG GCCAGCTGTT TACTGAGCAT AATACGAACA GCAGCAGTGC CAGCCAGTTA    2160
```

```
CGGTGACCGC GGTGGTGTGT TCGCCAGAAA ATCACCATGA ATACCAGAAT CGCGGCACTG  2220

ACCAGAAAAT GATAAACAGG AATCATCCCG GTAAACTCCG CTGCCTCATC AGTTGTGGTC  2280

TGCAGCAACG CAACAATAAA ACTGTTGTTG ATTTTACCGT ACGTCATACC GGCAGGCGCA  2340

TACAGTGCAC AACAGAACAG AAATAACAGC GCTGTAATGG ATGTGAGGGT ATTTCTGTGT  2400

GCAAGAAGCA GAAGAAAGAA CAGCAGCAAC ACATTCCCGG TGGTATTCTT CTCAGTGTAT  2460

CCGCATGCAA TTGTGGTTAT GACAGAAACA ACAAAAAAGA ATAAAAACAA TATAATCCTG  2520

AGAGTGTTGC CCGGACAAAA CAGTTTTCTG ATATTCATCG GAGTATATCG ACAACATTAT  2580

TATGAAGAGA ACAGGATAAT AAAAATCAGA AGTTATCTGT GAAACAGATA ACAGACANCC  2640

CTGCAGTATA ATATTACTGC AGGGTGTTCC TTTTTAATTA CAGAAATACG TAATTATCTT  2700

AATTGCAGAA ATATGCGCAA TTATCGTTCA GAAGCAGTGT CGTCAGAAGT TATAAGTCAC  2760

ACCAAGCAGG ATGTCATGAC TTTTAACATC AACCTCTGAT TTATATTTAT CCCCTTCTGT  2820

ATCCTTGTAA TACAGGGAGG ATTTACCAGC ATCCAGATAG CGATAGCTGA GGTCAAGAGC  2880

GATATCCGGG GTTACGTCAT AGCGAACACC GGCCCCAATG CTCCATGCGA AGTTGTCAGC  2940

AGAGCCTGAG CGTGATATAG AATAACGCAC TCGCTCACCG TAGCCATAAT CCCAACTACC  3000

GCTACCTGTT GATTCCTGAT GAATTCTGGC GTAACCAATT CCGGCAGACA CCCATGGCGT  3060

AAATGCACTG TCGTTTCTGA AATCATAGTA CGCATTCAGC ATCAGGCTGT TGACTGACAC  3120

CTCATTCTTC AGGTCACTAT GTCCCGCGTG GTCCTTATAG AGGTTGTATG TTGTGTCAGC  3180

TTTTCCACGG GCGTAAAACT CCAGTTCTGT ACGCACAGGA ATACTGAACT GCGGATGCAA  3240

GTCATAACCA AACGCTATAC CTCCACTGAA TACCGTGTTA TGGCCATCCC CCCCCTATAC  3300

TTTGATGTTT CCTCTTTATT TTCGGACAGG AAACTCTGGT CAGAAAGAGA TACTGCTGAA  3360

GTACCTGCTT TACCGGTCAG ATAAAAACCG CTTTTACCTT CCTCAGCACC CGCATTTGCT  3420

GCAANCATAC AGGCAGCGGT AACTGCTGAA ACAGCAAAAA CTTTTTTCAT TTCAATTAAC  3480

TCCATTATTT CACTATTTTT GTAAATAGCA CTCCTAATAT TTTAAAACCA GTCAAAAGAT  3540

AGTATCAAGC AAATTATTCA TGTCTAATGA ACAGATAAAA TCGACTATGT GTCGGCAAGA  3600

CTCTGCTCCA CCGATATTCC TCTTATTTCC GCCTCGATGA AATACCCCCG TTACCTTATT  3660

TGTACCCCTT ATAATGGGAT GTTGGCCAGC CAGACCCGGC ATGATTAGTT CTCCCTGTCG  3720

ACTATGCTCC GGGAGGGATG TCACCGGGTC TGGTGAGGCG CGGATAACCG CTAATAGGGG  3780

AAGGTCAGGT ATTTTACACC GGGACCGTCA GGGCAAGATA ACGAAAGCCA GCTCCCCGCA  3840

TGAACTGACG CCAGATAGTT TCTGTCCATT GCTGCTTTTC TCATCTTACG TCTTAACCCT  3900

GCCTTGAATA CCTTATCTCT CGTCAAAATA TTAATAGCGA TATGCCGTAT CCCTGAAAAT  3960

AATCCCGCTG CGTTTCCTCT TCTTACTTGC AGTCGTCTTC ATTCATTACC ACGTCCAGAC  4020

GCCATGCAGC TTATTCTCCA CGTGCCAGTG ATTTCGGATC GCTGTGACGA ACTTCTCTGC  4080

GGTTAAATCA GCAGAACTGA TATAATATCT GACCATTATT TCTGACTCTT GCTTTTGTTC  4140

TGCTATTATT GACCGAAAGG AGACTGCCAG GCATATTTTT TCAGCCCTTT CCATTCAAAC  4200

GTGAATTCAA TCAGCTCATC AGGGACNTCG CCAAACCATA TGAAGACGGG ATCCTNCTCT  4260

GCCGTGACTC TTGTCACTAA TTGCGTAACA GTCATGCTCN GGGATAATTA AATCTTTCAG  4320

CGGAAATAAA AAGATTATCA GATATGGGGA TGACACCACA GCACCGCTGA GGCCAGTATG  4380

GATAAACCAT GTACCTTATT AACCAAA                                     4407
```

(2) INFORMATION FOR SEQ ID NO: 76:

(i) SEQUENCE CHARACTERISTICS:
    (A) LENGTH: 824 base pairs
    (B) TYPE: nucleic acid
    (C) STRANDEDNESS: double
    (D) TOPOLOGY: linear (xi) SEQUENCE DESCRIPTION: SEQ ID NO: 76:

```
TTTTTTGCAA GAGAATTTCC CTGAACCTGA AGCTCATCAT CGCCATCTCC GCCGTTCAGG      60
TAATTATTAC CTGCTCCCCC AATTAACTTA TCGTTGCCAT CACCGCCATA GAGCTGGTCA     120
TCTCCGTTTC CACCACTCAG TGTGTCATTA CCTTTATCAC CATATAAGCG GTCATTCCCG     180
TCATTTCCTT CTATATGGTC ATCACCATCC GCGCCATGGA AGATATCAGC AAATTTACTG     240
CCAAAAAACT TGTCGGCACG CGTGGTCCCA ATAAGTTCTT CCACGGAATA TAAGTTATCA     300
GTCTCTGTTA AATTTTTACC ATTGATATGA GTGAATTCAT AACTCCGATA TTGCGTTTTT     360
TCAGTTCTTT TTCCAACTGA AACCTCCTGC TCCTTCACAA CTTCCTGTAA AACCTTAACA     420
TCACCACCAA GTACACGTGT TACCGTGTAA TTACCCGCTT CGGTTGCTTT TGTGCCATCA     480
ATGGTCAGAT AACCGGTGTC TGTTTTATCA TAATAAACAA CATCATGTCC TTTACCTGCG     540
TAGATATTGG CTGAGCCGGC AGATAAAAAG ACCTTATCAT CCCCGTCTCC CAGGTGTGAC     600
TCAATACGAA TTTCCCGATA CTGGTTATTA CCGACTGATG CATGCTGAAT CAGGTTAGAG     660
TAATCATATA CAGACCCCTT GTCCTGNAAC CCCCTTCACC GTCCATTTAT CAACACCCTT     720
GACTAATAAC TCGGTAATAT ATTCATATTT TCCGGACTGC CTCCTTTCAC GAATTTCCTC     780
ACCGGGAGTT TAACAATGGG CGTAACNAAT TTGCAATAAC GTGG                      824
```

(2) INFORMATION FOR SEQ ID NO: 77:

(i) SEQUENCE CHARACTERISTICS:
    (A) LENGTH: 550 base pairs
    (B) TYPE: nucleic acid
    (C) STRANDEDNESS: double
    (D) TOPOLOGY: linear (xi) SEQUENCE DESCRIPTION: SEQ ID NO: 77:

```
GNGGCCGCAG TACTGGATCA TCACCGAAGT TTCGCGCGGA AAAGCGTTAG AGAAAGATCT      60
AATGCTTCAT GATGGTGATG GACTTTTCCT GATGGTGAAA TCCAGCGGGA AATGCTCTGG     120
CGTTTCCGTT ATCAACATTC GACAACAAAG CAGCGGACAA TGATGGGACT CGGTGTCTTT     180
TCCACACTTT CACTTGCTGA TACCCGAGGG CTAAGAGTGG ATTATATTTC CTTATTAGCC     240
AACAGAATCG ACCCGCAAAT TCAAGCTAAA GCCGTAGACG AAGAGCAATA TTTGAAAAGG     300
TGGGCACCTA CGTTACCAAT ACTGGCTTAA TGGCTACATA CGGCGGTCAG GGTCAGTTTA     360
CGCTTACAAA ATATAAAACA ATTTGATACA AAATATTCCT CTTATTCTAA ATAAAAGTAT     420
CTTGAAAACC TTCCAACTGG AAGGTAGATT GAATTTATGC TAAACATAAA GAGGAATTGC     480
TTATGAATTA CGTTATCCGC ACTACCACCG TCGTCTTTAG TCTCATGCTG GGCAGGTTAC     540
GCAACTGCTG                                                            550
```

(2) INFORMATION FOR SEQ ID NO: 78:

(i) SEQUENCE CHARACTERISTICS:
    (A) LENGTH: 382 base pairs
    (B) TYPE: nucleic acid
    (C) STRANDEDNESS: double
    (D) TOPOLOGY: linear (xi) SEQUENCE DESCRIPTION: SEQ ID NO: 78:

```
CACTAAAGGC CCTGGATGTT TTTCGCTCAT TAGTAGACAT CTCGCTGATA ACGGCGCTCT      60

ACGCGCACTC ACTTAAAAAT TCATCCGCCG CTTCGGTGTC CATGCCACCA AATTCGGCAA     120

TCACTTCCAG AAGTGCCTGC TCAACGTCTT TCGCCATGCG ATTAGCGTCG CCGCAGACAT     180

AAATGTGGGC ACCATCATTG ATCCAGCGCC ACAGCTCCGC GCCCTGTTCG CGCAGTTTGT     240

CTTGTACGTA AACTTTTTCT TTTTGATCGC GCGACCAGGC AAGATCGATA CGTGTCAGCA     300

CGCCATCTTT GACGTAGCGC TGCCAMTCCA MCTGGTACAG GAAGTCTTCC GTAAAGTGCG     360

GATTACCAAA GAACAGCCAG TT                                              382

(2) INFORMATION FOR SEQ ID NO: 79:

(i) SEQUENCE CHARACTERISTICS:
        (A) LENGTH: 3576 base pairs
        (B) TYPE: nucleic acid
        (C) STRANDEDNESS: double
        (D) TOPOLOGY: linear (xi) SEQUENCE DESCRIPTION: SEQ ID NO: 79:

TAAATCAGCA GAACTGATAT AATATCTGAC CATTATTTCT GACTCTTGCT TTTGTTCTGC      60

TATTATTGAC CGAAAGGAGA CTGCCAGGCA TATTTTTTCA GCCCTTTCCA TTCAAACGTG     120

AATTCAATCA GCTCATCAGG AACATCGCAA ACAATATGAA GACGGATTTC TTCTCTGCCG     180

TGACTCTTGT CACTAATTGC GTAACAGTCA TGCTCTGGAT TATTTAATTC TTTCAGCGAA     240

AATAAAAGAT TATCAGATAT GGGATGCACA CAGCACCGC TGAGCAAGTA TGTATAACCA      300

TGTACTTATA ACAAAAGGAG ACGTAAGAAG GGGAACGGGT ATCAGAGGGC CAATCAAAGC     360

AGGTATAATG AACGCCAGTA TAATTGTCCG CAACCCAGAA ATATATTATT GAACTGGTTA     420

TCTCCTGCGA ATGCATATAC TGCAACGGCC GTTAAAATAG CATTATATCC ATAAAGCCCG     480

GCAGAGATTT TATCAGGAGA AAGCTCAGGA ATACAGAATG ATACCACCAC ACTCAGAAAC     540

GAAGCGACAA CCGTAATCAT CAGTAGTTTC CGGCTCCCTG CAAGTAGTCC CAGCATAACA     600

AGAATACCGC CGACAGCATC AGGAAACATA AAAATCTCCA TAAAGCTACC AGACAATGCC     660

ACCGGATAGT TTTTCAGCAA AACAGAACCT GCACTTCGCC CGAAGGTACT GACATATCAT     720

GAGGCATTAT TCCGGAATGT AATAACCACG TAGCGATAAT AAAGGGGCG GTCAATACGG      780

GTAACCCTCT GAGCACTGAC GACAACAGGG GAGTAAACAA AACAATACCA AGAGTTCCGA     840

CGATAAGTAC AGCAATTCCG GAGACTGACA CAGGGACAAG CATGCCACAG GCTATGCCAT     900

ACAGAACAGC ATTATATCCC CATATACCTT CATTAATCTC CTCATCAGGA TACCGCAAAC     960

ACCAGGCAAA GAACGGAGAA AGTGCTGCAC TGATGGCTGA GAAATACAGT ATTTCGGGGT    1020

GCCCCATATT AAAAGAGGCT ATTCCAGTCG CCAAAAAAAA GAACAAGCCA GAAACAACAT    1080

TGTTCTGTAA TAATACCTGT GAATACCCCT TACTAAAGGC GGTTATCACC TGTTTTACTC    1140

TCATGTAAAA TGTCACACAC ACCTCATACA TAAACCATTC TCCGCTTCTG CGGGACAGTA    1200

CCGCCCCTGA CTCCACCTCA CAGCGGATTG TGTATTTTTA AACAATCACA GTCTTCTCAT    1260

ATACTTTCCA TTCTGAAGCT TATCTCTTCC TCCGTGATAA GCTTCCGTCG CGGGATGTGT    1320

TATACGCCCT GTAAGACAGT TATAAAGGAC ATCAATGCCA TAGTTAATGA YTACCGAATT    1380

CCGGTGGATA GTCAGTACTG GTTTGCCACA AACAGTGCA GTCACACATG ACAGGAGAAG    1440

ATATGAGCCG GATACCGCTG CTCTGAGACT TAACGCTCAT GTAAACTTTC TGTTACAGAT    1500

TCTTCCAGGG ACTAAGAAGA TAACTGANTT ACGTTCGCAT TCCAGTSTTT ATTTCTGCAG    1560

TGACAGCCAT ACCCGAGCTT AATGGAATGT GCTTATTCCC GGTTGACAAA TCATTCTCTT    1620
```

```
CAACAGAAAC AATGACATTA AAAACGAGTC CCAGTTTCTG GTCTTCTATT GCATCTAAAT    1680

TTATATTTTT TACCTTACCC ACCAGATAAC CATATCGGGT GTAAGGAAAA GCCTCCACTT    1740

TAATGATGGC ATTCTGCCCG ACGTTAATAA AACCAATATC TTTATTTTGT ACCAGAGCAG    1800

TAACCTCCAG CGTGTCATCT TCCGGAACGA TGACCATCAG TGTTTCCGCT GTTGTAACAA    1860

CCCCACCTTC AGTATGAACC TTCAGTTGCT GAACTTTTCC CGAAACAGGG GCCCTGATTA    1920

CTGAAGCCTG TTGACGCTCT TCATTTTTCT CTAACTCCAG AGTTAATAAC TCAATGCTGT    1980

CTGTTGTTTG TCTTAGCTTG TCTAAAATTT CATTTTTAAA AAGCTGCGTG ACAAGCTGAT    2040

ATTCTTCTTT TGCAGACAAT ATCTCACTCT CAATTTGCTC CAGTTGCGAT TTATAAACCC    2100

GTAATTCATT TGCTGCCTCA ACATATTTAT TCTCCTGCTC AAGTACAGCA TGTTTTGCAA    2160

TTGCCTGTTT ATGCAACAGG CTCCTGAAAT CATCCAGACG GCTTTTTTCA ACCCTCGATA    2220

CATTTTCATA ACGTTTATA CGGGCAAGTA TTGTTAAWCG CTCTGCTCTT TTCTTATCCA    2280

GATTCAGTTC TTTTTGATAC TTCTGATTTT GCCATGTGGA AAACTGTTCT TTTATCAAAG    2340

AAGTTAAACG CAGTACTTCC TCTTCAGATA CATTCTGAAA ATAAGGCTCA TCAGGAAGTT    2400

TCAGTTCAGG AAGTTTATTT AATTCAATTG ACCGGCTCAG AATTTGATAC CGAATTTGTT    2460

CCAGCCTGGC CTGTAACAGT GATGACTGCG TTTTTAACGT ATCAGCTTCA GCTCCCAGCG    2520

CTGTAAGCTT TAATAACACA TCCCCTTTCC GGACTGACTC TCCTTCTTTT ACGAYAATTT    2580

CTTTAACTAT CGAGTTTTCA ATAGGTTTAA TTTCTTTNTA CGCCCACTGA GTGTTAATTT    2640

CCCATTTGCA GTGGCAACAA TTTCCACCTG GCCTAAAACA GATAAAATGA AAGCAATAAC    2700

CAGAAACCCC ATAATAAAAT AAGCAACCAG ACGCGGCCGT CTGGATACCG GCGTTTCAAT    2760

TAATTCCAGA TGAGCGGGTA AGAATTCATT TTCGTCCTTT TCACGTACCG GAGTATCTAA    2820

CTGCTTCCGG ATTTTCCATG TTTCACTCCA GACAAGTTTA TAGCGCAACA GGAACTCGCT    2880

GAACCCCATT AACCATGTTT TCATATTCTT CTGTTCTTTC TGTTAGTCTG ACTGTAACTG    2940

ATATAAGTAA CTGTATAAAC TTTCCGGTTC AGAAAGCAGC TCCTTATGTT TACCCTGTTC    3000

AACAATTTTC CCTTTTTCCA TGACAATAAT GCGGTCTGCA TTTTTTACTG TAGACAGACG    3060

ATGAGCAATG ATTATAACCG TTCTGCCCTT ACATATTTTG TGCATATTGC GCATGATGAC    3120

ATGCTCCGAC TCATAATCCA GAGCACTGGT TGCTTCATCA AAGATGAGTA TTTTAGGGTT    3180

GTTCACCAGC GCCCTTGCAA TTGCGATGCG TTGACGTTGA CCTCCGGATA ATCCTGCCCC    3240

CTGTTCCCCG ACAATGGTGT TATACCCCTC ACGCAATTCA GAAATAAAAT CATGAGCACC    3300

TGSTAATTTC GCTGCATAAA TAACTTTTTC GACGGACATG CCAGGATTAG CCAGTGAAAT    3360

ATTATCAATA ATACTGCGAT TAAGCAGCAC ATTGTCCTGC AACACAACCC CCACCTGACG    3420

ACGTAACCAG TTAGGATCGG CCAACGCAAG ATCATGTCCA TCAATTAAGA CCTGGCCATT    3480

TTCAGGAATA TAAAAACGTT GAATTAATTT AGTAATGTG  CTTTTTCCTG AACCAGAACG    3540

TCCGACAATA CCAATAACCT CCCCCTGCTT AATACT                              3576
```

(2) INFORMATION FOR SEQ ID NO: 80:

(i) SEQUENCE CHARACTERISTICS:
        (A) LENGTH: 3541 base pairs
        (B) TYPE: nucleic acid
        (C) STRANDEDNESS: double
        (D) TOPOLOGY: linear (xi) SEQUENCE DESCRIPTION: SEQ ID NO: 80:

```
TCAGCCCGGT GAGCGGGTTT GACAATTCCG CACTCACCAT TGGGCTAAGG GTTATCAGGT    60
```

```
GGGGTTAAGG AAATGGCAAA ACCTACCCCC GTCCAAACTC CAGTCGCTGC ACATTCACCA    120

TCCCTGGCTT CTCACCTGCG CTGACATCAA TTTGTGTCAC CCGCAGCGCA TATTTTTCAT    180

CCAGTGCTTT TAACCAGTTC AGCAGGTCAT TAAACACCAC AGGTTCTATC AGACCTGGA     240

TATTCTCCCC GCGCTCGGCA ATCCGTTTGA TGACCACCGA GTGCGCGGAA GCTGTCACTG    300

ATGACCCGCG ATACCTGTGC TGGCGTTGTC GTGCCGGATT TTCGCGCCGC AATAATATCC    360

GGCGCGGCGC TCTTCAGTCG CGCGTTCATC GCCACCAGCT GCTGCAACAT CGTCTCCTGT    420

TGCTCAATCC GTTCGCTCAA CGGCTGCCAG ATGAGAACGA AATATCCGGC GCTAAACAGG    480

AACACTACCG CTGCCAGTAA CATGCCTTTT TCACGCGGCG AACGCCCCGC CAGGTGTTGT    540

GTCAGCCAGT GTTCGCCACG GCTTAACTGG CGTTCACGCC ATTGCTGAAA ATAGTGAATA    600

AATTTATCGC GTAACATGTT ATTTCCTCCG CAACGTTACG CCGCCGGAAA CCGCATCACC    660

CTCTTTCTGT AACGCGTCCT GTTGCACAAC ATAATCTGCC GCCAGTGCGC TACGAGTTTA    720

TCGAAGCTGG CAAAGTTCGC AGCCCGTAGC TGGAGGTGAA GCGTCTGGCG TTTTTGATCA    780

AAGGTGAAAC ACGCATTTCG ATGTCGGTAA GTGACGCTGA TTTCAGGGTA CTGGCGATCG    840

CTGACAATTC TGCGAGCAGC CGGGTATCGT CGGTCTGTGG GCGATATTTT TTCAGCGCCA    900

TCGTCACCTG AGAGCGTAAA TTCACAATCC GCTTCTGCTC CGGGAATAGC GTTAAGAACT    960

GTTTCTCCGC CTGGGTGCGG CTTTGCGCCA CCTGTTCGCT GACGCTCCAT AACGTCACGC   1020

CCCGTTCCAC TACCAGCGCA ACCAGAATCA ACAATATCGG CAGAATCATC ACCCGCCAGC   1080

GCGCCCACTG TTTTCGGTAG CTGACACGAG GCTGCCACGG CCCTGTTAGC AGGTTCCCTT   1140

CCGGTTCGCC ATAAGTGGTA ATGGCGGGCA GAGCGTAACG GTCAGCGTTC GGCGTCTGCA   1200

CCAGCCCATG CAGACAGTTC TTCCGGTGCA ATGCCGACCA CGGTTAGTGA AAGCGGTAAA   1260

TCCTGCTCAT TGAGCTGTGC TCGGAACATG ACCGGAGCCA GCGCCCGCCC GGCGCTCCAT   1320

CCCCGGCATT CATCGATGCG GMAGATAACC CGTTGCGCAT CGCCAGCCAT AAACCCACAA   1380

GGAATGGACA TCCAGTCCGG CGCGACGATA GCGCGGGTGA TGCCGTTTGC CTGCAACCAC   1440

TGCGCAATGT TGCGCATATG CTGCTGGTGA ATCACAGCTA CGGTTGCCAG TTGCTGGTCG   1500

ATTTTCAACG GGGCGAAATG CAGTTCATCG ATATCCTGGT TCAGCTCTTC TTCCAGCAAG   1560

GCGGGCAGAA TCGTCGGTAT CTGCTTGCGG GGCACATCAG GCAGTTCAAC CTGCCAGACG   1620

CTGATCCATT CGCCGGGAAT GTAGAGTCGA ATCGCATCAG TTTGCAGCCA TTGCTGGAGA   1680

CATTCATCAG CAACGTCAGG CCAGATGCCG CACTCCACGT CGGCGGTACG ACGCTGCCAA   1740

CGGATGGGAG CGGAAMGNCA AAGCGGGAAA AAAATCTCAA GCATGGAACT CACTCACTTT   1800

CTCCTGTCTG ATGCCAGAGA ACAGAAAAGT GTTGTGGGCC CATGCGGACA ATTAACGAAT   1860

TCATCGTCAG TTCAATCTCA TTCACGGTGA TATCTGAACG CAGCCAGAAG TAATTGCTGT   1920

CCACGCTCAG GACGGTTTTT AGCTGTTTTT TAGTACGCTC ATCGACGTCA GCAAGTAACG   1980

GCTGTGCAAG AAACTGATCG ACATCTTCCC AGCCCTTCGC ATGACGTTGT TGTAATAACG   2040

CTCGCGCCTG AACAGGGCTT AACCACGGGT CAAACAGCGC TCAAGAATC ACACTTTGCG   2100

TGACGTCTAA GGTATTGATG TTGATTTGCT GGCGGGTCAT CGGCAGCGCA CAGACCAGCG   2160

GTTTCAGTTT TTGATAAAGC CCGGCGTCCA TTCCCTGCAC CACGCGCATC TCGCTGATAT   2220

CAGCCAGCGG TTGATTAGCG GCGTAAAACG GCACCGAACG GGCGAGATAC TCGCTGTCTT   2280

CACGGCCCAG ACGCGTCTGC ACGCTGCGGT CTTCGTCAAT AAACTCCCAC AGGCTTTCGG   2340

CTATCAGTTC GGCCCGATAA GCAGGCACAT CCAGGCGCGT GATCAGGGCA ATCAGTTGTT   2400

GTACCGCGAG CGGACGCGAC GCCGTCGTCG GCTGAGCGAG GGCATTCAGG TTAAAGCAAG   2460
```

```
CCTGTGCGTC ACGCAGAGTG ACGGCGATTT GCCCTGCGGC AGTGGGAAAA AACGCGGGCC   2520

GGAAGCCCNA CGTGCGCCAG ATGCACGCGC TTTTCATTTT TCAGGCTCAG ACTGAGTGCG   2580

CTCAACGCCA GGCTTTCCGC ACTGGCGCTG TACCACAGCG CCTGCTGGTA CTCCTGCTGG   2640

TGCGCGTTCG CCCAAGTTGT TTCTGCATCC GCCCGGAAAG CGTGATGGTC ACCAGCATCA   2700

TAACCGCCAG CAATACCAGC ACCACGACCA GTGCCATTCC GCGTTTTGGT GGTGAGGTGA   2760

TCATGATAAT TGCGGCCCGC GTAACAACCA GATGCGTTCA ATTTCGCCCC ATTGTGGCGA   2820

ATGCAGGGTT ATGCGTACTG CCACGGGGAT CGCCTGCACT GATGACCAGC TCTCCTGCCA   2880

GCGCGTGCCG TCGTAGAACT GCAAACGGAG CGAATCCGCC GGGATTAATT TTTGCGTTGT   2940

TGGCTTCACG CTGCCTGCCG CATCGGTCAG TGGCCAGGCT AACCGTTCGA GATAACCACC   3000

ATGAATGCGG TAACCGACGG TGAGCAGATT ACTGCGCGGC AGACGCATCA ACGGATTAAC   3060

CACGCCGCCA CGTACAAAAC GCATCCCTTC ACTCTCAGAC GCCAGCACGC CAGCGCCCGC   3120

CAGTAACGCT RGTTCACGCT GGCCCTGATC GCCTCTTACC GGACGCGGCA TCATTTGTGT   3180

CAGATCGTGG GTCAGAAAAC TCATCGTTTG CTGCATGAGG TTTAGTTTTT GATCGTGTCC   3240

GGCGACGGCG CTATTCACGC GTGTAACCCG TTTGTCACCT GCTGCGCCAT CATTGCCAGT   3300

GAGGCAAAAA TGGCTATTGC CACCAGCATT TCCAGTAACG TGAAACCAGC GCGAGTCCTT   3360

CTCACTGTTG GTCTCCCACG GCGCTAAACC ANGCGCGTCG TGACTGAATC ACTGACGAAA   3420

AGTCNTCATG AAGACTGACT TCAATATCCA CNGCATGGAG CAGCGCATTA NCGGTATTCA   3480

GTGGTGTTGG TTCGCCAGAA CCAAGCGGCT TTCCTGCCAT AATCGCTCTC GGCCCTGGGT   3540

G                                                                  3541

(2) INFORMATION FOR SEQ ID NO: 81:

(i) SEQUENCE CHARACTERISTICS:
        (A) LENGTH: 1234 base pairs
        (B) TYPE: nucleic acid
        (C) STRANDEDNESS: double
        (D) TOPOLOGY: linear (xi) SEQUENCE DESCRIPTION: SEQ ID NO: 81:

GTACTGGACA TCTTTGATGA ACAAGCTCCT CAGTGTAAAT TGTACGTCTC TGATCGTAAT     60

CTTCCTGAGG GCGTTGAACA TCTATCCGCT GAATTTATAC CCTATACTCC TGAGTCGGCA    120

GATTTTCTGA TTCAACGTTT TTTCTCTGAA ACTATCCATA TTGAAAGTGC AATTGTTGTT    180

ACAGCACTTA AAATTGCCAA TCAGATTGCT CTATCTCAAA ATGAGACCAA GAATGTGTAT    240

CTGCTTGGAT TTGATTTTAC GATAAAGGGG GGGTTCACTA GCAAGATCCC CTGCGCAGCC    300

TTGCATGCCG AACCAGAATA TCAAGAGCGA ATTATCAGTA GTCAAGAACA GCTATTGCAG    360

ATGCTCCTTG CAGAAAAAAC ACGCCTGAAT ATCAATATCA ATCATGTTGG TAATAAGCCT    420

TACAGCGTAT ATTCTGTTGA TGCATTTAAT CAAGTGTTCG CTGCCCGCCA TCGTGGAGTC    480

GTGCTGCCCA CACATGCCCA GATTTCCACT ACATCATCAC AAAATGGGGT GAAGGTGATC    540

GCAGAGATTA CTACTAATCA CTTTGGTGAT ATGGACCGAT TGAAGTCAAT GATTGTAGCG    600

GCCAAGCAGG CAGGGGCTGA CTATATCAAA CTGCAGAAGC GTGATGTTGA AAGTTTCTAT    660

AGCAGGGAGA AGCTGGAGTC ACCGTACAAC TCTCCTTTTG GCACCACCTT TAGGGACTAT    720

CGGCATGGCA TTGAACTCAA TGAAGAGCAA TTTTCCTTTG TCGACTCTTT CTGTAAAGAG    780

ATTGGTATCG GCTGGTTTGC TTCTATTTTA GATATGCCCT CGTATGAGTT CATTCGGCAA    840

TTTGAACCAG ATATGATCAA GCTACCATCA ACTATATCTG AACATAAAGA TTATTTGGCT    900
```

| | |
|---|---|
| GCTGTTGCTT CTGATTTTAC TAAAGATGTA GTAATTTCAA CTGGTTATAC TGATGAGGCC | 960 |
| TATGAGCGTT TTAYCCTKGA TAACTTTACC AAGGTTAGAA ATATTTATCT GCTGCAATGC | 1020 |
| ACCTCGGCTT ATCCCACACC GAATGAAGAT ACCCAGCTAG GTGTGATAAG ACATTATTAT | 1080 |
| AATTTGGCGA AAAAGGATCC ACGTATTATT CCTGGTTTTT CCAGCCATGA TATTGGTAGC | 1140 |
| CTTTGTTCCA TGATGNTGTC GCAGCCGGTG CAAAAATGAT TGAAAAGCAT GTTAAATTTG | 1200 |
| GCAATGTGGC TTGGTCTCAC TTTGATGAAG TTGC | 1234 |

(2) INFORMATION FOR SEQ ID NO: 82:

(i) SEQUENCE CHARACTERISTICS:
        (A) LENGTH: 6313 base pairs
        (B) TYPE: nucleic acid
        (C) STRANDEDNESS: double
        (D) TOPOLOGY: linear (xi) SEQUENCE DESCRIPTION: SEQ ID NO: 82:

| | |
|---|---|
| ATGGGACCTT TCTTCAATGA TGTTGCCGAG TGGTTAGAGT CATTAGGTCG TAACGCTGTG | 60 |
| AATGTTGTAT TCAATGGAGG AGATCGTTTT TACTGCCGTC ATCGACACTA TCTGGCTTAT | 120 |
| TACCAAACGC CGAAAGAATT TCCTGGTTGG TTACGAGATA TCCACCGGCA ATTTGACTTT | 180 |
| GATACCATTC TCTGTTTTGG TGACTGCCGT CCATTGCACA AAGAAGCAAA ACGTTGGGCG | 240 |
| AAGTCTAAAG GGATCCGCTT TCTGGCATTT GAAGAAGGAT ATTTACGTCC GCAATTTATT | 300 |
| ACTGTTGAAG AGGACGGTGT AAACGCGTAT TCATCGCTGC CGCGCGATCC TGACTTTTAT | 360 |
| CGTAAATTAC CAGATATGCC TGCACCACAT GTTGAGAACT TAAAACCCTC GACGATGAAA | 420 |
| CGTATTGGTC ATGCAATGTG GTATTACCTG ATGGGATGGC ATTACCGACA TGAATTCACT | 480 |
| CGCTACCGTC ATCACAAATC ATTTTCTCCT TGGTATGAGG CTCGTTGCTG GGGGCGTGCG | 540 |
| TACTGGCGTA ACTATTTTAC AAAATAATGC AACGTAATGT ATTGGCTCGG TTAGTGAATG | 600 |
| ATCTGGACCA ACGTTACTAT CTTGTTATTT TACAAGTTTA TAATGATAGC CAAATTCGTA | 660 |
| ATCACAGTAA TTATAATGAT GTGCGTGATT ATATTAACGA AGTTGTATAT TCATTTTCGC | 720 |
| ATAAGGCACC GAAAGAGAGT TATTTGGTGA TCAAACACCA TCCGATGGAT CGCGGTCACA | 780 |
| GACTCTATCG ACCATTAATT AAGCGGTTGA GTAAGGAATA TGGCTTAGGC GAGCGAGTCA | 840 |
| TATACGTACA CGATCTCCCA ATGCCGGAAT TATTACGCCA TGCAAAAGCG GTTGTGACAA | 900 |
| TTAACAGTAC AGTGGGGATC TCTGCACTGA TTCATAACAA ACCACTCAAA GTGATGGGTA | 960 |
| ATGCTCTGTA CGACATCAAG GGGTTGACGT ATCAAGGGCA TTTGCACCAA TTCTGGCAGG | 1020 |
| CCGATTTTAA ACCAGATATG AAACTGTTTA AGAAGTTTCG TGAATATTTA TTGATGAAGA | 1080 |
| CGCAAATTAA TGCTGTTTAT TATGGTGTAA AATCAAAAAG CAATAGAAGG TCCGCATTCC | 1140 |
| TAAACGGTAG CAGATGATGG TTTTCATGGG CGTTTCAGGT TACTCAATCA GCCAACAACC | 1200 |
| GCAGCGAAAA CCCTGCTTTC TCGACCAGTT CAGGCCGGTT TTACCTCCAA TGCTTTCCGT | 1260 |
| CAGAACTGAG ATTTCAGCCA GTTGCCGGAT AAGTGTGTCG ATTTGCAGCA GTATACTTTT | 1320 |
| TCGTACAGCC AGAATGTGGC AGACTGAGGT GGAATAGATA ACGTCCGTAT GCCCGCTCAC | 1380 |
| CACCTCCGGG CGGGAGTGTG TGGTATCTGA CATCATCATT TTTCCTTTCT GTTTATAAAT | 1440 |
| GAAAACGCCA GCCGTGTTCA GGCTGACGTC AGGGAAGTGA AATCGGGTGA GTGATCTTCA | 1500 |
| CTGGTTCTGG TGCAAAAGTT ACTGTTGGCG CAGGGTACGG ATACCCTCCC TGGCCTGTTC | 1560 |
| GATACAGGGC AACAGTGCTG CCGAATCTGT TTTATCCTCA TCGTTGTCGA AGATAATTCC | 1620 |
| CGATTCGCAG TCGATATTGT CCTGCAGCCA CGTAATCAGA ATATCCAGCG CTGTTTCCGT | 1680 |

```
GGTTAATGAT TTCATGTTGT GAATTTCCGG ATTACCAGTC GAAAGTGGGT AAACCTGGCA   1740

GACATCTGGC ACTGGCATCC AGATGAATGA GACTGACACC ATAACGCCGG ATGAGTGTGA   1800

CGACCAGACG ACGGAACGTA ACAGATAACC GGTACCGGTA AAATGAATCC ATTCTGATTC   1860

ACCAAAGTCA CTGGTCTGGT GTAACAGCGA GTACAGCCAG GCGTTGTCCT TTTCCGTGAT   1920

ATGTGCGGTA CTGCAGCGTA TGCCGGAAAG AGTCGTAAAC GGTTGTGGAG TGCAGGTTGA   1980

CTGTTGGTCA GATTCATCCA CCACGCGGAG TGAATAACCG TTTTCAGCGA CCTTGTTAAT   2040

CAGTTCAGCG AGATTAATAC CATCGACGTC AACGACAATG CGCCCCATAT TCAGTGCCTG   2100

TACGTTAACG CTGTCGGCTT CCGGCGTCAG GGAAAGTTTC ATTGTTTCAC CTCCGGGTGC   2160

TTACCCAGGA TAATATTATT TACCGCTCTG TAATTGTCGC GGGTCATCAG GCCGGTCGCC   2220

CTGCGAGCCC GGAGGATATC GATGCTGTTT ATTAACTGAG AGCGGGTACA GGCGCTGAAT   2280

CCCGGCTGGT CGGTACGCAC CAGCGCGTAT TTTTCCACGA GAAAGTTCAC CGCATCACAC   2340

AGTGAAATGC CTGCCTCAAT ATGCTGCTCG ATCACACGTT CATCGGCAAA CGGTGTGTCA   2400

TTCAGTGTGA GGCCGTAGTG CTGGTCCAGC AGTCGGGACA GAAGTATCTG CCAGATTTCA   2460

ACAGGAGACG GGCGAGAACT GGCCGCCTGC CCGGGTAATA CAGGTAATGT TTTCATACTG   2520

AAGATTTTCC TGATATGCAG ATATAAAAAT GGGAAAGTGG CGTGGTGAAA ACACCAGGCC   2580

GTAGCAGAAG GCTATTCTGG AGAGTTAATT TTTCATTTCG GGCGTCGGAT AAACAGCCAG   2640

ATAAACGTAA CCACAACTGC TGAGGGTATC GGCTTTGCAG GTCAGCCCTT TTGCATACAG   2700

CGTGACGGTA TGCTGATGGC GGGGATTCAG TTCACCGCTG GTGAGCATGA GTTCCAGTTG   2760

TTTCATCAGC AGCGGAAAGG CCTGGTCCAG GTGGTACGCA TCTGCATTGC TGTATAGGCC   2820

TCTGATACCG GCGCGGTCGG CAAGGTAATG CAACCGGTTA CCCTCCTGCA CCAGACGTGC   2880

CCCGAAACAG GGCGTCACGG TGCAGGGCAG CCCCCACCAG GGGCGGTCGT GATTGTCGTC   2940

GGGAAGTGTT GTCCCGGGGA GTGTGTCTGA CACGATAAAA TCCCTACAGA AAATCGGCTA   3000

AGAATGCTCC GGTATTGGCG ATAATTCTGC TCATCAGAAT TCCCACTCAG TTCAGGGTGA   3060

CGCTCATCAG CCGGACATAC GGGCCAAAAC TGTCCTTACG GCGTTCAGCA ACACGGCCA    3120

GCACACCGGG AATATCCTGT ACTTCACGAC CGGTATACGC CTCAGCACTG CCGTGCCAGC   3180

GGTACTTACC GGTGCAGAAC GGAAATAGAC GGGATGCAGG ATGCTGTTGG TGAATACGCA   3240

TGGCTTCACC ACGGGTGATG ATTTTCATAA TGGGATACCT CTGAAGACAG AAGATAAAAG   3300

TGAAAACAGG TGTGATGTGG TTGTGACGGT GACGGGTTAA AGCAGACCGT GTTCCGCAAA   3360

GGAGAAAACC TGACTGCCAC CAACTATCAG ATGGTCCGGT ACCCGGATAT CCACCAGGGC   3420

CAGTGCCTGT ACCAGACGTT CCGTGATAAG GCGGTCTGCC TTACTGGGGG TGACTTCACC   3480

GGACGGGTGA TTGTGTGCCA GTACCACGGC GGCGGCATTG TGGTACAGGG CGCGTTTAAT   3540

CACTTCCCGG GGATGGACTT CCGTGCGGTT GATGGTGCCG GTGAAGAGGG TTTCACCGGC   3600

AATCAGCTGA TTCTGGTTGT TCAGATACAG TACCCGGAAC TCTTCACGCT CCAGTCCCGC   3660

CATCTTCAGA ATCAGCCATT CCCGTGCCGC ACGGGTGGAG GTGAAGGCCA CGCCGGGTTC   3720

ATGAAGATGG CGGTCCAGGG TTTTCAGGGC CCGCAGAATG AGACTGCGCT CGCCGGGCGT   3780

CATCTCTCCG GGCAGAAAGG AAAGTTGTTG CATTGTGCTT CTCTCCATTC AGTCGATGAT   3840

GCGCATAATG GCGCTGCATT CCGGATGCTG CAGGGCGTAA TCCCGCAACC GGTAATAATG   3900

GATCGTCATG GCATAACACT CCGTACGACA GGCATGATGA CTGTACGTCA TCAGACAGGC   3960

GGCAATGCCG GCGGCTTCCG GGCTCATTTC AGCGCGGTTA CCGTTCATGG CATTGAACAG   4020
```

-continued

```
TACCCAGTTT TCGTCATCAT CGTCATCCGG TTCGGGTGCC ATAAATGCCC CGCCGTTGTT    4080

CAGGGTGTAC AGATTCCAGA TACCACCGCA GTAGTCTTCG CACAGACGGT CCATCCAGCC    4140

GAAGACACGG GGCTCCAGGG TCACCCACTG TGGAATGAGG CCAAAGTGCT GCGGCCAGAA    4200

GCTGATGCGC TGTTCATCAG GGACTATGGT GGCAACCAGC TGAGGCTGGT CATTCCCTGA    4260

TGCAGCGGTT ACGGAAACAG AAGGAGTGGT GGAATTATGC AAGACGGTTG TCATGAGATT    4320

ATTCCTTATA AAAGTAAAT GAATGGAAGA ACCCCGGGG GAAGGACAG ACGTGAGTCA    4380

GAACTGCGCT TTCAGGGAAA CGGCATCAGC GCATACTCTC CAGCAGCGTT TCAGCCATCA    4440

CCCACAATGC GCGGTTGAGC TTAATGTCGG TGTCGATGCT GTGAATGGCA CGGGTATGGA    4500

TACGTTTTCC TCTGGCACTG CGACCGGAAA TTCCGCCTTT CAGCATATTC TCCTGAATGG    4560

TCTGATAAGC ACTCCACAGG TCCTTACCGT AATCCTCCCG GCGTCGTGGT GTCAGAATGT    4620

CGGCGGTGGT GACGGGCTGA TGTTCGTCAC CATAACGGTA AGTCAGTGCC GCCTGTGCCA    4680

GCGCCTGGCG TGCCGGTGGC GGCAGAATCA GCGACTGCAT GGCATCACGC TTTTCCTCAA    4740

TCCGGTCAAA AACCCCCACC ACCTCGTAAG CCCCTTCAAT AACTTTCTCC ACCACATTTC    4800

CCCGGTGCGG AACACGCACT TCCCCCAGAG ACTGACCACA GACGCATCCG TTCTGGCAGA    4860

CGAACCTGAA GTAACCCGGC AGCATCTGGT AGCTGGAGGT ACCGTCATGA GAGTTGAGCA    4920

GAATAATTTC AGGGACATGT TCTCCGTTTA TCTCTCCGGC CCGCCGCAGA CGCAGCATGT    4980

GTTTGGTGTA TTCCCGGCGG TCCGGGTCAC GTACGCGGGT CTGGCAGGCG AAGAATGGCT    5040

GAAAGCCTTC CCGCTGCAGG CTTTCCAGTA CGGTGATGGT GGGGATGTAC GTATAGCGTT    5100

CACTGCGGGA GGTATGCCGG TCTTCACCGA AAATACCCGG TACATGGTGC ATCAGTTCTT    5160

CGTGTGTCAG CGGACGGTCA CGGCGTATCT GGTTCGCATA ACCAAAACGA CTGGCTAGTC    5220

GCATAATTTG CTCCTTATCG GTGGTTAAGA TTTACTGGTG TAATAAATGA AAAAGCCACG    5280

TCTCCCGGAG AAGACGCGGC CTGACAGATG AAATGAATGA CGTTTATTGT CTGAGAAGCC    5340

CTTAACTGGC GAGCTGAGTA TTAAGCTGTG TTCCGGCATC ACCAGCGCAA CTGACCTTCA    5400

GCATTACGGA TAACCAGCCG GGAATATGTT CCCTGGTCAT CTTCAGTAAA CACATTGCGG    5460

TAAGCTGTTA TGACAGCAAC CGCCTGCCCG TATGAGAAAG ATCCTTCAGC CAGGACATAC    5520

TCTGTGTGTA ACCCGGCATA TCTGGTTTCT CCTGATAAAT AGCCTCTGCC ATACGTTGTG    5580

GCAGAGGCTG AAGCATGAAA CTGACTTCAG GGATCAGTTA ACATTTTTTC CGGAAACGGT    5640

AATCAGCAGT GGATGGTAGT CCTGGGGATC GAAAACCGAT AACGGCAGAC TGACACGATG    5700

GCCGTTACTT TCTTCAGTTG CTTTAATGAT TTCGGTTGTG GCGACATTTT CCACGCACTC    5760

CGTTTCCAGA AATGCGTCTG TGGTTCGCGT GGCATTACTG TCACCAAAGG CTTCCGTTTC    5820

CATTTTTCTG GTCACCAGCG TCTGACCATA TTTGTCTTTG AGTTGCAGAG TGATGGTGAG    5880

GGGGCCAAAT CCTTCATCGT TTCCGCCATT ATCCAGCCGG AACTGGTAAG CACAAATATT    5940

TCCCGGGAGC CATATCGTAT CTGTATTGCG TATACTGATG TAACGTTGAT CCTGTGCCCG    6000

GAGTGGGGCA GACCACGTTA ACCCCAGAAT GAAGGCGGTA ATCATGCAGG TTTTGAACAG    6060

GTGAATCATG GTATTTACCT CTCTGAGTCA TGACGATTAC ACTGACAAAT CAGGTGATAA    6120

AACGTAAAAG GCGCAGAATA GCCGTTATGC CGGTAACTCC GGGGGTAATG TTTCTTCCAG    6180

TCGGTTAACC ATATTGCCGA GATGGGATGC ATCATATTCC ATGACGGGGC GTTGCCTGAT    6240

GATACTGACC ACCAGTGGTT TGATTAACAT GTTGGTCGCG GCCCGTTGTT GTATACCGGC    6300

GGCGAAAATG ATC                                                      6313
```

(2) INFORMATION FOR SEQ ID NO: 83:

(i) SEQUENCE CHARACTERISTICS:
        (A) LENGTH: 432 base pairs
        (B) TYPE: nucleic acid
        (C) STRANDEDNESS: double
        (D) TOPOLOGY: linear (xi) SEQUENCE DESCRIPTION: SEQ ID NO: 83:

```
CGTTGGCCGC TTGCGCAGAT AAAAGCGCGG ATATTCAGAC GCCAGCACCG GCTGCAAATA        60

CGTCTATTTC AGCAACACAA CAACCAGCTA TCCAGCAACC GAATGTCTCC GGTACCGTCT       120

GGATCCGTCA GAAAGTCGCA CTGCCGCCTG ATGCTGTGCT GACCGTGACA CTTTCTGACG       180

CGTCGTTAGC CGATGCACCG TCAAAAGTGT GGCGCAGAAA GCGGTGCGTA CTGAAGGTAA       240

ACAGTCACCA TTCAGCTTTG TTCTGTCATT TAACCCGGCA GATGTTCAGC CGAACGCGCG       300

TATTCTGTTG AGTGCGGCGA TTACCGTGAA TGACAAACTG GTATTTATCA CCGATACCGT       360

TCAGCCGGTG ATCAACCAGG GCGGAACTAA AGCCGACCTG ACATTGGTGC CGGTACAGCA       420

AACCGCCGTG CC                                                           432
```

(2) INFORMATION FOR SEQ ID NO: 84:

(i) SEQUENCE CHARACTERISTICS:
        (A) LENGTH: 3494 base pairs
        (B) TYPE: nucleic acid
        (C) STRANDEDNESS: double
        (D) TOPOLOGY: linear (xi) SEQUENCE DESCRIPTION: SEQ ID NO: 84:

```
GGGCTGATTA CGATTTTATC AATCTGTCTA TAGAACATGA ACTGAATGAA GGAATAGCTG        60

GCAGAGAGAG GTTATGCCGG ACTGGCGGAT AACCGGAACC GGTTGGCAGA GGTGGTTACC       120

CGTAAATTGC AGGACAGCTT TTATATGAAC TTTCCTGGGA TGCGCTGAAC ACGGCATACA       180

GTGAACACCC AGAGTGGTTT TCCGGGCTTG TCTCCGGGGA TGAGAATTAA AAAGTGGATT       240

ATGCTGCTAT AGCGCGGCGT GATTTCCTGC AGGGATTTCC ATTTATAAGA ATACGCCGCT       300

TCGGGGAATC TCCGGTTCTC CTGAGAGTTA CGATTGTTTT TTTACTCAAA TCCACAACAC       360

CTGAACTGGA ACTTGTGTTG CATCCCTGAT TGTTACTCTG CAGGAAACAT CTTTTTTACC       420

ATCAAAGGAT GACTGTTTTC CTTTCTCCCC TCCGTAAAAC ACAACTTCGA TCACATTTCT       480

GACATTTTTT CCAGATTTTA CATAACAGGA TTGTTTCTGT ATGTTTTTTA TCTGGTGTAA       540

ATTTCAGCAC TGACATTCCG CTTACGTTAA TTTACACTGA ATACCCCACG AGGAGAATAT       600

GCAGCACCGG CAGGATAACT TACTGGCGAG CAGAACGTCG TTGCCTGGTA TGGTTTCCGG       660

TCAGTGCGCA TTTAAGCTCC GCACTTTCTC TCCGGTGGCA CGCTATTTTT CCCTCCTCCC       720

CTGCCTTTGT ATTCTTTCGT TTTCGTCTCC GGCAGCCATG CTGTCTCCGG GTGACCGCAG       780

TGCAATTCAG CAGCAACAGC AACAGTTGCT GGATGAAAAC CAGCGCCAGC GTGATGCGCT       840

GAAGCGCAGT GCGCCGCTGA CTGTCATACC GTCTCCGGAA ATGTCTGCCG GTACTGAAGG       900

TCCCTGCTTT ACGGTGTCAC GCATTGTTGT CCGTGGGGCC ACCCGACTGA CGTCTGCAGA       960

AACCGACAGA CTGGTGGCAC CGTGGGTGAA TCAGTGTCTG AATATCACGG GGCTGACCGC      1020

GGTCACGGAT GCCGTGACGG ACAGCTATAT ACGCCGGGGA TATATCACCA GCCGGGCCTT      1080

TCTGACAGAG CAGGACCTTT CAGGGGGCGT ACTGCACATA ACGGTCATGG AAGGCAGGCT      1140

GCAGCAAATC CGGGCGGAAG CGCGCTGACCT TCCTGCCCGC ACCCTGAAGA TGGTTTTCCC      1200

GGGAATGGAG GGGAAGGTTC TGAACCTGCG GGATATTGAG CAGGGGATGG AGCAGATTAA      1260
```

```
TCGTCTGCGT ACGGAGCCGG TACAGATTGA AATATCGCCC GGTGACCGTG AGGGATGGTC    1320

GGTGGTGACA CTGACGGCAT TGCCGGAATG GCCTGTCACA GGGAGTGTGG GCATCGACAA    1380

CAGCGGGCAG AAGAATACCG GTACGGGGCA GTTAAATGGT GTCCTTTCCT TTAATAATCC    1440

TCTGGGGCTG GCTGACAACT GGTTTGTCAG CGGGGGACGG AGCAGTGACT TTTCGGTGTC    1500

ACATGATGCG AGGAATTTTG CCGCCGGTGT CAGTCTGCCG TATGGCTATA CCCTGGTGGA    1560

TTACACGTAT TCATGGAGTG ACTATCTCAG CACCATTGAT AACCGGGGCT GGCGGTGGCG    1620

TTCCACGGGA GACCTGCAGA CTCACCGGCT GGGACTGTCG CATGTCCTGT TCCGTAACGG    1680

GGACATGAAG ACAGCACTGA CCGGAGCTGC AGCACCGCAT TATTCACAAT TATCTGGATG    1740

ATGTTCTGCT TCAGGGCAGC AGCCGTAAAC TCACTTCATT TTCTGTCGGG CTGAATCACA    1800

CACACAAGTT TCTGGGGGGT GTCGGAACAC TGAATCCGGT ATTCACACGG GGATGCCCT     1860

GGTTCGGCGC AGAAAGCGAC CACGGGAAAA GGGGAGACCT GCCCGTAAAT CAGTTCCGGA    1920

AATGGTCGGT GAGTGCCAGT TTTCAGCGCC CCGTCACGGA CAGGGTGTGG TGGCTGACCA    1980

GCGCTTATGC CCAGTGGTCA CCGGACCGTC TTCATGGTGT GGAACAACTG AGCCTCGGGG    2040

GCGAGAGTTC AGTGCGTGGC TTTAAGGAGC AGTATATCTC CGGTAATAAC GGTGGTTATC    2100

TGCGAAATGA GCTGTCCTGG TCTCTGTTCT CCCTGCCATA TGTGGGAACT GTCCGTGCAG    2160

TGACTGCACT GGACGGTGGC TGGCTGCACT CTGACAGAGA TGACCCGTAC TCGTCCGGCA    2220

CGCTGTGGGG TGCTGCTGCC GGGCTCAGCA CCACCAGTGG CCATGTTTCC GGTTCGTTCA    2280

CTGCCGGACT GCCTCTTGTT TACCCGGACT GGCTTGCCCC TGACCATCTC ACGGTTTACT    2340

GGCGCGTTGC CGTCGCGTTT TAAGGGATTA TTACCATGCA TCAGCCTCCC GTTCGCTTCA    2400

CTTACCGCCT GCTGAGTTAC CTTATCAGTA CGATTATCGC CGGGCAGCCG TTGTTACCGG    2460

CTGTGGGGGC CGTCATCACC CCACAAAACG GGGCCGGAAT GGATAAAGCG GCAAATGGTG    2520

TGCCGGTCGT GAACATTGCC ACGCCGAACG GGGCCGGGAT TTCGCATAAC CGGTTTACGG    2580

ATTACAACGT CGGGAAGGAA GGGCTGATTC TCAATAATGC CACCGGTAAG CTTAATCCGA    2640

CGCAGCTTGG TGGACTGATA CAGAATAACC CGAACCTGAA AGCGGGCGGG GAAGCGAAGG    2700

GTATCATCAA CGAAGTGACC GGCGGTAACC GTTCACTGCT GCAGGGCTAT ACGGAAGTGG    2760

CCGGCAAAGC GGCGAATGTG ATGGTTGCCA ACCCGTATGG TATCACCTGT GACGGCTGTG    2820

GTTTTATCAA CACGCCGCAC GCGACGCTCA CCACAGGCAG ACCTGTGATG AATGCCGACG    2880

GCAGCCTGCA GGCGCTGGAG GTGACTGAAG GCAGTATCAC CATCAATGGC GCGGGCCTGG    2940

ACGGCACCCG GAGCGATGCC GTATCCATTA TTGCCCGTGC AACGGAAGTG AATGCCGCGC    3000

TTCATGCGAA GGATTTAACT GTCACTGCAG GCGCTAACCG GATAACTGCA GATGGTCGCG    3060

TCAGTGCCCT GAAGGGCGAA GGTGATGTGC CGAAAGTTGC CGTTGATACC GGCGCGCTCG    3120

GTGGAATGTA CGCCAGGCGT ATTCATCTGA CCTCCACTGA AAGTGGTGTC GGGGTTAATC    3180

TTGGTAACCT TTATGCCCGC GATGGCGATA TCACCCTGGA TGCCAGCGGC AGACTGACTG    3240

TCAACAACAG TCTCGCCACG GGGGCCGTCA CTGCAAAAGG TCAGGCGTC ACCTTAACCG     3300

GCGACCATAA AGCGGGAGGT AACCTGAGCG TCACAGCCGG AGCGATATCG TTCTCAGCAA    3360

TGGAACGCTT AACAGCGACA AGGACCTCAG CCTNGACCGC CGGCGGCAGA AATTCACTCA    3420

ACAGAATGAA AAACTGACTG CCGGCCGGGA TGTAACGCTT GCCGCGAAAA AACATCACAC    3480

AGGGTTACCG GCCA                                                    3494
```

(2) INFORMATION FOR SEQ ID NO: 85:

(i) SEQUENCE CHARACTERISTICS:
 (A) LENGTH: 9319 base pairs
 (B) TYPE: nucleic acid
 (C) STRANDEDNESS: double
 (D) TOPOLOGY: linear (xi) SEQUENCE DESCRIPTION: SEQ ID NO: 85:

```
GNCCCAAGCT TAGGTTCGCG GCCGCAGTAC TGGATCTATT GCCAGCTTCA CCGCCAGACT      60

GTCAGTCAGT ACATCACCGT ATTTCTGCTG GCAGGTTGCC GGGCGGCTGC ACAGTCACTG     120

ATCAGTTGCT TCTGCTGTGC CGTACTCAAC TCTTCGTACT TTTTGATAAT ACCGCCGCAG     180

TCACCGCCTT TCGCCTGACA GGACTTCATT TCAGCAGAGC AGGCATCTAT CTGCTTATTG     240

CTCAGGTAGT TATTCTCAAC AACAACCACA GGGGATTAGA AGCCTTTTAG CCTGAAATAT     300

TTTGCGAGAG CACATCCAAT ACCAATAAAT GAGCCAATCA CACATCCGAT AAACAAAACA     360

TGCCGAATCT CTTTCAAACT AATATTTAAA TTACCTGTTA TCAACCACTC CACCAAAGAA     420

AAAACACAT CAATACATAG GAATGACACC ACTATAGAAA GAAATGCGAT TATAAAAATA     480

ATAAACAATT CTGATAAGTG CTGAGAATTG CCGCTCATTT TTTCACCTCC GGAATGTAAG     540

ACTCAATCTT TTTACCTTCA TACTCAGAAG CAAAAGAAGC CGACACATCC CCAGCTATAC     600

CAGGAATCCT ACTGGGTGTC ATTTCTTTTG ATAGCCCCAA TTCTCCTTTA ATATCGGTAT     660

ATTTTTGAAG TGTTGGATTA AATTTCGGGT CCCAGCCGTC TTTTAACCAG TTAGCACCAC     720

TATTAATGCC CCATGAAAGG CCTTTACCAA TGCCATATCC AATAGCAGAA CCAGCACCAT     780

TGATCAACGC ACCAGATGTT GGGGCTTTTC CTTCGAGCCA GTTTCCTAAT GCTCCTCCAG     840

TTGCATTCCA GCCAACTGTG CCTACAACTC CATTCCCTGC ACTAATCACA TTAACCCAAC     900

CACCGATAAT CGCTGTTGTA GGATCTATAG TTCCATCCGT CAGATAGCTA ACACCTGCAT     960

TAGCTCCTGC CCCTAATCCC CACATGGCCT GAGCACCGCC AGTAAGAGAG CTACACTACC    1020

AGTGGCCAAC GCTCCGGCAT ACGCTTTATT GACTGCTTCT CCTCGCTTAC AGGCTTCACC    1080

GCCTGGGGCA TCGTTACAGG AAAGTACATC TGCGCCATGC GTCTGAGCAG CTTTGCTCTG    1140

CTCGGACTCT GTGCCACCAA CCAGGTTATT CTCAGCAATG TTCTTCCCGA CACCAGCCCC    1200

AGCAGCCGCG CCAGCCACAT CGCCACTGGC AATGCCGCCA GCCATACCCG CTGACAGCGT    1260

TGCCAGCGTG CTTACGGTTT GCTTCTGATC TTCTGTCAGT TTCGACGGAT CTACGTCCGG    1320

ATAGAGGCTT TTCGCAATGG CTGACGAGAT CACTTCACCA GTACCCGCAC CAATTGCGCC    1380

TGCTGCCGCA CTGTTGCCCT GAAGGGCTGC TGTCACACCA CCGAGAATGG CATGGGCAAT    1440

GGCTTTTGCC GCTGTATTGT CATCAATACC CGCGTGATGA CCGATGATGT TCGCCAGCTC    1500

CGGCGCCGAA GCTCCGGCCA GAGCACCTGC TAAATTACCC CCCGCCAGCC CCTGAAGTGC    1560

AGCCGTTGCA GCCTGGATAC CGCGCTGCAT ATCGCTGCCG GTACCATACT TTTCCTGTTC    1620

CTTTTTGTAT TCCGGCGTAT CACGCAGTTT TGCCAGATAT GCCTGCCGCT GTTCTTCCGT    1680

CGCATCCGCC GGAACAGGCC CATATTTATC CTGCGCAGCT TCAACGCATT CAGTTCCCCC    1740

TGCGTCCGCG CAATATCCGC CACCTGACTG CCTATGTCAC TGATAAGCCC CACTGTCTGC    1800

AGACGCCTCT GCTCCTTCTC CTTGTCAAAT ATCGGGCTGA TACTGTCATT AGCGTGCGCA    1860

GGGTCACGGC TCAGGTTCGC CAGATTCTGC TTCTGATTGC CCCTGTCCCG GATGGTGATA    1920

GTGCCTTCTG CCACTGCGGC CTGAGTCGTT CCTTCCGCAT GTCCGCTGTG ACCTCCGGCG    1980

GATATCATGC CACCCGGCAT GTTACCCTGA AATTTATCCC CGAAGCTGCC ACCACCGCTC    2040

AGACTGATTC CACTGTGACT GACTTTATAA TCCGCTTCGT TGTGAAGGTC ACTGAACCCC    2100

AGCGTTCCGG TATCCAGGTG GTTTTTATCC GGTGTGGCAG TGGAGGCAAT CACCGCACCA    2160
```

```
TCCAGTTGGG TATGTTTACC CACTGTGATG TCGAAGCCGC CGTCACCGGC AAACATTCCG    2220

GTTTGTTCAG CAACGGAGTC AAAGCGGCTC TTCATCTTAT CCCGGGAGGC AGCGATGTAA    2280

CCTGAGCCGG TCATGGAGCC AAAGGTAAAA CTGCCGCCGG CASCCACGCT GGTCTGTTTA    2340

CTGTCGTACT TACTGGTGTC CTGCTGGCTG CTTATCAGCA GGTCGTGGCC CACATCGGCG    2400

ATAATCCTGT TGCCGTTGAC CTGAGCACCG TTCAGTACCG TATCCCGACC ACTGTTGATG    2460

GTGACGGTTT TACCGCTGTC TGTTGTGGTT TCAGTCCACT CAGTACCGTT ACCTTTCTCG    2520

CTGCCTTTTG CCGCATTAAC GCTGGCAAAG ACACTGATAC CGGCACCTTT ACCTGCACCG    2580

ATACTGACAC CCACGCCACC GCCACTGCTG CTGTTCCTGC CCGTTGTTTT TTGTGTGTTT    2640

GCCGCGCCAC TCAACAGAAC ATCATTCGCA GCATCCAGGT TTGTGTTACC ACCGGCCTTA    2700

AGCTGGCTTC CGGCAATCAC AATATCTCCG CGGTTATCGC CCCTGTTTTT ACCGGTTGCG    2760

ACAACAGACA GATTATTCCC GGCATTCAGC GTACTGCCGG ATACTGTGTC ACTTTCAGAA    2820

TGTTGTTGTG ATTTCGATTT CTGGGTGGTG AGCGACAGGC TGACTCCCGT CGCATTCGGG    2880

TCACCGGTTG CGGAGGCCAT TGCCGCAGCC TGTCCGGCCT GCACACCAGA CAGCGCTGTC    2940

TTTGTAGCCT GCAGGGTTTT CAGACGGCTG TCACTGCTCT CCTTCGTCTC CTGTGCACTG    3000

GTGACCGCAT TATTGATGGC ACTGCCCACT GTGCCGGAAA GGGCAACCGT CAGCCCGCTT    3060

TTCTTCTGCT CAAATTTTTC GTCCACAGTA CGACGGTCAT GCCCCGGGTC AACCACCACA    3120

CTGTCACCGG TAATGCTGAT ATCCCGGTTC GCAATCACAT CCGAACCGCT GATATGAGCC    3180

TGTTTGCCCG CGGTAATACT GACATTACCG GCAGTGGAGC CGATGGTACT GGCACTCTGA    3240

CTCTGCGTTG TCCCGGCCTC GCGGCGGTCG TGCGTTGTCT TACTGCTGCC AATGGTGAAG    3300

CCAATACCGC CGGTACCCAT CAGACCGGAT TTCTTCGTTT CCTTAAAGCG CCAGGACGTA    3360

TCTGTACTGG TGGCAGCAAG AACATCAACA TGGTTACCCG CCGCCAGTGA CACATCCCGG    3420

TCAGCCACCA CATCCGAACC CTCTACCGTC AGGTTATCAC CGGCGTTAAC GGTCACGCGG    3480

TTCCCCGACA GCAGGGAACC TGYTTCACGG GAGGCACTGT CCTCACTGAT GGTGTGGGTG    3540

GTTTTCTTAC TGAGAAAACC TCCGCTTTTT TTCTTCGTTT CCAGATAGTG ATAGTCACTT    3600

TCTGTCGCCG TGGTCAGGGC AACATCACGA CCGGCATTCA CGCTGATATT GCCGGTTGCG    3660

GTAACGGATG ACGCAACAGC GGTGATATCC CGTCCTGCGG TGACGGTGGT GTCACCACCK    3720

CTGGCGATTT CCGTTCCCTG CTGACGGACT GTCTCGTTAA TCTCTTTCTT TTTCTTCGAC    3780

GTATAGCTGT CGCCTGCGCC GGCAGACTCT GCCACCAGGT TCACATCACG TCCGCCCCGG    3840

ATGACCACGT TATTTTCCGC AGCCATACCG GCAGCCTGAC TGGCAATATC ACGACCGGCA    3900

ACAAGGAGGA GGTTATCGCC CGCCGTCACC GTGGACACAG CTGCGTGGCT TTCATGACTT    3960

TCTGACCTGC CGTTGCGACT GTTTTTGCTT TCCCTGACTG CATTCAGACT CAGGTCGTTA    4020

CCTGCAGAAA GCAGGGCGCT GTGCCCGGCA GAAACAGAGG ATGCTGTGAC ATCCAGATTA    4080

TGGCCTGCAG CCATCGCCAG GTTACCGCCG GCGCTGATGC TGCTGCCCTG TGAGGTGGTG    4140

GATGATGAAC TGTTGTCATC AGTGTGCCAG AAACCGGACT GACTTTTGCT CCCGCTTATC    4200

AGGTTTACGG CAATGTTGAT GTCATTACCC GCAGACATTC CAAGGTCTCC ACCGGACGAG    4260

ACCGTTGCCC CGGTAATATC AATGTTTTTC CCTGCATCCA GTGAAAGTGA ATCAGTGCCT    4320

TTAATGGTCG CAACCGGACC GGTGTCCGTA CCGCTGAGAT GCACACCACC ATATCGGCTG    4380

TCACTGCCCG CATTCCATTG CTGACGCCGG GTGATATTGC TGATGTTGCC ACTCACGCTT    4440

TCCAGTTGTA CGGTTTTACC GCTGATGACT GAGCTGATAT TGCTGATATC CCCGATGGCG    4500
```

-continued

```
CTCAGGTCCA GGCTACCGCC CGCGCTTATC AGCCCTGCAT TCAGGTTGTC GATATAGCCG    4560

GTACTGTCGA GCGAAAGGTC GTTCTGTGCG TTGATGCTGC CGCCGCTGTT GGTGATATTG    4620

CCGTCCGCAA GCTGCACGTT GTTCCCGCTG ATAACGCTGC CGTTATGCAG GGTGATATCT    4680

TCCGGCGACA GATACAGTTT CGGGACCATG ACTGTCTGTC CGTTGATGGT GACTGACTCC    4740

CACCACAGCA TGCTGCCGTC AAGCTGAGCA ATCTGTTCAG CTGTCAGCGC ACACCAAAC    4800

TCTAATCCCA GTCCTTTCTG TTGTCTGGCC GCGTTATCCA TCAGATACCG CATCTGTTCC    4860

GTGTCTGAAC CCAGTCCGTT GAGATAACGT GAACCCGTCC GGCTCAGCAC CGCGTTACTG    4920

ACATACCGGG TATCAAAGAC CGCATCCCCC AGGAAACGAT AATCTTTTTC CGGTTTCAGC    4980

CCGAGGCGGT CAAGAAAATA CGATGAGCCC AGAAACTGTT TTTCATCGGT ATACGACGGA    5040

GCCGTTTCAC GTGGCGCCTG ACCCGGTTTC GCTCCAAGAA GCTCATACAG TCCGGCAAAC    5100

AAATGGCTGT CCACCTGTCC GAGACCATCC AGTTTCGGGT TCACCGTAAT CAGATACGGA    5160

CTGTCCGGGT CCGTGGACGG AACCAGGTAT CCATTGTTGC CGGAAGGCAG TGGCCAGTCA    5220

TCACTGATAC CGGTCTGACC GGTCAGTGGC GAACCTCCGG CAATATTTTT CAGGGCACCT    5280

GCCAGTTCAT CGTGCCATTG CGGAGAGCCA ACCACCACCG GCTCATACTG CTGCAGCGCT    5340

GTCTGTGTCA GACTGTCTCC GCCGGTCTGC TGACTTAACG TATTCAGTAC AGGTGCAGAG    5400

ACCACCGGAC TGACACTACC TGCATGTGCA GTGGTTGTTC CGTTATTGAT ACTGCTGGTA    5460

AAACGGGTCT TAACATCCCC GCCCGCCTGA ATAACGGAAT AATACGTCTT ACCGGGCGTG    5520

TAATCTTTTT CCCGGCCATC CAGTGAAAAT CTGATGGTAT TGTTTTCAAA TTCCGGTGAC    5580

AGCAGGGGCA GTTTATCCAG AGAGCCTGTT GCATAGCTAC CGTAAAACGT TTCGGGTCG    5640

TAGCGGTATA CCAGATATTC ATTCTCTGTC CCCGTCTGCC AGCTCTGATT GCTTAACTCT    5700

CTGCCCGAGA GTGCGATATC CCCATTCGCC AGGATAAATG ACGCCCGGTT TTCCAGTCGT    5760

TCAGCCTCAG CAGAAAGATT ACGCCCTGAC GCAATGCGGC CTGCCGGATT ATCAGCACCG    5820

GTTACTGTTG TGATGTTCTG GCTGCTGAGA AAGCGCTGTG TGGCACTGTC AGCAAACGGA    5880

GCGTAATAAT AAAGCGTATC CATTGTGATA TTGCATGCCC CGTGCCCGTT GCAGGGCGTA    5940

CCGTGCTGAT TTTCAACTTC ACGGGTGAAA TAGCCATAGC TGCCGTCAGG AAGAAGGGAA    6000

AGGGAATATA CAACCAGAGC ATTTCCCATT CCCTGAATGG ATGAGGGGTT AGTCCGGGTT    6060

GTTGTTGTGG CAGAAAATCC CTCCCGCTGG TTCAGAAGAT GCCCGGTTCT TACAACAATA    6120

TCGCCCTGAT GCGTCTCAAT ATTCCCGGAA GTATTGATAA TCTCTGTGTT TGCACCGCCG    6180

GAAGCATCCT TCTGTACCCA CAGACTGTTG CCGGCCAGGA TATCACCATG CTGGTTATGC    6240

AGACGGTCTG TAAACAGCTT CAGGTTATTC CCCGCATAAA TCAGCGCACT GTTCAGCAGG    6300

GTACCGGCCA CATTCATTGT CAGACTGCCT GCCGTGCCGG TAAAACCACT GATGGTGATA    6360

TCACTCCGGC TGTTCAGACT CACATCGCCA CCGGCCTGAA GTGAACCCGG TGCGTTAAGG    6420

AAAAGACGCT GTGCGCTGAA AACACTGTTG CCTTTACCGG CAGTCAGCGT TCCATTGTTG    6480

GTGAATGCCT CTCCGGCACC GAGCACCATG GCATCACCCT GCATGACACC GCCGTTGGTG    6540

ATGGCATTTT GCGACGTGAC GGAAAGGGTT TTCCCTGCGG CCAGGGTACC GTAATTCGTG    6600

AGGGCAGCAA TCAGTTTCAG TGTGACATCA CCGGTGGCCA CCACCTGCCC CTGACCACTG    6660

AAGTCCTGAG CGTCAAGCAG CAGGTTGCCT GCACTGTACA GCCGCCCTGT ACCATTTTGC    6720

AGCAGTGAAC TGCCCTTGAC GCCAAGCCCG GAGGTTCCCA GCAGGGTACC GCTGTTGCTG    6780

AATGTGTGGT AATTCACCAG CAGGTCCGCA CCCTGAAGCG TACCGGTATT ATTCAGCGTG    6840

GTTCCTTTAA CGTCGGCACT GCCGGTGGCA AGTACGCGTC CGCCGTTGAC AGTATTCACC    6900
```

-continued

```
ACATCCAGCA GCAGGGTGGC AGCCTGTACC AGTCCGCTGC CGGTGTTCGC CAGCACCTGC    6960
GCCGTCAGCG TGAGGTTACT GCCGGAGAGG ATTTTGCCGT CGTTCTGCAG ACGGTCAGTG    7020
GCGTTCAGGG AAACCCCGCC ACCACCCTGT ATCGTGCCCT GGTTACTCAG GGTCGCAGTA    7080
CTGACATTCA GTGCATTCCG GCTCATCAGA ACACCACCGG AACGGTTGTT CACGCCACCG    7140
GAGGCGGCCA GCGTCAGCGT TTCGCCCTGC AGATGCCCGC CGTTTGTGAG TTGTCCTGCC    7200
GTGATGGTGG TGGCATTTCC CTGTAATTGC CCGTCGTTTG TGACACTGTC TGCCTTCAGC    7260
GTCAGCACAC CTGCACTGAG CAGTTTTCCG CTCGCGTGAT TGTGCAGCGT CTGATTCACC    7320
GTGAGCGTGA GAGCATCCAC ACCGGTGATG TCACCCGCAC TGGTCAGTGA GTTCGCCTTC    7380
AGGGTCAGAT TTTTTGCAAT CCATTGTCCG CTGTTGCTTA AATTCAGTGC ACTGAGCGCC    7440
ATTTCACCGT TCGAGGTGAC TTTGCTGCCT GCTGTGCTGA CGAGCTCACC CGTCAGACGT    7500
GCAGTCAGGC TGTCAGCCGC CTGGATCGCC CCGCTGTTTG CCAGACTGTC TGCGGTGATC    7560
AGCACCCGTT TGCCCTGCCA GTGTCCGGAA CTGGTAATAC TGCCTGCGGT GATTGTCAGA    7620
TCGCCGCTGG TCAGCAATGA ACCTCCGTTA TTCATCAGCG CAGGTTGAGG GGATGCCATA    7680
CGGGCGGCAA GCGTCAGCGC GGCTATCCCG GTGAGCGTGC CACTGTTGGT GACACTGTTC    7740
TGGCGAATCG TGACATGGTT ACCCTGGACA GTGCCGCTGT TATCCAGTGA GTTTCCATCA    7800
AGGGAGAGCG TGCCGGCCGA AAGCAGACTG CCCCGGTTGT CCATGGTGGC TGCTTTCAGC    7860
GTGGTGTCAC CCTGGCTCAT GATATCGCCG GTACTGGTCA ACTGACCGGT TGCCGAAGCA    7920
GTAAGGTTAC CGGTTGCCAG CACGGAACCA CTGTTCGCCC AGTTGTCCCG CYTGCACGGT    7980
GAGATTCTGT CCCTGCGTGG TCCTGCGGTA TGCAGTGTTT TACCCCGGAG GGTGAGGTCG    8040
CCCGCCGTCA GCCAGCGCCC GTTACTACCC TGTGAGAGGG TGTCGCCAGC AAGCGCCAGT    8100
GCACCGGCGC CCTGCAACAG GCCGTCACCA TCCAGCGTGG TCGCCCTGAC GCTCAGCGTG    8160
TCAGCGATGA TTTTTCCCGG ATTGCTGAGG GAGACAGCAT TTAACATTAA ACCATTATCA    8220
CCGGTGATAA GCCCGCTGTT GCGGATGTCC GGTATATCCA GCGTCAGGTC TGCAGCACTG    8280
TACAGCGTGC CGTTCTGCTG ATTATCAAGC CTCTGTGTGT TAACGGTAAG TGAGGCCTCC    8340
CCCTGCAACA GACCGCTGTT GGTCAGGGTC TGTGACTGTG TATTCAGGGC GGAACCAACA    8400
AGTACGCCGC TGCTGGTCAG TTCCGGCGCA CTGAGGCTGA GCGACGGGGC ACTGCTTTTC    8460
CCGCTGTGGG TGAGCTTTTC ACTGGCGTTC ACCACCATGG TCTGTTGTGC TGCCTGCGTA    8520
CCTGCAAGAC GTGCATCTCT GGCGTTGATG CTGAGATTTT TACCGCTCTG AAGCTGTGCG    8580
CCCGCTGCGG TACTCAGTTT GTCTGCCTGA ACCGGAGGG TGTCACCGGC ACTGTTTTCC    8640
CCGTCCAGCG CCACTGTTGT CACATTCAGC GTCATCGCAG CATCGCTGTG GGTGACCGAT    8700
TTTTTACCGG AGCTCAGCGC CTGCGCACTG ACCGTCAGCC CTTTGCCGCC GGACAGCACA    8760
CCGTTCTGTG TCACATCCTG CGCCTTCAGC ACCAGTACAT CATCGCTCAC CAGCGAACCT    8820
GTACTGGTCA GTTTCCCACT GGCCGTGATA TCCACTTTGC CCTTCGCGCC AGTGCGGCCG    8880
CTCTGGGTAA AGTCGCGGGT ATTCACGGTC AGGGACCGC CACTGAGCAG GGAGCCACTG    8940
TTGCTGAGCG TTGTACTGCC GAGCGTCAGG GAAGCCCCCT GAACAGCACC ACTGTTATTC    9000
AGCGTGCCGG CATCGAGTCC CGCATGACCT TTCGCCAGCA ATATTCCGTC CTGTGTCAGC    9060
GTGGTGGCGC TGGCCGTGAG ATTCTGCCCG GCGGTTATCT GTCCCTGTGT TGTCAGCGTG    9120
TCACTGGCGA CAGTCACGAT ATCGCGGGCC GCGTTAATCT GGCTGGCGGT ATCCTGTGTG    9180
ATGTTTTTCG CGGCAAGCGT TACATCCCGG CCGGCAGTCA GTTTTTCATT CTGTTGAGTG    9240
```

```
ATTCTGCCGC CGGCGGTCAG GCTGAGGTCC TTGTCGCTGT TAAGCGTTCC ATTGCTGAGA      9300

ACGATAATCG CTCCGGGCT                                                   9319
```

(2) INFORMATION FOR SEQ ID NO: 86:

(i) SEQUENCE CHARACTERISTICS:
        (A) LENGTH: 551 base pairs
        (B) TYPE: nucleic acid
        (C) STRANDEDNESS: double
        (D) TOPOLOGY: linear (xi) SEQUENCE DESCRIPTION: SEQ ID NO: 86:

```
ATGAGGCGAT TAAAGCAACA TTGGGCAGTG ATAATGCCCC CACCCAGCCA CCTAACGCAG        60

CGAAGAGTAA TACATCGCCC ATGCCTAATG CTTCTTTACG CAGAACTATT CCGGCTATCC       120

AGCGSAGGGA GTAAAAAGTG ATAAATCCCA CCAGTACGCC GGTAACTGCG TCTTGTAGCG       180

TTAACGGACT CTGTTGCGCC CATGCTGCAA TCAGCCCGGT CCACAATACG CCCTGAGTAA       240

AAACATCGGG CAGCCATTGG TTGTCGAGGT CAATGACGCT CGCGGCAATC AGCCAGGCGG       300

ATAATATCAT CACCGCCAGC CCCCATCCAC TTTCTGGCCA CACCAGACTC GCCAGCAAAA       360

AAGTGAGTGC TGTCAATAAC TCAACCAGCG GATAACGTTG CTGATTTTCG CCTGACAGTC       420

GCGGCAGCCC TTTGAGCATC AACCATGAGA GCAGCGGAAT ATTGTCACGA ACGCGGATGG       480

TCTGCTGGCA ATGCGGGACA GTTGCGAACC GGGTTAGCCA AGGGCTTTAT TTTTTGGACT       540

GCGGCACTCG G                                                           551
```

(2) INFORMATION FOR SEQ ID NO: 87:

(i) SEQUENCE CHARACTERISTICS:
        (A) LENGTH: 595 base pairs
        (B) TYPE: nucleic acid
        (C) STRANDEDNESS: double
        (D) TOPOLOGY: linear (xi) SEQUENCE DESCRIPTION: SEQ ID NO: 87:

```
CATTTACCAA ACCCCGTTCG AATATCTTAT CTATTGCCCA TCTCATATTA AATATAACCG        60

ATAATTTGGT GGATACTAAT AGTAATTACC TTGTTATTGA AAATATAATT ATTGTTATTT       120

TTAGCCTCAT TAATTAAATT GAAAAATCCT CTCTAATTTT TGTCAGATTA GGGCTGTAGA       180

AAGGATCGAG TTCAAGATGT TTACCCCATT TGCTTTTCAT AAAGTCCACT TCCCTGGCAA       240

ATCTGGCTAG TTTCTCCGGT GAATCTTCGG CTCCTCGACT AATCGATTCA TAGTGGTAAA       300

GCTCGGCATA AGGTGTCCAG AGATTACGAT ACCCCGCTTC GNGTACTTTC AGACAGAAGT       360

CCACATCATT AAAAGCAACA TGCAGATTCT CTTCATCCAA CCCGGCAACT TCCTCATAAA       420

TATCTTTGCG AATAAGCAGG CAAGCCGCCG TGACGGCCGA GAGAGTTTGT GTCAACAACA       480

AACGGCTGAA ATAGCCCGGA TGGTGGCGAG GATAATGTTT ATGGGAGTGT CCAGCTACAC       540

CACCAATACC GAGAATCACT CCGCCATGTT GTAAAAGTAT CATTACTGTN ATAGG           595
```

(2) INFORMATION FOR SEQ ID NO: 88:

(i) SEQUENCE CHARACTERISTICS:
        (A) LENGTH: 399 base pairs
        (B) TYPE: nucleic acid
        (C) STRANDEDNESS: double
        (D) TOPOLOGY: linear (xi) SEQUENCE DESCRIPTION: SEQ ID NO: 88:

```
TGGCAGTTGA ACAGATTTTC ACATCAGCAA CAGATTAGCG AACGGGACTT GGCATTAGCC        60
```

```
GAGCGTTTTA GTGAANGTTT AGCTCTAACA CGTCTATTAG AAGAGCGCAC GCAGNATTAT    120

CACTGAACTA GAGATTGAAA ACAATTGCT TACCACCAAG TTGTCTGGCG TAGAGCAGCA    180

GTTAAGGGCT GAGCAAGAGT CGCTTCAGCA GGCCCAGTCT GCATTGCTCT CAGCAGCAAA    240

AGAAAAGCAA CATCAACTTG ATGAGTTGGA ATCGGTGCTC AATGAGCGGT ACAGTGAGAT    300

TGCAACCTTA ACCCGTTGGC TGGAAGAACG TGATCAGGCA CTCCTTAGTG CAGCAAGTGA    360

ACAACAACAG ACCAATGANA CCATATAGAG CTCAGCCAG                            399

(2) INFORMATION FOR SEQ ID NO: 89:

(i) SEQUENCE CHARACTERISTICS:
        (A) LENGTH: 1013 base pairs
        (B) TYPE: nucleic acid
        (C) STRANDEDNESS: double
        (D) TOPOLOGY: linear (xi) SEQUENCE DESCRIPTION: SEQ ID NO: 89:

ATACTCTGCT TGTTGAGCAG CCATTACGTC GCTTTGTGAC GCAATATTAG ACTCGTGCAC     60

TGCTATTAGT TGAGTCAGTT CATCACATTG TTTAGAAGCC GCAGCCAAAG CAAGAGTTTG    120

CTCATCTATG CTTTGCTGCA ATGTTTGTTG CACAAGTTGC CCTTCTTCCA GCTGTTGCTG    180

TAGATTTGCA CTTACCTTTT TCAGTGCATC ATATTCCAAG CCTAACGTAT CGTGCTGTGC    240

TTCCAGTAAT CCATAAGCAT GCTGCAACTG GTTTTTAGTT TGCTGCTCAC CGTCAAGCTG    300

TTGCTGCAAT GCATTAGCCT GCTGTTGCAA CAAGTTCACC ATATTGTCTC GCTCGGCCAG    360

TGTACGAACC TGTGTATCCT GGATATGTAG CGCTTGTTCC AACTGAAGCT GTAATTCGGT    420

AATTTGCCGC GAATGTTCGC TCAATGCTCT GTTGCTCTTG CTGAGCGCGA GAGTAAGGTG    480

AGATGCACGC TGTGTTTCTT CACTCAATTG TAACGTCAGG GTATTGACCT GTTGCTCCAG    540

TTGATGGCGA GCTTGCTCCT GGCTCGTGAT GCGACTCTGT TGCTGCTCTA GTTGATGCAG    600

AGCTGTATGC AACTCATCGT TGGCTTGTAT TCGCTCCTGC GACCATACAC TCAAGTTTGT    660

TTGGGCCTCA TTGAGCTGTT CTTGCAATAA TGCCACCTCA GATGTCAGCG AATTGATATG    720

TTGCTGGGCA AAAGATAGCT CATCAGATTG CACTTGAGCA TGTGCAAGCT GCTTTTCCAT    780

TTCTAATATG CTGTTATGTT GTGCAGTAAT GCGCTCGGCA AGACGCCCCC TTTCCAATGC    840

CTGCTGTTCT ACCAATAGCT GCCGTTCAGC CTGAATGTCA TCTTGTTGTG TAGACAACTG    900

ACGTTTTAAC TGGGAATTCT CCCAACTCTC GCTACAAGAT TTNCCCAAAC GACAAAAGAT    960

GTCTTGGACT TGTNTGGGTT ACACGAGCAT TTTCTGAGGA TTTTATACCA ATN          1013

(2) INFORMATION FOR SEQ ID NO: 90:

(i) SEQUENCE CHARACTERISTICS:
        (A) LENGTH: 689 base pairs
        (B) TYPE: nucleic acid
        (C) STRANDEDNESS: double
        (D) TOPOLOGY: linear (xi) SEQUENCE DESCRIPTION: SEQ ID NO: 90:

GATATCCACA TCGAGACGTT TGAAAAGAGT CTGGTGATCC GTTTTCGTGT TGACGGCACA     60

TTACATGAAA TGCTGCGTCC GGGGCGCAAA CTGGCCTCGC TGCTGGTGTC GCGTATCAAG    120

GTGATGGCGC GGCTGGACAT TGCCGAAAAG CGCGTGCCGC AGSATGGACG TATTGCGCTG    180

TTGCTGGGCG GCCGGGCGAT TGACGTGCGT GTATCAACCA TGCCTTCCGC CTGGGGGGAA    240

CGGGTGGTGC TGCGACTGCT GGACAAAAAC CAGGCTCGCC TGACGCTGGA GCGTCTGGGT    300

TTAAGTCTCG AACTGACTGC GCAGTTGCGC CACTGTTACA CAAACCGCAC GGCATTTTTC    360
```

```
TGGTGACGGG GCCGACCGGT TCCGGCAAAA GCACCACGCT GTACGCTGGA TTGCAGGAGC        420

TGAACAACCA CTCGCGTAAC ATTCTCACGG TTGAAGACCC TATCGAATAC ATGATTGAAG        480

GGATCGGTCA GACGCAGGTT AACACCCGCG TCGGCATGAC ATTCGCCCGT GGCCTGCGCG        540

CAATTTTGCG TCAGGACCCG GATGTGGTGA TGGTCSGTGA AATCCGCGAT ACCGAAACCG        600

CAGAAATCGC TGTTCAGGCT TCAACTGGAC CGGACACCTG GGNACTTTCN ACGCTGGNAT        660

ACCAAAAAAA AGGGGTGGGG GGATTATAC                                         689
```

(2) INFORMATION FOR SEQ ID NO: 91:

(i) SEQUENCE CHARACTERISTICS:
        (A) LENGTH: 1281 base pairs
        (B) TYPE: nucleic acid
        (C) STRANDEDNESS: double
        (D) TOPOLOGY: linear (xi) SEQUENCE DESCRIPTION: SEQ ID NO: 91:

```
CTCAGCAGAA CCGAGATCTT CCATCAGCTG GCGGGCCTCG GAAGANTCCC GCTGCCAGAC         60

CGCATTCAGC CGCTGTTCAA ATTCGGCCTC GTCGATTTGC CTCAGCGTAA AGGGCGCGTT        120

CAGCCCCCGT TGCAGCTCCT GCAAAACAGA GAGCGACAAC GGATGCACAT GGAGGATCTC        180

CAGCGACGCT TCGCACCATG CCACCAGGCT AAACCGACGG CTGAAACTAT AGGGCAGACG        240

CACGGTGTTA GCGGTGGTTT CCTGTGCTAC AGGCACCATT AACGCGTTCT CCCGGCATTA        300

AGGAACGCAC GAACTTCTGG CGGTAAGGCC TGATTTTGCG CAGGCAATAT CGCTGCGCAG        360

TGTGCGGCAT CAGGCTTAAG CCCTGCTCAT CGCGGTAGAT TTGCTCGGCG CGCATGTAGT        420

TATATTTGCG CTGCGACACA CCGTCTGCCG CCATACCGTC ACGCAGAATG GTCGGGCGGA        480

TAAACACCAT CAGGTTACGT TTTTCTTTTT TATCCGCCGT CGATTTAAAC AGGTTACCAA        540

TCAACGGGAT ATCGCCCAGC AGCGGCACTT CTCGCCACGC TTTCTCCCGC CTGGTCGTCC        600

ATCAGACCGC CAAGCACAAT TAGCTCACCA TCGTTAGCCA ACACGGTGGT TTTCAGTTTG        660

CGCTCACCAA ACACCACGTC GAGGCTGGTC TGTCCTTCCA CCTTCGACAC TTCCTGCTCA        720

ATCACCATCT GTACCGCGTT CCTTCGTTA ATCTGCGGCG TGACTTTCAG CATGATGCCG         780

ACTTTTTTCC TCTCTACCGT GTTGAAAGGA TTGCTGTTAT TGGAGCCAAC GGTAGATCCA        840

GTTAATACCG GAACGTCCTG GCCCACCATG AAGAAGGCTT CCTGGTTGTC CAGCGTGGTG        900

ATGCTCGGCG TGGAGAGCAC GTTCGAGCTG GAGTCGTTTT TGACCGCCTG TACCAGCGCC        960

ATCCAGTCGC CTTTCAMCAC GCCAACCGCC GTACCGCTAA AGCCAGAAAG AAGCTGAGCA       1020

AGCGTGGAGA GATCGCCGTT AGTATCCGGA TTTATGGTGG TAGCGCCGTT TTCACTGATC       1080

ACCGTGGAGC CTTTCTGCGG TTTTGCYTGA GAAATCGTGC GCCCAGCGTA CCAATAGGGA       1140

TCTGCGTACC GTTAGCAAAC TGCATTAATC CGGCATCTTT CGACGCCCAC TGCACGCCGA       1200

AATTGATAAT TCACCTTCGG CAACTTCCAC GATCAACGCC TCGACATGTA CCTGAGCACG       1260

GCGAATATCC AGTTGTTCAA T                                                 1281
```

(2) INFORMATION FOR SEQ ID NO: 92:

(i) SEQUENCE CHARACTERISTICS:
        (A) LENGTH: 421 base pairs
        (B) TYPE: nucleic acid
        (C) STRANDEDNESS: double
        (D) TOPOLOGY: linear (xi) SEQUENCE DESCRIPTION: SEQ ID NO: 92:

```
CAATATTAGC GCACGGCACC AAAGGTGATG AATGAGCAGG CTGRAATATT ATTTTCCCGC        60

GGTGCAGAAA TCCTTGTTCT TGGTTGTACA GAAATTCCGG TTATTCTGGC GCAACGTTAA       120

AGAGCAGCCT TCCCGCTATA TTGACTCACG GCGTCACTCG TTCGTGCCGG AATAAAATGG       180

TACGAAAATC GTGTCGGTAA ACATTATCTT TTAACCCAAT AATCATTTAA ATCGCAGCCA       240

GAAAGTTATT CGCTTTTAAC TGAATTATAT TTATAACGGA GAACATTATG GTTTGGCTGG       300

AAATTATCGT AGTACTTGGT GCAATAKTTT TTGGTATTCG CCAGGGGGA ATCGGTATTG        360

GTTTATGTGG CGGGCTTGGG CTTGCCATTC TGACTCTGGG ACTTGGTCTG CCTATGGGGG      420

G                                                                      421

(2) INFORMATION FOR SEQ ID NO: 93:

(i) SEQUENCE CHARACTERISTICS:
        (A) LENGTH: 1018 base pairs
        (B) TYPE: nucleic acid
        (C) STRANDEDNESS: double
        (D) TOPOLOGY: linear (xi) SEQUENCE DESCRIPTION: SEQ ID NO: 93:

GTTAACAATG GCGTAACAAA TTTCAATAAC GTAGAAGATT TGCTGTCAGA AAGGTCAATA        60

TTTCCTTTCA ATGGGTCAAA GACTTGCTTC TGGAATTCAT CCGGTTTTTT CTCCAGACGT       120

TTTCCTTCTT CATAATAGTC AATATAACTT TTACCACTGA GTGTTTTGKC YCCATTTCTG       180

GTGACACCAG CTAACTCACC TATCAGCGTA TCCCMATGTT GCTGGGTAAT GAGGACTGAT       240

CTTTCAACAG AATACTCTTT ATTATACTGA GATAATATTT TAAAGTTATC TTCTAAAAAT       300

GCAGCATGGC GGGCATCATA TCCCATTTTC AAAGTAATTT TTGCCGTGTT TTTTCTCCCA       360

TTCAGCAATA ACATCGGCCA TTTTACTGGC GACATGTTCA AACATTGCCT GTTTTGAAGC       420

CTCAAGGATG CCTGAAATTA TCCCCGTAAC AGCCCCTACC AGCGCGCTTA CCGGTGCACC       480

AACCAGAGAT GTCGTTGCAG CAGCACTAAT ACCTGAAGAT ACTGAAGCCA GAACAGTGCT       540

TATCGTTGTT AACGATGCAT CAATAGCTCC TGTTTCTTTG TGGAAAGCAG CAAGTAAACT       600

GTCACCATCG TATCCAAGTT TTTTGAATCG TTGTGAATAC TCCTCTATTT TATTGGCACG       660

TTTAAACTTA TCGGCAATGG ACAGGAATGA GAGGGGACTA ATTGCCAGTG TCACAACAGA       720

AGCAATTAAA CCGGCAGCAG CAGCAGATGT AGATAACCCC TGTGCTGCAC GCTGTGCGAY       780

NAATATATTG AGAAATACCT TTTCCAACAT TACCCAGTAC TTTCGTTGTT AATTCAACAC       840

CTGCTGCAGC TTTAGTTCCG GTATCTGCAT CTGCATTGCT CAGAATGAAA CTTGCTGAAA       900

TCGCAGATAA AATACCCGAT ACAGTATCTA ACCCTGCACC GATATTATCA AGGTTAGGTA       960

AATTCTGTAA CTTATTACCA ACACCGTTCN GGNCTGTTGG TATTGGGATA ATACACTT       1018

(2) INFORMATION FOR SEQ ID NO: 94:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 94:

GGCAATGTTC AAATCGATAT TGTGCAGCAC CTGGGTTGGG CCAAAGTGCT TGGAGACGTT        60

TTTAAATTCA ATCACAGGAT TTTCATCCTT CTTTCCAGAC GACGCAGAAT AAAGCTCAGC       120

ACCAGGGTAA TAATCAGATA GAACACCGCC ACGGCGCTCC AGATCTCAAG GGCGCGGAAG       180

TTACCGGCAA TAATTTCTTG CCCCTGACGG GTCAGTTCCG CCACGCCGAT CACAATAAAC       240
```

-continued

```
AGCGAGGTGT CTTTAATGCT GATGATCCAC TGGTTACCCA GCGGCGGCAG CATACGACGC        300

GTGCCAGCGG TAAAATGACG TAGCGAATGG TTTCCCMACG TGAAAGACCG AGCGCCAGTC        360

CTGCTTCACG AAAACCTTTG TGGATAGACA GCACCGCACC                              400
```

(2) INFORMATION FOR SEQ ID NO: 95:

(i) SEQUENCE CHARACTERISTICS:
        (A) LENGTH: 1857 base pairs
        (B) TYPE: nucleic acid
        (C) STRANDEDNESS: double
        (D) TOPOLOGY: linear (xi) SEQUENCE DESCRIPTION: SEQ ID NO: 95:

```
CGTGTTCCCC TGGCCNGCTT GGTTTCGCCA TAGACGTTGA GCGGGAAAT CACATCGGTT          60

TCCACCCAAG GACGTTCACC ACTTCCATCG AAAACATAGT CGGTGGAATA ATGTACTAGC        120

CACGCACCTA ATGCTTCAGC TTCTTTGGCA ATAACCGCCA CACTAGTTGC ATTGAGTAAC        180

TCGGCAAATT CCCGCTCACT CTCCGCTTTG TCGACTGCAG TATGGGCCGC TGCGTTAACA        240

ATCACATCCG GCTTGACGAG ACGTACCGTT TCAGCCACCC CTGCAGAATT GCTAAAATCA        300

CCGCAATAGT CGGTGGAGTC AAAATCAACG GCAGTGATGT GCCCCAGAGG CGCCAATGCA        360

CGCTGCAGCT CCCATCCTAC CTGACCATTT TTGCCAAACA ACAGAATATG CATCAGGTAC        420

GCTCCCTATA GTTTTGTTCA ATCCAGGATT GGTAGGCACC ACTCTTGACG TTGTTAATCC        480

ATTGTTGATT ATCCAGATAC CACTGCACGG TCTTGCGAAT ACCAGACTCA AAAGTCTCCT        540

CTGGCTGCCA ATCCAACGCA GCGCTCATCT TGCAAGCATC AATCGCATAT CGGCGATCGT        600

GTCCGGGGCG ATCCGCCACA TAAGTAATTT GATCGCGATA AGAGCCAGCT TTCGGTACCA        660

TCTCGTCAAG CAGATCACAA ATAGTATGTA CTACATCCAG GTTCTGCTTC TCGTTGTGAC        720

CGCCTATGTT ATAAGTCTCC CCGACCAAGC CAGTGGTCAC TACCTTGTAG AGTGCTCGTG        780

CATGATCTTC CACATACAAC CAGTCACGAA TTTGGTCACC TTTACCATAA ACCGGCAGCG        840

GCTTGCCATC CAGCGCATTG AGGATCACTA GCGGGATCAG CTTCTCGGGA AAGTGGTAAG        900

GGCCATAGTT GTTGGAGCAG TTAGTGACAA TGGTTGGCAG GCCGTACGTA CGGTACCAAG        960

CACGCACCAG ATGATCGCTG GAAGCCTTGG AGGCAGAATA GGGACTGCTA GGAGCGTAGG       1020

AGGTAGTTTC GGTAAAGAGC GGCAATGCCT CACCGGAGGC TACTTCATCC GGATGGGGCA       1080

GATCGCCATA TACTTCATCG GTAGAAATAT GGTGGAAGCG AAAGGCCGCC TTGCTCAACT       1140

CGCCCAGACT GCTCCAATAG GCGCGAGCCG CTTCCAGCAA TGTATAGGTG CCTACGATAT       1200

TGGTTTCGAT AAAGTCGGCT GGCCCTGTGA TAGAACGATC AACATGGCTT TCAGCAGCCA       1260

GATGCATCAC GGCATCTGGC TGGTGCAGAG CAAACACCCG ATCCAACTCA GCACGATTAC       1320

AGATATCAAC TTGTTCAAAC GAATAACGCT CACTTGACGA TACACTGGCC AAAGATTCCA       1380

AATTGCCAGC ATAGGTGAGT TTATCCAGAT TGATAACGGA GTCTCCAGTA TCACTAATGA       1440

TATGACGCAC CACGGCAGAG CCGANAAAAC CAGCACCGCC AGTAACGAGA ATCTTCATAT       1500

ATTTCGCTCT CTTATTTTAC AATTAATAGC TATTAAAAAT AAACTTGTTG ACTCCGATAT       1560

ATTAGAAATA TCGGGATACC GAACTAAATA TTTTTATATG CTTTTGCCAA GCAGACTCTA       1620

TATCCACCCT GTATCACTAT GCTTTCTGGC ATACAATATC CCATCATTGA CACAATGATA       1680

AACATATAAA TAAAGAAAAT TTTAAATCAT ATAACCAAAT TACTTTCATT TATTATCAAT       1740

AAGTATTTTG ATAAGAATAC CTATACCACA GGGAGCCCCC TGAAACATAA TATTAGCGAA       1800

GAATGATAAC TGATAGTTAC CATCTTAGAG ATAAAAACTT ATTTGTGTGG CGGGATG          1857
```

(2) INFORMATION FOR SEQ ID NO: 96:

(i) SEQUENCE CHARACTERISTICS:
        (A) LENGTH: 1128 base pairs
        (B) TYPE: nucleic acid
        (C) STRANDEDNESS: double
        (D) TOPOLOGY: linear (xi) SEQUENCE DESCRIPTION: SEQ ID NO: 96:

```
AGCTCTTTCG TGTAAAATAA AATACAGCAT ATCCTATATA GCTTACAATC ATTAAATGAA      60

GTCGCCAATA TTTATATGTT TTATCAATAT CAGCTTGACT CATTGTTATT TCTTTGTCAG     120

GAGACTCTGA AAATATGGAC ATATATAACC TCTTTTATTA TGAAATATTT TCAATAATAA     180

TAATCCGTTA GTAATCCTAT CATAGGGTAA TGTCTCATCA TGTTAAAATG ATCACATTTA     240

TAATCATGTC AAAAGAACA ACAGAAAAAA TCATATAAAA TCAATTAAAT ATAATTGCCA      300

CATATTGTTG TTATTWAAAC ATTGGTGGTG AATTTAAAGC GAGAACAGTT TGTAACAGTG     360

ACTCCTTGCA GACTAAGTTA GAGTCTCCTT CTAAAATTAG ACGGWKTTCT ATTGATGGAT     420

AATAGTAAGC GCACCGTGAA KGACGTGGGG TAAAAATTAG TTTACAGATT GAGTGACATT     480

CCAGGGCAAC AACTCTTTCA CGCGGTTGGC AGGCCAGGTG TTGATTACAC TGATCACGTG     540

GCGTACATTA CCGGACTCGA TTCCGTTAAG TTTGCAGCTA CCGATCAGGC TGTACATCAC     600

TGCCGCACTC TCGCCTCCAC CATCAGAGCC GAAGAACATG TAGTTACGCC GCCCCAGTGC     660

AATACCCGGA GGCGTTTTCA CACAGGTTAT TGTCGATCTC CACCCAGCCA TTGCGGCAGT     720

ATTCGTTCAG AGCGTCCCAT TGCTTCAGCA GATAGGTGAA CGCTTTCGCT GTATCCGAGT     780

GGCGCGACAG TGCTCATCTG CCCCTGGAGC CACTCATACA ACGACTGCAT TAGCGGTACC     840

GTTCTGGCTT TTCTGACCGC CAGTCGCTCT TCTGCCGGAC TGCCGCGGAT CTCAGCCTCG     900

ATAGCGTACA GTTCACCGAT ACGCTGCAGG GCTTCCGTGG TGATGTCAGG TGGCGCTCTT     960

GCATGCACAT CGTGGATTTT TCTCCGGGCA TGGGCCATAC AAGCCGCTTC GGTTACCTGA    1020

CCGCTTTCGT AAAGAGCATT GTAACCCGCA TATGCATCGG CCTGCAGGAT ACCTCTGTAG    1080

TCCGCCAGAT GTTGCTGTGG GTGGATGCCT TTGCGGTCGG GAGAGTAT               1128
```

(2) INFORMATION FOR SEQ ID NO: 97:

(i) SEQUENCE CHARACTERISTICS:
        (A) LENGTH: 439 base pairs
        (B) TYPE: nucleic acid
        (C) STRANDEDNESS: double
        (D) TOPOLOGY: linear (xi) SEQUENCE DESCRIPTION: SEQ ID NO: 97:

```
GTTTGCTTAC GAACCGTGAA ATATGACGGT CCCATATAAC TGCCTGATAC TTGTATATCA      60

TATACTTGTG CATGCATGTC ATCATTAAAA AGTACTTTGT CACCGTCTTT AAGTTGAAGA     120

CGTGTAAAAT CTTTATACGG CAAGTAGACG GAAAACGGGC GCTTTCCCTG TCGCCAATCA     180

CACCGACATG ACTGACTTTT GCGAGAGGAA GTGCATAATT CACCAATTCA GAGCCTAATG     240

CATTGCGCTG GGTAAGCTCA AATCGGAATG GGTTTCGAAC CTTTCCCGCA ACATTGATCA     300

TTGGACCTTG TTGCTCAACT GAAAATCACA TCTTGATCTT TTAATGCCAG CTTCGGGAGT     360

TTCCCATACC GTATGAAATC ATAAAGATCA ATTTGCKGTG NTTACTGCTA TTTTGTGCGT     420

GAACACCTTA ATTTTTGCG                                                 439
```

(2) INFORMATION FOR SEQ ID NO: 98:

(i) SEQUENCE CHARACTERISTICS:
    (A) LENGTH: 906 base pairs
    (B) TYPE: nucleic acid
    (C) STRANDEDNESS: double
    (D) TOPOLOGY: linear (xi) SEQUENCE DESCRIPTION: SEQ ID NO: 98:

```
TATTCGTAAT TAGTTATAAA CAGATGATGT AAACACCAGT TGACTAGAGT CAATCTTATA        60
CTGGCAACAT CTATGATTAA TTTGTGTGGT TATAATTTTA AATATCTTAT ATTTATGGGC       120
TATTATTGAT ATCTGTCAGA GTATCAATAA TAGAAGGTAA TTGTTTTACA TACTATCAAC       180
TTTTGGATAA CGTTTTAAAA TGCACCTTGC ACATCGTATT TTATTATTTT CACTAATCTT       240
TTTTATAACG GCCTGCGCAC ATGATCCAAA ACAAGTTGAA GCCTCTCGTC CATTGGTAAC       300
AGCGATTAAT TCTTCTTATT CTCTTATTCC TGAAGATTTG CAGGCACCAT TAAATAACCA       360
AGATCAAGGC ACGACATTCA ACAAAAATGG CGTAATTTAT ACTATTGAGG AAAGGTATAT       420
ATCGGCTTTA GGTTCTCAAT GCATAAAGTT AAGTTATGCG ATGAATAAAA ATTATTCAAA       480
GCGAAGTGTT GTATGTAAAG AGAATAACAA GTGGTATCAA GTACCTCAGT TGGAACAAAC       540
ATCAGTTAGC ACTTTGCTTA TTGAAGAATA AAGTTGAAGG TAGACGGTTA GAAAATAATG       600
AAAATTTCGC AACTTAGCAC TCTTCTCTTT CTTATTTCTG CATCAGCATT CGCCGCAATA       660
GAGCAAAATC AATCTAATGG TTCACATTTA GATTATGATC TTGCTGCCTC GACAGGAGAG       720
TCTCGGAAAA TGCTAGCAGA CATCACTGGA CAGCCTAATA CAACCTCCAC AACAGGAAGC       780
TTCACACAAC AGAATCGTAA TGGGATGTTG CTTCCAGGAG AGTCAGATGT ACGAAAATTA       840
CTGCCGCAAT CTGAAGCAGG CTTACCTCCT CCGTATGGTG CTAATTTATT TGCCGGAGGC       900
TATGAA                                                                  906
```

(2) INFORMATION FOR SEQ ID NO: 99:

(i) SEQUENCE CHARACTERISTICS:
    (A) LENGTH: 1395 base pairs
    (B) TYPE: nucleic acid
    (C) STRANDEDNESS: double
    (D) TOPOLOGY: linear (xi) SEQUENCE DESCRIPTION: SEQ ID NO: 99:

```
GCGGCCTGAT ATATGCCGTT ATTACAAAAA GAGGATCAAC CACACTGCCT TTTGGACCGT        60
GTTTAAGTCT GGGCGGTATA GCAACACTTT ATCTACAGGC ATTGTTTTAA TGATAACCAC       120
GTCATTATCA AAGTGACATT TTAACTCTTA TTAATAACCT TAGAGATTAT TTACCATGTC       180
GATAAAACAA ATGCCAGGGA GGGTATTAAT ATCGCTATTG TTGAGCGTTA CAGGATTATT       240
AAGTGGCTGT GCCAGCCATA ATGAAAATGC CAGTTTACTG GCGAAAAAAC AGGCGCAAAA       300
TATCAGCCAA AACCTGCCGA TTAAATCTGC GGGATATACC TTAGTGCTGG CGCAAAGTAG       360
TGGCACGACG GTAAAAATGA CCATTATCAG CGAATCGGGT ACTCAGACCA CGCAGACACC       420
TGACGCCTTT TTAACCAGCT ATCAACGACA AATGTGCGCT GACCCAACGG TGAAATTAAT       480
GATCACCGAG GGAATTAATT ACAGCATAAC GATTAATGAT ACACGTACAG GTAACCAGTA       540
TCAGCGGAAA CTGGATCGTA CCACCTGTGG AATAGTCAAA GCATAACGTC GGGTAGATAT       600
AAATTGGCGC GGGTTGTTTT TCGTGACGCA CGAATTTATC TCATTCAATG GCTGACAAAA       660
ATTCGTCACA CTCTTAACCA GAGACAATCT CTTAATACAG ACAAAGAGCA TCTGCGCAAA       720
ATTGCACGCG GGATGTTCTG GCTGATGCTG CTTATTATTT CTGCAAAAGT GGCGCATTCA       780
CTCTGGCGCT ATTTCTCCTT TTCTGCGGAA TATACGGCGG TTTCCCCATC GGCGAATAAA       840
```

```
CCGCTCCGTG CGRATGCAAA AGCGTTCGAT AAAAATGACG TGCAATTAAT CAGCCAGCAA      900

AACTGGTTTG GCAAATATCA GCCCGTCGCC ACGCCGGTAA AACAACCCGA ACCTGCACCT      960

GTGGCCGAAA CGCGTCTTRR TGTGGTGTTG CGTGGGATCG CCTTTGGTGC CAGACCCGGC     1020

GCGGTTATTG AAGAAGGTGG TAAACAGCAG GTCTATTTGC AGGGTGAACG CTTGGCTCGC     1080

ACAACGCAGT GATTGAGGAA ATCAACCGCG ACCATGTGAT NTGCGCTATC AGGGAAAAAT     1140

AGAGCGCCTG AGCCTGGCTG AAGAGGAGCG TTCCACCGTT GCCGCGACCA ACAAAAAAGC     1200

TGTCAGTGAC GAAGCAAAGC AAGCTGTTGC TGAACCTGCT GTCAGTGCGC CAGTTGAGAT     1260

CCCNGCTGCC GTGCGTCAGG CACTGGCGAA AGATCCGCAG AAAATTTTTA ACTATATCCA     1320

GCTTACGCCT GTGCGTAAGG AAGGGATTGT CGGTTATGCA GTGAAACCGG GGCAGATCG      1380

TTCTCTGTTC GATGC                                                      1395

(2) INFORMATION FOR SEQ ID NO: 100:

(i) SEQUENCE CHARACTERISTICS:
         (A) LENGTH: 380 base pairs
         (B) TYPE: nucleic acid
         (C) STRANDEDNESS: double
         (D) TOPOLOGY: linear (xi) SEQUENCE DESCRIPTION: SEQ ID NO: 100:

CACTTGAATA AAACTGACAC CGTTTACCTC CATAATAGTG AGCATAGCCG CCATTGCGGC       60

CTGATCGGCG AACCGGAAAT CGCAACCTGC GAACGACAAC CGAACCGGCA AGCGTGCGGG      120

AAGGACGGAT ACCGGACTCT TTCGCCACTT CAGCAATCAC CGGCAGCGTG GAAAAAACAA     180

TAAACCCAGT ACCGGCCATA ATGGTCATAG ACCAGGTGAT AATCGGCGCG ATTATGTTGA     240

TATATTTCGG GTTACGCCGC ATAAAATTAC CAGCGACGGT ACCAGATAAT CCATTCCCCT     300

GCGGCCTGTA AGGCTGAGGC CGCCACAACA ACGGTCATAA TAATCAGGAT CACGTCGACT     360

GGCGGCGACC CCATAGGCAG                                                 380

(2) INFORMATION FOR SEQ ID NO: 101:

(i) SEQUENCE CHARACTERISTICS:
         (A) LENGTH: 995 base pairs
         (B) TYPE: nucleic acid
         (C) STRANDEDNESS: double
         (D) TOPOLOGY: linear (xi) SEQUENCE DESCRIPTION: SEQ ID NO: 101:

CTTTACGGTT TAATAGGGGA ANGCCGACTG GATGNAAAAA TGGAATCTGG AGCCCAGAAT       60

AAATCTGAAT TTAATGTGGA CTGGATATGC TCCAATAACC CCGGCAGGGA GTCATCTGTG      120

CGAAGATATT TGCGTTATGC TGTAATATAA TAATTCAATG TATTTCAGGA ACAGTAATAT      180

ACTACAGTTT CTACTTTCTT GTATTTAATA AATTGTTCCG CATCGCTAAA AGCAGGTCTT     240

TCAGAAGCCA CAAGAATTCT GTGGTCCCAG TATTTTTAGT TATCCTATTT TTATATCTAA      300

CTTGTAATAC TTACAGCATT TTCATTCATC CTAATGAAGG CTGTAATAA TCTTTGAGCT      360

TAGAAACATC AAAATTATGC ATCTCATTAA TTTTGTCAGT CACACGACCT CTGGTAAAAA     420

TAAAACCCCC AGAAATATGC CATTTCTAGG GGGGCGTAA GAATCAATAT ATTTTAGTGT      480

TGTTACATTT AGCTCTTAGC TCTTAGCTCT TAGCTCTTAG CTCTTAGCTC TTAGCGTTTG      540

TAGTTTCATC GCAATGAGTA AAAGGACAAC AAGAATAAGT GATAACGTTA AGAGAAGAGC      600

ATAGAAACCA TTCCAGTGGT ATATTTCTAT TATTTTAGAC AATGGATAGC CAGCCGCGGA      660
```

```
CGCACCAAGA TATGCGAATA AACTAACAAA ACCAGTAGAA GCACCAGATG CATATTTATG    720

TGAGTTTTCA GCAGCTGCCA TTGCGATCAG AAATTGTGGC CCAAAGATAA AGAAGCCAGT    780

GATGAAAAAT AATAACGAAA AAACATATTT ACTATCAATA GAAACCAACC ATAGACATGC    840

AGAAGCAATG ATTATACCAA TTGTATAAAT AACATTCATT TGAGAGCGAT TGCCCTTAAA    900

CAGAATATCT GATCCCCATC CAGCTACGAT AGCACCAAAA AAGCCTCCAA CCTCAAACAT    960

CATTACTGTT GCATTTGCTG TTAGCAAGTC ATATT                               995

(2) INFORMATION FOR SEQ ID NO: 102:

(i) SEQUENCE CHARACTERISTICS:
        (A) LENGTH: 817 base pairs
        (B) TYPE: nucleic acid
        (C) STRANDEDNESS: double
        (D) TOPOLOGY: linear (xi) SEQUENCE DESCRIPTION: SEQ ID NO: 102:

TAAAAGCGAC TCCATGTGAA ATTTCTGTTT GTCGTTTTTT CCCCGTTGTA GCGGCTCTGC     60

TCCTGGCTTC CCTGATAGTC AGCCCGCAGG CGCCAGGGCC CCAGATTCCC CCCCACAGTC    120

CCGTTATAAC TGAACTGATG AGAGTCTCCT CCCTGATAAT TACGGGAAAC CGTCCCGTTG    180

AGGTTATAAT CCAGCATCAG TCCGGGAATG CCGTCGTCCC AGCGTGAGGG AGGCAGCCAG    240

GTGGCATCAG AATACTCAAG CCAGGCCTGC GGCATATTGA TGCGTAATAC GCCCGCTCCG    300

GTATCAGGAC GAATATCCAC TCCCGGCAAC CCATGAAAAT CCGCACACTG ACCATCATGC    360

CAGTAAACAA CTTTATCCAG AGATTCTGCT GTTAACCCCA TCAGTCTGAC CATATCTGAT    420

GTCAGACAGC TGCGGCAATT TTTTTTCTGC CTTATCTCCT GACAACGCAG GTTCAACAAA    480

TGAMATCTGT AACGATGCGG GAGAAATACT TTGCCCGTTA ACAATCACAT CCAGAAGATA    540

TTGCCCCGGC AGAACATAGC CGGCTTCTGA AAAACGGGTG AAGTCAATAT TTTTCTTGTC    600

CGCTGCGTCA AGTACATCTG TATTAAACTC AACGGCACTG GCTGCGTTAC AAAACAGAGA    660

CAACAATATC ACACAGGTAA TATTGTTGAC TGCAAAAGGT ATTCTGTCTT TCATTCCACG    720

CATCACCAGA TTCACAAAAA AGATAAATAA CCGGACATCT CACCGGAGTG ACTCACTCAT    780

AATCGACCCG GAATCCCAGC ACAGCAAAAT AATTTCC                             817

(2) INFORMATION FOR SEQ ID NO: 103:

(i) SEQUENCE CHARACTERISTICS:
        (A) LENGTH: 709 base pairs
        (B) TYPE: nucleic acid
        (C) STRANDEDNESS: double
        (D) TOPOLOGY: linear (xi) SEQUENCE DESCRIPTION: SEQ ID NO: 103:

TTTTTGTCAG AGCGTTCACT CTCTGGCTGG ATGATTTCGG CTCGGAAAT GCAGGCTTAA      60

TGTGGGACT GTCGGGATG TTTGAACGGG TAAAAATAAG TCATGAGTTT TTTCATTATG      120

TCCTGAAAAA CGGGTGTGCA ATGCCACTTC TCCGTGCTGT GGCAGACACT GTTGCCTGTC    180

ACAACAGAGG CGTGATACTC GAAGGTGTTG AAAATGAAGC GTTGTTCCGT ATTGCCAGAG    240

ACATGAATGT CCAGGGCTGT CAGGGATGGC TCTACAGGCG TGTGGGGGTT GATGAATTAT    300

CCGCGCTTAT TCAGCAGTAT GAATAATCCT TTTTCACAGA CTGGTCAGCT GTCAACATTT    360

ATGTTTTTTT ATCTGCGGGA ATTTATCCGT CTGCCTGTCG GGACTACTCT GTCATACAGA    420

AATCAGGCCA GAATAAATTG TTGTGGAAAG GTGAGATTTA CCGGATGACT GATGTGCTCT    480

TGTGCACAGG TATACAGGCA GTGTGTTTCC AGTATATGGA AAATGATTAA ATGAATAACA    540
```

```
CAGACTTATT AGAAAAAATC ATCAGGCATC AACAAAACAA AGATCCTGCA TATCCTTTCC      600

GGGAACATCT TTTGATGCAA CTCTGTATCC GTGTAAACAA AAAAATACAG AACAGTACAT      660

CTGAGTTTTT TGGTGCATAT GGTATAAATC ACTCAGTATA TATGGTTCT                  709
```

(2) INFORMATION FOR SEQ ID NO: 104:

(i) SEQUENCE CHARACTERISTICS:
        (A) LENGTH: 485 base pairs
        (B) TYPE: nucleic acid
        (C) STRANDEDNESS: double
        (D) TOPOLOGY: linear (xi) SEQUENCE DESCRIPTION: SEQ ID NO: 104:

```
TCATCAAGGG ACGGGCATA TCTGGATGCG ACAGGGCAAA CCAACCACTG AGAATCCAAC        60

CTGCCAAAGC CTGACCAGGA AGTCCGACGT TAAAGAAACC AGCTCGACTG GCAACGGCAA      120

AACCAAGACC AATCAAGACC AGAGGACCCA TAGCACGGAA GATTTCTCCA ATCCCACGCA      180

GACTGCCAAA GGCTGTATAG AACAATTCTT CGTAGCCCCA AATAGCATCA TAACCGAAGA      240

TCCACATGAC AATGGCTCCG AGTAAAATTC CTAGGAATAC AGAAATCAAG GGAACCGAAA      300

TTTGTTGTAA TTTTTTAGAC ATCACTCTTC TCCTTTCCCA AGTTYCCACC AGCCATCAAG      360

ACACCAAGTT CTTGTTTATT GGTTGTTTCT GGTGATACAA TACCTTGAAT CTTACCATCG      420

TGGATAACGG CAATACGGTC TGAGACGTTT AAAATCTCAT CCAATTCAAA GCTGACNACA      480

AGGAC                                                                  485
```

(2) INFORMATION FOR SEQ ID NO: 105:

(i) SEQUENCE CHARACTERISTICS:
        (A) LENGTH: 459 base pairs
        (B) TYPE: nucleic acid
        (C) STRANDEDNESS: double
        (D) TOPOLOGY: linear (xi) SEQUENCE DESCRIPTION: SEQ ID NO: 105:

```
AGCAGAATAG GCAACATCAC CACGCCGACA AACAGCGAGA AGAGAATGAC GCCAGCCGCC       60

AGGAACACCA GCTCATAGCG CGCCGGGAAG ACGTTACCAT CCGGCAAGAG CAGCGGGATA      120

GAGAGCACAC CGGCCAGAGT GATCGCCCCA CGCACCCCGG CGAAAGACGC GATCAGGATT      180

TCTCGTGTGG TCCACGAACC AAACTCCATC GGCTTCTTCT TCAGGAAGCG GTTGCTGAAC      240

TTTTTCATCG TCCACAGCCA GCCGAAACGG ACCAGCATCA GCGCCGCATA TATCAGAATA      300

ATATTGGTAA ACAGCATCCA GATTTCGACG TTAGGGTCGA TTTCTTGCTG GCCATCAGCG      360

GACGTCTTCC AGRATTACCC GGCAGCTGCA GACCTTAACA GCAGGGAACA CCATGGCCGT      420

TTTAAGGACA ATTTCNAGCA TCGGCCCANG TGCTGTTTT                             459
```

(2) INFORMATION FOR SEQ ID NO: 106:

(i) SEQUENCE CHARACTERISTICS:
        (A) LENGTH: 908 base pairs
        (B) TYPE: nucleic acid
        (C) STRANDEDNESS: double
        (D) TOPOLOGY: linear (xi) SEQUENCE DESCRIPTION: SEQ ID NO: 106:

```
TTAATAGCAC TAATACTGTC CTGCTCTATT CCGCTGACAT TTTCAGTCAG CTGCTGTATG       60

GGATGGGTTA CCCAAAACCA GACCAGCATA CCTGACAAGA GACCGCATAT CACTACCAGA      120

AACAGCGACC AGTACAGTGC ATTCCATAGT GCCTTTGTCC AGGCTGTATC AGTAAGAGCA      180
```

-continued

```
TTAAGTTCCT CTCCCTGTAA AATAATATAC AGATATCCTT TCGGTTCATC ACTCTGGTAA      240

AGCGGTGCGG TACTGAAAAC TTTTTGCTTA TTTACACTTC GGGGATCATC ACCATATACG      300

GGCCAGACAC TGCCGGAGAG AAATTTTTTC AACGGTGCAA TATTGATATA CCGGCGTTTG      360

AGATGACCCG GAGGGCGGCC TCCACAAGCA GTCGCCCTTC CGGTGAAACC ATATACAGCT      420

CCACACTGGG ATTAAGCGTC ATCAGACGCT CAAACAGACT CGTTAATGTC CGGTGTTACC      480

AGACAAAACA AGCATCGCAA GACGCCACAA ACGGTGCGCT TACTTAAATA AGCCGGTTAC      540

AGGTGAAAAA TCACGTCCTG ATATTCAAAT GTTTTTTCAG GTCATATTTT AGCAGGACAC      600

TACCAGCACC TAACAGCAGC ACATCTTTTA TAACAAAACT GTCAACTTTC CCCAGTTGTG      660

GTAACAGGCT GAGCGTGGTT ATTCCTGTAA CAATAACGAT AATATCTCCC AGTACACCAG      720

CAGCAGGCCT GAAGAAACCG ATAATCAATG CCAGAAATGT GATAGTTTCC ACTATGCCGA      780

GGAAATAGCT CCCTCCATGA ATACCAAATA TAATATACAG GATATTCAGC CAGGTGGGAT      840

ATATCAGGGG CTTGAGAGCC ATAACTTCAA AATCAAACCA TTTATAAGTC CCAAAAAGCA      900

TAAATATT                                                              908
```

(2) INFORMATION FOR SEQ ID NO: 107:

(i) SEQUENCE CHARACTERISTICS:
       (A) LENGTH: 1057 base pairs
       (B) TYPE: nucleic acid
       (C) STRANDEDNESS: double
       (D) TOPOLOGY: linear (xi) SEQUENCE DESCRIPTION: SEQ ID NO: 107:

```
CGGGCTAACC CAATATGCTT TATTAACCCG GGATAATTAC CCTGTTGCAT ATTGTAGTTG       60

GGCTAATTTA AGTTTAGAAA ATGAAATNAA ATATCTTAAT GATGTTACTT CATTAGTCGC      120

AGAAGACTGG ACTTCTGGTG ATCGTAAATG GTTCATTGAC TGGATTGCTC CTTTCGGGGA      180

TAACGGTGCC CTGTACAAAT ATATGCGAAA AAAATTCCCT GATGAACTAT TCAGAGCCAT      240

CAGGGTGGAT CCCAAAACTC ATGTTGGTAA AGTATCAGAA TTTCACGGAG GTAAAATTGA      300

TAAACAGTTA GCGAATAAAA TTTTTAAACA ATATCACCAC GAGTTAATAA CTGAAGTAAA      360

AAACAAGTCA GATTTCAATT TTTCATTAAC AGGTTAAGAG GTAATTAAAT GCCAACAATA      420

ACCGCTGCAC AAATTAAAAG CACACTGCAG TCTGCAAAGC AATCCGCTGC AAATAAATTG      480

CACTCAGCAG GACAAAGCAC GAAAGATGCA TTAAAAAAAG CAGCAGAGCA AACCCGCAAT      540

GCGGAAAACA GACTCATTTT ACTTATCCCT AAAGATTATA AAGGGCAGGG TTCAAGCCTT      600

AATGACCTTG TCAGGACGGC AGATGAACTG GGAATTGAAG TCCAGTATGA TGAAAAGAAT      660

GGCACGGCAA TTACTAAACA GGTATTCGGC ACAGCAGAGA AACTCATTGG CCTCACCGAA      720

CGGGGAGTGA CTATCTTTGC ACCACAATTA GACAAATTAC TGCAAAAGTA TCAAAAAGCG      780

GGTAATAAAT TAGGCGGCAG TGCTGAAAAT ATAGGTGATA ACTTAGGAAA GGCAGGCAGT      840

GTACTGTCAA CGTTTCAAAA TTTTCTGGGT ACTGCACTTT CCTCAATGAA ATAGACGAA       900

CTGATAAAGA AACAAAAATC TGGTGGCAAT GTCAGTTCTT CTGAACTGGG CAAAAGCGAG      960

TATTGAGCTA ATCAACCAAC TCGTGGGACA CAGCTGGCCA GCCTTTAATA ATAATGTTNA     1020

ACTCATTTTC TCAACAACTC AATAAGCTGG GGAAGTG                              1057
```

(2) INFORMATION FOR SEQ ID NO: 108:

(i) SEQUENCE CHARACTERISTICS:
       (A) LENGTH: 752 base pairs (B) TYPE: nucleic acid
        (C) STRANDEDNESS: double
        (D) TOPOLOGY: linear (xi) SEQUENCE DESCRIPTION: SEQ ID NO: 108:

```
TACCGGGCCC CCCCTCGAGG TCGACGGTAT CGATAAGCTT GATATCGAAT TCCTGCAGCC      60
CGGGGGATCC ACTAGTTCTA GAGCGGCCGC CACCGCGGTG GAGCTCCAGC TTTTGTTCCC     120
TTTAGTGAGG GTTAATTTCG AGCTTGGCGT AATCATGGTC ATAGCTGTTT CCTGTGTGAA     180
ATTGTTATCC GCTCACAATT CCACACAACA TACGAGCCGG AAGCATAAAG TGTAAAGCCT     240
GGGGTGCCTA ATGAGTGAGC TAACTCACAT TAATTGCGTT GCGCTCACTG CCCGCTTTCC     300
AGTCGGGAAA CCTGTCGTGC CAGCTGCATT AATGAATCGG CCAACGCGCG GGAGAGGCG      360
GTTTGCGTAT TGGGCGCTCT TCCGCTTCCT CGCTCACTGA CTCGCTGCGC TCGGTCGTTC     420
GGCTGCGGCG AGCGGTATCA GCTCACTCAA AGGCGGTAAT ACGGTTATCC ACAGAATCAG     480
GGGATAACGC AGGAAAGAAC ATGTGAGCAA AAGGCCAGCA AAAGGCCAGG AACCGTAAAA     540
AGGCCGCGTT GCTGGCGTTT TTCCATAGGC TCCGCCCCCT GACGAGCATC ACAAAAATCG     600
ACGCTCAAGT CAGAGGTGGC GAAACCCGAC AGGACTATAA AGATACCAGG CGTTTCCCCC     660
TGGAAGCTCC CTCGTGCGCT CTCCTGTTTC CGACCCTGCC GCTTTACCGG ATANCTGTNC     720
GGCTTTCTCC CTTCGGGAAG CGTGGCGCTT TC                                   752
```

(2) INFORMATION FOR SEQ ID NO: 109:

(i) SEQUENCE CHARACTERISTICS:
        (A) LENGTH: 486 base pairs
        (B) TYPE: nucleic acid
        (C) STRANDEDNESS: double
        (D) TOPOLOGY: linear (xi) SEQUENCE DESCRIPTION: SEQ ID NO: 109:

```
CTTGGGTAAT NGACCTCATA TCCCTCCGCC AAAAAAGGAT CTACATGCGA TTTTGCGAAG      60
CCAGCGTTGA TTGTAGGCGA GAGAATGGTT CTGTTGTTTT GGTACATTTC AGTTGTCATG     120
GATTTCACAA ATGTAGCATG ACCTTTCACC TGTCCAAGAG ACTGCAACAC CATCTGTCCA     180
AAACAATAAA TAGGAATCAA ACAGGCTACC AACATCAACA AGTATCCCAA TAAGGCTCGT     240
AGTTTAGTCC TTGACATGAC GCCCCTCCAA TTGCTTTTCT AGTCCTTTGA CAATCCGTCG     300
ATTACGATAC ACGCGATACA GCAAGAGAAG GATGACCGCC ATCGCTCCTA GTAATAACCA     360
CAACCAGAAT TGCCCACGCT CTCTCACCGC TCGATTCCGC TCTGCAATTG GTGCCGTATA     420
CGGAATCCGC TTCCCACGTA CCAACAGACG ATGACTGTTA ATCCTATACG GTGTACNAGT     480
CAACCA                                                               486
```

(2) INFORMATION FOR SEQ ID NO: 110:

(i) SEQUENCE CHARACTERISTICS:
        (A) LENGTH: 313 base pairs
        (B) TYPE: nucleic acid
        (C) STRANDEDNESS: double
        (D) TOPOLOGY: linear (xi) SEQUENCE DESCRIPTION: SEQ ID NO: 110:

```
TTACGCNTTC AACCAGGTCT TCTGGTTTAC CAACGCCCAT CAGGTAACGC GGTTTGTCTG      60
CCGGAATTTG CGGGCATACA TGCTCCAGAA TGCGGTGCAT ATCTGCTTTC GGCTCACCCA     120
CAGCCAGACC GCCGACAGCG TACCATCAAA ACCGATATCT ACCAGACCTT TAACAGAAAT     180
ATCACGTAAA TCTTCGTAAA CGCTGCCCTG GATGATACCA AACAGCGCAT TTTTGTTTCC     240
```

```
GAGACTGTCA AAACGCTCAC GGCTACGTCG CCCAACGCAG AGACATCTCC ATGGAGCGTT        300

TTGCGTAATC CCA                                                          313
```

(2) INFORMATION FOR SEQ ID NO: 111:

(i) SEQUENCE CHARACTERISTICS:
        (A) LENGTH: 1613 base pairs
        (B) TYPE: nucleic acid
        (C) STRANDEDNESS: double
        (D) TOPOLOGY: linear (xi) SEQUENCE DESCRIPTION: SEQ ID NO: 111:

```
CGGAAATCCC AGTAATTCCA TCCTCANATA TTCCACTCAN CCTCACTGTA ACAAAGTTTC         60

TTCGAATAAT AAAAATCATG CTTTCTGTTA TCAACGGAAA GGTATTTTTA TTCTCTGTGT        120

TTGCTTTATT TGTGAAATTT AGTGAATTTG CTTTTTGTTG GCTTTATNTG ATGTGTGTCA        180

CATTTTGTGT GTTATTTTTC TGTGAAAAGA AAGTCCGTAA AAATGCATTT AGACGATCTT        240

TTATGCTGTA AATTCAATTC ACCATGATGT TTTTATCTGA GTGCATTCTT TTTGTTGGTG        300

TTTTATTCTA GTTTGATTTT GTTTTGTGGG TTAAAAGATC GTTTAAATCA ATATTTACAA        360

CATAAAAMMC TAAATTTAAC TTATTGCGTG AAGAGTATTT CCGGGCCGGA AGCATATATC        420

CAGGGGCCCG ACAGAAGGGG GAAACATGGC GCATCATGAA GTCATCAGTC GGTCAGGAAA        480

TGCGTTTTTG CTGAATATAC GCGAGAGCGT ACTGTTGCCC GGCTCTATGT CTGAAATGCA        540

TTTTTTTTTA CTGATAGGTA TTTCTTCTAT TCACAGTGAC AGGGTCATTC TGGCTATGAA        600

GGACTATCTG GTAGGTGGGC ATCCCGTAAG GAGGTCTGCG AGAAATACCA GATGAATAAT        660

GGGTATTTCA GTACAACACT GGGGAGACTT ATACGGCTGA ATGCTCTTGC AGCAAGGCTT        720

GCACCTTATT ATACAGATGA GTCGTCGGCA TTTGACTAAA TTATGGCATT CCGGAGTTTC        780

TGGAAGATAA AAAAGAAGC CCTTATCAGA AAGCAGACAG GTTATATCAG TATTCTGTCG         840

ATAAATAACC TGCCCTGAAA ATACGAGAAT ATTATTTGTA TTGATCTGGT TATTAAAGGT        900

AATCGGGTCA TTTTAAATTG CCAGATATCT CTGGTGTGTT CAGTAATGAA AAAGAGGTTG        960

TTATTTATGA TTAAGTCGGT TATTGCCGGT GCGGTRCTAT GGCAGTGGTG TCTTTTGGTG       1020

TAAATGCTGC TCCAACTATT CCACAGGGGC AGGGTAAAGT AACTTTTAAC GGAACTGTTG       1080

TTGATGCTCC ATGCAGCATT TCTCAGAAAT CAGCTGATCA GTCTATTGAT TTTGGACAGC       1140

TTTCAAAAAG CTTCCTTGAG GCAGGAGGTG TATCCAAACC AATGGACTTA GATATTGAAT       1200

TGGTTAATTG TGATATTACT GCCTTTAAAG GTGGTAATGG CGCCAAAAAA GGGACTGTTA       1260

AGCTGGCTTT TACTGGCCCG ATAGTTAATG GACATTCTGA TGAGCTAGAT ACAAATGGTG       1320

GTACGGGCAC AGCTATCGTA GTTCAGGGGG CAGGTAAAAA CGTTGTCTTC GATGGCTCCG       1380

AAGTGATGCT AATACCCTGA AAGATGGTGA AAACGTGCTG CATTATACTG CTGTTGTTAA       1440

GAAGTCGTCA GCCGTTGGTG CCGCTGTTAC TGAAGGTGCC TTCTCAGCAG TTGCGAATTT       1500

CAACCTGACT TATCAGTAAT ACTGATAATC CGGTCGGTAA ACAGCGGAAA TATTCCGCTG       1560

TTTATTTCTC AGGGTATTTA TCATGAGACT GCGATTCTCT GTTCCACTTT TCT             1613
```

(2) INFORMATION FOR SEQ ID NO: 112:

(i) SEQUENCE CHARACTERISTICS:
        (A) LENGTH: 930 base pairs
        (B) TYPE: nucleic acid
        (C) STRANDEDNESS: double
        (D) TOPOLOGY: linear (xi) SEQUENCE DESCRIPTION: SEQ ID NO: 112:

| | | | | | |
|---|---|---|---|---|---|
| NTAGTCCATG | GCCCCATGGA | GCGAANTCCA | AAGTGTGGAT | ATTGTCGTTT | TAATTCATCC | 60
| CAAAAGCTGA | AATACGCCAA | AACCCACGTT | CCCTAACATT | GGTATCATGC | ATAATGACCA | 120
| CAGCCNTTCA | GAAAGCTTTG | GCAACCAGCT | TTCAAAATCA | TGGGTACCGC | TTCAAACGTA | 180
| TGCAAACCAT | CAATATGAAG | CAGATCAATG | CTACCTTGTG | AAAAATGCTC | TAACGCTTGG | 240
| TCAAATGTAC | TGCGAATGAG | AGTAGAAAAA | CCTGAATAGT | GCTGTTGATT | ATATTCTGAT | 300
| ACTTGCCTGT | AAACTTCTTC | GCCATACAGC | CCCGCATGTT | CATCTCCCCC | CCAGGTATCA | 360
| ACGGCAAAGC | AGCATGTTTC | TAAATCTAGT | TTAGAGACTG | CTTGGCAAAA | TGAGAAATAA | 420
| GAACTTCCAT | AATGAGTTCC | CAGCTCAACA | ATATTTCTTG | GCCGCAGTGT | GTCAACTAAC | 480
| CAGAAAGCAA | AAGGAATGTG | TTCTAGCCAA | GCAGATTGTG | CAAGGTATGT | AGGACACCAN | 540
| AAAAGAGATG | GTTTGAAAAT | GAAATTCAAT | TCCCTGCCAA | TATCAGTGAT | GGGATATAAC | 600
| TCACGATTCT | CTACTAACTG | ACTAATTTTT | TGACTATCCA | TTGAGGAAAA | CTCACATGTA | 660
| TTTATAGAAT | TAAATCAAGA | AACCTGAAAA | TACCTATAGT | GCGGTAACTT | ATTAACTAAC | 720
| ATTTAAATAT | TAACAATACA | CTTGGAAATA | TTAGTTAAAA | ATAAATCATT | ATGATTTCTC | 780
| ATCAATCCTG | GTGCTCACGC | AAAGTTGCCA | GCCCCATAAT | AATAAGACCA | TAGAACAAGC | 840
| AAAGTAATAC | ACCCACAGTC | GCAAGATTAT | AGAATCGCCG | TGGATATTCG | GCATCTTCCG | 900
| CTAAAGTTGG | TTGGGTAATA | ACCAATAGAT | | | | 930

(2) INFORMATION FOR SEQ ID NO: 113:

(i) SEQUENCE CHARACTERISTICS:
        (A) LENGTH: 659 base pairs
        (B) TYPE: nucleic acid
        (C) STRANDEDNESS: double
        (D) TOPOLOGY: linear (xi) SEQUENCE DESCRIPTION: SEQ ID NO: 113:

| | | | | | |
|---|---|---|---|---|---|
| ACGATATCCC | CCCTCTGCTT | TTGAGAGGCA | ATCTGCTTTA | ATACATGATT | CATCACAACA | 60
| CCTCTTGCTG | CGCTTTGATC | TTAATTTTAT | ATTTTTGGGT | AGGGAAAAGT | AATTGCCCCT | 120
| GATACGGCTC | ACCATTTACC | AACGTTTCAC | AGCTATGTTC | CAGAGCTAAA | TTAAGACCTG | 180
| GTAGAATATC | CCAGCAATTC | ACCCCTTTGA | CATTTTCAAA | GCTGTCATAA | GCACCGGNNA | 240
| AGGGGGGGCC | AACATGTTAT | ACATGGAGCA | GCCAATGATA | CGATATTCAA | AGCCCTCTTC | 300
| CAGTTGCATC | AGATCCTGCT | TGGTAASGGA | GGAAGAGAGG | CCACGAATAC | GAGAGCGATG | 360
| ATGTGTAATC | GGCATACCTG | TGATATGAAG | ATCATTCAAT | TCAGGTAAGA | AGATGCAGGA | 420
| CTCTTGATGT | TTCCCCTCGG | TGTAAATGCT | GATACCAATG | CCCCACTCTT | TGAGCCCAGA | 480
| GACAAAGTTT | TCTGTGCCAT | CAATTGGATC | TAGAACAATG | TAAGAACCTT | TGGGATTCCA | 540
| CTCAATATCT | CCTAAAGGGG | CTAATTCCTC | TGAAATTAGC | ACATGCCCTG | GTAGATGCTT | 600
| TCTACAGAGT | TCGAAAACTA | TATCTTGAAC | TTTTAGATCC | AGTACTGCGG | CCGCGATCC | 659

(2) INFORMATION FOR SEQ ID NO: 114:

(i) SEQUENCE CHARACTERISTICS:
        (A) LENGTH: 556 base pairs
        (B) TYPE: nucleic acid
        (C) STRANDEDNESS: double
        (D) TOPOLOGY: linear (xi) SEQUENCE DESCRIPTION: SEQ ID NO: 114:

| | | | | | |
|---|---|---|---|---|---|
| CCCGGATATA | CATCAGGAGA | AATTGGAGCA | GCAATTGGAT | GCGCCATTAA | TGCCTGGTTA | 60

```
GGGATCCCCG CATGTGGGCA CGCAAATGGC TCAGAATATG ATCGACCTTC ACCAGATAAA      120

CCAAATCTGA GCGAACCATT TATCCCAAGA CCCACGTATG ACGCTTCACT TCATTCCTGG      180

CATGGCGGAT ACTGAGTAAA TCATCCTGAA TCATTATGTT CAACATCATC AATTCTCCGG      240

ACTTGTTGTC AGATGTCCGG AGAATATTAA CCTTTTCTTC AGAAACAGAW TGATCAAGAA      300

TCACACTCCT TCTTTAAGAG GATTTTATCC AGAAAACTGA CTTTCTTCTA TCAAAATMAC      360

AGTATCCTGT TTTATCAGGA ATAATCTTTA CCTCCGGTAT CATTCCCATA ATCAGATATC      420

AGAAAAATGT GCCAGTAATT TTTTACTGAT GACTTCAAAC ATTTCACATT CATCACACGT      480

CAGATTACTC CAAAGTTCTT TCAGATATGT GTTCTGCGCC AGAGTGAGTC TCTGAATAAA      540

AAACATACCT TCAGAC                                                     556
```

(2) INFORMATION FOR SEQ ID NO: 115:

(i) SEQUENCE CHARACTERISTICS:
        (A) LENGTH: 503 base pairs
        (B) TYPE: nucleic acid
        (C) STRANDEDNESS: double
        (D) TOPOLOGY: linear (xi) SEQUENCE DESCRIPTION: SEQ ID NO: 115:

```
TACCTGTTTG TGGAATTTGA CCCAGAAGTG ATTCATACCA CGACTATCAA CGCGACCCGN       60

GTGTNCAGCC ACTTCGTGCG CTTTGGCGTN CGCAGCGATA GTCCCATCGG CGGTTATTCA      120

TCAGCTATCG GTATATAAAC CGAAAGACAT TGTCGATTCC GGCAACCCCT TATCCGGGTG      180

ATAAGGTGAT TATTACCGAA GCGCGTTCGA AGGCTTTCAG GCCATTTTCA CCGAACCCGA      240

TGGTGAGGCT CGCTCCATGC TATTGCTTAA TCTTATTAAT AAAGAGATTA AGCACAGTGT      300

GAAGAATACC GAGTTCCGCA AACTCTAAAA CGCAATCCCA AACAGTGTTT TGACATTAGC      360

ATCCGTGGTG GCAGCCAGCC ATGCGGCATC TTCTCCACGC CAGTGCGCAA TACGTTGCAA      420

AATATGGGGC AGATGGGCTG GCTCGTTGCG CCGGGATGAN GGCTTTGGCG TGAGATCGCG      480

AGGGAGCAGA TACGGNGCAT CAG                                             503
```

(2) INFORMATION FOR SEQ ID NO: 116:

(i) SEQUENCE CHARACTERISTICS:
        (A) LENGTH: 433 base pairs
        (B) TYPE: nucleic acid
        (C) STRANDEDNESS: double
        (D) TOPOLOGY: linear (xi) SEQUENCE DESCRIPTION: SEQ ID NO: 116:

```
TTTAACATCA AAATTACCTG CAGCTGAAAT GATTTTGCTG ATTTCATTAA TTAATGGATT       60

AAGATTACCC TGACTTCCAT AGGCTAATGC ATCATTCCCA TACACATAAC TTGCCTTATT      120

ATTACTCTGT TGATACTNAA GTGCCTTTTT AAGGGAATCT GGTGTGATTA CCCTGCCGTC      180

TTTATCAAAA ATCTGCTCTA TCTGGTGATT AGAGATATCA CCTGACTCTT TTTCAAACCA      240

GTTTTTAAAT GTAATACCAT TTTTGTGGCC AATGGAAAGA ACATTACCTT CAGCTTTATA      300

CATGATGAGG TCATTACCTT CTCGCCTGAA GGCCACATCC CGGAAATCAA TATCAGCCAA      360

ACTGAGTTTA TCGTCTTTCC CCCCATCATC GTCAATAATA TGATGGCCAT ATCCTGAAAG      420

ATAACGATAA ATA                                                        433
```

(2) INFORMATION FOR SEQ ID NO: 117:

(i) SEQUENCE CHARACTERISTICS:

(A) LENGTH: 302 base pairs
        (B) TYPE: nucleic acid
        (C) STRANDEDNESS: double
        (D) TOPOLOGY: linear (xi) SEQUENCE DESCRIPTION: SEQ ID NO: 117:

| | | | | | |
|---|---|---|---|---|---|
| GCGCTCTGTT | CCCGTTCCTG | TTCATCACCA | TCGCCTGTGG | TGCGGTATCT | GGCTTCCACG | 60
| CGCTGATCTC | TTCCGGTACG | ACGCCAAAAC | TGCTGGCTAA | TGAAACCGAC | GCGCGTTTCA | 120
| TCGGCTACGG | CGCAATGCTG | ATGGAGTCCT | TCGTGGCGAT | TATGGCGCTG | GTTGCTGCGT | 180
| CCATCATCGA | ACCGGGTCTT | TACTTCGCGA | TGAACACCCC | GCCTGCTGGC | CTTGGCATCA | 240
| CCATGCCTAA | CCTGCATGAA | ATGGGGTGGC | GAGAACGCGN | CGGATTCATC | ATGGCGCANT | 300
| GA | | | | | | 302

(2) INFORMATION FOR SEQ ID NO: 118:

(i) SEQUENCE CHARACTERISTICS:
        (A) LENGTH: 656 base pairs
        (B) TYPE: nucleic acid
        (C) STRANDEDNESS: double
        (D) TOPOLOGY: linear (xi) SEQUENCE DESCRIPTION: SEQ ID NO: 118:

AATTAATAAG CCAAATACTA CATCACGTAA TACTTGCAAA GAAGTGCGTG GAGTTTGACT        60

AATAATGGGT TTGTCCATTA ATACTTACCC AAATAATCGG CTCATTATAG CAACGAGCCT       120

CCGATTAAAA TTTAAAATAC TCAATCATTT AATAGCAACG TTAGCAGCTA CAGCGATTTG       180

ATAAATAATT TGTGTGATAT CTTTAAATGA TTGCATGGTT TTGCTATCAA CCTGAGGTAG       240

AACCAATATC TGATCCCCCG GTTGTACTTT ACCTTGCCCT TTAAATTCTA CAAGACCATT       300

TGCATGTACA ATAGCAATTC GCTTGTCGTT AGCTCGCTCA GTAAAACCTC CGGCCCATGC       360

AACATAATCA TCCAAATTAG CATCGGCATT ATATACTACT GCTTGTGGCA TCAACACTTC       420

ACCCCCCACT TGAATAAGAT CAGTCTTATT TGGAATAACT ATTTGATCGC CTTGTTCTAA       480

TTGGATAWTG GCAATAACAC CTTTATCTGC AACTACTACT TTACCAAGCG GTKGAACTTT       540

ACGAGCCTTT YCAACAAACT GCATCACTAA CTCTGCTTCT TTAGCACGTA TATTCGCCTC       600

ACCATCAGAT CGCGCGGGTG TGGTAAANTT CATACGTTCC AAGCGGTTTA GAGATT          656

(2) INFORMATION FOR SEQ ID NO: 119:

(i) SEQUENCE CHARACTERISTICS:
        (A) LENGTH: 436 base pairs
        (B) TYPE: nucleic acid
        (C) STRANDEDNESS: double
        (D) TOPOLOGY: linear (xi) SEQUENCE DESCRIPTION: SEQ ID NO: 119:

ATATGTTATC TGGATCCAGA TAAAGAGCGT TCTTGACCCG CTATATCCAG ACAGGTCAGT        60

TACACCCTGT CCGGAAAAAC TGATCGGAAT AACAACAGTA TATTTCTAA TACACTGGCA        120

AATGGTGCCG GCGGTGTGGG GATTCAGCTT CTGGATAGCG CTGGTAATGC GGTTGCTGCT       180

GGACAGAAGA AATATCTGGG ACAGGTAGGA CCATCAACAT CTCTCAATAT TGGATTAAGG       240

GCATCTTATG CACTGACCAA TGGACAGACT CCACCTACTC CCGGACGAGT TCAGGCGTTA       300

GTTGATGTTA CCTTCGAGTA TAATTAGGAA TGTCGGGGAT GGGCTATCCC CGATATTATT       360

GCAGGATTAG TCTGTGATAC AGATATACAG CCCATATGAA CAACTGTTTG CATATATAAA       420

AATGATGATA ATTTTA                                                      436

(2) INFORMATION FOR SEQ ID NO: 120:

(i) SEQUENCE CHARACTERISTICS:
        (A) LENGTH: 559 base pairs
        (B) TYPE: nucleic acid
        (C) STRANDEDNESS: double
        (D) TOPOLOGY: linear (xi) SEQUENCE DESCRIPTION: SEQ ID NO: 120:

```
AATAATTAAA TTTGGAGGGA TCAGTTTTCT GATAATGTTC TGTTATTAAA ACATTATCCC      60

ATGGGGCGTA GTTATATCAA TTAGCAGGAT CTTATGAGTT AACTAACATC AGTTTTGAAT     120

TTTTAATGGG GGTAATTTAT CTTTTACTAA AAATATTTTA ACTATTAATA TAGCATCATG     180

GTTGTTACGG TTTGTTTTAA TTCTATTTTA TAATGTGCTA TATATTGTAT TTTTGTGCTT     240

AGATAAAATAT GTTTTTTCAT TACTTTAGTG ATGTTAATAT TTTGCGTGTA GTAAAAATCA    300

TTGTTATAAC AAATGTCACT GTTGCTATAC TTTGCTGAAC TGTTTATCGG TCATTTTGAT     360

TCAATCACTG GTTCTATATT TTTTAATAAC CGTTCTGTAG CGATTAATAT ATTGCTCTCC     420

AGAGGATACA CTATATGAAA TATATTAAAA GTCATTAATT TTNATTCAAT GTTGTTTAGA     480

GTTATGTTCA GTGTTTGGNA ATAGGATGTG TTTCTAAACC GTCTTGGGTT CTATAATAAA     540

TTCTATTCTT ANAGGTTTT                                                  559
```

(2) INFORMATION FOR SEQ ID NO: 121:

(i) SEQUENCE CHARACTERISTICS:
        (A) LENGTH: 481 base pairs
        (B) TYPE: nucleic acid
        (C) STRANDEDNESS: double
        (D) TOPOLOGY: linear (xi) SEQUENCE DESCRIPTION: SEQ ID NO: 121:

```
CATGTCCCTT CCTGAATACT GGGGAGAAGA GCACGTATGG TGGGACGGCA GGGCTGCTTT      60

TCATGGTGAG GTTGTCAGAC CTGCCTGTAC TCTGGCGATG GAAGACGCCT GGCAGATTAT     120

TGATATGGGG GAAACCCCGG TACGGATTTA CAGAATGGTT TCTCCGGACC TGAAAGAAAA     180

TTCAGCCTCC GGCTCAGGAA TTGTGAATTT AACAGTCAGG GTGGGAACCT TTTCTCTGAT     240

TCCCGGATAA GGGTGACTTT CGATGGCGTC CGGGGTGAAA CGCCGGATAA GTTTAATTTA     300

TCCGGTCAGG CAAAAGGCAT TAATCTGCAG ATAGCTGATG TCAGGGGAAA TATTGCCCGG     360

GCAGGAAAAG TAATGCCTGC AATACCATTG ACGGGTAATG AAGAAGCGCT GGATTACACC     420

CTCAGAATTG TGAGAACGGA AAAAAACTTG AAGCCGGAAA TTATTTTGCT GTCTGGGATT     480

A                                                                     481
```

(2) INFORMATION FOR SEQ ID NO: 122:

(i) SEQUENCE CHARACTERISTICS:
        (A) LENGTH: 535 base pairs
        (B) TYPE: nucleic acid
        (C) STRANDEDNESS: double
        (D) TOPOLOGY: linear (xi) SEQUENCE DESCRIPTION: SEQ ID NO: 122:

```
CCATATAGTG ACTTCATTGA ACAAAATGTA AATGGAATCT TGCTGGAGAA TGACCCACAT      60

ATATGGATAA AAGCTCTTTC ATTACTTGTT AGTGCAGATC ATAAACGTAG CGAGTTGGCG     120

TTCAATGCTA AAAATATGC TTGTAAAATT GTAGGTGTCG AGTAAAAAGA TATTTTTATT      180

TAATTGGTGC TATTGAATGT TTAAAAATCG AACTGATTGG TGTTTTAATA TTAATCATAG     240
```

```
GTTATGATGC AAAAATATAT TAGGCATTGC CTGCTTCAAT TAACTTGAGA GTGTAAGTTG    300

AATTGAAATA TGGTTATATG ATAAAGCAAT ATATGTTAAT ACATATGTCA ACCGAAAATG    360

CCATTATGTG TTTTTTACTT TATCTGTAAC GACACAATAT ATAAAATAAG CTAATAATC     420

AAAACGCTTT TTAATTTGAT TGTTTTGAAT CAAGTGACTA AGAAATTCTC TTGCTGCAAA    480

TAACTCCCTT AGTGATTTTT TTTGAGTCTA TTTTATTCTC TGGGCATGGT CATGC         535

(2) INFORMATION FOR SEQ ID NO: 123:

(i) SEQUENCE CHARACTERISTICS:
        (A) LENGTH: 412 base pairs
        (B) TYPE: nucleic acid
        (C) STRANDEDNESS: double
        (D) TOPOLOGY: linear (xi) SEQUENCE DESCRIPTION: SEQ ID NO: 123:

CCGGCCCCAT AATGATGGTT TTATTAAGGT TAGCGCCGAC GGTTTCGATG AACGATTTCA     60

GGTCGGTATC TTTAAAATTA GCGGTGAAAG TGGCTTCTTC CGCCCAGACC GGTGAACTGC    120

ATAATGCCGC TGCCAGCACC AGCGGCAGTA AACGCTTTTT TGTTTTGAGG CCAGTTGTCT    180

TCTTACGCCA GACCGACAAC GTCATATCAC GCCAAAACAC GATGAATGAT TCTCCTGGAT    240

TAAATGCGGT TAGCGCAGCG CGATGGAAAT GTCGTGGCGC GCACCCTTGC GTAAAACCGT    300

AAGTTGAATG GAATCCATTG AAGGTAACTG CCGCATCAGA GCAATCATTG CTCGTGGATC    360

AGTGAAATCC TGCTGATTTA GCGCAAATGC GATATCGCCT TCCTTAAAAC CG           412

(2) INFORMATION FOR SEQ ID NO: 124:

(i) SEQUENCE CHARACTERISTICS:
        (A) LENGTH: 576 base pairs
        (B) TYPE: nucleic acid
        (C) STRANDEDNESS: double
        (D) TOPOLOGY: linear (xi) SEQUENCE DESCRIPTION: SEQ ID NO: 124:

TAGCCTGTTC AGCGTATATT TGGGATGAGA AGCCAAAGTG GCTTTGGTGG TGTCCCAGCC     60

CAGGTTTTTA TTACTGCTGG TTATTTACCT TTCATGTTTT TCAATAAAGT TGTGACTCAG    120

TTGAAATCTG CTGTCAATGC TAATATGGGA CTTTTTTGTT ATAGACAAGT GACTCCTTTT    180

GCAACTTTTA TAGCACGTTT TATGCTAGAA ACAATGGTGG GCATGATTGT CGGTATAATC    240

CTAGTACTAG GATTATTGTG GTTTGGCTTT GATGCAATAC CTGCGGATCC ATTGCAAGTG    300

ATCCTTGGTT ATTCTCTTCT GATGCTGTTT TCTTTTTCTC TTGGTATTGT ATTTTGTGTT    360

ATTTGTAATT KRGCGARAGA GGCAGATAAA TTTCTTAGCT TGTTAATGAT GCCTTTGATG    420

TTTATCTCTT GTGTTATGTT TCCTCTTGCT ACTATTCCCC CTCAATATCA GCATTGGGTT    480

TTTATGGAAT CCACTTGTGC ATGCTGTAGA ACTAATCCGA AGGGCATGGG ATATCTGGGT    540

TATCGTAGTC CTGATGTAAG TTGGGCGTAT CTGTCG                              576

(2) INFORMATION FOR SEQ ID NO: 125:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (xi) SEQUENCE DESCRIPTION: SEQ ID NO: 125:

TTACCAAGCA GGATCTGATG CAACTGGAAG AAGGCTTTGA ATATCGTATC ATTGGCTGCT     60
```

```
CCATGTATAA CATGTTGGCC GCCGTACGCG GTGCCTATGA CAGCTTTGAA AATGTCAAAG      120

GGGTGAATTG CT                                                         132

(2) INFORMATION FOR SEQ ID NO: 126:

(i) SEQUENCE CHARACTERISTICS:
        (A) LENGTH: 542 base pairs
        (B) TYPE: nucleic acid
        (C) STRANDEDNESS: double
        (D) TOPOLOGY: linear (xi) SEQUENCE DESCRIPTION: SEQ ID NO: 126:

GATTAGGGGT CACTCAGGAT TATAAAAAAG CGGCAGAATA CTATAAAAAA GGTGATAAAA       60

ATAATGATAT TACAGCACAA TACCGTCTGG CAAAACTTTA TGAACAAGGT AACGGTGTAA      120

AACGTGATTA TCAACAAGCG ATAAACCTTT ACCTTAAACA TATCAACAGA ATGGATCACA      180

TCACTGCCCC CAGTTTTGTG GCTCTGGGTG ATATCTATTC TCTGGGATTS GGGGTAGAGA     240

AAAACCCACA ACTGGCTGAA AAATGGTATC AAAAAGCGAT AGATGCAGCT AATACACAAC      300

ATAACCAGGA ATAAATCAT TAAACGACAA CACTTAATAC CATATTGTGA AGATGTTCAG      360

ACATGGCGGA ATTCCCCTAT TCTTTGTTGG CGCTTACAAC AGACTATATT CCGCCATATC      420

TGTCTTTATT GTGTATAAAC CATCGATACT GATGTTTGAT AGTGCTAAAT AATCATTGGC     480

GCAATCACAA AGCCTAATGC CACTCCAGCA ATAATTCCCC CCAACCCAGG CAGCATAAAT      540

GG                                                                    542

(2) INFORMATION FOR SEQ ID NO: 127:

(i) SEQUENCE CHARACTERISTICS:
        (A) LENGTH: 382 base pairs
        (B) TYPE: nucleic acid
        (C) STRANDEDNESS: double
        (D) TOPOLOGY: linear (xi) SEQUENCE DESCRIPTION: SEQ ID NO: 127:

GAACCACTTA GCGGCAGCTA TCGGAATCG CCTGCTGAAA GACGGTCAGA CAGTGATTGT       60

GGTTACCGTG GCTGATGTTA TGAGTGCCCT GCACGCCAGC TATGACGATG GGCAGTCAGG      120

CGAAAAATTT TTGCGGGAAC TGTGCGAAGT GGATCTGCTG GTTCTTGATG AAATTGGCAT      180

TCAGCGCGAG ACGAAAAACG AAGCAGGTGG TACTGCACCA GATTGTTGAT CGCCGGACAG     240

CGTCGATGCG CACGTGGGGA TRCTGACAAA CCTGAACTAT GAGGCCATGA AACATTGCT      300

CGGCGARCGG ATTATGGATC RCATGACCAT GAACGGCGGG CGATGGGTGA ATTTTAACTG     360

GGAGACTGGC GTCCGAATGT CG                                              382

(2) INFORMATION FOR SEQ ID NO: 128:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (xi) SEQUENCE DESCRIPTION: SEQ ID NO: 128:

CGTCCCGCAC CCGGAAATGG TCAGCGAACC AATCAGCAGG GTCATCGCTA GAAATCATCC       60

TTAGCGAAAG CTAAGGATTT TTTTTATCTG AATTCTAGCC AGATCCCCGC TGATTTATGC     120

TGGTTA                                                                126

(2) INFORMATION FOR SEQ ID NO: 129:
```

(i) SEQUENCE CHARACTERISTICS:
        (A) LENGTH: 258 base pairs
        (B) TYPE: nucleic acid
        (C) STRANDEDNESS: double
        (D) TOPOLOGY: linear (xi) SEQUENCE DESCRIPTION: SEQ ID NO: 129:

| | | | | | |
|---|---|---|---|---|---|
|ACCCCCAGCC|TAGCTGGGGG|TTTTCTGTGC|ACAAAAAATC|CCGGCATAAT|GGCCGGGATT|60|
|TGCGAGCTTT|CCCACTATTT|CTTGATTCCT|AAACGGAACA|TATCAGTTGG|GAATAAAGGT|120|
|TGTATTATCA|CTTCATCATT|ANAAATGAAT|AATTTGGGCG|ATAAAGCTGT|TACGTCATAG|180|
|ATATTTTCAG|CGATTAATCT|TAGANTTGAC|CTAAAAACTG|GAATACTTGC|ATCATCTGCA|240|
|AAGACAAACA|TGTCATCG| | | | |258|

(2) INFORMATION FOR SEQ ID NO: 130:

(i) SEQUENCE CHARACTERISTICS:
        (A) LENGTH: 399 base pairs
        (B) TYPE: nucleic acid
        (C) STRANDEDNESS: double
        (D) TOPOLOGY: linear (xi) SEQUENCE DESCRIPTION: SEQ ID NO: 130:

| | | | | | |
|---|---|---|---|---|---|
|AACCAGCGGT|TCGCATCATC|TCATCCCACT|GACTCTCCGC|TTTTGACAGA|TCTGCATATC|60|
|CTCGGGCCAA|CTTATCCAGT|ACTCCGTAGT|TTGCCGATTT|ATTCACCCGC|CAGAACACCG|120|
|CCTCACCTGC|ATCGGCAAGC|CGGGGGGAAA|ACTGATACCC|CAGTAGCCAG|AACAGACCGA|180|
|AAATAATATC|GCTGCTACCC|GCAGTGTCTG|TCATGATTTC|AACTGGATTC|AGCCCTGTCT|240|
|GCTGCTCAAG|AAGTCCTTCC|AGTACAAAAA|TCGAATCCCG|TAATGTACCG|GGTACCACAA|300|
|TGCCATGGAA|CCCAGAGTAC|TGATCAGATA|CGAATTATAC|CAGGTGATGC|CTCGTCCAGA|360|
|ACCAAAATAT|TTTCTGTTAG|ATCCTGAGTT|GATGGTCTT| | |399|

(2) INFORMATION FOR SEQ ID NO: 131:

(i) SEQUENCE CHARACTERISTICS:
        (A) LENGTH: 745 base pairs
        (B) TYPE: nucleic acid
        (C) STRANDEDNESS: double
        (D) TOPOLOGY: linear (xi) SEQUENCE DESCRIPTION: SEQ ID NO: 131:

| | | | | | |
|---|---|---|---|---|---|
|AAATAACATC|AACATACATT|TGACTCGCGG|GGGAAACGTT|TACGGAGTCT|TCATACTGGC|60|
|ACTTTTTTAT|GCTGCTGACT|ACTCTTCGTC|ATCGCCATCA|ACATGCGCAC|GAATCAGCGC|120|
|CATAAACGGT|TTGCCAAAGC|GTTCCAGCTT|GCGCATCCCA|ACGCCGTTAA|CGCTGAGCAT|180|
|TTCGCTGGCG|GTGATCGGCA|TCTGTTCAGC|CATCTCAATC|AAGGTTGCGT|CGTTAAACAC|240|
|CACGTACGGC|GGGACATTAC|TTTCATCGGC|TATCGATTTA|CGCAGTTTGC|GTAATTNGGC|300|
|GAACAGTTTG|CGATCATAGT|TGNCGCCGAN|CGATNTCTGC|ATCGCTTTCG|GTTTGAGCGC|360|
|CACGATACGC|GGCACGGCAA|TTGCAAAGAG|GATTCGCCGC|GCAGCACCGG|GCGCGCGGCC|420|
|TCTGTCAGTT|GTAGGGCAGA|ATGCTGGGCA|ATATTTTGCG|TCACCAGGCC|GAGGTGAATC|480|
|AGCTGGCGGA|TCACGCTCAC|CCAATGTTCA|TGGCTTTTAT|CACGGCCCAT|GCCATAGACT|540|
|TTCAGTTTGT|CATGACCATA|GTCGCGGATA|CGCTGGTTAT|TAGCACCACG|AATCACTTCC|600|
|ACCACATAAC|CCATCCCAAA|CCGCTGATTC|ACACGACCAA|TGGTGGAAAG|GGCAATCTGA|660|
|GCATCGGTTG|AACCGTCGTA|CTGTTTCGGC|GGATCGAGGC|AGATATCGCA|GTTCNCCGCA|720|

CGGCTCCTGA CGCCCTTCGC CAAAA  745

(2) INFORMATION FOR SEQ ID NO: 132:

(i) SEQUENCE CHARACTERISTICS:
        (A) LENGTH: 439 base pairs
        (B) TYPE: nucleic acid
        (C) STRANDEDNESS: double
        (D) TOPOLOGY: linear (xi) SEQUENCE DESCRIPTION: SEQ ID NO: 132:

AGAATGGCGG CTTCTTGCCC CCCTTTGCCC CGGTCCTGAC TAGCATGGCT GGAGTCCAGT  60

GTCCAGGCCA CGACCATGCT CATCATGGAA GCAGCTTTTG TAGTACANTC GCAGCTTATT  120

TTCCTGGAAC GAAATGTCTG GCATCGTGGT GCATAACATA ACCCCCAATG CCCAGCAGAT  180

GCACAGAAGG TTCTAGAATC GCCCACTGAT ATCCCATACA AAATTTACCA AAACGTGTTC  240

GTATTTCTCG TATAAATAAT GTCTCTATGG TGACGTTCTA GACTTCAAAC CCACTTTTTG  300

AATTTGATGA TGTGCTCCTA ATCTCTTCAG GAATGTAACG CCCTTGGTTT ACAGCTACCA  360

ATACACTGGA GGTATACTTA TCTGCAACTG GATGAACTAG ATGTACTTGA GCAAACATTT  420

CATAAGCTCG ACGACAGTT  439

(2) INFORMATION FOR SEQ ID NO: 133:

(i) SEQUENCE CHARACTERISTICS:
        (A) LENGTH: 350 base pairs
        (B) TYPE: nucleic acid
        (C) STRANDEDNESS: double
        (D) TOPOLOGY: linear (xi) SEQUENCE DESCRIPTION: SEQ ID NO: 133:

CTGGAAAGCG ACGTTGATGG ATTAATGCAG TCGGTAAAAC TGAACGCTGC TCAGGCAAGG  60

CAGCAACTTC CTGATGACGC GACGCTGCGC CACCAANTCA TGGAACGTTT GATCATGGAT  120

CAAMTCATCC TGCAGATGGG GCAGAAAATG GGAGTGAAAA TCTCCGATGA GCAGCTGGAT  180

CAGGCGATTG CTAACATCGC GAAACAGNAC AACATGACGC TGGATCAGAT GCGCACCGTC  240

TGGCTTACGA TGGACTGAAC TACAACACCT ATCGTAACCA GATCCGCAAA GAGATGATTA  300

TCTCTGAAGT GCGTAACAAC GAGGTGCGTC GTCGNATCAC CATCCTGCCG  350

(2) INFORMATION FOR SEQ ID NO: 134:

(i) SEQUENCE CHARACTERISTICS:
        (A) LENGTH: 400 base pairs
        (B) TYPE: nucleic acid
        (C) STRANDEDNESS: double
        (D) TOPOLOGY: linear (xi) SEQUENCE DESCRIPTION: SEQ ID NO: 134:

CCCCAAGATT GCTAACAAAT GCGCGTTGTT CATGCCGGAT GCGGCGTGAC CGCCTTATCC  60

GGCCTACGAA ACCGCAAGAA TTCAATATAT TGCAGGAGCG GTGTAGGCCT GATAAGCGTA  120

GCGAWTCAGG CAGTTTTGCG TTTGCCCGCA ACCTTAGGGG ACATTTAGCG ACCCCATTTA  180

TTTCTCACTT TTCCGCCTCA TCATCGCGCG TTAATTTCTT TCATGAATCA CGCTTTACAA  240

TATCCAGCGC GCGCANAACG GTACTGGCAG GGATCTGAAT TTTCCTCCAG CAGCACAATC  300

AAATCGACAG CCAGTTTGAC ATCGTCAAGG GGCATTTTCC CAGTGACATA ATCTCTCCAT  360

TGCTAAGCGG GTTAAAACGC GCTAACCTGT TTCGATTTTT  400

(2) INFORMATION FOR SEQ ID NO: 135:

(i) SEQUENCE CHARACTERISTICS:
    (A) LENGTH: 463 base pairs
    (B) TYPE: nucleic acid
    (C) STRANDEDNESS: double
    (D) TOPOLOGY: linear (xi) SEQUENCE DESCRIPTION: SEQ ID NO: 135:

```
CTATCCTTAT GACCACCCAA CTACNTCATT TACACCCAAA CCAGCGATCT GAATAAAGAA      60
GCGATTGCCC AGTTACGACT GGGCGGAAAA TGCGCGTAAG GATGAAGTAA AGTTTCAGTT     120
GAGCCTGGCA TTTCCCTGTG GCGTGGGATT TTAGGCCCGA ACTCGGTGTT GGGTGCGTCT     180
TATACGCAAA AATCCTGGTG GCAACTGTCC AATAGCGAAG AGTCTTCACC GTTTCGTGAA     240
ACCAACTACG AACCGCAATT GTTCCTCGGT TTTGCCACCG ATTACCGTTT TGCAGGTTGG     300
ACTGCGCGAT GTGGAGATGG GGTATAACCA CGACTCTAAA CGGGCGTTCC GACCCGACCT     360
CCCGCAGCTG AACCGCCTT TATACTCGCC TGATGGCAGA AAACGGTAAC TGGCTGGTAG      420
AAGTGAAGCC GNGGTATGTG GTGGGTAATA CTGACGATAA CCC                       463
```

(2) INFORMATION FOR SEQ ID NO: 136:

(i) SEQUENCE CHARACTERISTICS:
    (A) LENGTH: 584 base pairs
    (B) TYPE: nucleic acid
    (C) STRANDEDNESS: double
    (D) TOPOLOGY: linear (xi) SEQUENCE DESCRIPTION: SEQ ID NO: 136:

```
TTGGTCAGCC GTACCTGAAT GGGGGCTGAT GCCCGGCTGG TTAATGGCAG GTGGTCTGAT      60
CGCCTGGTTT GTCGGTTGGC GCAAAACACG CTGATTTTTT CATCGCTCAA GGCGGGCCGT     120
GTAACGTATA ATGCGGCTTT GTTTAATCAT CATCTACCAC AGAGGAACAT GTATGGGTGG     180
TATCAGTATT TGGCAGTTAT TGATTATTGC CGTCATCGTT GTACTGCTTT TTGGCACCAA     240
AAAGCTCGGC TCCATCGGTT CCGATCTTGG TGCGTCGATC AAAGGCTTTA AAAAAGCAAT     300
GAGCGATGAT GAACCAAAGC AGGATAAAAC CAGTCAGGAT GCTGATTTTA CTGCGAAAAC     360
TATCGCCGAT AAGCAGGCGG ATACGAATCA GGAACAGGCT AAAACAGAAG ACGCGAAGCC     420
TACGNTAAAG AGCAGGTGTA ATCCGTGTTT GATATCGGTT TTAGCGNACT GCTATTGGTG     480
TTCATCATCG GCCTCGTCGT TCTGGGGGCG CAACGACTGC CTGTGGCGGT AAAAACGGTA     540
GCGGGCTGGA TTCGCGCGTT GCGTTCACTG GCGACAACGG TGCA                      584
```

(2) INFORMATION FOR SEQ ID NO: 137:

(i) SEQUENCE CHARACTERISTICS:
    (A) LENGTH: 527 base pairs
    (B) TYPE: nucleic acid
    (C) STRANDEDNESS: double
    (D) TOPOLOGY: linear (xi) SEQUENCE DESCRIPTION: SEQ ID NO: 137:

```
GCAGGCAGGA GGAACTGCCC AGTGATACGG TTATTCGTGA TGGCGGAGGG CAGAGCCTTA      60
ACGGACTGGC GTTGAACACC ACGCTGGATA ACAGAGTTGA GCATTGGNTA CACGGGGGAG     120
GGAAAGCAGA CGTTACAATT ATTAACCAGG ATGTTTACCC AGACCATAAA ACATGGCGGA     180
TTGGCAACCG NAACCATCGT CAACACCGTT GCAGAAGKTG GTCCGGAGTC TGAAAATGTG     240
TCCAGCGGTC AGATGGTCGG AGGGACGGCT GAATCCACCA CCATCAACAA AAATGGCCGG     300
CAGTTATCTG GTCTTCGGGG ATGGCACGGG ACACCCTCAT TTGCGCTGGT GGTGACCAGA     360
```

```
CGGTACACGG AGAGGCACAT AACACCCGAC TGGAGGGAGG TTAACCAGTA TGTACACAAC      420

GGTGGCACGG CAACAGAGAC GCTGATAAAC CGTGATGGCT GGCAGGTGAT TAAGGAAGGA      480

GGGAACTGCC GGCGCATTAC CACCATCAAN CCNGAAAAGG GAAANCT                   527

(2) INFORMATION FOR SEQ ID NO: 138:

(i) SEQUENCE CHARACTERISTICS:
        (A) LENGTH: 441 base pairs
        (B) TYPE: nucleic acid
        (C) STRANDEDNESS: double
        (D) TOPOLOGY: linear (xi) SEQUENCE DESCRIPTION: SEQ ID NO: 138:

GTCAGTCTCT GGGGGAAGTG CGTGTTCCGA CCGGGGAAAT GTGGTGGAGA AAGTTATTGA       60

AGGGGCTTAC GAGGTGGTGG GGGTTTTTGA CCGGATTGAG GAAAAGCGTG ATGCCATGCA      120

GTCGCTGATT CTGCCGCCAC CGGACGCCAG GCGCTGGCAC AGGCGGCACT GACTTACCGT      180

TATGGTGACG AACMTCARCC CGTCACCACC GCCGACATTC TGACACCACG ACGCCGGGAR      240

GATTACGGTA AGGACCTGTG GAGTGCTTAT CAGACCATTC AGGAGAATAT GCTGAAAGGC      300

GGAATTTCCG GTCGCAGTGC CAGAGGAAAA CGTATCCATA CCCGTGCCAT TCACAGCATC      360

GACACCGACA TTAAGCTCAA CCGCGCATTG TGGGTGATGG CTGAAACGCT GCTGGAGAGT      420

ATGCGCTGAT GCCGTTTCCN T                                               441

(2) INFORMATION FOR SEQ ID NO: 139:

(i) SEQUENCE CHARACTERISTICS:
        (A) LENGTH: 398 base pairs
        (B) TYPE: nucleic acid
        (C) STRANDEDNESS: double
        (D) TOPOLOGY: linear (xi) SEQUENCE DESCRIPTION: SEQ ID NO: 139:

CGAGCGAGAT GAACTTCGAG GGCGGTGTGA GCCAGTCGGC TTACGAGACA CTGGCGGCGC       60

TTAATCTGCC GAAACCGCAG CAAGGGCCGG AAACCATTAA TCAGGTTACC GAGCATAAGA      120

TGTCAGCTGA GTAAGCCTGT ATGCCGGATA AGGCGCTCGC GCCNATTCCG ATGAAATAAG      180

GCGCATCGGG CCTGAAGGAA AGCCGTATGN ATACACCCGC AGCCCGCATC CGGCAAGTTA      240

CAACAAATAA CCTTTAACCA TGCTTTTTGA TGTTTTTCAG CAATACCCCG CGGCGATGCC      300

CATACTGGCA ACCGTCGGGA GGGATTGATC ATCGGCAGTT TTTTGAATGT GGTGATTTGG      360

GCGTTACCCC ATCATGCTGC GCCAACAAAT GGCGGAGT                             398

(2) INFORMATION FOR SEQ ID NO: 140:

(i) SEQUENCE CHARACTERISTICS:
        (A) LENGTH: 580 base pairs
        (B) TYPE: nucleic acid
        (C) STRANDEDNESS: double
        (D) TOPOLOGY: linear (xi) SEQUENCE DESCRIPTION: SEQ ID NO: 140:

GCCGAACAGA CACAGCAATA TGAACCCTGC CAGCGCAGAC GCTTGCTGAT TAATGCTCTG       60

AACAAAAGGC GAAGAATGGC AAATCCTGCG ATCAGCAAAG TCAGCGCACC GACTATCTGT      120

AACATAGTCA CTCCGTGATG AATATCATGT GTATTGTGAA TGCCAGTGAA TGTGGCACTG      180

AAGCGTTTGC ACCTGTCCGG GTCCCGGTCA TGATGACCGS AACAGAGAGA CAATGCCGAA      240

TTATCAGAAG GTCACATTCA GTGTGGCTTG GCCGTTATAA CCTTCAGCGC TGCTGCCGCT      300
```

-continued

```
GACGCTGTGG GCATAACCGG CCTGAACGCC CAGGGTGATA TTTTCCCGGA CACGGGCTTC      360

CAGTCCGGCC TGCAGCTCCA GTGACGTGCC ATTCCGGGAC GGTGAGAACG TCATGTTACT      420

GCCGGCTGCG GCTGTACCCA TGCTCATGTC TCCCCGGGAG CTGAAGGTGC GGATAACAGA      480

AGGCTGTACC CACCCGTTCA CCGGCAGTTC ACGCACACTG TGTTTTGCAC TGTCACGCAA      540

GGTGTCACGG GATGAGGTGC CTTCANCAAA AGGTCATATT                            580

(2) INFORMATION FOR SEQ ID NO: 141:

(i) SEQUENCE CHARACTERISTICS:
        (A) LENGTH: 446 base pairs
        (B) TYPE: nucleic acid
        (C) STRANDEDNESS: double
        (D) TOPOLOGY: linear (xi) SEQUENCE DESCRIPTION: SEQ ID NO: 141:

TGCGGACATC CAGCGTTCCG CCATCATCCA CACGGGTTCT GGTGGCTGTG TGTCCGGTCA       60

GCACATCCAG ACGGCCGCCA TTTTCCAGTA CGACATTATC AGCTTTACCC TCCACAACAG      120

AGAATGCTCC CAGGCGGTTT GTGCCGGTGA CGGTTGCAGC AGTGCTGGTA ACCAGTGCTC      180

CGCCCGTGTT CTGGGTGACA TCAGACGCTT TACCGCCGGC ATTCACCTGC AGCTTTCCTT      240

TCTGGTTGAT GGTGGTATGC GCGGCAGTTC CTCCTTCCTT AATCAMCTGC CAGCCATCAC      300

GGTTTATCAG CGTCTCTGTT GCCGTGCCAA CGTTGTGTAC ATACTGGTTA MCTCCCTCCA      360

GTCGGGTGTT AWGTGSCTCT CCGTGTANCG TCTGGTCANC AACAACGCAA ATGANGGTGT      420

CCCGTGCCAT CCCCGAAGAC CAGTAA                                          446

(2) INFORMATION FOR SEQ ID NO: 142:

(i) SEQUENCE CHARACTERISTICS:
        (A) LENGTH: 327 base pairs
        (B) TYPE: nucleic acid
        (C) STRANDEDNESS: double
        (D) TOPOLOGY: linear (xi) SEQUENCE DESCRIPTION: SEQ ID NO: 142:

TGAATACGTT AAGTCAGCAG ACCGGCGGAG ACAGTCTGAC ACAGACAGCG CTGCAGCAGT       60

ATGAGCCGGT GGTGGTTGGC TCTCCGCAAT GGCACGATGA ACTGGCAGGT GCCCTGAATA      120

ATATTGCCGG AGTTCGCCAC TGACCGGTCA GACCGGTATC AGTGATGACT GGCCACTGCC      180

TTCCGTCAAC AATGGATACC TGGTTCCGTC CACGGACCCG GACAGTCCGT ATCTGATTAC      240

GGTGAACCCG AAACTGGATR GTCTCGGACA GGTGGACAGC CATTTGTTTN CCGGACTGTA      300

TGAGCTTCTT GGAGCGAAAC CGGGTCA                                         327
```

NUCLEOTIDE SEQUENCE OF *ESCHERICHIA COLI* PATHOGENICITY ISLANDS

This application claims priority benefit of U.S. Provisional Application Nos. 60/061,953, filed Oct. 14, 1997 and 60/031,626, filed Nov. 22, 1996, both incorporated herein by reference.

This invention was made with United States government support awarded by the following agencies:

NIH Grant #AI20323; AI125547.

The United States has certain rights in this invention.

BACKGROUND OF THE INVENTION

1. Field of the Invention

The present invention relates to novel genes located in two chromosomal regions within *E. coli* that are associated with virulence. These chromosomal regions are known as pathogenicity islands (PAIs).

2. Related Background Art

*Escherichia coli* (*E. coli*) is a normal inhabitant of the intestine of humans and various animals. Pathogenic *E. coli* strains are able to cause infections of the intestine (intestinal *E. coli* strains) and of other organs such as the urinary tract (uropathogenic *E. coli*) or the brain (extraintestinal *E coli*). Intestinal pathogenic *E. coli* are a well established and leading cause of severe infantile diarrhea in the developing world. Additionally, cases of newborn meningitis and sepsis have been attributed to *E. coli* pathogens.

In contrast to non-pathogenic isolates, pathogenic *E. coli* produce pathogenicity factors which contribute to the ability of strains to cause infectious diseases (Mühldorfer, I. and Hacker, J., *Microb. Pathogen*. 16:171–181 1994). Adhesions facilitate binding of pathogenic bacteria to host tissues. Pathogenic *E. coli* strains also express toxins including haemolysins, which are involved in the destruction of host cells, and surface structures such as O-antigens, capsules or membrane proteins, which protect the bacteria from the action of phagocytes or the complement system (Ritter, et al., *Mol. Microbiol*. 17:109–212 1995).

The genes coding for pathogenicity factors of intestinal *E. coli* are located on large plasmids, phage genomes or on the chromosome. In contrast to intestinal *E. coli*, pathogenicity determinants of uropathogenic and other extraintestinal *E. coli* are, in most cases, located on the chromosome. Id.

Large chromosomal regions in pathogenic bacteria that encode adjacently located virulence genes have been termed pathogenicity islands ("PAIs"). PAIs are indicative of large fragments of DNA which comprise a group of virulence genes behaving as a distinct molecular and functional unit much like an island within the bacterial chromosome. For example, intact PAIs appear to transfer between organisms and confer complex virulence properties to the recipient bacteria.

Chromosomal PAIs in bacterial cells have been described in increasing detail over recent years. For example, J. Hacker and co-workers described two large, unstable regions in the chromosome of uropathogenic *Escherichia coil* strain 536 as PAI-I and PAI-II (Hacker J., et al., *Microbiol. Pathog*. 8:213–25 1990). Hacker found that PAI-I and PAI-II containing virulence regions can be lost by spontaneous deletion due to recombination events. Both of these PAIs were found to encode multiple virulence genes, and their loss resulted in reduced hemolytic activity, serum resistance, mannose-resistant hemagglutination, uroepithelial cell binding, and mouse virulence of the *E. coli*. (Knapp, S et al., *J Bacteriol*. 168:22–30 1986). Therefore, pathogenicity islands are characterized by their ability to confer complex virulence phenotypes to bacterial cells.

In addition to *E. coli*, specific deletion of large virulence regions has been observed in other bacteria such as *Yersinia pestis*. For example, Fetherston and co-workers found that a 102-kb region of the *Y. pestis* chromosome lost by spontaneous deletion resulted in the loss of many *Y. pestis* virulence phenotypes. (Fetherston, J. D. and Perry, R. D., *MoL Microbiol*. 13:697–708 1994, Fetherston, et al., *Mol. Microbiol*. 6:2693–704 1992). In this instance, the deletion appeared to be due to recombination within 2.2-kb repetitive elements at both ends of the 102-kb region.

It is possible that deletion of PAIs may benefit the organism by modulating bacterial virulence or genome size during infection. PAIs may also represent foreign DNA segments that were acquired during bacterial evolution that conferred important pathogenic properties to the bacteria. Observed flanking repeats, as observed in *Y. pestis* for example, may suggest a common mechanism by which these virulence genes were integrated into the bacterial chromosomes.

Integration of the virulence genes into bacterial chromosomes was further elucidated by the discovery and characterization of a locus of enterocyte effacement (the LEE locus) in enteropathogenic *E. coli* (McDaniel, et al., *Proc. Natl Acad. Sci*. (USA) 92:1664–8 1995). The LEE locus comprises 35-kb and encodes many genes required for these bacteria to "invade" and degrade the apical structure of enerocytes causing diarrhea. Although the LEE and PAI-I loci encode different virulence genes, these elements are located at the exact same site in the *E. coli* genome and contain the same DNA sequence within their right-hand ends, thus suggesting a common mechanism for their insertion.

Besides being found in enteropathogenic *E. coli*, the LEE element is also present in rabbit diarrheal *E. coli, Hafnia alvei*, and *Citrobacter freundii* biotype 4280, all of which induce attaching and effacing lesions on the apical face of enterocytes. The LEE locus appears to be inserted in the bacterial chromosome as a discrete molecular and functional virulence unit in the same fashion as PAI, PAI-II, and Yersinia PAI.

Along these same lines, a 40-kb *Salmonella typhimurium* PAI was characterized on the bacterial chromosome which encodes genes required for Salmonella entry into nonphagocytic epithelial cells of the intestine (Mills, D. M., et al., *Mol. Microbiol*. 15:749–59 1995). Like the LEE element, this PAI confers to Salmonella the ability to invade intestinal cells, and hence may likewise be characterized as an "invasion" PAI.

The pathogenicity islands described above all possess the common feature of conferring complex virulence properties to the recipient bacteria. However, they may be separated into two types by their respective contributions to virulence. PAI-I, PAI-II, and the *Y. pestis* PAI confer multiple virulence phenotypes, while the LEE and the *S. typhimurium* "invasion" PAI encode many genes specifying a single, complex virulence process.

It is advantageous to characterize closely-related bacteria that contain or do not contain the PAI by the isolation of a discrete molecular and functional unit on the bacterial chromosome. Since the presence versus the absence of essential virulence genes can often distinguish closely-related virulent versus avirulent bacterial strains or species, experiments have been conducted to identify virulence loci and potential PAIs by isolating DNA sequences that are unique to virulent bacteria (Bloch, C. A., et al, *J Bacteriol.* 176:7121–5 1994, Groisman, E. A., *EMBO J*. 12:3779–87 1993).

At least two PAIs are present in *E. coli* J96. These PAIs, PAI:IV and PAI V are linked to tRNA loci but at sites different from those occupied by other known *E. coli* PAIs. Swenson et al., *Infect. and Immun*. 64:3736–3743 (1996).

The era of true comparative genomics has been ushered in by high through-put genomic sequencing and analysis. The first two complete bacterial genome sequences, those of *Haemophilus influenzae* and *Mycoplasma genitalium* were recently described (Fleischmann, R. D., et al., *Science* 269:496 (1995); Fraser, C. M., et al., *Science* 270:397 (1995)). Large scale DNA sequencing efforts also have produced an extensive collection of sequence data from eukaryotes, including *Homo sapiens* (Adams, M. D., et al., *Nature* 377:3 (1995)) and *Saccharomyces cerevisiae* (Levy, J., *Yeast* 10:1689 (1994)).

The need continues to exist for the application of high through-put sequencing and analysis to study genomes and subgenomes of infectious organisms. Further, a need exists for genetic markers that can be employed to distinguish closely-related virulent and avirulent strains of a given bacteria.

SUMMARY OF THE INVENTION

The present invention is based on the high through-put, random sequencing of cosmid clones covering two pathogenic islands (PAIs) of uropathogenic *Escherichia coli* strain J96 (04:K6; *E. coli* J96). PAIs are large fragments of DNA which comprise pathogenicity determinants. PAI IV is located approximately at 64 min (near pheV) on the *E. coli* chromosome and is greater than 170 kilobases in size. PAI V is located at approximately 94 min (at pheR) on the *E. coli* chromosome and is approximately 106 kb in size. These PAIs differ in location from the PAIs described by Hacker and colleagues for uropathogenic strain 536 (PAI I, 82 minutes {selC} and PAI II, 97 minutes {leuX}).

The location of the PAIs relative to one another and the cosmid clones covering the J96 PAIs is shown in FIG. 1. The present invention relates to the nucleotide sequences of 142 fragments of DNA (contigs) covering the PAI IV and PAI V regions of the *E. coli* J96 chromosome. The nucleotide sequences shown in SEQ ID NOs: 1 through 142 were obtained by shotgun sequencing eleven *E. coli* J96 subclones, which were deposited in two pools on Sep. 23, 1996 at the American Type Culture Collection, 12301 Park Lawn Drive, Rockville, Md. 20852, and given accession numbers 97726 (includes 7 cosmid clones covering PAI (IV) and 97727 (includes 4 cosmid clones covering PAI V). The deposited sets or "pools" of clones are more fully described in Example 1. In addition, *E. coli* strain J96 was also deposited at the American Type Culture Collection on Sep. 23, 1996, and given accession number 98176.

Three hundred fifty-one open reading frames have been thus far identified in the 142 contigs described by SEQ ID NOs: 1 through 142. Thus, the present invention is directed to isolated nucleic acid molecules comprising open reading frames (ORFs) encoding *E. coli* J96 PAI proteins, and fragments of said nucleic acid molecules.

The present invention also relates to variants of the nucleic acid molecules of the present invention, which encode portions, analogs or derivatives of *E. coli* J96 PAI proteins. Further embodiments include isolated nucleic acid molecules comprising a polynucleotide having a nucleotide sequence at least 90% identical, and more preferably at least 95%, 96%, 97%, 98% or 99% identical, to the nucleotide sequence of an *E. coli* J96 PAI ORF described herein, and fragments of said nucleic acid molecules.

The present invention also relates to recombinant vectors, which include the isolated nucleic acid molecules of the present invention and fragments thereof, host cells containing the recombinant vectors, as well as methods for making such vectors and host cells for *E. coli* J96 PAI protein production by recombinant techniques.

The invention further provides isolated polypeptides encoded by the *E. coli* J96 PAI ORFs or fragments of said ORFs. It will be recognized that some amino acid sequences of the polypeptides described herein can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

In another aspect, the invention provides a peptide or polypeptide comprising an epitope-bearing portion of a polypeptide of the invention. The epitope-bearing portion is an immunogenic or antigenic epitope useful for raising antibodies.

The invention further provides a vaccine comprising one or more *E. coli* J96 PAI antigens together with a pharmaceutically acceptable diluent, carrier, or excipient, wherein the one or more antigens are present in an amount effective to elicit protective antibodies in an animal to pathogenic *E. coli*, such as strain J96.

The invention also provides a method of eliciting a protective immune response in an animal comprising administering to the animal the abovedescribed vaccine.

The invention further provides a method for identifying pathogenic *E. coli* in an animal comprising analyzing tissue or body fluid from the animal for one or more of:

(a) polynucleic acids encoding an open reading frame listed in Tables 1–4 or a fragment of said polynucleic acid;

(b) full length or mature polypeptides encoded for by an open reading frame listed in Tables 1–4; or (c) antibodies specific to polypeptides encoded for by an open reading frame listed in Tables 1–4.

The invention further provides a nucleic acid probe for the detection of the presence of one or more *E. coli* PAI nucleic acids (nucleic acids encoding one or more ORFs as listed in Tables 1–4) in a sample from an individual comprising one or more nucleic acid molecules sufficient to specifically detect under stringent hybridization conditions the presence of the above-described molecule in the sample.

The invention also provides a method of detecting *E. coli* PAI nucleic acids in a sample comprising:

a) contacting the sample with the above-described nucleic acid probe, under conditions such that hybridization occurs, and b) detecting the presence of the probe bound to an *E. coli* PAI nucleic acid.

The invention further provides a kit for detecting the presence of one or more *E. coli* PAI nucleic acids in a sample comprising at least one container means having disposed therein the above-described nucleic acid probe.

The invention also provides a diagnostic kit for detecting the presence of pathogenic *E. coli* in a sample comprising at least one container means having disposed therein one or more of the above-described antibodies.

The invention also provides a diagnostic kit for detecting the presence of antibodies to pathogenic *E. coli* in a sample comprising at least one container means having disposed therein one or more of the above-described antigens.

DETAILED DESCRIPTION OF THE INVENTION

Figure 1:
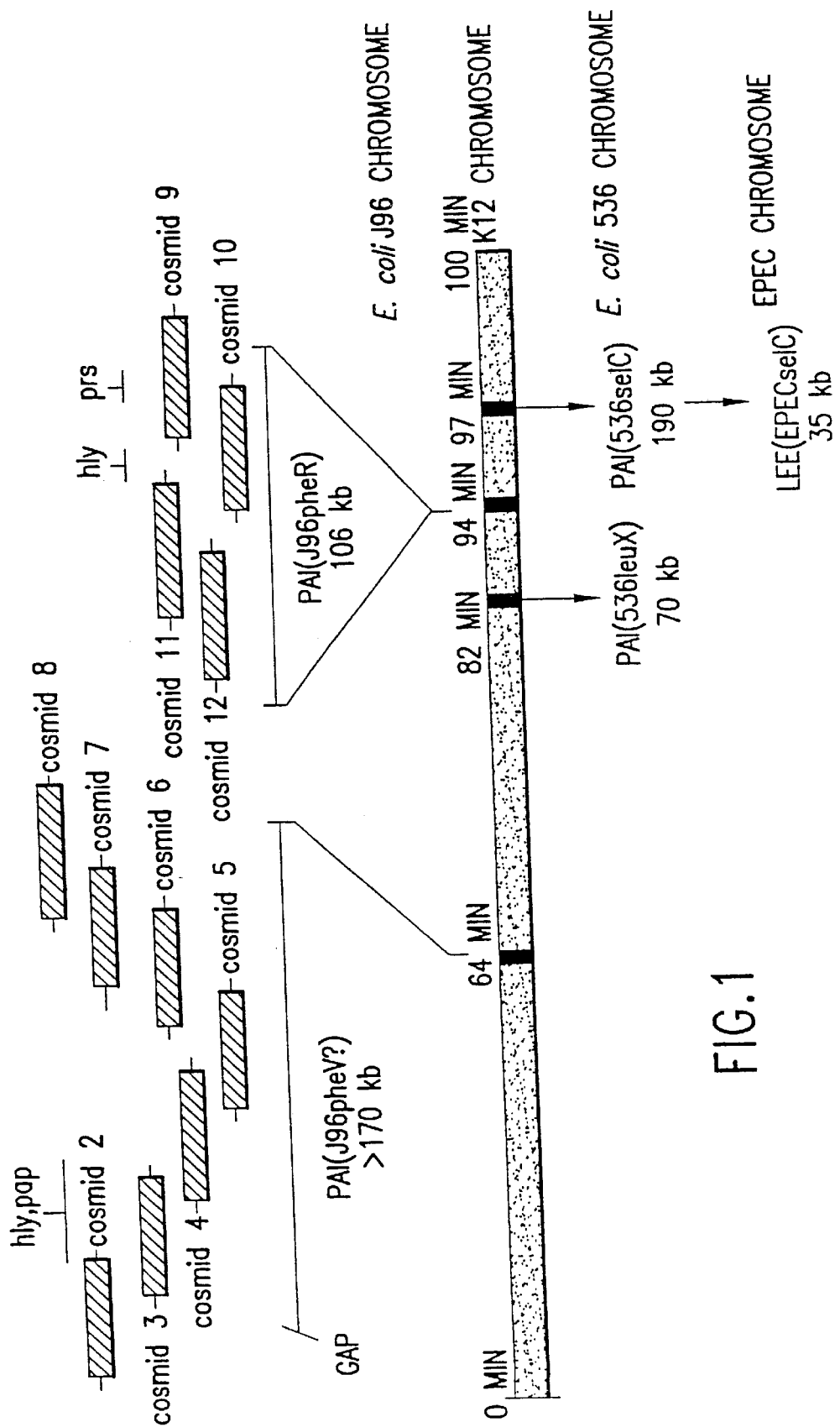
FIG. 1 is a schematic diagram of cosmid clones derived from *E. coli* J96 pathogenicity island and map positions of known *E. coli* PAIs (not drawn to scale). The gray bar represents the *E. coli* K-12 chromosome with minute demarcations of PAI junction points located above the bar. *E. coli* J96 overlapping cosmid clones are represented by hatched bars (overlap not drawn to scale) with positions of hly, pap, and prs operons indicated above bar. The PAIs and estimated sizes are shown above and below the K-12 chromosome map.

The present invention is based on high through-put, random sequencing of a uropathogenic strain of *Escherichia coli*. The DNA sequences of contiguous DNA fragments covering the pathogenicity islands, PAI IV (also referred to as $PAI_{J96(pheV)}$) and PAI V (also referred to as $PAI_{J96(ph,U)}$) from the chromosome of the *E. coli* uropathogenic strain, J96 (04:K6) were determined. The sequences were used for DNA and protein sequence similarity searches of the database.

The primary nucleotide sequences generated by shotgun sequencing cosmid clones of the PAI IV and PAI V regions of the *E. coli* chromosome are provided in SEQ ID NOs: 1 through 142. These sequences represent contiguous fragments of the PAI DNA. As used herein, the "primary sequence" refers to the nucleotide sequence represented by the IUPAC nomenclature system. The present invention provides the nucleotide sequences of SEQ ID NOs: 1 through 142, or representative fragments thereof, in a form that can be readily used, analyzed, and interpreted by a skilled artisan. Within these 142 sequences, there have been thus far identified 351 open reading frames (ORFs) that are described in greater detail below.

As used herein, a "representative fragment" refers to *E. coli* J96 PAI protein-encoding regions (also referred to herein as open reading frames or ORFs), expression modulating fragments, and fragments that can be used to diagnose the presence of *E. coli* in a sample. A non-limiting identification of such representative fragments is provided in Tables 1 through 6, preferably in Tables 1 through 4. As described in detail below, representative fragments of the present invention further include nucleic acid molecules having a nucleotide sequence at least 95% identical, preferably at least 96%, 97%, 98%, or 99% identical, to an ORF identified in Tables 1 through 6, or more preferably Tables 1 through 4.

As indicated above, the nucleotide sequence information provided in SEQ ID NOs: 1 through 142 was obtained by sequencing cosmid clones covering the PAIs located on the chromosome of *E. coli* J96 using a megabase shotgun sequencing method. The sequences provided in SEQ ID NOs: 1 through 142 are highly accurate, although not necessarily a 100% perfect, representation of the nucleotide sequences of contiguous stretches of DNA (contigs) which include the ORFs located on the two pathogenicity islands of *E. coli* J96. As discussed in detail below, using the information provided in SEQ ID NOs: 1 through 142 and in Tables 1 through 6 together with routine cloning and sequencing methods, one of ordinary skill in the art would be able to clone and sequence all "representative fragments" of interest including open reading frames (ORFs) encoding a large variety of *E. coli* J96 PAI proteins. In rare instances, this may reveal a nucleotide sequence error present in the nucleotide sequences disclosed in SEQ ID NOs: 1 through 142. Thus, once the present invention is made available (i.e., once the information in SEQ ID NOs: 1 through 142 and in Tables 1 through 6 is made available), resolving a rare sequencing error would be well within the skill of the art. Nucleotide sequence editing software is publicly available. For example, Applied Biosystem's (AB) AutoAssembler™ can be used as an aid during visual inspection of nucleotide sequences.

Even if all of the rare sequencing errors were corrected, it is predicted that the resulting nucleotide sequences would still be at least about 99.9% identical to the reference nucleotide sequences in SEQ ID NOs: 1 through 142. Thus, the present invention further provides nucleotide sequences that are at least 99.9% identical to the nucleotide sequence of SEQ ID NOs: 1 through 142 in a form which can be readily used, analyzed and interpreted by the skilled artisan. Methods for determining whether a nucleotide sequence is at least 99.9% identical to a reference nucleotide sequence of the present invention are described below.

Nucleic Acid Molecules

The present invention is directed to isolated nucleic acid fragments of the PAIs of *E. coli* J96. Such fragments include, but are not limited to, nucleic acid molecules encoding polypeptides, nucleic acid molecules that modulate the expression of an operably linked ORF (hereinafter expression modulating fragments (EMFs)), and nucleic acid molecules that can be used to diagnose the presence of *E. coli* in a sample (hereinafter diagnostic fragments (DFs)).

By "isolated nucleic acid molecule(s)" is intended a nucleic acid molecule, DNA or RNA, that has been removed from its native environment. For example, recombinant DNA molecules contained in a vector are considered isolated for the purposes of the present invention. Further examples of isolated DNA molecules include recombinant DNA molecules maintained in heterologous host cells, purified (partially or substantially) DNA molecules in solution, and nucleic acid molecules produced synthetically. Isolated RNA molecules include in vitro RNA transcripts of the DNA molecules of the present invention.

In one embodiment, *E. coli* J96 PAI DNA can be mechanically sheared to produce fragments about 15–20 kb in length, which can be used to generate an *E. coli* J96 PAI DNA library by insertion into lambda clones as described in Example I below. Primers flanking an ORF described in Tables 1 through 6 can then be generated using the nucleotide sequence information provided in SEQ ID NOs: 1 through 142. The polymerase chain reaction (PCR) is then used to amplify and isolate the ORF from the lambda DNA library. PCR cloning is well known in the art. Thus, given SEQ ID NOs: 1 through 142, and Tables 1 through 6, it would be routine to isolate any ORF or other representative fragment of the *E. coli* J96 PAI subgenomes. Isolated nucleic acid molecules of the present invention include, but are not limited to, single stranded and double stranded DNA, and single stranded RNA, and complements thereof.

Tables 1 through 6 herein describe ORFs in the *E. coli* J96 PAI cosmid clone library.

Tables 1 and 3 list, for PAI IV and PAI V, respectively, a number of ORFs that putatively encode a recited protein based on homology matching with protein sequences from an organism listed in the Table. Tables 1 and 3 indicate the location of ORFs (i.e., the position) by reference to its position within the one of the 142 *E. coli* J96 contigs described in SEQ ID NOs: 1 through 142. Column 1 of Tables 1 and 3 provides the Sequence ID Number (SEQ ID NO) of the contig in which a particular open reading frame is located. Column 2 numerically identifies a particular ORF on a particular contig (SEQ ID NO) since many contigs comprise a plurality of ORFs. Columns 3 and 4 indicate an ORF's position in the nucleotide sequence (contig) provided in SEQ ID NOs: 1 through 142 by referring to start and stop positions in the contig sequence.

One of ordinary skill in the art will appreciate that the ORFs may be oriented in opposite directions in the *E. coli* chromosome. This is reflected in columns 3 and 4. For these ORFs, the sense strand is complementary to the actual sequence given. The corresponding sense-strand of the ORF must be read as the 5'-3' complement of the antisense strand actually shown in the Sequence Listing, wherein the location is specified 3'-5'.

Column 5 provides a database accession number to a homologous protein identified by a similarity search of public sequence databases (see, infra). Column 6 describes the matching protein sequence and the source organism is identified in brackets. Column 7 of Tables 1 and 3 indicates the percent similarity of the protein sequence encoded by an ORF to the corresponding protein sequence from the organism appearing in parentheses in the sixth column. Column 8 of Tables 1 and 3 indicates the percent identity of the protein sequence encoded by an ORF to the corresponding protein sequence from the organism appearing in parentheses in the sixth column. The concepts of percent identity and percent similarity of two polypeptide sequences are well understood in the art and are described in more detail below. Identified genes can frequently be assigned a putative cellular role category adapted from Riley (see, Riley, M., *Microbiol. Rev.* 57:862 (1993)). Column 9 of Tables 1 and 3 provides the nucleotide length of the open reading frame.

Tables 2 and 4, below, provide ORFs of *E. coli* J96 PAI IV and PAI V, respectively, that did not elicit a homology match with a known sequence from either *E. coli* or another organism. As above, the first column in Tables 2 and 4 provides the contig in which the ORF is located and the second column numerically identifies a particular ORF in a particular contig. Columns 3 and 4 identify an ORF's position in one of SEQ ID NOs: 1 through 142 by reference to start and stop nucleotides.

Tables 5 and 6, below, provide the *E. coli* J96 PAI IV ORFs and PAI V ORFs, respectively, identified by the present inventors that provided a significant match to a previously published *E. coli* protein. Columns 1–6 correspond to columns 1–6 appearing in Tables 1 and 3. Column 7 indicates the percent identity of the protein sequence encoded by an ORF to the corresponding protein sequence from the organism appearing in parentheses in the sixth column. Column 8 indicates the length of the high-scoring segment pair (HSP). Column 9 provides the nucleotide length of the open reading frame.

As used herein, "open reading frame" or "ORF" refers to the nucleotide sequences as described in Tables 1 through 6. In Tables 1 through 6, each ORF is designated by a nucleotide sequence start position and stop position according to numbering of contig nucleotides in the Sequence Listing provided (Contig ID=SEQ ID NO).

In a first embodiment, the invention comprises a nucleotide sequence described in Tables 1 through 4 which begins with the nucleotide following the last nucleotide of an upstream stop codon (first nucleotide of the "ORF"), an initiation codon, in-frame putative polypeptide-encoding sequence, and nucleotides of an in-frame stop codon.

In a second embodiment, the invention comprises a nucleotide sequence of Tables 1 through 4 which contains an initiation codon (e.g a methionine or valine codon) on their 5' end and a stop codon on their 3' end. The sequences of this embodiment are present within the nucleotide sequence described in Tables 1 through 4 by start and stop position as numbered in the Sequence Listing. To determine the 5' start position of this embodiment, one simply reads 5' to 3' from the designated 5' end position until an initiation codon is found.

In a third embodiment, the invention comprises a nucleotide sequence of the second embodiment, except that the 3' stop codon is not present.

In a fourth embodiment, the invention comprises a nucleotide sequence encoding a putative protein which is a sequence of Tables 1 through 4 excluding sequence encoding amino acids subject to removal by post-translational processing and sequences 3' of the last codon coding for an amino acid present in the putative polypeptide (e.g., sequences not containing the stop codon and encoding the mature form of the polypeptide).

Certain embodiments of the invention may therefore either include or exclude initiation codons for methionine or valine and either include or exclude the stop codon.

Further details concerning the algorithms and criteria used for homology searches are provided in the Examples below. A skilled artisan can readily identify ORFs in the *Escherichia coli* J96 cosmid library other than those listed in Tables 1 through 6, such as ORFs that are overlapping or encoded by the opposite strand of an identified ORF in addition to those ascertainable using the computer-based systems of the present invention.

Isolated nucleic acid molecules of the present invention include DNA molecules having a nucleotide sequence substantially different than the nucleotide sequence of an ORF described in Tables 1 through 4, but which, due to the degeneracy of the genetic code, still encode a *E. coli* J96 PAI protein. The genetic code is well known in the art. Thus, it would be routine to generate such degenerate variants.

The present invention further relates to variants of the nucleic acid molecules of the present invention, which encode portions, analogs or derivatives of an *E. coli* protein encoded by an ORF described in Table 1 through 4. Non-naturally occurring variants may be produced using art-known mutagenesis techniques and include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the *E. coli* protein or portions thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical, to the nucleotide sequence of an ORF described in Tables 1 through 6, preferably 1 through 4. By a polynucleotide having a nucleotide sequence at least, for example, 95% identical to the reference E. coli ORF nucleotide sequence is intended that the nucleotide sequence of the polynucleotide is identical to the reference sequence except that the polynucleotide sequence may include up to five point mutations per each 100 nucleotides of the ORF sequence. In other words, to obtain a polynucleotide having a nucleotide sequence at least 95% identical to a reference ORF nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to the nucleotide sequence of an *E. coli* J96 PAI ORF can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Preferred are nucleic acid molecules having sequences at least 90%, 95%, 96%, 97%, 98% or 99% identical to the nucleic acid sequence of an *E. coli* J96 PAI ORF that encode a functional polypeptide. By a "functional polypeptide" is intended a polypeptide exhibiting activity similar, but not necessarily identical, to an activity of the protein encoded by the *E. coli* J96 PAI ORF. For example, the *E. coli* ORF [Contig ID 84, ORF ID 3 (84/3)] encodes a hemolysin. Thus, a "functional polypeptide" encoded by a nucleic acid molecule having a nucleotide sequence, for example, 95% identical to the nucleotide sequence of 84/3, will also possess hemolytic activity. As the skilled artisan will appreciate, assays for determining whether a particular polypeptide is "functional" will depend on which ORF is used as the reference sequence. Depending on the reference ORF, the assay chosen for measuring polypeptide activity will be readily apparent in light of the role categories provided in Tables 1, 3, 5 and 6.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of a reference ORF will encode a functional polypeptide. In fact, since degenerate variants all encode the same amino acid sequence, this will be clear to the skilled artisan even without performing a comparison assay for protein activity. It will be further recognized in the art that, for such nucleic acid molecules that are not degenerate variants, a reasonable number will also encode a functional polypeptide. This is because the skilled artisan is fully aware of amino acid substitutions that are either less likely or not likely to significantly affect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

The present invention is further directed to fragments of the isolated nucleic acid molecules described herein. By a fragment of an isolated nucleic acid molecule having the nucleotide sequence of an *E. coli* J96 PAI ORF is intended fragments at least about 15 nt, and more preferably at least about 20 nt, still more preferably at least about 30 nt, and even more preferably, at least about 40 nt in length that are useful as diagnostic probes and primers as discussed herein. Of course, larger fragments 50–500 nt in length are also useful according to the present invention as are fragments corresponding to most, if not all, of the nucleotide sequence of an *E. coli* J96 PAI ORF. By a fragment at least 20 nt in length, for example, is intended fragments that include 20 or more contiguous bases from the nucleotide sequence of an *E. coli* J96 PAI ORF. Since *E. coli* ORFs are listed in Tables 1 through 6 and the sequences of the ORFs have been provided within the contig sequences of SEQ ID NOs: 1 through 142, generating such DNA fragments would be routine to the skilled artisan. For example, restriction endonuclease cleavage or shearing by sonication could easily be used to generate fragments of various sizes from the PAI DNA that is incorporated into the deposited pools of cosmid clones. Alternatively, such fragments could be generated synthetically.

Preferred nucleic acid fragments of the present invention include nucleic acid molecules encoding epitope-bearing portions of an *E. coli* J96 PAI protein. Methods for determining such epitope-bearing portions are described in detail below.

In another aspect, the invention provides an isolated nucleic acid molecule comprising a polynucleotide that hybridizes under stringent hybridization conditions to a portion of the polynucleotide in a nucleic acid molecule of the invention described above, for instance, an ORF described in Tables 1 through 6, preferably an ORF described in Tables 1, 2, 3 or 4. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65°C.

By a polynucleotide that hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g., a E. coli ORF), for instance, a portion 50–500 nt in length, or even to the entire length of the reference polynucleotide, are also useful as probes according to the present invention, as are polynucleotides corresponding to most, if not all, of an E. coli J96 PAI ORF.

By "expression modulating fragment" (EMF), is intended a series of nucleotides that modulate the expression of an operably linked, putative polypeptide-encoding region (encoding region). A sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments that induce the expression of an operably linked encoding region in response to a specific regulatory factor or physiological event. EMF sequences can be identified within the E. coli genome by their proximity to the encoding regions within ORFs described in Tables 1 through 6. An intergenic segment, or a fragment of the intergenic segment, from about 10 to 200nucleotides in length, taken 5' from any one of the encoding regions of ORFs of Tables 1 through 6 will modulate the expression of an operably linked 3' encoding region in a fashion similar to that found within the naturally linked ORF sequence. As used herein, an "intergenic segment" refers to the fragments of the E. coli J96 PAT subgenome that are between two encoding regions herein described. Alternatively, EMFs can be identified using known EMFs as a target sequence or target motif in the computer-based systems of the present invention.

The presence and activity of an EMF can be confirmed using an EMF trap vector. An EMF trap vector contains a cloning site 5' to a marker sequence. A marker sequence encodes an identifiable phenotype, such as antibiotic resistance or a complementing nutrition auxotrophic factor, which can be identified or assayed when the EMF trap vector is placed within an appropriate host under appropriate conditions. As described above, an EMF will modulate the expression of an operably linked marker sequence. A more detailed discussion of various marker sequences is provided below.

A sequence that is suspected as being an EMF is cloned in all three reading frames in one or more restriction sites upstream from the marker sequence in the EMF trap vector. The vector is then transformed into an appropriate host using known procedures and the phenotype of the transformed host in examined under appropriate conditions. As described above, an EMF will modulate the expression of an operably linked marker sequence.

By a "diagnostic fragment" (DF), is intended a series of nucleotides that selectively hybridize to E. coli sequences. DFs can be readily identified by identifying unique sequences within the E. coli J96 PAI subgenome, or by generating and testing probes or amplification primers consisting of the DF sequence in an appropriate diagnostic format for amplification or hybridization selectivity.

Each of the ORFs of the E. coli J96 PAI subgenome disclosed in Tables 1 through 4, and EMFs found 5' to the encoding regions of the ORFs, can be used in numerous ways as polynucleotide reagents. The sequences can be used as diagnostic probes or diagnostic amplification primers to detect the presence of uropathogenic E. coli in a sample. This is especially the case with the fragments or ORFs of Table 2 and 4 which will be highly selective for uropathogenic E. coli J96, and perhaps other uropathogenic or extraintestinal strains that include one or more PAIs.

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla. (1988)).

Triple helix—formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

Vectors and Most Cells

The present invention further provides recombinant constructs comprising one or more fragments of the E. coli J96 PAIs. The recombinant constructs of the present invention comprise a vector, such as a plasmid or viral vector, into which, for example, an E. coli J96 PAI ORF is inserted. The vector may further comprise regulatory sequences, including for example, a promoter, operably linked to the encoding region of an ORF. For vectors comprising the EMFs of the present invention, the vector may further comprise a marker sequence or heterologous ORF operably linked to the EMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are pKK232–8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention further provides host cells containing any one of the isolated fragments (preferably an ORF) of the E. coli J96 PAIs described herein. The host cell can be a higher eukaryotic host cell, such as a mammalian cell, a lower eukaryotic host cell, such as a yeast cell, or the host cell can be a procaryotic cell, such as a bacterial cell. Introduction of the recombinant construct into the host cell can be effected by calcium phosphate transfection, DEAE, dextran mediated transfection, or electroporation (Davis, L. et al., Basic Methods in Molecular Biology (1986)). Host cells containing, for example, an E. coli J96 PAI ORF can be used conventionally to produce the encoded protein.

Polypeptides and Fragments

The invention further provides isolated polypeptides having the amino acid sequence encoded by an E. coli PAI ORF described in Tables 1 through 6, preferably Tables 1 through 4, or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of E. coli polypeptides can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of polypeptides encoded for by ORFs listed in Tables 1 through 6 which show substantial pathogenic activity or which include regions of particular E. coli PAI proteins such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," Science 247:1306–1310 (1990).

Thus, the fragment, derivative or analog of a polypeptide encoded by an ORF described in one of Tables 1 through 6, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of said proteins. The prevention of aggregation is highly desirable.

Aggregation of proteins not only results in a loss of activity but can also be problematic when preparing pharmaceutical formulations, because they can be immunogenic. (Pinckard et al., Clin Exp. Immunol. 2:331–340 (1967); Robbins et al., Diabetes 36:838–845 (1987); Cleland et al. Crit. Rev. Therapeutic Drug Carrier Systems 10:307–377 (1993)).

The replacement of amino acids can also change the selectivity of binding to cell surface receptors. Ostade et al., Nature 361:266–268 (1993) describes certain mutations resulting in selective binding of TNF-α to only one of the two known types of TNF receptors. Thus, proteins encoded for by the ORFs listed in Tables 1, 2, 3, 4, 5, or 6, and that bind to a cell surface receptor, may include one or more amino acid substitutions, deletions or additions, either from natural mutations or human manipulation.

As indicated, changes are preferably of a minor nature, such as 15 conservative amino acid substitutions that do not significantly affect the folding or activity of the protein (see Table 7).

TABLE 7

| Conservative Amino Acid Substitutions | |
|---|---|
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

Amino acids in the proteins encoded by ORFs of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of the polypeptides can be substantially purified by the one-step method described in Smith and Johnson, *Gene* 67:31–40 (1988).

The polypeptides of the present invention include the polypeptide encoded by the ORFs listed in Tables 1–6, preferably Tables 1–4, as well as polypeptides which have at least 90% similarity, more preferably at least 95% similarity, and still more preferably at least 96%, 97%, 98% or 99% similarity to those described above, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 *Science Drive, Madison, Wis.* 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of a polypeptide is intended that the amino acid sequence of the polypeptide is identical to the reference sequence except that the polypeptide sequence may include up to five amino acid alterations per each 100 amino acids of the reference amino acid of said polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence encoded by the ORFs listed in Tables 1, 2, 3, 4, 5, or 6 can be determined conventionally using known computer programs such the Bestfit program (Wisconsin Sequence Analysis Package, Version 8 for Unix, Genetics Computer Group, University Research Park, 575 *Science Drive, Madison, Wis.* 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting pathogenic protein expression as described below or as agonists and antagonists capable of enhancing or inhibiting protein function of important proteins encoded by the ORFs of the present invention. Further, such polypeptides can be used in the yeast two-hybrid system to "capture" protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Nat. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe el al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et a, Cell 37:767–778 (1984) at 777. The anti- peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al, supra; Chow, M. et al., Proc. Nall. Acad. Sci. USA 82:910–914; and Bittle, F. J. et al., J. Gen. Virol. 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 $\mu$g peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, E. coli PAI polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker et al., Nature 331:84–86 (1988)). Fusion proteins that have a disulfide-linked dimeric structure due to the IgG part can also be more efficient in binding and neutralizing other molecules than the monomeric E. coli J96 PAI proteins or protein fragments alone (Fountoulakis et al., J. Biochem 270:3958–3964 (1995)).

Vaccines

In another embodiment, the present invention relates to a vaccine, preferably in unit dosage form, comprising one or more E. coli J96 PAI antigens together with a pharmaceutically acceptable diluent, carrier, or excipient, wherein the one or more antigens are present in an amount effective to elicit a protective immune response in an animal to pathogenic E. coli. Antigens of E. coli J96 PAI IV and V may be obtained from polypeptides encoded for by the ORFs listed in Tables 1–6, particularly Tables 1–4, using methods well known in the art.

In a preferred embodiment, the antigens are E. coli J96 PAI IV or PAI V proteins that are present on the surface of pathogenic E. coli. In another preferred embodiment, the pathogenic E. coli J96 PAI IV or PAI V protein-antigen is conjugated to an E. coli capsular polysaccharide (CP), particularly to capsular polypeptides that are more prevalent in pathogenic strains, to produce a double vaccine. CPs, in general, may be prepared or synthesized as described in Schneerson et al. J. Exp. Med. 152:361–376 (1980); Marburg et al. J. Am. Chem. Soc. 108:5282 (1986); Jennings et al., J. Immunol. 127:1011–1018 (1981); and Beuvery et al, Infect. Immunol. 40:39–45 (1983). In a further preferred embodiment, the present invention relates to a method of preparing a polysaccharide conjugate comprising: obtaining the above-described E. coli J96 PAI antigen; obtaining a CP or fragment from pathogenic E. coli; and conjugating the antigen to the CP or CP fragment.

In a preferred embodiment, the animal to be protected is selected from the group consisting of humans, horses, deer, cattle, pigs, sheep, dogs, and chickens. In a more preferred embodiment, the animal is a human or a dog.

In a further embodiment, the present invention relates to a prophylactic method whereby the incidence of pathogenic E. coli-induced symptoms are decreased in an animal, comprising administering to the animal the above-described vaccine, wherein the vaccine is administered in an amount effective to elicit protective antibodies in an animal to pathogenic E. coli. This vaccination method is contemplated to be useful in protecting against severe diarrhea (pathogenic intestinal E. coli strains), urinary tract infections (uropathogenic E. coli) and infections of the brain (extraintestinal E. coli). The vaccine of the invention is used in an effective amount depending on the route of administration. Although intra-nasal, subcutaneous or intramuscular routes of administration are preferred, the vaccine of the present invention can also be administered by an oral, intraperitoneal or intravenous route. One skilled in the art will appreciate that the amounts to be administered for any particular treatment protocol can be readily determined without undue experimentation. Suitable amounts are within the range of 2 micrograms of the protein per kg body weight to 100 micrograms per kg body weight.

The vaccine can be delivered through a vector such as BCG. The vaccine can also be delivered as naked DNA coding for target antigens.

The vaccine of the present invention may be employed in such dosage forms as capsules, liquid solutions, suspensions or elixirs for oral administration, or sterile liquid forms such as solutions or suspensions. Any inert carrier is preferably used, such as saline, phosphate-buffered saline, or any such carrier in which the vaccine has suitable solubility properties. The vaccines may be in the form of single dose preparations or in multi-dose flasks which can be used for mass vaccination programs. Reference is made to Remington's Pharmaceutical Sciences, Mack Publishing Co., Easton, Pa., Osol (ed.) (1980); and New Trends and Developments in Vaccines, Voller et al. (eds.), University Park Press, Baltimore, Md. (1978), for methods of preparing and using vaccines.

The vaccines of the present invention may further comprise adjuvants which enhance production of antibodies and immune cells. Such adjuvants include, but are not limited to, various oil formulations such as Freund's complete adjuvant (CFA), the dipeptide known as MDP, saponins (ex. Quillajasaponin fraction QA-21, U.S. Pat. No. 5,047,540), aluminum hydroxide, or lymphatic cytokines. Freund's adjuvant is an emulsion of mineral oil and water which is mixed with the immunogenic substance. Although Freund's adjuvant is powerful, it is usually not administered to humans. Instead, the adjuvant alum (aluminum hydroxide) may be used for administration to a human. Vaccine may be absorbed onto the aluminum hydroxide from which it is slowly released after injection. The vaccine may also be encapsulated within liposomes according to Fullerton, U.S. Pat. No. 4,235,877.

Protein Function

Each ORF described in Tables 1 and 3 possesses a biological role similar to the role associated with the identified homologous protein. This allows the skilled artisan to determine a function for each identified coding sequence. For example, a partial list of the E. coli protein functions provided in Tables 1 and 3 includes many of the functions associated with virulence of pathogenic bacterial strains. These include, but are not limited to adhesins, excretion pathway proteins, O-antigen/carbohydrate modification, cytotoxins and regulators. A more detailed description of several of these functions is provided in Example 1 below.

Diagnostic Assays

In another preferred embodiment, the present invention relates to a method of detecting pathogenic E. coli nucleic acid in a sample comprising:

a) contacting the sample with the above-described nucleic acid probe, under conditions such that hybridization occurs, and b) detecting the presence of the probe bound to pathogenic E. coli nucleic acid.

In another preferred embodiment, the present invention relates to a diagnostic kit for detecting the presence of pathogenic *E. coli* nucleic acid in a sample comprising at least one container means having disposed therein the above-described nucleic acid probe.

In another preferred embodiment, the present invention relates to a diagnostic kit for detecting the presence of pathogenic *E. coli* antigens in a sample comprising at least one container means having disposed therein the above-described antibodies.

In another preferred embodiment, the present invention relates to a diagnostic kit for detecting the presence of antibodies to pathogenic *E. coli* antigens in a sample comprising at least one container means having disposed therein the above-described antigens.

The present invention provides methods to identify the expression of an ORF of the present invention, or homolog thereof, in a test sample, using one of the antibodies of the present invention. Such methods involve incubating a test sample with one or more of the antibodies of the present invention and assaying for binding of the antibodies to components within the test sample.

In a further embodiment, the present invention relates to a method for identifying pathogenic *E. coli* in an animal comprising analyzing tissue or body fluid from the animal for a nucleic acid, protein, polypeptide-antigen or antibody specific to one of the ORFs described in Tables 1–4 herein from *E. coli* J96 PAI IV or V. Analysis of nucleic acid specific to pathogenic *E. coli* can be by PCR techniques or hybridization techniques (cf. *Molecular Cloning: A Laboratory Manual, second edition*, edited by Sambrook, Fritsch, & Maniatis, Cold Spring Harbor Laboratory, 1989; Eremeeva et al., *J. Clin. Microbiol.* 32:803–810 (1994) which describes differentiation among spotted fever group Rickettsiae species by analysis of restriction fragment length polymorphism of PCR-amplified DNA).

Proteins or antibodies specific to pathogenic *E. coli* may be identified as described in *Molecular Cloning: A Laboratory Manual, second edition*, Sambrook et al., eds., Cold Spring Harbor Laboratory (1989). More specifically, antibodies may be raised to *E. coli* J96 PAI proteins as generally described in *Antibodies: A Laboratory Manual*, Harlow and Lane, eds., Cold Spring Harbor Laboratory (1988). *E. coli* J96 PAI-specific antibodies can also be obtained from infected animals (Mather, T. et al., *JAMA* 205:186–188 (1994)).

In another embodiment, the present invention relates to an antibody having binding affinity specifically to an *E. coli* J96 PAI antigen as described above. The *E. coli* J96 PAI antigens of the present invention can be used to produce antibodies or hybridomas. One skilled in the art will recognize that if an antibody is desired, a peptide can be generated as described herein and used as an immunogen. The antibodies of the present invention include monoclonal and polyclonal antibodies, as well as fragments of these antibodies. The invention further includes single chain antibodies. Antibody fragments which contain the idiotype of the molecule can be generated by known techniques, for example, such fragments include but are not limited to: the F(ab')$_2$ fragment; the Fab' fragments, Fab fragments, and Fv fragments.

Of special interest to the present invention are antibodies to pathogenic *E. coli* antigens which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et aL, *Science* 240:1041–1043 (1988); Liu, A.Y. et al., *Proc. Natl. Acad. Sci. USA* 84:3439–3443 (1987); Liu, A. Y. et al., *J Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Nail. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980)).

In another embodiment, the present invention relates to a method of detecting a pathogenic *E. coli* antigen in a sample, comprising: a) contacting the sample with an above-described antibody, under conditions such that immunocomplexes form, and b) detecting the presence of said antibody bound to the antigen. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier *Science Publishers, Amsterdam, The Netherlands (*1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985); and *Antibodies: A Laboratory Manual*, Harlow and Lane, eds., Cold Spring Harbor Laboratory (1988).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

In another embodiment, the present invention relates to a method of detecting the presence of antibodies to pathogenic *E. coli* in a sample, comprising: a) contacting the sample with an above-described antigen, under conditions such that immunocomplexes form, and b) detecting the presence of said antigen bound to the antibody. In detail, the methods comprise incubating a test sample with one or more of the antigens of the present invention and assaying whether the antigen binds to the test sample.

In another embodiment of the present invention, a kit is provided which contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits.

One skilled in the art will readily recognize that the antibodies described in the present invention can readily be incorporated into one of the established kit formats which are well known in the art.

Screening Assay for Binding Agents

Using the isolated proteins described herein, the present invention further provides methods of obtaining and identifying agents that bind to a protein encoded by an *E. coli* J96 PAI ORF or to a fragment thereof.

The method involves:

(a) contacting an agent with an isolated protein encoded by a *E. coli* J96 PAI ORF, or an isolated fragment thereof; and (b) determining whether the agent binds to said protein or said fragment.

The agents screened in the above assay can be, but are not limited to, peptides, carbohydrates, vitamin derivatives, or other pharmaceutical agents. The agents can be selected and screened at random or rationally selected or designed using protein modeling techniques. For random screening, agents such as peptides, carbohydrates, pharmaceutical agents and the like are selected at random and are assayed for their ability to bind to the protein encoded by an ORF of the present invention.

Alternatively, agents may be rationally selected or designed. As used is herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide ligands, for example see Hurby et al., Application of Synthetic Peptides: Antisense Peptides, In *Synthetic Peptides, A User's Guide*, W. H. Freeman, NY (1992), pp. 289–307, and Kaspczak et al., *Biochemistry* 28:9230–8 (1989).

In addition to the foregoing, one class of agents of the present invention, can be used to control gene expression through binding to one of the ORF encoding regions or EMFs of the present invention. As described above, such agents can be randomly screened or rationally designed and selected. Targeting the encoding region or EMF allows a skilled artisan to design sequence specific or element specific agents, modulating the expression of either a single ORF encoding region or multiple encoding regions that rely on the same EMF for expression control.

One class of DNA binding agents are those that contain nucleotide base residues that hybridize or form a triple helix by binding to DNA or RNA. Such agents can be based on the classic phosphodiester, ribonucleic acid backbone, or can be a variety of sulfhydryl or polymeric derivatives having base attachment capacity.

Agents suitable for use in these methods usually contain 20 to 40 bases and are designed to be complementary to a region of the gene involved in transcription (triple helix— see Lee et al., *Nucl. Acids Res.* 6:3073 (1979); Cooney et al., *Science* 241:456 (1988); and Dervan et al., *Science* 251: 1360 (1991)) or to the mRNA itself (antisense—Okano, *J. Neurochem.* 56:560 (1991); *Oligodeoxynucleotides as Antisense Inhibitors of Gene Expression*, CRC Press, Boca Raton, Fla.(1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents.

Computer Related Embodiments

The nucleotide sequence provided in SEQ ID NOs: 1 through 142, representative fragments thereof, or nucleotide sequences at least 99.9% identical to the sequences provided in SEQ ID NOs: 1 through 142, can be "provided" in a variety of media to facilitate use thereof. As used herein, "provided" refers to a manufacture, other than an isolated nucleic acid molecule, that contains a nucleotide sequence of the present invention, i.e., the nucleotide sequence provided in SEQ ID NOs: 1 through 142, a representative fragment thereof, or a nucleotide sequence at least 99.9% identical to SEQ ID NOs: 1 through 142. Such a manufacture provides the *E. coli* J96 PAI subgenomes or a subset thereof (e.g., one or more *E. coli* J96 PAI open reading frame (ORF)) in a form that allows a skilled artisan to examine the manufacture using means not directly applicable to examining the *E. coli* J96 PAI subgenome or a subset thereof as it exists in nature or in purified form.

In one application of this embodiment, one or more nucleotide sequences of the present invention can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently know methods for recording information on computer readable medium to generate manufactures comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and MicroSoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention.

By providing the nucleotide sequence of SEQ ID NOs: 1 through 142, representative fragments thereof, or nucleotide sequences at least 99.9% identical to SEQ ID NOs: 1 through 142, in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403–410 (1990)) and BLAZE (Brutlag et al., *Comp. Chem.* 17:203–207 (1993)) search algorithms on a Sybase system can be used to identify open reading frames (ORFs) within the *E. coli* J96 PAI subgenome that contain homology to ORFs or proteins from other organisms. Such ORFs are protein-encoding fragments within the *E. coli* J96 PAI subgenome and are useful in producing commercially important proteins such as enzymes used in modifying surface 0-antigens of bacteria. A comprehensive list of ORFs encoding commercially important *E. coli* J96 PAI proteins is provided in Tables 1 through 6.

The present invention provides a DNA sequence—gene database of pathogenicity islands (PAIs) for *E. coli* involved in infectious diseases. This database is useful for identifying and characterizing the basic functions of new virulence genes for *E. coli* involved in uropathogenic and extraintestinal diseases. The database provides a number of novel open reading frames that can be selected for further study as described herein.

Selectable insertion mutations in plasmid subclones encoding PAI genes with potentially significant phenotypes for *E. coli* uropathogenesis and sepsis can be isolated. The mutations are then crossed back into wild type, uropathogenic *E. coli* by homologous recombination to create wild-type strains specifically altered in the targeted gene. The significance of the genes to *E. coli* pathogenesis is assessed by in vitro assays and in vivo murine models of sepsis/peritonitis and ascending urinary tract infection.

New virulence genes and PAI sites in uropathogenic *E. coli* may be identified by the transposon signature-tagged mutagenesis system and negative selection of *E. coli* mutants avirulent in murine models of ascending urinary tract infection or peritonitis.

Epidemiological investigations of new virulence genes and PAIs may be used to test for their occurrence in the genomes of other pathogenic and opportunistic members of the Enterobacteriaceae.

One can choose from the ORFs included in SEQ ID NOs: 1 through 142, using Tables 1 through 6 as a useful guidepost for selecting, as candidates for targeted mutagenesis, a limited number of candidate genes within the PAIs based on their homology to virulence, export or regulation genes in other pathogens. For the large number of apparent genes within the PAIs that do not share sequence similarity to any entries in the database, the transposon signature-tagged mutagenesis method developed by David Holden's laboratory can be employed as an independent means of virulence gene identification.

Allelic knock-outs are constructed using different pir-dependent suicide vectors (Swihart, K. A. and R. A. Welch, *Infect. Immun.* 58:1853–1869 (1990)). In addition, two different animal model systems can be employed for assessment of pathogenic determinants. The initial identification of *E. coli* hemolysin as a virulence factor came from the construction of isogenic *E. coli* strains that were tested in a rat model of intra-abdominal sepsis (Welch, R. A. et al., *Nature* (London) 294:665–667 (1981)). The ascending UTI (Urinary Tract Infection) mouse model was also successfully performed with allelic knock-outs of the hptmA hemolysin of *Proteus mirabilis* (Swihart, K. A. and R. A. Welch, *Infect. Immun.* 58:1853–1869 (1990)).

The present invention further provides systems, particularly computer-based systems, which contain the sequence information described herein. Such systems are designed to identify commercially important fragments of the *E. coli* J96 PAI subgenome. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the *E. coli* genome that match a particular target sequence or target motif. A variety of known algorithms are disclosed publicly and a variety of commercially available software for conducting search means are available and can be used in the computer-based systems of the present invention. Examples of such software include, but are not limited to, MacPattern (EMBL), BLASTN and BLASTX (NCBIA). A skilled artisan can readily recognize that any one of the available algorithms or implementing software packages for conducting homology searches can be adapted for use in the present computer-based systems.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that during searches for commercially important fragments of the E. coli J96 PAI subgenome, such as sequence fragments involved in gene expression and protein processing, may be of shorter length.

As used herein, "a target structural motif,"or " target motif," refers to any arationally selected sequence or combination of sequences in which the sequence(s) are chosen based on a three-dimensional configuration which is formed upon the folding of the target motif. There are a variety of target motifs known in the art. Protein target motifs include, but are not limited to, enzymic active sites and signal sequences. Nucleic acid target motifs include, but are not limited to, promoter sequences, hairpin structures and inducible expression elements (protein binding sequences).

Thus, the present invention fuirther provides an input means for receiving a target sequence, a data storage means for storing the target sequence and the homologous E. coli J96 PAI sequence identified using a search means as described above, and an output means for outputting the identified homologous E. coli J96 PAI sequence. A variety of structural formats for the input and output means can be used to input and output information in the computer-based systems of the present invention. A preferred format for an output means ranks fragments of the E. coli J96 PAI subgenome possessing varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments of the E. coli J96 PAI subgenomes. For example, implementing software which implement the BLAST and BLAZE algorithms (Altschul et al., J. Mol. Biol. 215:403–410 (1990)) can be used to identify open reading frames within the E. coli J96 PAI subgenome A skilled artisan can readily recognize that any one of the publicly available homology search programs can be used as the search means for the computer-based systems of the present invention.

Figure 2:
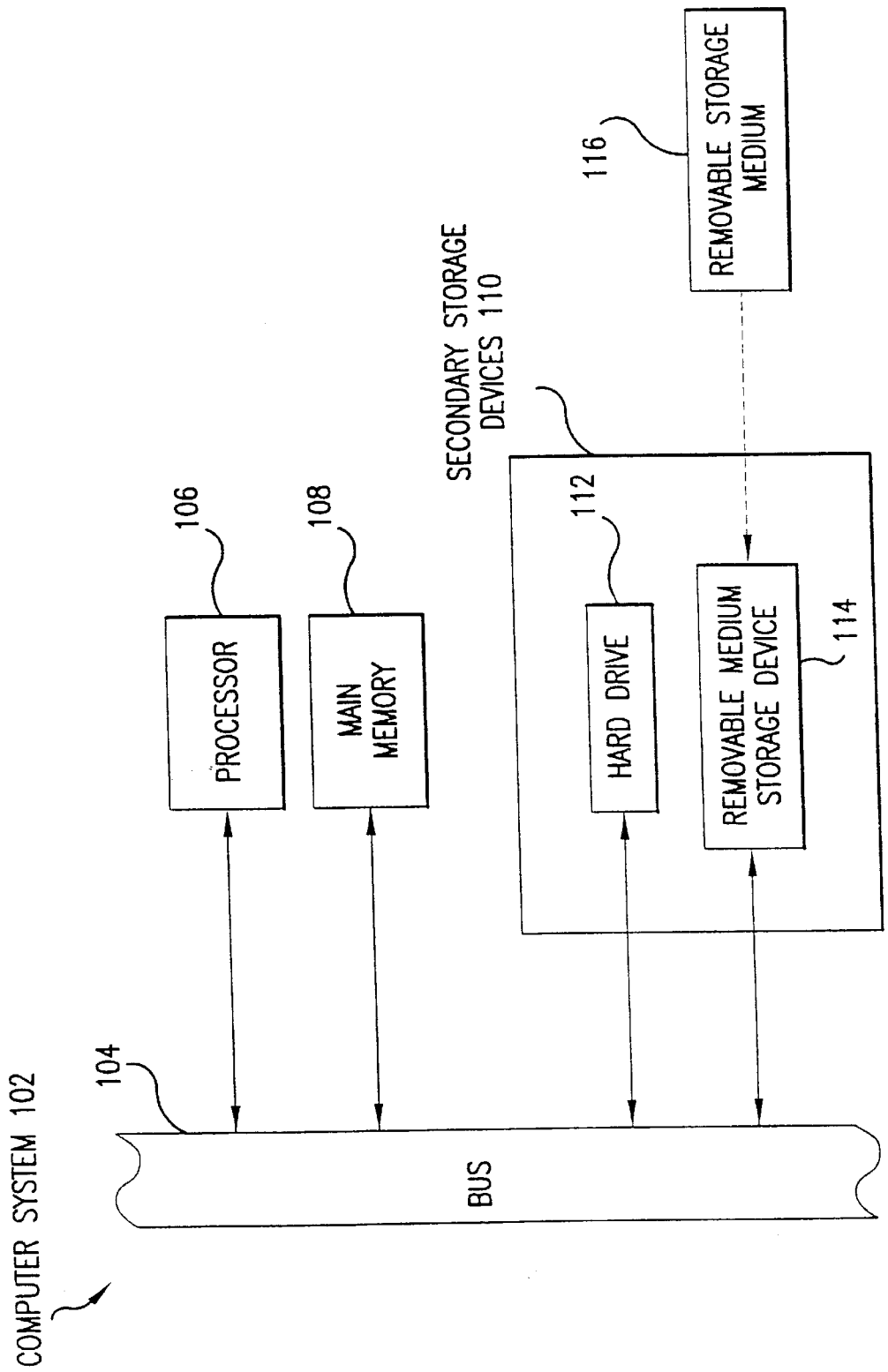
FIG. 2 is a block diagram of a computer system 102 that can be used to implement the computer-based systems of present invention.

One application of this embodiment is provided in FIG. 2. FIG. 2 provides a block diagram of a computer system 102 that can be used to implement the present invention. The computer system 102 includes a processor 106 connected to a bus 104. Also connected to the bus 104 are a main memory 108 (preferably implemented as random access memory, RAM) and a variety of secondary storage devices 110, such as a hard drive 112 and a removable medium storage device 114. The removable medium storage device 114 may represent, for example, a floppy disk drive, a CD-ROM drive, a magnetic tape drive, etc. A removable storage medium 116 (such as a floppy disk, a compact disk, a magnetic tape, etc.) containing control logic and/or data recorded therein may be inserted into the removable medium storage device 114. The computer system 102 includes appropriate software for reading the control logic and/or the data from the removable medium storage device 114 once inserted in the removable medium storage device 114.

A nucleotide sequence of the present invention may be stored in a well known manner in the main memory 108, any of the secondary storage devices 110, and/or a removable storage medium 116. Software for accessing and processing the genomic sequence (such as search tools, comparing tools, etc.) reside in main memory 108 during execution.

Having generally described the invention, the same will be more readily understood by reference to the following examples, which are provided by way of illustration and are not intended as limiting.

EXPERIMENTAL

EXAMPLE 1

High Through-put Sequencing of Cosmid Clones Covering PAI IV and PAI V in E. coli J96

The complete DNA sequence of the pathogenicity islands, PAI IV and PAI V (respectively >170 kb and ~110 kb), from uropathogenic E. coli strain, J96 (04:K6) was determined using a strategy, cloning and sequencing method, data collection and assembly software essentially identical to those used by the TIGR group for determining the sequence of the *Haemophilus influenzae* genome (Fleischmann, R. D., et al., Science 269:496 (1995)). The sequences were then used for DNA and protein sequence similarity searches of the databases as described in Fleischmann, Id.

The analysis of the genetic information found within the PAIs of E. coil J96 was facilitated by the use of overlapping cosmid clones possessing these unique segments of DNA. These cosmid clones were previously constructed and mapped (as further described below) as an overlapping set in the laboratory of Dr. Doug Berg (Washington University). A gap exists between the left portion of cosmid 2 and the end of the PAI IV that would represent the pheV junction to the E. coli K-12 genome.

Uropathogenic strain E. coli J96 (04:K6) was used as a source of chromosomal DNA for construction of a cosmid library. E. coli K-12 DH5α and DH12 (Gibco/BRL, Gaithersburg, Md.) were used as hosts for maintaining cosmid and plasmid clones. The cosmid library of E. coli J96 DNA was constructed essentially as described by Bukanow & Berg (Mol. Microbiol 11:509–523 (1994)). DNA was digested with Sau3AI under conditions that generated fragments with an average size of 40 to 50 kb and electrophoresed through 1% agarose gels. Fragments of 35 to 50 kb were isolated and cloned into Lorist 6 vector that had been linearized with BamIII and treated with bacterial alkaline phosphatase to block self-ligation. (Lorist 6 is a 5.2-kb moderate-copy-number cosmid vector with T7 and SP6 promoters close to the cloning site.) Cloned DNA was packaged in lambda phage particles in vitro by using a commercial kit (Amersham, Arlington Heights, Ill.) and cosmid-containing phage particles were used to transduce E. coli DH5α. Transductant colonies were transferred to 150 μL of Luria-Bertani broth supplemented with kanamycin in 96-well microtiter plates and grown overnight at 37° C. with shaking. Two sets of clones, one for each PAI were ultimately assembled, as previously described (Swenson et al., Infection and Immunity 64:3736–3743 (1996)), fully incorporated by reference herein).

The two sets of clones contain eleven sub-clones that were employed in the sequencing method described below. One set of four overlapping cosmid clones covers the prs-containing PAI V, ATCC Deposit No. 97727, deposited Sep. 23, 1996. A second set of seven subclones covers much of the pap-containing PAI V, ATCC Deposit No.97726, deposited Sep. 23, 1996. See FIG. 1.

A high through-put, random sequencing method (Fleischmann et al., *Science* 269:496 (1995); Fraser et al., *Science* 270:397 (1995)) was used to obtain the sequences for 142 (contigs) fragments of *E. coli* J96 PAIs. All clones were sequenced from both ends to aid in the eventual ordering of contigs during the sequence assembly process. Briefly, random libraries of ~2 kb clones covering the two J96 PAIs were constructed, ~2,800 clones were subjected to automated sequencing (~450 nt/clone) and preliminary assemblies of the sequences accomplished which result in 142 contigs for each of the two PAIs that total 95 and 135 kb respectively. The estimated sizes of the PAI IV and PAI V based on the overlapping cosmid clones are $1.7 \times 10^5$ and $1.1 \times 10^5$ bp respectively. The 142 sequences were assembled by means of the TIGR Assembler (Fleischmann et al.; Fraser et al.); Sutton et al., *Genome Sci. Tech.* 1:9 (1995)). Sequence and physical gaps were closed using a combination of strategies (Fleischmann et al.; Fraser et al.). Presently the average depth of sequencing for each base assembled in the contigs is 6-fold. The tentative identity of many genes based on sequence homology is covered in Tables 1, 3, 5 and 6.

Open reading frames (ORFs) and predicted protein-coding regions were identified as described (Fleischmann et al.; Fraser et al.) with some modification. In particular, the statistical prediction of uropathogenic *E. coli* J96 pathogenicity island genes was performed with GeneMark (Borodovsky, M. & McIninch, *J. Comput. Chem.* 17:123 (1993)). Regular GeneMark uses nonhomogeneous Markov models derived from a training set of coding sequences and ordinary Markov models derived from a training set of noncoding sequences. The ORFs in Tables 1–6 were identified by GeneMark using a second-order Markov model trained from known *E. coli* coding regions and known *E. coli* non-coding regions.

Among the important genes that are implicated in the virulence of *E. coli* J96 PAIs are adhesins, excretion pathway proteins, proteins that participate in alterations of the 0-antigen in the PAIs, cytotoxins, and two-component (membrane sensor/DNA binding) proteins.

I Adhesins.

It is believed that the principal adhesin determinants involved in uropathogenicity that are present within PAIs of uropathogenic *E. coli* are the pili encoded by the pap-related operons (Hultgren et al., *Infect. Immun.* 50:370–377 (1993), Stromberg et al., *EMBO J* 9:2001–2010 (1990), High et al., *Infect. Immun.* 56:513–517 (1988)) and the distantly related afimbrial adhesins (Labigne-Roussel et al, *Infect. Immun.* 46:251–259 (1988)). The presence of two of these (pap, and prs) has been confirmed. In addition potential genes for five other adhesins including sla (described above), AIDA-I (diffuse adherence-DEAC), hra (heat resistant hemagglutinin-ETEC), fha (filamentous hemagglutinin— *Bordetella pertussis*) and the arg-gingipain proteinase of *Porphyromonas gingivalis* have been found.

II. Type II Exoprotein Secretion Pathway.

Highly significant statistics support the presence of multiple genes involved in the type II exoprotein pathway. Curiously, perhaps two different determinants appear to be present in PAI IV where one set of genes has the highest sequence similarity to eps-like genes (*Vibrio cholerae* Ctx export) and the other has greatest similarity to exe genes (*Aeromonas hydophilia* aerolysin and protease export). At present, the assembly of contigs involving these potential genes is incomplete. Thus, it is uncertain if two separate and complete determinants are present. However, it is clear that these genes are newly discovered and novel to pathogenic *E. coli* because the derived sequences do not have either the bfp or hop genes as the highest matches. The gene products that are the target of the type II export pathway are not evident at this time.

Within PAI IV there are sequences which suggest genes very similar to secD and secF. These two linked genes encode homologous products that are localized to the inner membrane and are hypothesized to play a late role in the translocation of leader-peptide containing proteins across the inner membrane of gram-negative bacteria. In addition, in each PAI, sequences are found that are reminiscent of the heat-shock htrA/degA gene that encodes a piroplasmic protease. They may perform endochaperone-like function as Pugsley et al. have hypothesized for different exoprotein pathways.

III. O-antigen/capsule/Carbolhydrate Modification (Nod genes).

J96 has the O4. The O-antigen portion of lipopolysaccharide is encoded by rfb genes that are located at 45 min. on the *E. coli* chromosome. We have found in both PAIs a cumulative total of five possible rfb-like genes which could participate alterations of the O-antigen in the PAIs. Overall these data suggest that PAIs provide the genetic potential for greater change of the cell surface for uropathogenic *E. coli* strains than what was previously known.

The apparent capsule type for strain J96 is a non-sialic acid K6-type. Sequence similarity "hits" were made in PAI IV region to two region-1 capsule genes, kpsS and kpsE involved in the stabilization of polysaccharide synthesis and polysaccharide export across the inner membrane. This is not altogether surprising based on the genetic mapping of the kps locus to serA at 63 minutes on the genome of the K1 capsular type of *E. coli*. This suggests that these kps-like genes either are participating in the K6-biosynthesis or perhaps are involved in complex carbohydrate export for other purposes.

An intriguing discovery are the hits made on genes involved in bacteria-plant interactions by Rhizobium, Bradyrhizobium and Agrobacterium. Four potential genes identified thus far share significant sequence similarity to genes encoding products that modify lipo-oligosaccharides that influence nodule morphogenesis on legume roots. These are: ORF140, carbamyl phosphate synthetase; nodulation protein 1265; phosphate-regulatory protein; and an ORF at a plant-inducible locus in Agrobacterium. To date there are no descriptions in the literature of such gene products being utilized by human or animal bacterial pathogens for the purposes of modification or secretion of extracellular carbohydrate. However, the sequence similarity to the capsular region-2 genes and to lipooligosaccharide biosynthetic genes in Rhizobium spp has been recently noted by Petit (1995).

IV. Cytotoxins.

Besides the previously known hemolysin and CNF toxins in the PAIs, in each PAI sequences similar to the shlBA operon (cosmid 5 and 12) were found for a cytolytic toxin from *Serratia marcescens* and *Proteus mirabilis*. Ironically, the *P. mirabilis* hemolysin (HpmA) member of this family of toxins was discovered by Uphoff and Welch (1990), but not thought to exist in other members of the Enterobacteriaceae (Swihart (1990)). A shlB-like transporter does also appear to be involved in the export of the filamentous hemagglutinin of *Bordetella pertussis* which was described above and a cell surface adhesin of *Haemophilus influenzae*. It has been demonstrated that cosmid #5 of *E. coli* J96 encodes an extracellular protein that is ~180 kDa and cross-reactive to polyclonal antisera to the *P. mirabilis* HpmA hemolysin.

Thus, there is evidence suggesting there is new member of this family of proteins in extraintestinal *E. coli* isolates. In addition, there is also a hit on the FhaC hemolysin-like gene within the PAI V although its statistical significance for the sequence thus far available is only 0.0043.

V. Regulators.

A common regulatory motif in bacteria are the two-component (membrane sensor/DNA binding) proteins. In numerous instances in pathogenic bacteria, external signals in the environment cause membrane-bound protein kinases to phosphorylate a cytoplasmic protein which in turn acts as either a negative or positive effector of transcription of large sets of operons. On cosmid 11 representing PAI V were found, in two different PstI clones, sequences for two-component regulators (similar probabilities for OmpR/ AIGB and separately RcsC, probabilities at the $10^{-22}$ level).

In addition, the phosphoglycerate transport system (pgtA, pg/C, and pgtP) including the pgtB regulator is present in PAI IV. This transport system which was originally described in *S. typhimurium* is not appreciated as a component of any pathogenic *E. coli* genome. The operon had been previously mapped at 49 minutes, near or within one of the *S. typhimurium* chromosome specific-loops not present in the K-12 genome. It should be noted that the *E. coli* K-12 gIpT gene product is similar to pgtP gene product (37% identity), but the *E. coli* J96 genes are clearly homologs to the pgt genes and their linkage within the middle of PAI IV element (cosmid #4) is suspicious.

VI. Mobile Genetic Elements.

There are numerous sequences that share similarity to genes found on insertion elements, plasmids and phages. The temperate bacteriophage P4 inserts within tRNA loci in the *E. coli* chromosome. The hypothesis was made that PAIs are the result of bacteriophage P4-virulence gene recombination events (Blum et al., *Infect. Immun.* 62:606–614 (1994). Data supporting this hypothesis was found during our sequencing with the identification of P4-like sequences in each of the PAIs (cosmids 7 and 9). This is a very important preliminary result which supports the hypothesis that PAIs can be identified by common sequence or genetic elements. However, there are indications that multiple mobile genetic elements involved in the evolution of the J96 PAIs. Conjugal plasmid-related sequences may also be present at two different locations (F factor and R1 plasmid). Sequences for multiple transposable elements are present that are likely to have originated from different bacterial genera (Tn1000, IS630, IS911, IS100, IS21, IS 1203, IS5376 (*B. stearothermophlus*) and RHS). Of particular interest is IS100, which was originally identified in *Yersinia pestis* (Fetherston et al, *Mol. Microbiol.* 6:2693–2704 (1992)). The presence of IS100 is significant because it has been associated with the termini of a large chromosomal element encoding pigmentation and some aspect of virulence in *Y. pestis*. This element undergoes spontaneous deletions similar to the PAIs from *E. coli* 536 (Fetherston et al, *Mol. Microbiol.* 6:2693–2704 (1992)) and appears to participate in plasmid-chromosome rearrangements. This element was not previously known to be in genera outside of Yersinia.

The discovery of the apparent att site for bacteriophage P2 in the PAIs is interesting. P2 acts as a helper phage for the P4 satellite phage. The P2 att site is at 44 min in the K-12 genome. The significance of this hit is unknown at present, but may be explained as either a cloning artifact (some K-12 fragments in the Pst I library of cosmid 5) or evidence of some curious chromosomal-P4/P2 phage history. It may indicate that the J96 PAIs are composites of multiple smaller PAIs.

EXAMPLE 2

Preparation of PCR Primers and Amplification of DNA

Various fragments of the sequenced *E. coli* J96 PAIs, such as those disclosed in Tables 1 through 6 can be used, in accordance with the present invention, to prepare PCR primers. The PCR primers are preferably at least 15 bases, and more preferably at least 18 bases in length. When selecting a primer sequence, it is preferred that the primer pairs have approximately the same G/C ratio, so that melting temperatures are approximately the same. The PCR primers are useful during PCR cloning of the ORFs described herein.

EXAMPLE 3

Gene Expression from DNA Sequences Corresponding to ORFs

A fragment of an *E. coli* J96 PAI (preferably, a protein-encoding sequence provided in Tables 1 through 6) is introduced into an expression vector using conventional technology (techniques to transfer cloned sequences into expression vectors that direct protein translation in mammalian, yeast, insect or bacterial expression systems are well known in the art). Commercially available vectors and expression systems are available from a variety of suppliers including Stratagene (La Jolla, Calif. Promega (Madison, Wis. and Invitrogen (San Diego, Calif. If desired, to enhance expression and facilitate proper protein folding, the codon context and codon pairing of the sequence may be optimized for the particular expression organism, as explained by Hatfield et al., U.S. Pat. No. 5,082,767, which is hereby incorporated by reference.

The following is provided as one exemplary method to generate polypeptide(s) from a cloned ORF of an *E. coli* J96 PAI whose sequence is provided in SEQ ID NOs: 1 through 142. A poly A sequence can be added to the construct by, for example, splicing out the poly A sequence from pSG5 (Stratagene) using BglI and SalI restriction endonuclease enzymes and incorporating it into the mammalian expression vector pXT1 (Stratagene) for use in eukaryotic expression systems. pXT1 contains the LTRs and a portion of the gag gene from Moloney Murine Leukemia Virus. The position of the LTRs in the construct allow efficient stable transfection. The vector includes the Herpes Simplex thymidine kinase promoter and the selectable neomycin gene. The *E. coli* J96 PAI DNA is obtained by PCR from the bacterial vector using oligonucleotide primers complementary to the *E. coli* J96 PAI DNA and containing restriction endonuclease sequences for PstI incorporated into the 5' primer and BglII at the 5' end of the corresponding *E. coli* J96 PAI DNA 3' primer, taking care to ensure that the *E. coli* J96 PAI DNA is positioned such that its followed with the poly A sequence. The purified fragment obtained from the resulting PCR reaction is digested with PstI, blunt ended with an exonuclease, digested with BglII, purified and ligated to pXT1, now containing a poly A sequence and digested BglII.

The ligated product is transfected into mouse NIH 3 T3 cells using Lipofectin (Life Technologies, Inc., Grand Island, N.Y. under conditions outlined in the product specification. Positive transfectants are selected after growing the transfected cells in 600 ug/ml G418 (Sigma, St. Louis, Mo.). The protein is preferably released into the supernatant. However if the protein has membrane binding domains, the protein may additionally be retained within the cell or expression may be restricted to the cell surface.

Since it may be necessary to purify and locate the transfected product, synthetic 15-mer peptides synthesized from the predicted E. coli J96 PAI DNA sequence are injected into mice to generate antibody to the polypeptide encoded by the E. coli J96 PAI DNA.

If antibody production is not possible, the E. coli J96 PAI DNA sequence is additionally incorporated into eukaryotic expression vectors and expressed as a chimeric with, for example, β-globin. Antibody to β-globin is used to purify the chimeric. Corresponding protease cleavage sites engineered between the β-globin gene and the E. coli J96 PAI DNA are then used to separate the two polypeptide fragments from one another after translation. One useful expression vector for generating β-globin chimerics is pSG5 (Stratagene). This vector encodes rabbit βglobin. Intron II of the rabbit βglobin gene facilitates splicing of the expressed transcript, and the polyadenylation signal incorporated into the construct increases the level of expression. These techniques as described are well known to those skilled in the art of molecular biology. Standard methods are available from the technical assistance representatives from Stratagene, Life Technologies, Inc., or Promega. Polypeptides may additionally be produced from either construct using in vitro translation systems such as In vitro Express™ Translation Kit (Stratagene).

EXAMPLE 4

E. coli Expression of an E. coli J96 PAI ORF and Protein Purification

An E. coli J96 PAI ORF described in Tables 1 through 6 is selected and amplified using PCR oligonucleotide primers designed from the nucleotide sequences flanking the selected ORF and/or from portions of the ORF's $NH_2$- or COOH-terminus. Additional nucleotides containing restriction sites to facilitate cloning are added to the 5' and 3' sequences, respectively.

The restriction sites are selected to be convenient to restriction sites in the bacterial expression vector pQE60. The bacterial expression vector pQE60 is used for bacterial expression in this example. (QIAGEN, Inc., 9259 Eton Avenue, Chatsworth, Calif. 9131 1). pQE60 encodes ampicillin antibiotic resistance ("Amnpr") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6x His tag") covalently linked to the carboxyl terminus of that polypeptide.

The DNA sequence encoding the desired portion of an E. coli J96 PAI is amplified from the deposited cDNA clone using PCR oligonucleotide primers which anneal to the amino terminal sequences of the desired portion of the E. coli protein and to sequences in the deposited construct 3' to the cDNA coding sequence. Additional nucleotides containing restriction sites to facilitate cloning in the pQE60 vector are added to the 5' and 3' sequences, respectively.

The amplified E. coli J96 PAI DNA fragments and the vector pQE60 are digested with one or more appropriate restriction enzymes, such as SalI and XbaI, and the digested DNAs are then ligated together. Insertion of the E. coli J96 PAI DNA into the restricted pQE60 vector places the E. coli J96 PAI protein coding region, including its associated stop codon, downstream from the IPTG-inducible promoter and in-frame with an initiating AUG. The associated stop codon prevents translation of the six histidine codons downstream of the insertion point.

The ligation mixture is transformed into competent E. coli cells using standard procedures such as those described in Sambrook et al, *Molecular Cloning: a Laboratory Manual*, 2nd Ed.; Cold Spring Harbor Laboratory Press, Cold Spring Harbor, N.Y. (1989). E. coli strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing an E. coli J96 PAI protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("OJN") in lliquid culture in LB media supplemented with both ampicillin (100 μg/ml) and kanamycin (25 μg/ml). The O/N culture is used to inoculate a large culture, at a dilution of approximately 1:25 to 1:250. The cells are grown to an optical density at 600 nm ("OD600") of between 0.4 and 0.6. isopropyl-β-D-thiogalactopyranoside ("IPTG") is then added to a final concentration of 1 mM to induce transcription from the lac repressor sensitive promoter, by inactivating the laci repressor. Cells subsequently are incubated further for 3 to 4 hours. Cells then are harvested by centrifugation.

The cells are then stirred for 3–4 hours at 4° C. in 6 M guanidine-HCl, pH8. The cell debris is removed by centrifugation, and the supernatant containing the E. coli J96 PAI protein is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure E. coli J96 PAI protein. The purified protein is stored at 4° C. or frozen at −80° C.

EXAMPLE 5

Cloning and Expression of an E. coli J96 PAI Protein in a Baculovirus Expression System A E. coli J96 PAI ORF described in Tables 1 through 6 is selected and amplified as above. The plasmid is digested with appropriate restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. E. coli HB101 or other suitable E. coli hosts such as XL-1 Blue (Stratagene Cloning Systems, La Jolla, Calif.) cells are transformed with the ligation mixture and spread on culture plates. Bacteria are identified that contain the plasmid with the E. coli J96 PAI gene by digesting DNA from individual colonies using appropriate restriction enzymes and then analyzing the digestion product by gel electrophoresis. The sequence of the cloned fragment is confirmed by DNA sequencing. This plasmid is designated herein pBac E. coli J96.

Five μg of the plasmid pBac E. coli J96 is co-transfected with 1.0 μg of a commercially available linearized baculovirus DNA ("BaculoGold™ baculovirus DNA", Pharmingen, San Diego, Calif.), using the lipofection method described by Felgner et al., Proc. Natl. Acad. Sci. USA 84:7413–7417 (1987). 1 μg of BaculoGold™ virus DNA and 5 μg of the plasmid pBac E. coli J96 are mixed in a sterile well of a microliter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is. performed, as described by Summers and Smith, supra. An agarose gel with "Blue Gal" (Life Technologies Inc.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., page 9–10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-E. coli J96.

To verify the expression of the E. coli gene Sf9 cells are grown in Grace's medium supplemented with 10% heat inactivated FBS. The cells are infected with the recombinant baculovirus V-E. coli J96 at a multiplicity of infection ("MOI") of about 2. Six hours later the medium is removed and is replaced with SF900 II medium minus methionine and cysteine (available from Life Technologies Inc.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretary signal peptide.

EXAMPLE 6

Cloning and Expression in Mammalian Cells

Most of the vectors used for the transient expression of an E. coli J96 PAI gene in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, 1HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2 dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV I, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., Biochem J. 227:277–279 (199 1); Bebbington etal., Bio/Technology 10: 169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BamHI, Xbal and Asp718, facilitate the cloning of the gene of interest. The vectors contain in addition the 3' intron, the polyadenylation and termination signal of the rat preproinsulin gene.

EXAMPLE 6(a)

Cloning and Expression in COS Cells

The expression plasmid, p E. coli J96HA, is made by cloning a cDNA encoding E. coli J96 PAI protein into the expression vector pcDNAI/Amp or pcDNAIII (which can be obtained from Invitrogen, Inc.).

The expression vector pcDNAI/amp contains: (1) an E. coli origin of replication effective for propagation in E. coli and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the E. coli J96 PAI protein is cloned into the polylinker region of the vector so that recombinant protein expression is directed by the CMV promoter. The plasmid construction strategy is as follows. The E. coli cDNA of the deposited clone is amplified using primers that contain convenient restriction sites, much as described above for construction of vectors for expression of E. coli J96 PAI protein in E. coli.

The PCR amplified DNA fragment and the vector, pcDNAI/Amp, are digested with appropriate restriction enzymes for the chosen primer sequences and then ligated. The ligation mixture is transformed into E. coli strain SURE (available from Stratagene Cloning Systems, La Jolla, Calif. 92037), and the-transformed culture is plated on ampicillin media plates which then are incubated to allow growth of ampicillin resistant colonies. Plasmid DNA is isolated from resistant colonies and examined by restriction analysis or other means for the presence of the E. coli J96 PAI protein-encoding fragment.

For expression of recombinant E. coli J96 PAI protein, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of E. coli J96 PAI protein by the vector.

Expression of the E. coli J96 PAI—HA fusion protein is detected by radiolabeling and immunoprecipitation, using methods described in, for example Harlow et al., Antibodies. A Laboratory Manual, 2nd Ed.; Cold Spring Harbor Laboratory Press, Cold Spring Harbor, N.Y. (1988). To this end, two days after transfection, the cells are labeled by incubation in media containing $_{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

EXAMPLE 6(b)

Cloning and Expression in CHO Cells

The vector pC4 is used for the expression of an E. coli J96 PAI protein. Plasmid pC4 is a derivative of the plasmid pSV2-dhfr (ATCC Acc. No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies, Inc.) supplemented with the chemotherapeutic agent methotrexate. The amplification of the DHFR genes in cells resistant to methotrexate (MTX) has been well documented (see, e.g., Alt, F. W. et al, 1978, J. Biol. Chem. 253:1357–1370, Hamlin, J. L. and Ma, C. 1990, Biochim. et Biophys. Acta, 1097:107–143, Page, M. J. and Sydenham, M. A. 1991, Biotechnology 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., Molecular and Cellular Biology, March 1985:438–447) plus a fragment isolated from the enhancer of the immediate early gene of human cytomegalovirus (CMV) (Boshart et al., Cell 41:521–530 (1985)). Downstream of the promoter is BamHI restriction enzyme site that allows the integration of the gene. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the E. coli protein in a regulated way in mammalian cells (Gossen, M., & Bujard, H. 1992, Proc. Natl. Acad Sci. USA 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with appropriate restriction enzymes and then dephosphorylated using calf intestinal phosphates by procedures known in the art. The vector is then isolated from a 1% agarose gel.

The DNA sequence encoding the complete E. coli J96 PAI protein including its leader sequence is amplified using PCR oligonucleotide primers corresponding to the 5' and 3' sequences of the gene.

The amplified fragment is digested with appropriate endonucleases for the chosen primers and then purified again on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSVneo using lipofectin (Felgner et al, supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nm, 800 nM). Clones growing at the highest concentrations of methotrexate are then transferred to new 6-well plates containing even higher concentrations of methotrexate (1 µM, 2 µM, 5 µM, 10 µM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

EXAMPLE 7

Production of an Antibody to an *E. coli* J96 Patliogenicity Island Protein

Substantially pure *E. coli* J96 PAI protein or polypeptide is isolated from the transfected or transformed cells described above using an art-known method. The protein can also be chemically synthesized. Concentration of protein in the final preparation is adjusted, for example, by concentration on an Amicon filter device, to the level of a few micrograms/ml. Monoclonal or polyclonal antibody to the protein can then be prepared as follows:

Monoclonal Antibody Production by Hybridoma Fusion

Monoclonal antibody to epitopes of any of the peptides identified and isolated as described can be prepared from murine hybridomas according to the classical method of Kohler and Milstein, *Nature* 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and modified methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2 (1989).

Polyclonal Antibody Production by Immunization

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than other molecules and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al., *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall (See Ouchterlony, 0. et al., Chap. 19 in: *Handbook of Experimental Immunology*, Wier, D., ed, Blackwell (1973)). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology*, 2nd ed., Rose and Friedman, (eds.), Amer. Soc. For Microbio., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample.

TABLE 1

(PAI IV)
Putative coding regions of novel *E. coli* PAI IV proteins similar to known proteins

| Contig ID | ORF ID | Start (nt) | Stop (nt) | match acession | match gene name | % sim | % ident | length (nt) |
|---|---|---|---|---|---|---|---|---|
| 65 | 2 | 1902 | 1042 | gi\|1655838 | ORFB; putative transposase [*Yersinia pestis*] | 100 | 100 | 861 |
| 65 | 3 | 2096 | 1821 | gi\|467612 | ORF1 [*Yersinia pestis*] | 100 | 100 | 276 |
| 63 | 11 | 7856 | 9238 | gi\|154262 | transporter protein pgtP [*Salmonella typhimurium*] | 98 | 93 | 1383 |
| 65 | 4 | 2889 | 1915 | gi\|1655837 | ORFA; putative transposase [*Yersinia pestis*] | 97 | 96 | 975 |
| 138 | 1 | 2 | 172 | gi\|1208992 | unknown [*Escherichia coli*] | 97 | 78 | 171 |
| 64 | 6 | 4075 | 4338 | gi\|1143207 | Description: IS630 insertion element; ORF5 protein; Method: conceptual translation supplied by author [*Shigella sonnei*] | 92 | 92 | 264 |
| 67 | 1 | 1 | 273 | gi\|809648 | ExeF gene product [*Aeromonas hydrophila*] | 92 | 71 | 273 |
| 73 | 4 | 3029 | 2511 | gi\|799234 | glucose-1-phosphate thymidylyltransferase [*Escherichia coli*] | 92 | 86 | 519 |
| 73 | 5 | 3139 | 2996 | gi\|454900 | rfbC gene product [*Shigella flexneri*] | 92 | 92 | 144 |
| 64 | 5 | 3741 | 4088 | gi\|47542 | ORF (343 AA) [*Shigella sonnei*] | 91 | 85 | 348 |
| 73 | 3 | 2613 | 2242 | gi\|46985 | glucose-1-phosphate thymidylyltransferase [*Salmonella enterica*] | 91 | 82 | 372 |

TABLE 1-continued (PAI IV)
Putative coding regions of novel *E. coli* PAI IV proteins similar to known proteins

| Contig ID | ORF ID | Start (nt) | Stop (nt) | match acession | match gene name | % sim | % ident | length (nt) |
|---|---|---|---|---|---|---|---|---|
| 90 | 1 | 1 | 366 | gi\|38826 | ExeE gene product [*Aeromonas hydrophila*] | 91 | 77 | 366 |
| 91 | 2 | 604 | 248 | gi\|609625 | putative [*Vibrio cholerae*] | 91 | 67 | 357 |
| 63 | 9 | 6301 | 5234 | gi\|858753 | regulatory protein pgtB [*Salmonella typhimurium*] | 89 | 84 | 1068 |
| 73 | 2 | 2179 | 1811 | gi\|294899 | dTDP-6-deoxy-L-mannose-dehydrogenase [*Shigella flexneri*] | 89 | 84 | 369 |
| 90 | 2 | 201 | 689 | gi\|38826 | ExeE gene product [*Aeromonas hydrophila*] | 89 | 80 | 489 |
| 95 | 2 | 1519 | 413 | gi\|581654 | dTDP-glucose 4,6-dehydratase [*Salmonella enterica*] | 88 | 81 | 1107 |
| 96 | 1 | 729 | 457 | pir\|S43483\|S434 | Orf104 homolog — *Escherichia coli* | 88 | 72 | 273 |
| 63 | 6 | 4281 | 3019 | gi\|154255 | phosphoglycerate transport system activator protein [*Salmonella typhimurium*] | 87 | 79 | 1263 |
| 67 | 2 | 251 | 745 | gi\|609628 | putative [*Vibrio cholerae*] | 87 | 72 | 495 |
| 82 | 12 | 5254 | 4406 | gi\|1208992 | unknown [*Escherichia coli*] | 87 | 74 | 849 |
| 60 | 1 | 693 | 4 | gi\|609625 | putative [*Vibrio cholerae*] | 86 | 57 | 690 |
| 95 | 1 | 428 | 3 | gi\|508238 | dTDP-6-deoxy-L-mannose-dehydrogenase [*Escherichia coli*] | 85 | 74 | 426 |
| 64 | 7 | 4336 | 4731 | gi\|47542 | ORF (343 AA) [*Shigella sonnei*] | 84 | 81 | 396 |
| 80 | 8 | 2800 | 2582 | gi\|38832 | ExeK gene product [*Aeromonas hydrophila*] | 84 | 53 | 219 |
| 82 | 10 | 4380 | 3829 | gi\|1033137 | ORF_o152 [*Escherichia coli*] | 84 | 72 | 552 |
| 63 | 8 | 5399 | 4830 | sp\|P37433\|PGTB_ | PHOSPHOGLYCERATE TRANSPORT SYSTEM SENSOR PROTEIN PGTB (EC 2.7.3.—). | 83 | 75 | 570 |
| 63 | 10 | 7572 | 6259 | gi\|154258 | regulatory protein pgtC [*Salmonella typhimurium*] | 83 | 78 | 1314 |
| 65 | 7 | 3351 | 3100 | gi\|1196999 | unknown protein [Transposon Tn3411] | 82 | 80 | 252 |
| 100 | 1 | 337 | 2 | gi\|41004 | URF 2 [*Escherichia coli*] | 82 | 64 | 336 |
| 138 | 2 | 109 | 429 | gi\|1033128 | ORF_o273 [*Escherichia coli*] | 80 | 62 | 321 |
| 74 | 4 | 1331 | 831 | gi\|38826 | ExeE gene product [*Aeromonas hydrophila*] | 79 | 62 | 501 |
| 63 | 7 | 4873 | 4256 | sp\|P37433\|PGTB_ | PHOSPHOGLYCERATE TRANSPORT SYSTEM SENSOR PROTEIN PGTB (EC 2.7.3.—). | 78 | 72 | 618 |
| 70 | 13 | 5759 | 5529 | gi\|1773143 | Hha protein [*Escherichia coli*] | 78 | 58 | 231 |
| 91 | 3 | 1154 | 534 | gi\|609625 | putative [*Vibrio cholerae*] | 77 | 65 | 621 |
| 75 | 5 | 3524 | 3255 | gi\|463911 | heat resistant agglutinin 1 [*Escherichia coli*] | 76 | 62 | 270 |
| 63 | 1 | 2 | 667 | gi\|1574313 | *H. influenzae* predicted coding region HI1472 [*Haemophilus influenzae*] | 75 | 56 | 666 |
| 104 | 2 | 485 | 315 | gi\|530438 | arabinose transport protein [*Mycoplasma capricolum*] | 72 | 41 | 171 |
| 63 | 3 | 2180 | 1629 | gi\|622948 | transposase [*Escherichia coli*] | 71 | 60 | 552 |
| 63 | 12 | 9688 | 10005 | sp\|P39213\|YI91_ | INSERTION ELEMENT IS911 HYPOTHETICAL 12.7 KD PROTEIN. | 71 | 57 | 318 |
| 61 | 3 | 1283 | 876 | gi\|581535 | ORF140 gene product [Rhizobium sp.] | 70 | 54 | 408 |
| 84 | 3 | 2361 | 3437 | gi\|1772623 | HecA [*Erwinia chrysanthemi*] | 70 | 60 | 1077 |
| 91 | 1 | 300 | 4 | gi\|295430 | epsE [*Vibrio cholerae*] | 70 | 49 | 297 |
| 74 | 1 | 541 | 2 | gi\|609627 | putative [*Vibrio cholerae*] | 69 | 54 | 540 |
| 67 | 4 | 1297 | 1581 | gi\|151469 | PilD-dependent protein [*Pseudomonas aeruginosa*] | 68 | 50 | 285 |
| 84 | 1 | 578 | 1741 | gi\|1772622 | HecB [*Erwinia chrysanthemi*] | 68 | 54 | 1164 |
| 84 | 2 | 1698 | 2363 | gi\|1772622 | HecB [*Erwinia chrysanthemi*] | 67 | 48 | 666 |
| 63 | 2 | 1734 | 1393 | gi\|1323798 | transposase [Plasmid pRL1063a] | 65 | 46 | 342 |
| 71 | 1 | 1134 | 4 | gi\|397405 | kpsE gene product [*Escherichia coli*] | 65 | 36 | 1131 |
| 64 | 2 | 2828 | 1839 | gi\|310632 | hydrophobic membrane protein [*Streptococcus gordonii*] | 64 | 38 | 990 |
| 74 | 2 | 861 | 355 | gi\|148436 | secretory component [*Erwinia chrysanthemi*] | 64 | 54 | 507 |
| 66 | 1 | 556 | 2 | gi\|1235662 | RfbC [*Myxococcus xanthus*] | 62 | 39 | 555 |
| 70 | 6 | 3017 | 2814 | gi\|1657478 | similar to *E. coli* ORF_o208 [*Escherichia coli*] | 62 | 41 | 204 |
| 85 | 1 | 278 | 66 | pir\|A45253\|A452 | activator 1 37K chain — human | 62 | 56 | 213 |
| 126 | 1 | 3 | 323 | gi\|1778562 | hypothetical protein [*Escherichia coli*] | 62 | 45 | 321 |
| 73 | 1 | 773 | 3 | pir\|S32879\|S328 | lipA protein — *Neisseria meningitidis* | 61 | 46 | 771 |
| 96 | 2 | 796 | 644 | gnl\|PID\|e276217 | T03F6.f [*Caenorhabditis elegans*] | 61 | 46 | 153 |
| 67 | 3 | 743 | 1312 | gi\|609629 | putative [*Vibrio cholerae*] | 60 | 43 | 570 |
| 70 | 10 | 4666 | 4292 | gi\|1657478 | similar to *E. coli* ORF_o208 [*Escherichia coli*] | 60 | 45 | 375 |
| 81 | 1 | 1 | 1179 | gi\|1591717 | spore coat polysaccharide biosynthesis protein E [*Methanococcus jannaschii*] | 60 | 44 | 1179 |
| 80 | 5 | 2563 | 1790 | gi\|609632 | putative [*Vibrio cholerae*] | 59 | 41 | 774 |
| 137 | 1 | 73 | 528 | gi\|1736670 | Adhesin AIDA-I precursor. [*Escherichia coli*] | 59 | 45 | 456 |
| 61 | 1 | 773 | 3 | gi\|1196968 | unknown protein [Insertion sequence IS66] | 58 | 41 | 771 |
| 63 | 5 | 2831 | 2178 | gi\|622948 | transposase [*Escherichia coli*] | 58 | 41 | 654 |
| 64 | 3 | 3568 | 2690 | gi\|1335913 | unknown [*Erysipelothrix rhusiopathiae*] | 57 | 36 | 879 |
| 64 | 1 | 1819 | 917 | gi\|153826 | adhesin B [*Streptococcus sanguis*] | 55 | 30 | 903 |
| 64 | 9 | 7008 | 6685 | gi\|152259 | lcrB gene product [Rhizobium sp.] | 55 | 42 | 324 |
| 70 | 14 | 6481 | 6753 | pir\|G42465\|G424 | hypothetical protein 88 — phage phi-R73 | 53 | 30 | 273 |
| 85 | 5 | 9317 | 1530 | gi\|144048 | filamentous hemagglutinin [*Bordetella pertussis*] | 52 | 37 | 7788 |
| 64 | 8 | 5063 | 4806 | gn1\|PID\|e264304 | F53C11.6 [*Caenorhabditis elegans*] | 51 | 27 | 258 |
| 80 | 9 | 3411 | 2761 | gi\|149309 | pulJ [*Klebsiella pneumoniae*] | 50 | 40 | 651 |
| 88 | 1 | 98 | 388 | gi\|156087 | [*Brugia malayi* myosin heavy chain gene, complete cds.], gene product [*Brugia malayi*] | 50 | 32 | 291 |
| 96 | 3 | 1127 | 687 | gi\|1196964 | unknown protein [Plasmid Ti] | 50 | 38 | 441 |
| 89 | 1 | 981 | 4 | gi\|57633 | neuronal myosin heavy chain [*Rattus rattus*] | 48 | 22 | 978 |
| 113 | 1 | 657 | 199 | gi\|147899 | extragenic suppressor [*Escherichia coli*] | 48 | 25 | 459 |
| 118 | 1 | 654 | 145 | pir\|S27564\|S275 | polysaccharide translocation-related protein — *Escherichia coli* | 48 | 25 | 510 |
| 58 | 2 | 2101 | 4245 | gi\|1235662 | RfbC [*Myxococcus xanthus*] | 47 | 35 | 2145 |

TABLE 1-continued (PAI IV)
Putative coding regions of novel *E. coli* PAI IV proteins similar to known proteins

| Contig ID | ORF ID | Start (nt) | Stop (nt) | match acession | match gene name | % sim | % ident | length (nt) |
|---|---|---|---|---|---|---|---|---|
| 87 | 1 | 595 | 134 | gi\|1235662 | RfbC [*Myxococcus xanthus*] | 42 | 28 | 462 |
| 85 | 2 | 1018 | 515 | bbs\|117606 | glycine-rich protein, atGRP (clone atGRP-1) [*Arabidopsis thaliana*, C24, Peptide Partial, 210 aa] [*Arabidopsis thaliana*] | 36 | 36 | 504 |
| 85 | 3 | 1779 | 973 | bbs\|157676 | silk fibroin heavy chain (C-terminal) [*Bombyx mori* = silkworms, Peptide Partial, 633 aa] [*Bombyx mori*] | 34 | 29 | 807 |

TABLE 2

(PAI IV)
Putative coding regions of novel *E. coli* PAI IV proteins not similar to known proteins

| Contig ID | ORF ID | Start (nt) | Stop (nt) |
|---|---|---|---|
| 58 | 1 | 1176 | 2120 |
| 61 | 2 | 54 | 560 |
| 63 | 4 | 1875 | 2639 |
| 64 | 4 | 3911 | 3627 |
| 65 | 6 | 3009 | 3239 |
| 65 | 12 | 6027 | 6683 |
| 66 | 2 | 1289 | 978 |
| 70 | 2 | 1418 | 861 |
| 70 | 3 | 1886 | 1476 |
| 70 | 4 | 2124 | 1900 |
| 70 | 5 | 2795 | 2220 |
| 70 | 7 | 3645 | 3259 |
| 70 | 8 | 4078 | 3680 |
| 70 | 9 | 4220 | 4513 |
| 70 | 11 | 4950 | 4498 |
| 70 | 12 | 4594 | 4866 |
| 70 | 15 | 6805 | 7449 |
| 70 | 16 | 9520 | 10806 |
| 73 | 7 | 3247 | 3666 |
| 74 | 3 | 720 | 1301 |
| 75 | 1 | 1 | 165 |
| 79 | 1 | 719 | 354 |
| 80 | 6 | 2108 | 2575 |
| 80 | 7 | 2831 | 2469 |
| 80 | 10 | 3223 | 3387 |
| 80 | 11 | 3541 | 3362 |
| 82 | 8 | 3313 | 4260 |
| 82 | 11 | 4340 | 5218 |
| 82 | 13 | 6090 | 5614 |
| 84 | 4 | 3487 | 3281 |
| 85 | 4 | 1485 | 2285 |
| 85 | 6 | 8373 | 9320 |
| 104 | 1 | 358 | 2 |
| 112 | 1 | 677 | 105 |
| 142 | 1 | 3 | 143 |
| 142 | 2 | 119 | 328 |

TABLE 3

(PAI V)
Putative coding regions of novel *E. coli* PAI V proteins similar to known proteins

| Contig ID | ORF ID | Start (nt) | Stop (nt) | match acession | match gene name | % sim | % ident | length (nt) |
|---|---|---|---|---|---|---|---|---|
| 14 | 3 | 2826 | 3686 | gi\|1655838 | ORFB; putative transposase [*Yersinia pestis*] | 100 | 100 | 861 |
| 14 | 2 | 1837 | 2907 | gi\|1655837 | ORFA; putative transposase [*Yersinia pestis*] | 99 | 99 | 1071 |
| 3 | 9 | 7927 | 7595 | gi\|1657499 | putative transposase for insertion sequence IS3 [*Escherichia coli*] | 89 | 85 | 333 |
| 20 | 6 | 3462 | 4304 | gi\|1208992 | unknown [*Escherichia coli*] | 87 | 73 | 843 |
| 6 | 6 | 3541 | 3263 | pir\|S43483\|S434 | Orf104 homolog — *Escherichia coli* | 81 | 62 | 279 |
| 20 | 3 | 1616 | 2332 | gi\|1033129 | ORF_o233 [*Escherichia coli*] | 80 | 61 | 717 |
| 9 | 1 | 1 | 681 | gi\|537112 | ORF_o396 [*Escherichia coli*] | 77 | 55 | 681 |
| 15 | 3 | 1899 | 1672 | pir\|S43483\|S434 | Orf104 homolog — *Escherichia coli* | 75 | 55 | 228 |
| 20 | 9 | 4302 | 4880 | gi\|1552816 | similar to *E. coli* ORF_o152 [*Escherichia coli*] | 74 | 60 | 579 |
| 14 | 13 | 12972 | 15359 | gi\|1772623 | HecA [*Erwinia chrysanthemi*] | 70 | 60 | 2388 |

TABLE 3-continued (PAI V)
Putative coding regions of novel *E. coli* PAI V proteins similar to known proteins

| Contig ID | ORF ID | Start (nt) | Stop (nt) | match acession | match gene name | % sim | % ident | length (nt) |
|---|---|---|---|---|---|---|---|---|
| 5 | 3 | 1112 | 1570 | gi\|1001717 | regulatory components of sensory transduction system [*Synechocystis* sp.] | 68 | 45 | 459 |
| 3 | 1 | 2572 | 1373 | gi\|849022 | Lactate oxidase [*Aerococcus viridans*] | 66 | 46 | 1200 |
| 3 | 8 | 6869 | 6498 | gi\|581535 | ORF140 gene product [*Rhizobium* sp.] | 66 | 45 | 372 |
| 6 | 5 | 3265 | 2951 | gi\|642184 | F19C6.1 [*Caenorhabditis elegans*] | 66 | 44 | 315 |
| 14 | 12 | 11775 | 12974 | gi\|1772622 | HecB [*Erwinia chrysanthemi*] | 66 | 50 | 1200 |
| 20 | 1 | 545 | 1450 | gi\|1033127 | ORF_o289 [*Escherichia coli*] | 66 | 45 | 906 |
| 57 | 1 | 696 | 124 | gi\|1772622 | HecB [*Erwinia chrysanthemi*] | 66 | 47 | 573 |
| 3 | 3 | 3320 | 3700 | gi\|431950 | similar to a *B. subtilis* gene (GB: BACHEMEHY_5) [*Clostridium pasteurianum*] | 65 | 34 | 381 |
| 5 | 7 | 4565 | 4239 | sp\|P39213\|YI91_ | INSERTION ELEMENT IS911 HYPOTHETICAL 12.7 KD PROTEIN. | 65 | 38 | 327 |
| 22 | 2 | 1651 | 557 | gi\|290430 | adhesin [*Escherichia coli*] | 64 | 48 | 1095 |
| 5 | 4 | 1455 | 1841 | gi\|1575577 | DNA-binding response regulator [*Thermotoga maritima*] | 61 | 47 | 387 |
| 14 | 11 | 11161 | 11937 | gi\|1772622 | HecB [*Erwinia chrysanthemi*] | 60 | 39 | 777 |
| 14 | 1 | 930 | 1700 | gi\|1657478 | similar to *E. coli* ORF_o208 [*Escherichia coli*] | 58 | 47 | 771 |
| 5 | 6 | 3834 | 3391 | gi\|155032 | ORF B [Plasmid pEa34] | 56 | 36 | 444 |
| 3 | 5 | 6500 | 5982 | gi\|1633572 | *Herpesvirus saimiri* ORF73 homolog [Kaposi's sarcoma-associated herpes-like virus] | 54 | 25 | 519 |
| 14 | 7 | 8429 | 8809 | gi\|1196729 | unknown protein [Bacteriophage P4] | 54 | 41 | 381 |
| 14 | 14 | 15191 | 21793 | gi\|144048 | filamentous hemagglutinin [*Bordetella pertussis*] | 52 | 37 | 6603 |
| 14 | 16 | 21427 | 22671 | bbs\|117613 | glycine-rich protein, atGRP (clone atGRP-4) [*Arabidopsis thaliana*, C24, Peptide Partial, 112 aa] [*Arabidopsis thaliana*] | 52 | 39 | 1245 |
| 5 | 2 | 1004 | 381 | gi\|48518 | HydC [*Wolinella succinogenes*] | 51 | 34 | 624 |
| 5 | 5 | 1941 | 3311 | gi\|143331 | alkaline phosphatase regulatory protein [*Bacillus subtilis*] | 51 | 21 | 1371 |
| 14 | 4 | 3968 | 5431 | gi\|1033120 | ORF_o469 [*Escherichia coli*] | 51 | 29 | 1464 |
| 32 | 1 | 481 | 227 | gi\|1673731 | (AE000010) *Mycoplasma pneumoniae*, fructose-permease IIBC component; similar to Swiss-Prot Accession Number P20966, from *E. coli* [*Mycoplasma pneumoniae*] | 50 | 41 | 255 |
| 20 | 17 | 7039 | 7284 | gi\|1123054 | coded for by *C. elegans* cDNA CEESN53F; similar to protein kinases including CDC15 in yeast [*Caenorhabditis elegans*] | 48 | 28 | 246 |

TABLE 4

(PAI V)
Putative coding regions of novel *E. coli* PAI V proteins not similar to known proteins

| Contig ID | ORF ID | Start (nt) | Stop (nt) |
|---|---|---|---|
| 1 | 1 | 809 | 1165 |
| 3 | 2 | 3275 | 2640 |
| 3 | 6 | 6006 | 6425 |
| 3 | 7 | 6423 | 6833 |
| 4 | 1 | 3 | 455 |
| 5 | 1 | 501 | 4 |
| 6 | 1 | 2168 | 1749 |
| 6 | 2 | 2527 | 2114 |
| 6 | 3 | 2648 | 2331 |
| 6 | 4 | 3099 | 2626 |
| 14 | 5 | 7112 | 7699 |
| 14 | 6 | 7800 | 8507 |
| 14 | 8 | 9040 | 9624 |
| 14 | 10 | 10586 | 10846 |
| 14 | 15 | 21721 | 20921 |
| 15 | 1 | 575 | 826 |
| 15 | 2 | 850 | 1365 |
| 20 | 2 | 904 | 605 |
| 20 | 4 | 2330 | 3157 |
| 20 | 5 | 3139 | 3396 |
| 20 | 7 | 3812 | 3492 |
| 20 | 8 | 4373 | 3828 |
| 20 | 18 | 7282 | 7950 |
| 22 | 1 | 356 | 3 |
| 24 | 1 | 492 | 4 |

TABLE 5

(PAI IV)
Putative coding regions of novel *E. coli* PAI IV containing known *E. coli* sequences

| Contig ID | ORF ID | Start (nt) | Stop (nt) | match acession | match gene name | percent ident | HSP nt length | ORF nt length |
|---|---|---|---|---|---|---|---|---|
| 59 | 1 | 968 | 54 | emb\|X61239\|ECPA | *E. coli* papABCDEFGHIJK genes for F13 P-pili proteins | 99 | 790 | 915 |
| 59 | 2 | 1551 | 805 | emb\|Y00529\|ECPA | *E. coli* papC gene involved in formation of pap pili | 99 | 518 | 747 |

TABLE 5-continued (PAI IV)
Putative coding regions of novel *E. coli* PAI IV containing known *E. coli* sequences

| Contig ID | ORF ID | Start (nt) | Stop (nt) | match acession | match gene name | percent ident | HSP nt length | ORF nt length |
|---|---|---|---|---|---|---|---|---|
| 59 | 3 | 1742 | 1494 | emb\|Y00529\|ECPA | *E. coli* papC gene involved in formation of pap pili | 99 | 182 | 249 |
| 61 | 4 | 1975 | 1220 | emb\|X61239\|ECPA | *E. coli* papABCDEFGHIJK genes for F13 P-pili proteins | 100 | 69 | 756 |
| 63 | 13 | 10097 | 10480 | gb\|AE000133\| | *Escherichia coli* from bases 263572 to 274477 (section 23 of 400) of the complete genome | 91 | 216 | 384 |
| 65 | 1 | 886 | 671 | gb\|U06468\| | *Escherichia coli* O111:H- insertion sequence IS1203 12.7 kDa protein and putative transposase genes, complete cds | 93 | 164 | 216 |
| 65 | 5 | 3218 | 2868 | gb\|U06468\| | *Escherichia coli* O111:H- insertion sequence IS1203 12.7 kDa protein and putative transposase genes, complete cds | 85 | 285 | 351 |
| 65 | 8 | 4064 | 3216 | gb\|U06468\| | *Escherichia coli* O111:H- insertion sequence IS1203 12.7 kDa protein and putative transposase genes, complete cds | 86 | 145 | 849 |
| 65 | 9 | 4939 | 4337 | emb\|Y00976\|ECHN | *E. coli* hns gene for DNA-binding protein H-NS (5'-region) | 96 | 53 | 603 |
| 65 | 10 | 4919 | 5266 | emb\|Y00976\|ECHN | *E. coli* hns gene for DNA-binding protein H-NS (5'-region) | 98 | 310 | 348 |
| 65 | 11 | 5206 | 5781 | gb\|AE000133\| | *Escherichia coli* from bases 263572 to 274477 (section 23 of 400) of the complete genome | 89 | 431 | 576 |
| 68 | 1 | 1575 | 1315 | emb\|X61239\|ECPA | *E. coli* papABCDEFGHIJK genes for F13 P-pili proteins | 100 | 186 | 261 |
| 68 | 2 | 2468 | 1848 | emb\|X51704\|ECPA | *Escherichia coli* papJ gene for PapJ protein | 99 | 621 | 621 |
| 68 | 3 | 2232 | 2594 | emb\|X61239\|ECPA | *E. coli* papABCDEFGHIJK genes for F13 P-pili proteins | 99 | 363 | 363 |
| 68 | 4 | 3212 | 2466 | emb\|X61239\|ECPA | *E. coli* papABCDEFGHIJK genes for F13 P-pili proteins | 100 | 747 | 747 |
| 69 | 1 | 300 | 4 | gb\|M14040\| | *E. coli* apt gene encoding adenine phosphoribosyl-transferase (APRT), complete cds | 98 | 225 | 297 |
| 69 | 2 | 383 | 117 | gb\|M14040\| | *E. coli* apt gene encoding adenine phosphoribosyl-transferase (APRT), complete cds | 95 | 162 | 267 |
| 70 | 1 | 832 | 149 | gb\|U09857\| | *Escherichia coli* 4787 o115:v165:f165 fimbrial regulatory f1652I, f1652B and f1652 A genes, complete cds | 89 | 225 | 684 |
| 70 | 17 | 10799 | 11767 | gb\|AE000291\| | *Escherichia coli*, asnV, erfK, cobT, cobS, cobU, yi52_6, yi22_3, yi21_3 genes from bases 2060089 to 2072765 (section 181 of 400) of the complete genome | 95 | 553 | 969 |
| 70 | 18 | 11809 | 11045 | gb\|AE000291\| | *Escherichia coli*, asnV, erfK, cobT, cobS, cobU, yi52_6, yi22_3, yi21_3 genes from bases 2060089 to 2072765 (section 181 of 400) of the complete genome | 94 | 595 | 765 |
| 70 | 19 | 12022 | 15222 | dbj\|D90838\|D908 | *E. coli* genomic DNA, Kohara clone #348(44.5–44.9 min.) | 89 | 2667 | 3201 |
| 70 | 20 | 15316 | 16836 | gb\|AE000292\| | *Escherichia coli*, yeeA, sbmC, yeeC, sbcB, yeeD, yeeE genes from bases 2072708 to 2083664 (section 182 of 400) of the complete genome | 96 | 1488 | 1521 |
| 70 | 21 | 16722 | 17711 | gb\|AE000292\| | *Escherichia coli*, yeeA, sbmC, yeeC, sbcB, yeeD, yeeE genes from bases 2072708 to 2083664 (section 182 of 400) of the complete genome | 96 | 82 | 990 |
| 70 | 22 | 17426 | 16776 | gb\|AE000292\| | *Escherichia coli*, yeeA, sbmC, yeeC, sbcB, yeeD, yeeE genes from bases 2072708 to 2083664 (section 182 of 400) of the complete genome | 96 | 63 | 651 |
| 72 | 1 | 12 | 1061 | gb\|M10133\| | *E. coli* (J96) hlyC, hlyA, hlyB and hlyD genes coding for chromosomal hemolysins C, A, B and D | 99 | 1024 | 1050 |
| 72 | 2 | 947 | 1285 | gb\|M10133\| | *E. coli* (J96) hlyC, hlyA, hlyB and hlyD genes coding for chromosomal hemolysins C, A, B and D | 96 | 261 | 339 |
| 73 | 6 | 4437 | 3205 | gb\|AE000379\| | *Escherichia coli* from bases 3102169 to 3112339 (section 269 of 400) of the complete genome | 95 | 392 | 1233 |
| 73 | 8 | 6177 | 4555 | gb\|U28377\| | *Escherichia coli* K-12 genome; approximately 65 to 68 minutes | 90 | 1133 | 1623 |
| 73 | 9 | 6835 | 6128 | gb\|AE000380\| | *Escherichia coli*, glcB, glcG, glcD genes from bases 3112500 to 3126189 (section 270 of 400) of the complete genome | 93 | 703 | 708 |
| 75 | 2 | 1553 | 1059 | gb\|AE000498\| | *Escherichia coli* from bases 4493507 to 4503769 (section 388 of 400) of the complete genome | 90 | 385 | 495 |
| 75 | 3 | 2579 | 1566 | gb\|AE000498\| | *Escherichia coli* from bases 4493507 to 4503769 (section 388 of 400) of the complete genome | 92 | 464 | 1014 |
| 75 | 4 | 3297 | 2743 | gb\|U07174\| | *Escherichia coli* O9:H10:K99 heat resistant agglutinin 1 gene, complete cds | 81 | 283 | 555 |
| 76 | 1 | 698 | 3 | gb\|M10133\| | *E. coli* (J96) hlyC, hlyA, hlyB and hlyD genes coding for chromosomal hemolysins C, A, B and D | 99 | 693 | 696 |
| 78 | 1 | 382 | 59 | gb\|AE000360\| | *Escherichia coli* from bases 2885166 to 2897277 (section 250 of 400) of the complete genome | 99 | 315 | 324 |
| 79 | 2 | 2620 | 1529 | gb\|M10133\| | *E. coli* (J96) hlyC, hlyA, hlyB and hlyD genes coding for chromosomal hemolysins C, A, B and D | 99 | 1084 | 1092 |
| 79 | 3 | 2925 | 2587 | gb\|M10133\| | *E. coli* (J96) hlyC, hlyA, hlyB and hlyD genes coding for chromosomal hemolysins C, A, B and D | 97 | 322 | 339 |
| 79 | 4 | 3576 | 2923 | gb\|M10133\| | *E. coli* (J96) hlyC, hlyA, hlyB and hlyD genes coding for chromosomal hemolysins C, A, B and D | 99 | 654 | 654 |
| 80 | 1 | 376 | 83 | gb\|U05251\| | *Escherichia coli* polysialic acid gene cluster region 3, promoter region | 93 | 210 | 294 |
| 80 | 2 | 638 | 210 | gb\|AE000379\| | *Escherichia coli* from bases 3102169 to 3112339 (section 269 of 400) of the complete genome | 95 | 347 | 429 |
| 80 | 3 | 1246 | 710 | gb\|AE000379\| | *Escherichia coli* from bases 3102169 to 3112339 (section 269 of 400) of the complete genome | 96 | 388 | 537 |
| 80 | 4 | 1796 | 1182 | gb\|AE000379\| | *Escherichia coli* from bases 3102169 to 3112339 (section 269 of 400) of the complete genome | 94 | 397 | 615 |

TABLE 5-continued

(PAI IV)
Putative coding regions of novel E. coli PAI IV containing known E. coli sequences

| Contig ID | ORF ID | Start (nt) | Stop (nt) | match acession | match gene name | percent ident | HSP nt length | ORF nt length |
|---|---|---|---|---|---|---|---|---|
| 82 | 1 | 1 | 567 | emb\|X74567\|ECKP | E. coli K5 antigen gene cluster region 1 kpsE, kpsD, kpsU, kpsC and kpsS genes | 87 | 551 | 567 |
| 82 | 2 | 549 | 1157 | emb\|X74567\|ECKP | E. coli K5 antigen gene cluster region 1 kpsE, kpsD, kpsU, kpsC and kpsS genes | 88 | 554 | 609 |
| 82 | 3 | 1500 | 1180 | gb\|AE000292\| | Escherichia coli, yeeA, sbmC, yeeC, sbcB, yeeD, yeeE genes from bases 2072708 to 2083664 (section 182 of 400) of the complete genome | 90 | 62 | 321 |
| 82 | 4 | 2163 | 1519 | gb\|AE000292\| | Escherichia coli, yeeA, sbmC, yeeC, sbcB, yeeD, yeeE genes from bases 2072708 to 2083664 (section 182 of 400) of the complete genome | 89 | 143 | 645 |
| 82 | 5 | 2594 | 2139 | gb\|AE000292\| | Escherichia coli, yeeA, sbmC, yeeC, sbcB, yeeD, yeeE genes from bases 2072708 to 2083664 (section 182 of 400) of the complete genome | 97 | 456 | 456 |
| 82 | 6 | 3000 | 2605 | gb\|AE000292\| | Escherichia coli, yeeA, sbmC, yeeC, sbcB, yeeD, yeeE genes from bases 2072708 to 2083664 (section 182 of 400) of the complete genome | 98 | 396 | 396 |
| 82 | 7 | 3463 | 3047 | gb\|AE000292\| | Escherichia coli, yeeA, sbmC, yeeC, sbcB, yeeD, yeeE genes from bases 2072708 to 2083664 (section 182 of 400) of the complete genome | 96 | 283 | 417 |
| 82 | 9 | 3831 | 3337 | gb\|AE000292\| | Escherichia coli, yeeA, sbmC, yeeC, sbcB, yeeD, yeeE genes from bases 2072708 to 2083664 (section 182 of 400) of the complete genome | 96 | 453 | 495 |
| 83 | 1 | 3 | 311 | gb\|AE000151\| | Escherichia coli, ybaE, cof, mdlA, mdlB, glnK, amtB, tesB, ffs genes from bases 464774 to 475868 (section 41 of 400) of the complete genome | 99 | 207 | 309 |
| 83 | 2 | 176 | 433 | gb\|AE000151\| | Escherichia coli, ybaE, cof, mdlA, mdlB, glnK, amtB, tesB, ffs genes from bases 464774 to 475868 (section 41 of 400) of the complete genome | 100 | 223 | 258 |
| 86 | 1 | 529 | 2 | gb\|AE000379\| | Escherichia coli from bases 3102169 to 3112339 (section 269 of 400) of the complete genome | 93 | 398 | 528 |
| 93 | 1 | 440 | 3 | gb\|M10133\| | E. coli (J96) hlyC, hlyA, hlyB and hlyD genes coding for chromosomal hemolysins C, A, B and D | 95 | 351 | 438 |
| 94 | 1 | 368 | 72 | emb\|X14180\|ECGL | Escherichia coli glutamine permease glnHPQ operon | 100 | 229 | 297 |
| 99 | 1 | 161 | 586 | gb\|AE000379\| | Escherichia coli from bases 3102169 to 3112339 (section 269 of 400) of the complete genome | 98 | 426 | 426 |
| 99 | 2 | 643 | 476 | gb\|AE000379\| | Escherichia coli from bases 3102169 to 3112339 (section 269 of 400) of the complete genome | 99 | 168 | 168 |
| 99 | 3 | 532 | 1092 | gb\|AE000379\| | Escherichia coli from bases 3102169 to 3112339 (section 269 of 400) of the complete genome | 95 | 537 | 561 |
| 99 | 4 | 1094 | 1396 | gb\|AE000379\| | Escherichia coli from bases 3102169 to 3112339 (section 269 of 400) of the complete genome | 94 | 274 | 303 |
| 102 | 1 | 527 | 3 | emb\|Y00529\|ECPA | E. coli papC gene involved in formation of pap pili | 100 | 427 | 525 |
| 102 | 2 | 762 | 373 | emb\|Y00529\|ECPA | E. coli papC gene involved in formation of pap pili | 99 | 333 | 390 |
| 105 | 1 | 377 | 3 | gb\|AE000480\| | Escherichia coli from bases 4277211 to 4288813 (section 370 of 400) of the complete genome | 100 | 343 | 375 |
| 107 | 1 | 2 | 397 | gb\|M10133\| | E. coli (J96) hlyC, hlyA, hlyB and hlyD genes coding for chromosomal hemolysins C, A, B and D | 99 | 390 | 396 |
| 107 | 2 | 406 | 966 | gb\|M10133\| | E. coli (J96) hlyC, hlyA, hlyB and hlyD genes coding for chromosomal hemolysins C, A, B and D | 99 | 549 | 561 |
| 110 | 1 | 148 | 2 | emb\|X56175\|ECSE | Escherichia coli secD and secF genes for membrane proteins involved in protein export | 99 | 143 | 147 |
| 110 | 2 | 312 | 40 | gb\|M63939\| | E. coli tRNA-guanine-transglycosylase (tgt) gene, complete cds | 100 | 125 | 273 |
| 115 | 1 | 501 | 325 | gb\|AE000459\| | Escherichia coli from bases 4013123 to 4024654 (section 349 of 400) of the complete genome | 98 | 177 | 177 |
| 117 | 1 | 3 | 302 | gb\|AE000506\| | Escherichia coli from bases 4584059 to 4594314 (section 396 of 400) of the complete genome | 100 | 263 | 300 |
| 121 | 1 | 2 | 250 | gb\|M16202\| | E. coli papH gene encoding a pilin-like protein | 98 | 148 | 249 |
| 123 | 1 | 361 | 2 | gb\|AE000379\| | Escherichia coli from bases 3102169 to 3112339 (section 269 of 400) of the complete genome | 99 | 113 | 360 |
| 127 | 1 | 2 | 229 | gb\|AE000233\| | Escherichia coli, racC, ydaD, sieB, trkG genes from bases 1415432 to 1425731 (section 123 of 400) of the complete genome | 100 | 200 | 228 |
| 127 | 2 | 227 | 382 | gb\|AE000233\| | Escherichia coli, racC, ydaD, sieB, trkG genes from bases 1415432 to 1425731 (section 123 of 400) of the complete genome | 97 | 113 | 156 |
| 130 | 1 | 337 | 2 | emb\|X60200\|ECTN | E. coli transposon Tn1000 (gamma delta) tnpR and tnpA genes for resolvase and transposase | 99 | 335 | 336 |
| 131 | 1 | 510 | 79 | gb\|M30198\| | E. coli recQ gene complete cds, and pldA gene, 3' end | 98 | 304 | 432 |
| 131 | 2 | 743 | 270 | gb\|M30198\| | E. coli recQ gene complete cds, and pldA gene, 3' end | 99 | 314 | 474 |
| 133 | 1 | 1 | 258 | gb\|AE000115\| | Escherichia coli, yabF, kefC, folA, apaH, apaG, ksgA, pdxA, surA, imp genes from bases 47163 to 57264 (section 5 of 400) of the complete genome | 98 | 237 | 258 |

TABLE 5-continued

(PAI IV)
Putative coding regions of novel *E. coli* PAI IV containing known *E. coli* sequences

| Contig ID | ORF ID | Start (nt) | Stop (nt) | match acession | match gene name | percent ident | HSP nt length | ORF nt length |
|---|---|---|---|---|---|---|---|---|
| 133 | 2 | 192 | 350 | gb\|AE000115\| | *Escherichia coli*, yabF, kefC, folA, apaH, apaG, ksgA, pdxA, surA, imp genes from bases 47163 to 57264 (section 5 of 400) of the complete genome | 99 | 115 | 159 |
| 135 | 1 | 103 | 327 | emb\|X02143\|ECPL | *Escherichia coli* K-12 pldA gene for DR-phospholipase A | 97 | 178 | 225 |
| 135 | 2 | 152 | 409 | emb\|X02143\|ECPL | *Escherichia coli* K-12 pldA gene for DR-phospholipase A | 98 | 157 | 258 |
| 136 | 1 | 122 | 532 | gb\|AE000459\| | *Escherichia coli* from bases 4013123 to 4024654 (section 349 of 400) of the complete genome | 97 | 237 | 411 |
| 140 | 1 | 576 | 244 | gb\|AE000291\| | *Escherichia coli*, asnV, erfK, cobT, cobS, cobU, yi52_6, yi22_3, yi21_3 genes from bases 2060089 to 2072765 (section 181 of 400) of the complete genome | 89 | 329 | 333 |
| 141 | 1 | 445 | 2 | gb\|AE000291\| | *Escherichia coli*, asnV, erfK, cobT, cobS, cobU, yi52_6, yi22_3, yi21_3 genes from bases 2060089 to 2072765 (section 181 of 400) of the complete genome | 77 | 432 | 444 |

TABLE 6

(PAI V)
Putative coding regions of novel *E. coli* PAI V containing known *E. coli* sequences

| Contig ID | ORF ID | Start (nt) | Stop (nt) | match acession | match gene name | percent ident | HSP nt length | ORF nt length |
|---|---|---|---|---|---|---|---|---|
| 3 | 4 | 6150 | 4855 | gb\|AE000292\| | *Escherichia coli*, yeeA, sbmC, yeeC, sbcB, yeeD, yeeE genes from bases 2072708 to 2083664 (section 182 of 400) of the complete genome | 91 | 129 | 1296 |
| 3 | 10 | 8214 | 7723 | emb\|X02311\|ECIS | *E. coli* insertion sequence IS3 | 76 | 274 | 492 |
| 3 | 11 | 7867 | 8319 | emb\|Z11606\|ECIS | *E. coli* DNA for insertion sequence IS3 | 80 | 378 | 453 |
| 3 | 12 | 8462 | 8157 | emb\|Z11606\|ECIS | *E. coli* DNA for insertion sequence IS3 | 90 | 267 | 306 |
| 3 | 13 | 8487 | 8663 | gb\|L19084\| | *Escherichia coli* RhsD genetic element; core protein (rhsD) gene, complete cds; complete ORF-D2; complete ORF-D3 | 96 | 112 | 177 |
| 4 | 2 | 1441 | 815 | gb\|AE000498\| | *Escherichia coli* from bases 4493507 to 4503769 (section 388 of 400) of the complete genome | 91 | 577 | 627 |
| 4 | 3 | 923 | 1372 | gb\|AE000498\| | *Escherichia coli* from bases 4493507 to 4503769 (section 388 of 400) of the complete genome | 92 | 448 | 450 |
| 4 | 4 | 2343 | 1324 | gb\|AE000498\| | *Escherichia coli* from bases 4493507 to 4503769 (section 388 of 400) of the complete genome | 92 | 244 | 1020 |
| 7 | 1 | 3 | 743 | emb\|X61239\|ECPA | *E. coli* papABCDEFGHIJK genes for F13 P-pili proteins | 100 | 741 | 741 |
| 7 | 2 | 977 | 615 | emb\|X61239\|ECPA | *E. coli* papABCDEFGHIJK genes for F13 P-pili proteins | 99 | 363 | 363 |
| 7 | 3 | 741 | 1214 | emb\|X51704\|ECPA | *Escherichia coli* papJ gene for PapJ protein | 98 | 459 | 474 |
| 8 | 1 | 438 | 4 | emb\|X60200\|ECTN | *E. coli* transposon Tn1000 (gamma delta) tnpR and tnpA genes for resolvase and transposase | 99 | 435 | 435 |
| 10 | 1 | 1932 | 2426 | emb\|X61238\|ECPR | *E. coli* prsEFG genes for F13 pili tip proteins | 97 | 462 | 495 |
| 11 | 1 | 903 | 1550 | gb\|M10133\| | *E. coli* (J96) hlyC, hlyA, hlyB and hlyD genes coding for chromosomal hemolysins C, A, B and D | 99 | 452 | 648 |
| 12 | 1 | 2559 | 1531 | gb\|U82598\| | *Escherichia coli* genomic sequence of minutes 9 to 12 | 100 | 1029 | 1029 |
| 12 | 2 | 1594 | 1860 | emb\|X13668\|ECIS | *E. coli* insertion element 5 (IS5) DNA | 100 | 267 | 267 |
| 12 | 3 | 1858 | 2235 | gb\|U95365\| | *Escherichia coli* transposon IS5, transposase (is5B) gene, complete cds | 99 | 354 | 378 |
| 13 | 1 | 93 | 1424 | emb\|X61239\|ECPA | *E. coli* papABCDEFGHIJK genes for F13 P-pili proteins | 99 | 885 | 1332 |
| 14 | 9 | 9832 | 10515 | gb\|U09857\| | *Escherichia coli* 4787 o115:v165:f165 fimbrial regulatory f1652I, f1652B and f1652 A genes, complete cds | 92 | 225 | 684 |
| 16 | 1 | 1 | 375 | gb\|U07174\| | *Escherichia coli* O9:H10:K99 heat resistant agglutinin 1 gene, complete cds | 94 | 320 | 375 |
| 16 | 2 | 263 | 616 | gb\|U07174\| | *Escherichia coli* O9:H10:K99 heat resistant agglutinin 1 gene, complete cds | 98 | 283 | 354 |
| 17 | 1 | 282 | 4 | emb\|Y00529\|ECPA | *E. coli* papC gene involved in formation of pap pili | 98 | 240 | 279 |
| 17 | 2 | 410 | 174 | emb\|Y00529\|ECPA | *E. coli* papC gene involved in formation of pap pili | 100 | 168 | 237 |
| 19 | 1 | 1 | 369 | gb\|AE000418\| | *Escherichia coli* from bases 3550279 to 3561054 (section 308 of 400) of the complete genome | 99 | 347 | 369 |
| 20 | 10 | 5401 | 4829 | gb\|AE000292\| | *Escherichia coli*, yeeA, sbmC, yeeC, sbcB, yeeD, yeeE genes from bases 2072708 to 2083664 (section 182 of 400) of the complete genome | 96 | 468 | 573 |
| 20 | 11 | 4874 | 5371 | gb\|AE000292\| | *Escherichia coli*, yeeA, sbmC, yeeC, sbcB, yeeD, yeeE genes from bases 2072708 to 2083664 (section 182 of 400) of the complete genome | 96 | 453 | 498 |
| 20 | 12 | 5245 | 5679 | gb\|AE000292\| | *Escherichia coli*, yeeA, sbmC, yeeC, sbcB, yeeD, yeeE genes from bases 2072708 to 2083664 (section 182 of 400) of the complete genome | 89 | 235 | 435 |

TABLE 6-continued (PAI V)
Putative coding regions of novel *E. coli* PAI V containing known *E. coli* sequences

| Contig ID | ORF ID | Start (nt) | Stop (nt) | match acession | match gene name | percent ident | HSP nt length | ORF nt length |
|---|---|---|---|---|---|---|---|---|
| 20 | 13 | 5732 | 6139 | gb\|AE000292\| | *Escherichia coli*, yeeA, sbmC, yeeC, sbcB, yeeD, yeeE genes from bases 2072708 to 2083664 (section 182 of 400) of the complete genome | 93 | 329 | 408 |
| 20 | 14 | 6316 | 5822 | gb\|AE000292\| | *Escherichia coli*, yeeA, sbmC, yeeC, sbcB, yeeD, yeeE genes from bases 2072708 to 2083664 (section 182 of 400) of the complete genome | 95 | 239 | 495 |
| 20 | 15 | 6048 | 6590 | gb\|AE000292\| | *Escherichia coli*, yeeA, sbmC, yeeC, sbcB, yeeD, yeeE genes from bases 2072708 to 2083664 (section 182 of 400) of the complete genome | 87 | 406 | 543 |
| 20 | 16 | 6569 | 7075 | gb\|AE000292\| | *Escherichia coli*, yeeA, sbmC, yeeC, sbcB, yeeD, yeeE genes from bases 2072708 to 2083664 (section 182 of 400) of the complete genome | 87 | 136 | 507 |
| 20 | 19 | 8686 | 9915 | gb\|M67452\| | *Escherichia coli* lysine decarboxylase (cadB, and cadC, complete cds, and cadA, 5' end) genes | 98 | 1205 | 1230 |
| 20 | 20 | 10604 | 11938 | gb\|U14003\| | *Escherichia coli* K-12 chromosomal region from 92.8 to 00.1 minutes | 98 | 1308 | 1335 |
| 20 | 21 | 11940 | 12368 | gb\|M76411\| | *E. coli* cadA gene, 5' cds and cadB and cadC genes, complete cds | 100 | 363 | 429 |
| 21 | 1 | 369 | 4 | emb\|X03391\|ECPA | *E. coli* major pilu subunit genes genes papI, papB, papA and papH 5'-region | 98 | 201 | 366 |
| 23 | 1 | 1 | 879 | gb\|U14003\| | *Escherichia coli* K-12 chromosomal region from 92.8 to 00.1 minutes | 98 | 879 | 879 |
| 23 | 2 | 900 | 16 | gb\|U14003\| | *Escherichia coli* K-12 chromosomal region from 92.8 to 00.1 minutes | 98 | 885 | 885 |
| 23 | 3 | 953 | 1186 | emb\|X77707\|ECCY | *E. coli* ORF112, DIPZ and ORF191 genes | 99 | 225 | 234 |
| 23 | 4 | 1223 | 2677 | emb\|X77707\|ECCY | *E. coli* ORF112, DIPZ and ORF191 genes | 97 | 1454 | 1455 |
| 25 | 1 | 536 | 171 | emb\|X60200\|ECTN | *E. coli* transposon Tn1000 (gamma delta) tnpR and tnpA genes for resolvase and transposase | 100 | 164 | 366 |
| 25 | 2 | 1128 | 562 | emb\|X60200\|ECTN | *E. coli* transposon Tn1000 (gamma delta) tnpR and tnpA genes for resolvase and transposase | 99 | 459 | 567 |
| 27 | 1 | 708 | 436 | emb\|X61239\|ECPA | *E. coli* papABCDEFGHIJK genes for F13 P-pili proteins | 100 | 252 | 273 |
| 28 | 1 | 309 | 4 | emb\|X77707\|ECCY | *E. coli* ORF112, DIPZ and ORF191 genes | 98 | 278 | 306 |
| 28 | 2 | 431 | 213 | emb\|X77707\|ECCY | *E. coli* ORF112, DIPZ and ORF191 genes | 96 | 150 | 219 |
| 30 | 1 | 399 | 4 | gb\|M26893\| | *E. coli* amidophosphoribosyltransferase (purF) gene, complete cds | 98 | 295 | 396 |
| 31 | 1 | 706 | 170 | emb\|X56780\|ECRR | *E. coli* terminator sequence of RNA G operon gene | 99 | 513 | 537 |
| 37 | 1 | 2 | 400 | gb\|M63703\| | *E. coli* pyruvate kinase type II (pykA) gene, complete cds | 98 | 399 | 399 |
| 38 | 1 | 463 | 2 | emb\|X13463\|ECGU | *Escherichia coli* gutM gene and gutR gene for activator and repressor proteins | 99 | 363 | 462 |
| 42 | 1 | 413 | 3 | gb\|M64367\| | *Escherichia coli* DNA recombinase (recG) gene, complete cds, spoU gene, 3' end, and gltS gene, 3' end | 97 | 316 | 411 |
| 42 | 2 | 115 | 591 | gb\|M64367\| | *Escherichia coli* DNA recombinase (recG) gene, complete cds, spoU gene, 3' end, and gltS gene, 3' end | 98 | 266 | 477 |
| 46 | 1 | 2 | 277 | emb\|X77707\|ECCY | *E. coli* ORF112, DIPZ and ORF191 genes | 98 | 187 | 276 |
| 48 | 1 | 1 | 171 | gb\|AE000491\| | *Escherichia coli* from bases 4413548 to 4424699 (section 381 of 400) of the complete genome | 98 | 162 | 171 |
| 48 | 2 | 105 | 464 | gb\|AE000491\| | *Escherichia coli* from bases 4413548 to 4424699 (section 381 of 400) of the complete genome | 98 | 144 | 360 |
| 49 | 1 | 2 | 172 | gb\|U00800\| | *Escherichia coli* cloning vector Pk184, complete sequence, kanamycin phosphotransferase (kan) and (lacZalpha) genes, complete cds | 98 | 167 | 171 |
| 50 | 1 | 414 | 4 | gb\|AE000341\| | *Escherichia coli*, glyA, hmpA, glnB, yfhA, yfhG genes from bases 2677406 to 2687636 (section 231 of 400) of the complete genome | 99 | 411 | 411 |
| 52 | 1 | 2 | 307 | emb\|X60200\|ECTN | *E. coli* transposon Tn1000 (gamma delta) tnpR and tnpA genes for resolvase and transposase | 100 | 284 | 306 |
| 53 | 1 | 280 | 41 | gb\|M36536\| | *E. coli* htrA gene, complete cds | 100 | 131 | 240 |
| 53 | 2 | 558 | 214 | gb\|M36536\| | *E. coli* htrA gene, complete cds | 99 | 315 | 345 |
| 54 | 1 | 9 | 263 | gb\|AE000381\| | *Escherichia coli* from bases 3125914 to 3136425 (section 271 of 400) of the complete genome | 94 | 111 | 255 |
| 55 | 1 | 1 | 675 | gb\|AE000179\| | *Escherichia coli*, modA, modB, modC, ybhA, ybhE, ybhD genes from bases 794199 to 805132 (section 69 of 400) of the complete genome | 98 | 332 | 675 |

While the present invention has been described in some detail for purposes of clarity and understanding, one skilled in the art will appreciate that various changes in form and detail can be made without departing from the true scope of the invention.

All patents, patent applications and publications recited herein are hereby incorporated by reference.

What is claimed is:

1. An isolated polynucleotide fragment comprising a nucleic acid sequence encoding an amino acid sequence encoded by an ORF selected from the group consisting of:
   (a) ORF ID NO:14 of Contig ID NO:14, represented by nucleotides 15191–21793 of SEQ ID NO:14;
   (b) ORF ID NO:1 of Contig ID NO:63, represented by nucleotides 2–667 of SEQ ID NO:63;
   (c) ORF ID NO:1 of Contig ID NO:64, represented by nucleotides 917–1819 of SEQ ID NO:64;
   (d) ORF ID NO:2 of Contig ID NO:64, represented by nucleotides 1839–2828 of SEQ ID NO:64;
   (e) ORF ID NO:9 of Contig ID NO:64, represented by nucleotides 6685–7008 of SEQ ID NO:64;
   (f) ORF ID NO:3 of Contig ID NO:84, represented by nucleotides 2361–3437 of SEQ ID NO:84;
   (g) ORF ID NO: 1 of Contig ID NO:89, represented by nucleotides 4–981 of SEQ ID NO:89;
   (h) ORF ID NO: 1 of Contig ID NO:137, represented by nucleotides 73–528 of SEQ ID NO:137;
   (i) ORF ID NO: 1 of Contig ID NO: 140, represented by nucleotides 244–576 of SEQ ID NO: 140, and
   (j) ORF ID NO: 1 of Contig ID NO: 141, represented by nucleotides 2–445 of SEQ ID NO: 141.

2. The isolated polynucleotide of claim 1, wherein said polynucleotide comprises a heterologous polynucleotide sequence.

3. The isolated polynucleotide of claim 2, wherein said heterologous polynucleotide sequence encodes a heterologous polypeptide.

4. A method for making a recombinant vector comprising inserting the isolated polynucleotide of claim 1 into a vector.

5. A recombinant vector comprising the isolated polynucleotide of claim 1.

6. The recombinant vector of claim 5, wherein said polynucleotide is operably associated with a heterologous regulatory sequence that controls gene expression.

7. A recombinant host cell comprising the isolated polynucleotide of claim 1.

8. The recombinant host cell of claim 7, wherein said polynucleotide is operably associated with a heterologous regulatory sequence that controls gene expression.

9. The isolated polynucleotide fragment of claim 1, wherein said ORF is the ORF of (a).

10. The isolated polynucleotide fragment of claim 1, wherein said ORF is the ORF of (b).

11. The isolated polynucleotide fragment of claim 1, wherein said ORF is the ORF of (c).

12. The isolated polynucleotide fragment of claim 1, wherein said ORF is the ORF of (d).

13. The isolated polynucleotide fragment of claim 1, wherein said ORF is the ORF of (e).

14. The isolated polynucleotide fragment of claim 1, wherein said ORF is the ORF of (f).

15. The isolated polynucleotide fragment of claim 1, wherein said ORF is the ORF of (g).

16. The isolated polynucleotide fragment of claim 1, wherein said ORF is the ORF of (h).

17. The isolated polynucleotide fragment of claim 1, wherein said ORF is the ORF of (i).

18. The isolated polynucleotide fragment of claim 1, wherein said ORF is the ORF of (j).

19. An isolated polynucleotide comprising a nucleic acid sequence encoding at least 15 contiguous amino acid residues of an amino acid sequence encoded by an ORF selected from the group consisting of:
(a) ORF ID NO:14 of Contig ID NO:14, represented by nucleotides 15191–21793 of SEQ ID NO:14;
(b) ORF ID NO: 1 of Contig ID NO:63, represented by nucleotides 2–667 of SEQ ID NO:63;
(c) ORF ID NO:1 of Contig ID NO:64, represented by nucleotides 917–1819 of SEQ ID NO:64;
(d) ORF ID NO:2 of Contig ID NO:64, represented by nucleotides 1839–2828 of SEQ ID NO:64;
(e) ORF ID NO:9 of Contig ID NO:64, represented by nucleotides 6685–7008 of SEQ ID NO:64;
(f) ORF ID NO:3 of Contig ID NO:84, represented by nucleotides 2361–3437 of SEQ ID NO:84;
(g) ORF ID NO:1 of Contig ID NO:89, represented by nucleotides 4–981 of SEQ ID NO:89;
(h) ORF ID NO:1 of Contig ID NO:137, represented by nucleotides 73–528 of SEQ ID NO:137;
(i) ORE ID NO:1 of Contig ID NO:140, represented by nucleotides 244–576 of SEQ ID NO:140; and
(j) ORF ID NO:1 of Contig ID NO:141, represented by nucleotides 2–445 of SEQ ID NO:141.

20. An isolated polynucleotide comprising a nucleic acid sequence complementary to the polynucleotide of claim 19.

21. The isolated polynucleotide of claim 19, wherein said polynucleotide comprises a nucleic acid sequence encoding at least 30 contiguous amino acid residues of an amino acid sequence encoded by an ORF selected from the group consisting of:
(a) ORF ID NO:14 of Contig ID NO:14, represented by nucleotides 15191–21793 of SEQ ID NO:14;
(b) ORF ID NO:1 of Contig ID NO:63, represented by nucleotides 2–667 of SEQ ID NO:63;
(c) ORF ID NO:1 of Contig ID NO:64, represented by nucleotides 917–1819 of SEQ IDNO:64;
(d) ORF ID NO:2 of Contig ID NO:64, represented by nucleotides 1839–2828 of SEQ ID NO:64,
(e) ORF ID NO:9 of Contig ID NO:64, represented by nucleotides 6685–7008 of SEQ ID NO:64;
(f) ORF ID NO:3 of Contig ID NO:84, represented by nucleotides 2361–3437 of SEQ ID NO:84;
(g) ORF ID NO:1 of Contig ID NO:89, represented by nucleotides 4–981 of SEQ ID NO:89;
(h) ORF ID NO:1 of Contig ID NO:137, represented by nucleotides 73–528 of SEQ ID NO:137;
(i) ORF ID NO:1 of Contig ID NO:140, represented by nucleotides 244–576 of SEQ ID NO:140; and
(j) ORF ID NO:1 of Contig ID NO:141, represented by nucleotides 2–445 of SEQ ID NO:141.

22. An isolated polynucleotide comprising a nucleic acid sequence complementary to the polynucleotide of claim 21.

23. The isolated polynucleotide of claim 21, wherein said ORF is the ORF of (a).

24. The isolated polynucleotide of claim 21, wherein said ORF is the ORF of (b).

25. The isolated polynucleotide of claim 21, wherein said ORF is the ORF of (c).

26. The isolated polynucleotide of claim 21 wherein said ORF is the ORF of (d).

27. The isolated polynucleotide of claim 21 wherein said ORF is the ORF of (e).

28. The isolated polynucleotide of claim 21, wherein said ORF is the ORF of (f).

29. The isolated polynucleotide of claim 21, wherein said ORF is the ORF of (g).

30. The isolated polynucleotide of claim 21, wherein said ORF is the ORF of (h).

31. The isolated polynucleotide of claim 21, wherein said ORF is the ORF of (i).

32. The isolated polynucleotide of claim 21, wherein said ORF is the ORF of (j).

33. The isolated polynucleotide of claim 21, wherein said polynucleotide comprises a heterologous polynucleotide sequence.

34. The isolated polynucleotide of claim 33, wherein said heterologous polynucleotide sequence encodes a heterologous polypeptide.

35. A method for making a recombinant vector comprising inserting the isolated polynucleotide of claim 21 into a vector.

36. A recombinant vector comprising the isolated polynucleotide of claim 21.

37. The recombinant vector of claim 36, wherein said polynucleotide is operably associated with a heterologous regulatory sequence that controls gene expression.

38. A recombinant host cell comprising the isolated polynucleotide of claim 21.

39. The recombinant host cell of claim 38, wherein said polynucleotide is operably associated with a heterologous regulatory sequence that controls gene expression.

40. The isolated polynucleotide of claim 19, wherein said ORF is the ORF of (a).

41. The isolated polynucleotide of claim 19, wherein said ORF is the ORF of (b).

42. The isolated polynucleotide of claim 19, wherein said ORF is the ORF of (c).

43. The isolated polynucleotide of claim 19, wherein said ORF is the ORF of (d).

44. The isolated polynucleotide of claim 19, wherein said ORF is the ORF of (e).

45. The isolated polynucleotide of claim 19, wherein said ORF is the ORF of (f).

46. The isolated polynucleotide of claim 19, wherein said ORF is the ORF of (g).

47. The isolated polynucleotide of claim 19, wherein said ORF is the ORF of (h).

48. The isolated polynucleotide of claim 19, wherein said ORF is the ORF of (i).

49. The isolated polynucleotide of claim 19, wherein said ORF is the ORF of (j).

50. The isolated polynucleotide of claim 19, wherein said polynucleotide comprises a heterologous polynucleotide sequence.

51. The isolated polynucleotide of claim 50, wherein said heterologous polynucleotide sequence encodes a heterologous polypeptide.

52. A method for making a recombinant vector comprising inserting the isolated polynucleotide of claim 19 into a vector.

53. A recombinant vector comprising the isolated polynucleotide of claim 19.

54. The recombinant vector of claim 53, wherein said polynucleotide is operably associated with a heterologous regulatory sequence that controls gene expression.

55. A recombinant host cell comprising the isolated polynucleotide of claim 19.

56. The recombinant host cell of claim 55, wherein said polynucleotide is operably associated with a heterologous regulatory sequence that controls gene expression.

57. An isolated polynucleotide fragment comprising a nucleic acid sequence which hybridizes under hybridization conditions, comprising a wash buffer consisting of 0.1×SSC at 65° C., to the complementary strand of an ORF selected from the group consisting of:
（a) ORF ID NO:14 of Contig ID NO:14, represented by nucleotides 15191–21793 of SEQ ID NO:14;
（b) ORF ID NO:1 of Contig ID NO:63, represented by nucleotides 2–667 of SEQ ID NO:63;
（c) ORF ID NO:1 of Contig ID NO:64, represented by nucleotides 917–1819 of SEQ ID NO:64;
（d) ORF ID NO:2 of Contig ID NO:64, represented by nucleotides 1839–2828 of SEQ ID NO:64;
（e) ORF ID NO:9 of Contig ID NO:64, represented by nucleotides 6685–7008 of SEQ ID NO:64;
（f) ORF ID NO:3 of Contig ID NO:84, represented by nucleotides 2361–3437 of SEQ ID NO:84;
（g) ORF ID NO:1 of Contig ID NO:89, represented by nucleotides 4–981 of SEQ ID NO:89;
（h) ORF ID NO:1 of Conitig ID NO:137 represented by nucleotides 73–528 of SEQ ID NO:137;
（i) ORF ID NO:1 of Contig ID NO:140, represented by nucleotides 244–576 of SEQ ID NO:140; and
（j) ORF NO:1 of Contig ID NO:141, represented by nucleotides 2–445 of SEQ ID NO:141.

58. An isolated polynucleotide comprising a nucleic acid sequence complementary to the polynucleotide of claim 57.

59. The isolated polynucleotide fragment of claim 57, wherein said ORF is the ORF of (a).

60. The isolated polynucleotide fragment of claim 57, wherein said ORF is the ORF of (b).

61. The isolated polynucleotide fragment of claim 57, wherein said ORF is the ORF of (c).

62. The isolated polynucleotide fragment of claim 57, wherein said ORF is the ORF of (d).

63. The isolated polynucleotide fragment of claim 57, wherein said ORF is the ORF of (e).

64. The isolated polynucleotide fragment of claim 57, wherein said ORF is the ORF of (f).

65. The isolated polynucleotide fragment of claim 57, wherein said ORF is the ORF of (g).

66. The isolated polynucleotide fragment of claim 57, wherein said ORF is the ORF of (h).

67. The isolated polynucleotide fragment of claim 57, wherein said ORF is the ORF of (i).

68. The isolated polynucleotide fragment of claim 57, wherein said ORF is the ORF of (j).

69. The isolated polynucleotide of claim 57, wherein said polynucleotide comprises a heterologous polynucleotide sequence.

70. The isolated polynucleotide of claim 69, wherein said heterologous polynucleotide sequence encodes a heterologous polypeptide.

71. A method for making a recombinant vector comprising inserting the isolated polynucleotide of claim 57 into a vector.

72. A recombinant vector comprising the isolated polynucleotide of claim 57.

73. The recombinant vector of claim 72, wherein said polynucleotide is operably associated with a heterologous regulatory sequence that controls gene expression.

74. A recombinant host cell comprising the isolated polynucleotide of claim 57.

75. The recombinant host cell of claim 74, wherein said polynucleotide is operably associated with a heterologous regulatory sequence that controls gene expression.

76. An isolated polynucleotide comprising at least 50 contiguous nucleotides of an ORF selected from the group consisting of:
（a) ORF ID NO:14 of Contig ID NO:14, represented by nucleotides 15191 –21793 of SEQ ID NO:14;
（b) ORF ID NO:1 of Contig ID NO:63, represented by nucleotides 2–667 of SEQ ID NO:63;
（c) ORF ID NO:1 of Contig ID NO:64, represented by nucleotides 917–1819 of SEQ ID NO:64;
（d) ORF ID NO:2 of Contig ID NO:64, represented by nucleotides 1839–2828 of SEQ ID NO:64;
（e) ORF ID NO:9 of Contig ID NO:64, represented by nucleotides 6685–7008 of SEQ ID NO:64;
（f) ORF ID NO:3 of Contig ID NO:84, represented by nucleotides 2361–3437 of SEQ ID NO:84;
（g) ORF ID NO:1 of Contig ID NO:89, represented by nucleotides 4–981 of SEQ ID NO:89;
（h) ORF ID NO:1 of Contig ID NO:137, represented by nucleotides 73–528 of SEQ ID NO:137;
（i) ORF ID NO:1 of Contig ID NO:140, represented by nucleotides 244–576 of SEQ ID NO:140; and
（j) ORF ID NO:1 of Contig ID NO:141, represented by nucleotides 2–445 of SEQ ID NO:141.

77. An isolated polynucleotide comprising a nucleic acid sequence complementary to the polynucleotide of claim 76.

78. The isolated polynucleotide of claim 76 comprising at least 100 contiguous nucleotides of an ORF selected from the group consisting of:
（a) ORF ID NO:14 of Contig ID NO:14, represented by nucleotides 15191–21793 of SEQ ID NO:14;
（b) ORF ID NO:1 of Contig ID NO:63, represented by nucleotides 2–667 of SEQ ID NO:63;

(c) ORF ID NO:1 of Contig ID NO:64, represented by nucleotides 917–1819 of SEQ ID NO:64;

(d) ORF ID NO:2 of Contig ID NO:64, represented by nucleotides 1839–2828 of SEQ ID NO:64;

(e) ORF ID NO:9 of Contig ID NO:64, represented by nucleotides 6685–7008 of SEQ ID NO:64;

(f) ORF ID NO:3 of Contig ID NO:84, represented by nucleotides 2361–3437 of SEQ ID NO:84;

(g) ORF ID NO:1 of Contig ID NO:89, represented by nucleotides 4–981 of SEQ ID NO:89;

(h) ORF ID NO:1 of Contig ID NO:137, represented by nucleotides 73–528 of SEQ ID NO:137;

(i) ORF ID NO:1 of Contig ID NO:140, represented by nucleotides 244–576 of SEQ ID NO:140; and (j) ORF ID NO:1 of Contig ID NO:141, represented by nucleotides 2–445 of SEQ ID NO:141.

79. An isolated polynucleotide comprising a nucleic aicd sequence complementary to the polynucleotide of claim 78.

80. The isolated polynucleotide of claim 78, wherein said ORF is the ORF of (a).

81. The isolated polynucleotide of claim 78, wherein said ORF is the ORF of (b).

82. The isolated polynucleotide of claim 78, wherein said ORF is the ORF, of (c).

83. The isolated polynucleotide of claim 78, wherein said ORF is the ORF of (d).

84. The isolated polynucleotide of claim 78, wherein said ORF is the ORF of (e).

85. The isolated polynucleotide of claim 78, wherein said ORF is the ORF of (f).

86. The isolated polynucleotide of claim 78, wherein said ORF is the ORF of (g).

87. The isolated polynucleotide of claim 78, wherein said ORF is the ORF of (h).

88. The isolated polynucleotide of claim 78, wherein said ORF is the ORF of (i).

89. The isolated polynucleotide of claim 78, wherein said ORF is the ORF of (j).

90. The isolated polynucleotide of claim 78, wherein said polynucleotide comprises a heterologous polynucleotide sequence.

91. The isolated polynucleotide of claim 90, wherein said heterologous polynucleotide sequence encodes a heterologous polypeptide.

92. A method for making a recombinant vector comprising inserting the isolated polynucleotide of claim 78 into a vector.

93. A recombinant vector comprising the isolated polynucleotide of claim 78.

94. The recombinant vector of claim 93, wherein said polynucleotide is operably associated with a heterologous regulatory sequence that controls gene expression.

95. A recombinant host cell comprising the isolated polynucleotide of claim 78.

96. The recombinant host cell of claim 95, wherein said polynucleotide is operably associated with a heterologous regulatory sequence that controls gene expression.

97. The isolated polynucleotide of claim 76, wherein said ORF is the ORF of (a).

98. The isolated polynucleotide of claim 76, wherein said ORF is the ORF of (b).

99. The isolated polynucleotide of claim 76, wherein said ORE, is the ORF of (c).

100. The isolated polynucleotide of claim 76, wherein said ORF is the ORF of (d).

101. The isolated polynucleotide of claim 76, wherein said ORF is the ORF of (e).

102. The isolated polynucleotide of claim 76, wherein said ORF is the ORF of (f).

103. The isolated polynucleotide of claim 76, wherein said ORF is the ORF of (g).

104. The isolated polynucleotide of claim 76, wherein said ORF is the ORF of (h).

105. The isolated polynucleotide of claim 76, wherein said ORF is the ORF of (i).

106. The isolated polynucleotide of claim 76, wherein said ORF is the ORF of (j).

107. The isolated polynucleotide of claim 76, wherein said polynucleotide comprises a heterologous polynucleotide sequence.

108. The isolated polynucleotide of claim 107, wherein said heterologous polynucleotide sequence encodes a heterologous polypeptide.

109. A method for making a recombinant vector comprising inserting the isolated polynucleotide of claim 76 into a vector.

110. A recombinant vector comprising the isolated polynucleotide of claim 76.

111. The recombinant vector of claim 110, wherein said polynucleotide is operably associated with a heterologous regulatory sequence that controls gene expression.

112. A recombinant host cell comprising the isolated polynucleotide of claim 76.

113. The recombinant host cell of claim 112, wherein said polynucleotide is operably associated with a heterologous regulatory sequence that controls gene expression.

* * * * *